United States Patent
Willey et al.

(10) Patent No.: US 9,683,261 B2
(45) Date of Patent: *Jun. 20, 2017

(54) STANDARDIZED MIXTURES FOR ASSESSING AMOUNTS OF TARGET NUCLEIC ACIDS IN A SAMPLE, AND KITS THEREFORE

(71) Applicant: The University of Toledo, Toledo, OH (US)

(72) Inventors: James C. Willey, Toledo, OH (US); Erin L. Crawford, Rossford, OH (US)

(73) Assignee: The University of Toledo, Toledo, OH (US)

( * ) Notice: Subject to any disclaimer, the term of this patent is extended or adjusted under 35 U.S.C. 154(b) by 87 days.

This patent is subject to a terminal disclaimer.

(21) Appl. No.: 14/659,101

(22) Filed: Mar. 16, 2015

(65) Prior Publication Data

US 2015/0184240 A1 Jul. 2, 2015

Related U.S. Application Data

(60) Continuation of application No. 12/404,992, filed on Mar. 16, 2009, now Pat. No. 8,981,068, which is a division of application No. 11/338,860, filed on Jan. 23, 2006, now Pat. No. 7,527,930.

(60) Provisional application No. 60/646,157, filed on Jan. 21, 2005.

(51) Int. Cl.
| | |
|---|---|
| *C07H 21/04* | (2006.01) |
| *C12Q 1/68* | (2006.01) |
| *C12P 19/34* | (2006.01) |
| *G06F 19/28* | (2011.01) |
| *G06F 19/20* | (2011.01) |

(52) U.S. Cl.
CPC ............ *C12Q 1/6876* (2013.01); *C12P 19/34* (2013.01); *C12Q 1/6834* (2013.01); *C12Q 1/6844* (2013.01); *C12Q 1/6851* (2013.01); *G06F 19/28* (2013.01); *C12Q 2600/156* (2013.01); *C12Q 2600/158* (2013.01); *C12Q 2600/16* (2013.01); *C12Q 2600/166* (2013.01); *G06F 19/20* (2013.01)

(58) Field of Classification Search
USPC ................................. 435/6.12, 91.2
See application file for complete search history.

(56) References Cited

U.S. PATENT DOCUMENTS

| | | | | |
|---|---|---|---|---|
| 5,213,961 A | * | 5/1993 | Bunn .................... | C12Q 1/6851 435/6.12 |
| 5,643,765 A | * | 7/1997 | Willey .................... | B01D 57/02 435/6.12 |
| 5,712,125 A | * | 1/1998 | Uhlen .................... | C12Q 1/6851 435/810 |
| 5,824,516 A | * | 10/1998 | Collu .................... | C12Q 1/6851 435/91.1 |
| 5,837,501 A | * | 11/1998 | Beumer ................ | C12Q 1/6851 435/5 |
| 2004/0197785 A1 | * | 10/2004 | Willey .................... | C12Q 1/686 435/6.12 |
| 2005/0239116 A1 | * | 10/2005 | Willey ................. | C12Q 1/6804 435/6.12 |
| 2006/0194216 A1 | * | 8/2006 | Willey ................. | C12Q 1/6858 435/6.12 |

* cited by examiner

*Primary Examiner* — Kenneth Horlick
(74) *Attorney, Agent, or Firm* — MacMillan, Sobanski & Todd, LLC

(57) ABSTRACT

Described herein are compositions for evaluating nucleic acids, standardized mixture for assessing amounts of at least one target nucleic acid in a sample, and kits comprising the same.

29 Claims, 39 Drawing Sheets

|  | Primary Mean | NSCLC SD2 | % of mean | n |
|---|---|---|---|---|
| BCL-2 | ND3 | | | |
| Catalase | 1.83E+05 | 3.60E+04 | 20 | 5 |
| GSTP1 | 8.96E+06 | 5.80E+06 | 65 | 3 |
| SOD1 | 7.50E+05 | 2.21E+05 | 30 | 3 |
| DNASE1 | 3.55E+04 | 1.04E+04 | 29 | 4 |
| GSTM3 | 1.19E+04 | 5.80E+03 | 49 | 5 |
| GSTM1-5 | 1.59E+04 | 2.50E+04 | 157 | 4 |
| ICAM1 | 7.33E+04 | 3.89E+04 | 53 | 5 |
| BCLX-lg | 1.83E+04 | 2.70E+03 | 15 | 5 |
| BCLX-sm | 9.99E+04 | 2.16E+04 | 22 | 5 |
| ERCC1 | 5.05E+05 | 1.31E+05 | 26 | 3 |
| MLH1 | 2.15E+04 | 9.40E+03 | 44 | 5 |
| MSH2 | 2.39E+04 | 3.70E+04 | 155 | 3 |
| MSH6 | 9.70E+04 | 2.69E+04 | 28 | 2 |
| ERCC4 | NE5 | | | |
| p53 | 5.64E+02 | 2.10E+02 | 37 | 3 |
| E2F-1 | 6.16E+04 | 1.50E+04 | 24 | 4 |
| p21 | NE5 | | | |
| GJA1 | 1.13E+05 | 1.41E+04 | 13 | 5 |
| GSR | NE5 | | | |
| MSK2 | NE5 | | | |
| FPGS | 5.32E+04 | 1.48E+04 | 28 | 4 |

1Gene expression values (mean) are reported as molecules per 10677-actin molecules 2SD= standard deviation 3ND= non detectable 4p values were determined by student t test between H460 and H1435 cells, bold numbers = significant, p<.05

5NE= not evaluated

*FIG. 1*

Gene Expression Measurement in Lung Donor Airway Epithelial Cells by Multiplex StaRT-PCR

| lung section | morphology | ARNT[1] | BCLX-L | BCLX-S | C-MYC | CJUN | CYP1A1 |
|---|---|---|---|---|---|---|---|
| RMS H | dysplastic | 1.10E+04 | 7.07E+03 | 1.93E+05 | NA[2] | >5,000[3] | NA |
| LLL 2 | normal | 1.10E+04 | 3.23E+04 | 2.58E+05 | 1.05E+04 | >50,000 | NA |
| LLL 4 | normal | 8.18E+03 | 1.57E+04 | 2.32E+05 | 1.41E+04 | 4.30E+05 | 2.64E+01 |

| lung section | ERBB2 | HNF3A | ICAM1 | IVL | MUC1 | NSE | PCNA |
|---|---|---|---|---|---|---|---|
| RMS H | >5,000 | 1.24E+03 | 1.43E+04 | <5,000 | <500 | 9.14E+04 | 1.55E+05 |
| LLL 2 | 4.46E+06 | 4.79E+03 | 1.16E+04 | <500 | <500 | 1.78E+05 | 9.40E+04 |
| LLL 4 | 8.52E+05 | 2.88E+03 | 5.89E+03 | <500 | 5.52E+04 | 6.60E+04 | 7.70E+04 |

| lung section | RARA | RB | SPR1 | TGM2 | TNFRF1A |
|---|---|---|---|---|---|
| RMS H | 9.10E+03 | <500 | >5,000 | <5,000 | >5,000 |
| LLL 2 | 1.34E+04 | <500 | <500 | <5,000 | 8.33E+04 |
| LLL 4 | 6.59E+03 | 4.16E+02 | <500 | <5,000 | 9.90E+03 |

[1] Expression values for each target gene presented as molecules/$10^6$ β-actin molecules
[2] NA = not assessed
[3] assessment were not completed for values listed as < or > but values could be approximated by measurement of CT or NT.

FIG. 2

Mean Gene Expression in Universal Human Reference cDNA as Measured by Methods Disclosed Herein

| Gene | Genbank Accession | Mean Expression Two-Step | Mean Expression Non-Two-Step | Seq. ID. No. R | Seq. ID. No. CT |
|---|---|---|---|---|---|
| HRD1l | M75664/M62487 | ND | ND | 1 | 2 | 3 |
| ACR1 | M55040 | 140 | NA | 4 | 5 | 6 |
| ALAS1 | X56351 | 7300 | 13000 | 7 | 8 | 9 |
| ARHT | M69238 | 8300 | NA | 10 | 11 | 12 |
| BCL2 | M14745 | 410 | 530 | 13 | 14 | 15 |
| BCL2L1 | Z23115/Z23116 | 3300 | 12000 | 16 | 17 | 18 |
| BCL2L1 | Z23115/Z23116 | 8500 | 2300 | 19 | 20 | 21 |
| MYC | V00568 | 81000 | 47000 | 22 | 23 | 24 |
| CALR | X56667 | NA | NA | 25 | 26 | 27 |
| CSK1 | X04856/X51818 | 6700 | 34000 | 28 | 29 | 30 |
| CAT | X04076 | 5400 | 7900 | 31 | 32 | 33 |
| CDC2 | X03360 | 49000 | 40000 | 34 | 35 | 36 |
| CDK7 | X79193 | 6000 | 17000 | 37 | 38 | 39 |
| CDK8 | X85753 | 1200 | NA | 40 | 41 | 42 |
| CIA1 | X52947 | 20000 | 13000 | 43 | 44 | 45 |
| JUN | J04111 | 60000 | 210000 | 46 | 47 | 48 |
| CLND | X78520 | 1600 | 4400 | 49 | 50 | 51 |
| COL3A | X14420 | 25 | 25 | 52 | 53 | 54 |
| SOD1 | X02317/K00065 | 220000 | 130000 | 55 | 56 | 57 |
| CCNA2 | X51688 | 4000 | 6700 | 58 | 59 | 60 |
| CCNG2 | U47414 | 3600 | 3300 | 61 | 62 | 63 |
| CCNH | U11791 | 2300 | 3400 | 64 | 65 | 66 |
| CYP1A | K03191 | 540 | 240 | 67 | 68 | 69 |
| CYP1B | U03688 | 1900 | 800 | 70 | 71 | 72 |
| CYP2B | M29874/M02864 | ND | ND | 73 | 74 | 75 |
| CYP2E | J02843 | 46 | 18 | 76 | 77 | 78 |
| CYP1F1 | J02906 | ND | ND | 79 | 80 | 81 |
| DAO | X13227 | 96 | 59 | 82 | 83 | 84 |
| SULT2 | U08024 | 2600 | 4700 | 85 | 86 | 87 |
| DNASE | M55983 | Low | 540 | 88 | 89 | 90 |
| TFDP2 | U18422 | 13000 | 20000 | 91 | 92 | 93 |
| DPYS | D78011 | 57 | 22 | 94 | 95 | 96 |
| E2F1 | M96577 | 2400 | 6300 | 97 | 98 | 99 |
| E2F3 | L22846 | 1400 | 710 | 100 | 101 | 102 |
| E2F4 | U15641 | 12000 | 15000 | 103 | 104 | 105 |
| E2F5 | U15642 | 3200 | 2000 | 106 | 107 | 108 |
| ERCC1 | M13194 | 61000 | 25000 | 109 | 110 | 111 |
| ERCC3 | D64315 | 630 | 170 | 112 | 113 | 114 |
| EDN1 | NM_001955 | 770 | 610 | 115 | 116 | 117 |
| FN1 | X02761/K00799 | 180000 | 140000 | 118 | 119 | 120 |
| GGH | U55205 | 18000 | 14000 | 121 | 122 | 123 |
| FPGS | M68045 | 4350 | 2600 | 124 | 125 | 126 |
| FOXL1 | X15707 | 40000 | 93000 | 127 | 128 | 129 |
| GAED | M33197 | 250000 | 360000 | 130 | 131 | 132 |
| GLCLC | M90656 | 980 | 1700 | 133 | 134 | 135 |
| GL2 | NM_002210 | 5000 | 1700 | 136 | 137 | 138 |
| GLUCT | M57899 | Low | ND | 139 | 140 | 141 |
| GLUCT | M57951 | 930 | 1000 | 142 | 143 | 144 |
| GSR | X15722 | 14000 | 12000 | 145 | 146 | 147 |

FIG. 4A

Mean Gene Expression in Universal Human Reference cDNA as Measured by Methods Disclosed Herein

| Gene | Accession | Val1 | Val2 | S1 | S2 | S3 |
|---|---|---|---|---|---|---|
| GPX3 | D00632 | 2500 | NA | 148 | 149 | 150 |
| GSTM1 | J03817/M63509 | 16000 | 19000 | 151 | 152 | 153 |
| GSTM3 | J05459 | 14000 | 17000 | 154 | 155 | 156 |
| GSTP1 | X06547 | 210000 | 230000 | 157 | 158 | 159 |
| GSTT1 | X79389 | NA | 180 | 160 | 161 | 162 |
| ERBB2 | X03363 | 84000 | 66000 | 163 | 164 | 165 |
| HNF3A | U39840 | 360 | 730 | 166 | 167 | 168 |
| HSPD1 | XM_012182 | 130000 | NA | 169 | 170 | 171 |
| HSPA9 | L15189 | 17000 | 13000 | 172 | 173 | 174 |
| ICAM1 | X06990 | 4300 | 6100 | 175 | 176 | 177 |
| IVL | M13902 | Low | Low | 178 | 179 | 180 |
| JUNB | X51345 | 1300 | 11000 | 181 | 182 | 183 |
| KRT5 | M19723 | ND | Low | 184 | 185 | 186 |
| IL16 | M90391 | Low | 690 | 187 | 188 | 189 |
| MAD | L06895 | 1200 | 1500 | 190 | 191 | 192 |
| MAX | X60287 | ND | ND | 193 | 194 | 195 |
| MLH1 | U07343 | 15000 | 6000 | 196 | 197 | 198 |
| MSH2 | L47581 | 9200 | 9600 | 199 | 200 | 201 |
| MSH6 | U28946 | 180000 | 57000 | 202 | 203 | 204 |
| MSK2 | AF074715 | 4300 | 2000 | 205 | 206 | 207 |
| MUC1 | X52229 | ND | ND | 208 | 209 | 210 |
| NADH | M28705 | 170000 | 28000 | 211 | 212 | 213 |
| POR | S90469 | 29000 | 15000 | 214 | 215 | 216 |
| NSE | M27810 | 76000 | 62000 | 217 | 218 | 219 |
| RBL2 | X74594 | 1700 | 5000 | 220 | 221 | 222 |
| CDKN2 | L27211 | ND | Low | 223 | 224 | 225 |
| CDKN2 | U17074 | 9300 | 17000 | 226 | 227 | 228 |
| CDKN2 | U40343 | 1800 | 3500 | 229 | 230 | 231 |
| CDKN1 | U03106 | 4000 | 9280 | 232 | 233 | 234 |
| CDKN1 | U10906 | 9000 | 8600 | 235 | 236 | 237 |
| TP53 | K03199 | 7200 | 3300 | 238 | 239 | 240 |
| SAM68 | M88108 | 190000 | 130000 | 241 | 242 | 243 |
| PCNA | J04718 | 120000 | 54000 | 244 | 245 | 246 |
| PMS2L | D38437 | 1400 | 3900 | 247 | 248 | 249 |
| SULT1 | L19999 | 6100 | 4000 | 250 | 251 | 252 |
| SULT1 | U08032 | 28000 | 22000 | 253 | 254 | 255 |
| RAP1A | M22995 | NA | 38000 | 256 | 257 | 258 |
| RARA | X06614 | 4200 | 3200 | 259 | 260 | 261 |
| RB1 | M15400 | 3900 | 3600 | 262 | 263 | 264 |
| SPARC | J03040 | 120000 | 110000 | 265 | 266 | 267 |
| SPRIB | M84757 | 13 | 62 | 268 | 269 | 270 |
| STX1A | L37792 | 1400 | 2400 | 271 | 272 | 273 |
| TGM2 | M55153 | NA | 3200 | 274 | 275 | 276 |
| TNF | X02910/X02159 | ND | ND | 277 | 278 | 279 |
| TNFRF | M58286/M33480 | 2400 | 7600 | 280 | 281 | 282 |

[2] ND = None detected. No NT was detected when CT mix F was used.

[3] NA = Not assessed.

[4] Low = expression levels are less than 600 mRNA/10⁶ β-actin mRNA. Low expression is reported when no NT is seen when mix E was used and neither NT nor CT were measurable when mix F was used.

FIG. 4B

Source of Variation in Quantitative RT-PCR Gene Expression Measurement and Control Methods

| Source of Variation | Embodiments of methods described herein | Real-time |
|---|---|---|
| cDNA loading: Due to variation in pipetting, quantification, reverse transcription. Consequence: unreliable comparison of expression for same gene in two different samples | Multiplex Amplify with Reference Gene (e.g. β-actin) | Multiplex Amplify with Reference Gene (e.g. β-actin) |
| Intra-nucleic acid Amplification Efficiency Cycle-to-Cycle Variation: early slow, log-linear, and late slow plateau phases Consequence: unreliable comparison of expression for same gene in different samples | Internal standard CT for each gene in a Standardized Mixture of Internal Standards (SMIS) | Real-time measurement |
| Inter-nucleic acid amplification Efficiency: in efficiency of primers Consequence: unreliable comparison of expression for different genes in the same or different samples | Internal standard CT for each gene in a SMIS | External standard curve for each gene measured |
| Inter-specimen Amplification Efficiency: variable presence of an inhibitor of PCR Consequence: unreliable comparison of expression for same or different gene in same or different samples | Internal standard CT for each gene in a SMIS | Standard curve of reference sample compared to test sample[2] |
| Inter-sample Amplification Efficiency: in quality and/or concentration of PCR reagents (e.g. primers); in presence of an inhibitor of PCR Consequence: unreliable comparison of expression for same or different gene in same or different samples | Internal standard CT for each gene in a SMIS | None[2] |
| Inter-sample amplification Efficiency: in thermocycler efficiency Consequence: e.g., unreliable comparison of expression for same or different gene in same or different samples | Internal standard CT for each gene | None[2] |

*FIG. 22*

**Standardized Data
Enabling Virtually Indefinite Multiplexed Analysis**

Example:
A gene expression test to augment diagnosis of lung cancer incytomorphologic samples
c-myc x E2F1/p21
Diagnostic sensitivity of 100% and specificity of 96%

Bivariate Analysis of Cell Cycling Genes in Normal and Malignant Human Bronchial Epithelial Cells The E2F1/p21 Relationship Observed in Lung Tissue is Not Observed in Bladder Tissue Data sets from different experiments, different laboratories, different days may all be compared in the Standardized Expression Database

*FIG. 25*

| Gene | Round one cycles | Round two cycles | Maximum dilution[1] | Gene expression values[2] |
|---|---|---|---|---|
| β-actin | 35 | 0 | 1/10 | NA[3] |
| | 5 | 35 | 1/100 | NA |
| | 8 | 35 | 1/100 | NA |
| | 10 | 35 | 1/1,000 | NA |
| | 35 | 35 | 1/100,000 | NA |
| c-*myc* | 35 | 0 | 1/1,000 | 8.99E+04 |
| | 5 | 35 | 1/1,000 | 8.24E+04 |
| | 8 | 35 | 1/10,000 | 7.02E+04 |
| | 10 | 35 | 1/10,000 | 3.30E+04 |
| | 35 | 35 | 1/1,000,000 | 3.40E+04 |
| catalase | 35 | 0 | 1/1,000 | 1.40E+04 |
| | 5 | 35 | 1/1,000 | 3.75E+04 |
| | 8 | 35 | 1/10,000 | 8.76E+03 |
| | 10 | 35 | 1/10,000 | 1.20E+04 |
| | 35 | 35 | 1/1,000,000 | 9.25E+03 |

[1] Maximum dilution at which quantifiable PCR products could be detected. For uniplex reactions (round two cycles = 0), the dilution shown is of the starting mixture of cDNA and CT mix. For multiplex reactions, the dilutions shown are of round one products (e.g. 1/100 = 1 ml of the 10 ml round one product + 9 ml water).
[2] Gene expression values are reported as molecules per $10^6$ β-actin molecules.
[3] NA = not applicable

*FIG. 29*

Densitometric Data from First Sample Lane of Fig. 34

|  | Length (base pairs) | Zeineh densitometric values | Size correction | Relative densitometric values |
|---|---|---|---|---|
| (A) GAPDH | | | | |
| Native GAPDH and heterodimer ($N^2$ + 2NM) | 788 | 10,095 | | 0.820 |
| Mutanted GAPDH ($M^2$) | 588 | 1,652 | X788/588 ~ 2214 | 0.180 |
| (B) GSH-Px | | | | |
| Mutated GSH-Px and heterodimer ($N^2$ + 2NM) | 354 | 6,709 | | 0.442 |
| Native GSH-Px ($N^2$) | 280 | 6,692 | X354/280 = 8461 | 0.558 |

*FIG. 35*

| GENE | Expression Data using some embodiments disclosed herein | | | MicroArray Expression Data |
|---|---|---|---|---|
| | SVpgC2a | HOE | Fold Difference: SVpgC2a / HOE | Fold Difference: SVpgC2a / HOE |
| AHR | 420 | 125 | 3.3 | +3.2 |
| GSTM1, 2,4,5 | 260 | 30 | 8.6 | +9 |
| GSTP1 | 10200 | 26,000 | -2.5 | -1.8 |
| SOD2 | 2300 | 420 | 5.5 | 5.1 |
| GPX1 | 17500 | 27,000 | -1.5 | -2.4 |

Comparison to microarray gene expression (cDNA chip technique) data in normal or immortalized Human Oral Epithelial cells confirmed the concept that gene arrays are valuaable screening methods where other techniques, like methods described herein, allow for more detailed gene expression analysis.

STANDARDIZED MIXTURES FOR ASSESSING AMOUNTS OF TARGET NUCLEIC ACIDS IN A SAMPLE, AND KITS THEREFORE

CROSS-REFERENCE TO RELATED APPLICATIONS

This application is a continuation application of U.S. Ser. No. 12/404,992 filed Mar. 16, 2009, now U.S. Pat. No. 8,981,068 issued Mar. 17, 2015, which is a divisional application of Ser. No. 11/338,860 filed Jan. 23, 2006, now U.S. Pat. No. 7,527,930 issued May 5, 2009, which claims the benefit of U.S. Provisional Application No. 60/646,157, filed Jan. 21, 2005, which is incorporated herein by reference in its entirety.

STATEMENT REGARDING FEDERALLY SPONSORED RESEARCH

Certain embodiments of the present invention were made under research grant number ES02679 and ES01247 from the National Institute of Health; Grant No. RR00044 from the Division of Research Resources, Health Institute Contract 91-2, and International Lead Zinc Organization contract CH61, who may have certain rights thereto. Certain embodiments of the invention were made under Research Grant No. NIH CA85147, CA 95806 and CA 103594 who may have certain rights thereto. Certain embodiments of the present invention were made under research grant number E01640 from the National Institute of Health who may have certain rights thereto.

BACKGROUND OF THE INVENTION

With the sequencing of the human genome comes the hope of accelerating drug development and discovering better diagnostic tests. This hope has engendered a need to develop improved methods for multi-gene expression measurement. Methods amenable to appropriate quality control, for example, to meet regulatory guidelines, are particularly needed. The present invention relates to compositions and methods directed to addressing these hopes and needs.

Other methods and compositions directed thereto are provided in U.S. patent application Ser. No. 10/109,349, filed Mar. 28, 2002, and Ser. No. 10/471,473; and U.S. Provisional Application Ser. Nos. 60/368,288 and 60/368,409, filed Mar. 28, 2002; 60/550,278, filed Mar. 5, 2004 and 60/561,841, filed Apr. 12, 2004.

SEQUENCE LISTING

The instant application contains a Sequence Listing which has been submitted via EFS-web and is hereby incorporated by reference in its entirety. The ASCII copy, created on Mar. 4, 2015, is named 604_56771_SEQ_LIST_D2006-14-6.txt, and is 41 kb in size.

SUMMARY OF THE INVENTION

A first aspect of the invention is a method comprising providing a first sample comprising a first nucleic acid; amplifying said first nucleic acid; and obtaining a relationship wherein said relationship can enumerate less than about 1,000 molecules of said first nucleic acid in said first sample. In some embodiments of the invention said relationship can enumerate less than about 100 molecules, less than about 10 molecules, or less than about 1 molecule of said first nucleic acid in said first sample. In other embodiments, said relationship compares a first relationship of amplified product of said first nucleic acid to co-amplified product of a competitive template for said first nucleic acid to a second relationship of amplified product of a second nucleic acid in said first sample to co-amplified product of a competitive template for said second nucleic acid. Typically, the said first nucleic acid and said competitive template for said first nucleic acid are co-amplified in a first vessel and said second nucleic acid and said competitive template for said second nucleic acid are co-amplified in a second vessel. The competitive template for the first or second nucleic acid can comprise a sequence referenced in Table 4. In some embodiments, the second nucleic acid serves as a first reference nucleic acid, for example as a control for loading. The first reference nucleic acid can correspond to at least one gene selected from GADP, ACTB, and β-actin. The relationship can further compare amplified product of a number of other nucleic acid(s) to co-amplified product of competitive template(s) for said number of other nucleic acid(s). At least one of said other nucleic acids can serve as a second reference nucleic acid. The second reference nucleic acid can correspond to at least one gene selected from GADP, ACTB, and β-actin. In various embodiments, the relationship comprises a use of microfluidic capillary electrophoresis, an oligonucleotide array, mass spectrometry, or a chromatography. In some embodiments, the relationship does not involve taking real-time measurements nor generation of a standard curve. The relationship can control for sources of variation selected from cDNA loading, intra-nucleic acid amplification efficiency, inter-nucleic acid amplification efficiency, inter-specimen amplification efficiency, inter-sample amplification efficiency, and intra-sample amplification efficiency. The relationship is capable of detecting less than about a two-fold difference or less than about a one-fold difference. The relationship is capable of detecting less than about an 80% difference, less than about a 50% difference, less than about a 30% difference, or less than about a 20% difference. In some embodiments, the relationship is capable of detecting less than about a two-fold difference or less than about a one-fold difference in about 100 molecules or less or in about 10 molecules or less of said first nucleic acid in said first sample. The difference detected can be less than about an 80% difference, less than about a 50% difference, less than about a 30% difference, or less than about a 20% difference. In some embodiments, the relationship provides a coefficient of variation of less than about 25%, less than about 20%, less than about 15%, less than about 10%, or less than about 5% between said first sample and a second sample of said first nucleic acid. In some embodiments, the first and said second samples are amplified at different times, first and said second samples are amplified in different laboratories, or the first and said second samples are provided from different subjects. The first nucleic acid can comprise a sequence referenced in Table 1 or 2. The methods described herein can reduce or eliminate the false negatives, preferably the false positives are reduced to a statistically insignificant number. The nucleic acid can be an RNA molecule or a DNA molecule. Typically, the relationship is substantially constant beyond an exponential phase of said amplification of said first nucleic acid.

Another embodiment is a method of assessing a first nucleic acid provided in a first sample, comprising co-amplifying said first nucleic acid, a number of other nucleic acid(s), a competitive template for said first nucleic acid and a competitive template(s) for said other nucleic acid(s)

wherein said competitive templates are at known concentrations relative to one another, to produce first amplified product thereof, diluting said first amplified product; and further co-amplifying said diluted first amplified product of said first nucleic acid and of said competitive template for said first nucleic acid, to produce second amplified product thereof. Typically, the number is at least about one other nucleic acid, at least about 100 other nucleic acids, or the number is at least about 1,000 other nucleic acids. Typically, the diluting produces at least about a 100-fold dilution, at least about a 1.000-fold dilution, or at least about a 10.000-fold dilution. Preferably, the method enumerates less than about 1,000 molecules of said first nucleic acid in said sample, less than about 100 molecules of said first nucleic acid in said first sample, less than about 10 molecules of said first nucleic acid in said first sample, or about 1 molecule of said first nucleic acid in said first sample. Preferably, at least one of said competitive templates comprises a sequence referenced in Table 4. The first nucleic acid can comprise a sequence referenced in Table 1 or 2. One of the other nucleic acids can serve as a first reference nucleic acid, such as a control for loading. The first reference nucleic acid can correspond to at least one gene selected from GADP, ACTB, and β-actin. In one embodiment, the method of assessing comprises obtaining a first relationship, said first relationship comparing said second amplified product of said first nucleic acid to said second amplified product of said competitive template for said first nucleic acid; obtaining a second relationship, said second relationship comparing said first amplified product of said first reference nucleic acid to said first amplified product of said competitive template for said first reference nucleic acid; and comparing said first and said second relationships. In some embodiments, another one of said other nucleic acids serves as a second reference nucleic acid. The second reference nucleic acid can corresponds to at least one gene selected from GADP, ACTB, and β-actin. In another embodiment, the method of assessing comprises obtaining a first relationship, said first relationship comparing said second amplified product of said first nucleic acid to said second amplified product of said competitive template for said first nucleic acid; obtaining a third relationship, said third relationship comparing said first amplified product of said second reference nucleic acid to said first amplified product of said competitive template for said second reference nucleic acid; and comparing said first and said third relationships. In some embodiments, the method further comprises diluting and further co-amplifying said diluted first amplified product of said first reference nucleic acid and of said competitive template for said first reference nucleic acid, to produce second amplified products thereof. In yet another embodiment, the assessing comprises obtaining a first relationship, said first relationship comparing said second amplified product of said first nucleic acid to said second amplified product of said competitive template for said first nucleic acid; obtaining a fourth relationship, said fourth relationship comparing said second amplified product of said first reference nucleic acid to said second amplified product of said competitive template for said first reference nucleic acid; and comparing said first and said fourth relationships. In various embodiments, the relationship comprises a use of microfluidic capillary electrophoresis, an oligonucleotide array, mass spectrometry, or a chromatography. In some embodiments, the relationship does not involve taking real-time measurements nor generation of a standard curve. The relationship can control for sources of variation selected from cDNA loading, intra-nucleic acid amplification efficiency, inter-nucleic acid amplification efficiency, inter-specimen amplification efficiency, inter-sample amplification efficiency, and intra-sample amplification efficiency. The assessing can detect less than about a two-fold difference, less than about a one-fold difference, less than about an 80% difference, less than about a 50% difference, less than about a 30% difference, or less than about a 20% difference. In some embodiments, the relationship provides a coefficient of variation of less than about 25%, less than about 20%, less than about 15%, less than about 10%, or less than about 5% between said first sample and a second sample of said first nucleic acid. In some embodiments, the first and said second samples are amplified at different times, first and said second samples are amplified in different laboratories, or the first and said second samples are provided from different subjects. The first nucleic acid can comprise a sequence referenced in Table 1 or 2. The methods described herein can reduce or eliminate the false negatives, preferably the false positives are reduced to a statistically insignificant number. The nucleic acid can be an RNA molecule or a DNA molecule. Typically, the relationship is substantially constant beyond an exponential phase of said amplification of said first nucleic acid. In some embodiments, the samples are diluted prior to amplification.

Another aspect of the invention is a method of assessing a first nucleic acid in a first sample, comprising providing a standardized mixture comprising a competitive template for said first nucleic acid and a competitive template for a second nucleic acid in said first sample wherein said competitive templates are at known concentrations relative to each other; combining said first sample with said standardized mixture; co-amplifying said first nucleic acid and said competitive template for said first nucleic acid to produce first amplified product thereof; diluting said first amplified product; further co-amplifying said diluted first amplified product of said first nucleic acid and of said competitive template for said first nucleic acid, to produce second amplified product thereof, and co-amplifying said second nucleic acid and said competitive template for said second nucleic acid to produce first amplified product thereof. The first nucleic acid and said competitive template for said first nucleic acid can be co-amplified in a first vessel and said second nucleic acid and said competitive template for said second nucleic acid can be co-amplified in a second vessel. Typically, the diluting produces at least about a 100-fold dilution, at least about a 1,000-fold dilution, or at least about a 10,000-fold dilution. The method can enumerate less than about 1,000 molecules of said first nucleic acid in said first sample, less than about 100 molecules of said first nucleic acid in said first sample, less than about 10 molecules of said first nucleic acid in said first sample, or about 1 molecule of said first nucleic acid in said first sample. The standardized mixture can further comprise sufficient amounts of said competitive templates for assessing said first nucleic acid in more than about $10^6$ other samples, more than about $10^8$ other samples, more than about $10^{10}$ other samples, more than about $10^{11}$ other samples, or more than about $10^{12}$ other samples. The standardized mixture can further comprise a number of other competitive template(s) for other nucleic acid(s) wherein said competitive template(s) are at known concentrations relative to one another; thereby allowing assessment of said other nucleic acids in said first sample. The number of other competitive templates can be at least about 100 or at least about 1,000. In some embodiments, the second nucleic acid serves as a first reference nucleic acid, such as a control for loading. The first reference nucleic acid can correspond to at least one gene selected from GADP, ACTB, and β-actin. In some embodiments, the method of assessing comprises obtaining a first relationship, said first relationship comparing said second amplified product of said first nucleic acid to said second amplified product of said competitive template for said first nucleic acid; obtaining a second relationship, said second relationship comparing said first amplified product of said first reference nucleic acid to said first amplified product of said competitive template for said first reference nucleic acid; and comparing said first and said second relationships. At least one of said other nucleic acids serves as a second reference nucleic acid and said second reference nucleic acid can correspond to at least one gene selected from GADP, ACTB, and β-actin. The method can further comprise co-amplifying said second reference nucleic acid and said competitive template for said second reference nucleic acid to produce first amplified product thereof. The assessing can comprise obtaining a first relationship, said first relationship comparing said second amplified product of said first nucleic acid to said second amplified product of said competitive template for said first nucleic acid; obtaining a third relationship, said third relationship comparing said first amplified product of said second reference nucleic acid to said first amplified product of said competitive template for said second reference nucleic acid; and comparing said first and said third relationships. The standardized mixture can further comprise sufficient amounts of said competitive templates for assessing said first nucleic acid in more than about $10^6$ other samples, more than about $10^8$ other samples, more than about $10^{10}$ other samples, more than about $10^{11}$ other samples, or more than about $10^{12}$ other samples. The method can further comprise diluting and further co-amplifying said diluted first amplified product of said first reference nucleic acid and of said competitive template for said first reference nucleic acid, to produce second amplified products thereof. In one embodiment, the first nucleic acid and said competitive template for said first nucleic acid are further co-amplified in a first vessel and said first reference nucleic acid and said competitive template for said first reference nucleic acid are further co-amplified in a second vessel. In another embodiment, the assessing comprises obtaining a first relationship, said first relationship comparing said second amplified product of said first nucleic acid to said second amplified product of said competitive template for said first nucleic acid; obtaining a fourth relationship, said fourth relationship comparing said second amplified product of said first reference nucleic acid to said second amplified product of said competitive template for said first reference nucleic acid; and comparing said first and said fourth relationships. In various embodiments, the relationship comprises a use of microfluidic capillary electrophoresis, an oligonucleotide array, mass spectrometry, or a chromatography. In some embodiments, the relationship does not involve taking real-time measurements nor generation of a standard curve. The relationship can control for sources of variation selected from cDNA loading, intra-nucleic acid amplification efficiency, inter-nucleic acid amplification efficiency, inter-specimen amplification efficiency, inter-sample amplification efficiency, and intra-sample amplification efficiency. The assessing can detect less than about a two-fold difference, less than about a one-fold difference, less than about an 80% difference, less than about a 50% difference, less than about a 30% difference, or less than about a 20% difference. In some embodiments, the relationship provides a coefficient of variation of less than about 25%, less than about 20%, less than about 15%, less than about 10%, or less than about 5% between said first sample and a second sample of said first nucleic acid. In some embodiments, the first and said second samples are amplified at different times, first and said second samples are amplified in different laboratories, or the first and said second samples are provided from different subjects. The first nucleic acid can comprise a sequence referenced in Table 1 or 2. The methods described herein can reduce or eliminate the false negatives, preferably the false positives are reduced to a statistically insignificant number. The nucleic acid can be an RNA molecule or a DNA molecule.

Another aspect of the invention is a method for assessing a first nucleic acid, comprising providing a series of serially-diluted standardized mixtures comprising a competitive template for said first nucleic acid and a competitive template for a second nucleic acid present in a number of samples comprising said first nucleic acid, wherein said competitive templates are at known concentrations relative to each other; combining one of said samples comprising said first nucleic acid with a first one of said serially-diluted standardized mixtures; co-amplifying said first nucleic acid and said competitive template for said first nucleic acid to produce amplified product thereof, obtaining a first relationship, said first relationship comparing said amplified product of said first nucleic acid to said amplified product of said competitive template for said first nucleic acid; determining whether said first relationship is within about 1:10 to about 10:1; if not, repeating said combining, co-amplifying, obtaining and determining steps with a second one of said serially-diluted standardized mixtures; co-amplifying said second nucleic acid and said competitive template for said second nucleic acid to produce amplified product thereof, obtaining a second relationship, said second relationship comparing said amplified product of said second nucleic acid to said amplified product of said competitive template for said second nucleic acid; and comparing said first and said second relationships. The method can further comprise diluting said amplified product of said first nucleic acid and said competitive template for said first nucleic acid; and further co-amplifying said diluted amplified product to produce further amplified product thereof. In addition, the method can further comprise diluting said amplified product of said second nucleic acid and said competitive template for said second nucleic acid; and further co-amplifying said diluted amplified product to produce further amplified product thereof. The number of samples can comprise a series of serially-diluted samples of said second nucleic acid. In one embodiment of the one of said samples is selected to provide said second nucleic acid approximately calibrated to said competitive template for said second nucleic acid in said first one of said serially-diluted standardized mixtures. In another embodiment of the method said first nuclei acid and said competitive template for said first nucleic acid are co-amplified in a first vessel and said second nucleic acid and said competitive template for said second nucleic acid are co-amplified in a second vessel. The second nucleic acid can serve as a first reference nucleic acid, such as a control for loading. The first reference nucleic acid can be GADP, ACTB, or β-actin. The first reference nucleic acid can be present at two different concentrations in two of said serially-diluted standardized mixtures. The series of serially-diluted standardized mixtures can further comprise sufficient amounts of said competitive templates for assessing said first nucleic acid in more than about $10^6$ samples, more than about $10^8$ samples, more than about $10^{10}$ samples, more than about $10^{11}$ samples, or more than about $10^{12}$ samples. The series of serially-diluted standardized mixtures can further comprise a number of other competitive template(s) for other nucleic acid(s) wherein said competitive template(s) are at known concentrations relative to one another, thereby allowing assessment of said other nucleic acid(s). This number can be at least about 100 other competitive templates or at least about 1,000 other competitive templates. The at least one of said other nucleic acids can serve as a second reference nucleic acid. The second reference nucleic acid can correspond to at least one gene selected from GADP, ACTB, and β-actin. The method of assessing can further comprise co-amplifying said second reference nucleic acid and said competitive template for said second reference nucleic acid to produce amplified product thereof, obtaining a third relationship, said third relationship comparing said amplified product of said second reference nucleic acid to said amplified product of said competitive template for said second reference nucleic acid; and comparing said first and said third relationships. The series of serially-diluted standardized mixtures can further comprise sufficient amounts of said number of other competitive template(s) for assessing said other nucleic acid(s) in more than about $10^6$ samples, in more than about $10^8$ samples, or in more than about $10^{10}$ samples. The series of serially-diluted standardized mixtures can further comprise sufficient amounts of said number of other competitive template(s) for assessing said other nucleic acid(s). The series of serially-diluted standardized mixtures can further comprise sufficient amounts of said number of other competitive template(s) for assessing said other nucleic acid(s) in more than about $10^{11}$ samples or in more than about $10^{12}$ samples. The method can be performed such that said first nucleic acid and said other nucleic acid(s) vary in amount over a range of more than about 2 orders of magnitude. The method can detect less than about a two-fold difference over said range, less than about a 50% difference over said range, or less than about a 20% difference over said range. In some embodiments of the method, said first nucleic acid and said other nucleic acid(s) vary in amount over a range of about 3 or more orders of magnitude and said assessing detects less than about a two-fold difference over said range, less than about a 50% difference over said range, or less than about a 20% difference over said range. In other embodiments of the method, the first nucleic acid and said other nucleic(s) vary in amount over a range of about 4 or more orders of magnitude and the assessing detects less than about a two-fold difference over said range, less than about a 50% difference over said range or less than about a 20% difference over said range. In some embodiments, the first nucleic acid and said other nucleic acid(s) vary in amount over a range of about 6 or more orders of magnitude and the assessing detects less than about a two-fold difference over said range, less than about a one-fold difference over said range, less than about an 80% difference over said range, less than about a 50% difference over said range, less than about a 30% difference over said range, or less than about a 20% difference over said range. In some methods, the first nucleic acid and said other nucleic acid(s) vary in amount over a range of about 7 or more orders of magnitude and said enumerating detects less than about a two-fold difference over said range, detects less than about a one-fold difference over said range, less than about an 80% difference, less than about a 50% difference, or less than about a 20% difference. The range can also be about 8, about 9, about 10, or about 15. In some methods the about 7 orders of magnitude span about a 7-log range of gene expression and said about 7 orders of magnitude can include about $10^{-3}$, about $10^{-2}$, about 0.1, about 1, about 10, about $10^2$, about $10^3$, and about $10^4$ copies/cell. The first nucleic acid can comprise a sequence referenced in Table 1 or 2. The competitive template for said first or said second nucleic acid can comprise a sequence referenced in Table 4. The competitive template for said first nucleic acid can be at a series of concentrations relative to said competitive template for said second nucleic acid. The series of concentrations can provide 10-fold serial dilutions of said competitive template for said first nucleic acid relative to said competitive template for said second nucleic acid. At least two of said series of concentrations can span about one order of magnitude, at least two of said series of concentrations span about three orders of magnitude, or at least two of said series of concentrations span about 6 orders of magnitude. The series of concentrations can include at least two concentrations selected from about $10^{-11}$ M, about $10^{-12}$ M, about $10^{-13}$ M, about $10^{-1}4$ M, about $10^{-15}$ M, and about $10^{-16}$M. The series of concentrations can include at least three concentrations selected from about $10^{-11}$ M, about $10^{-12}$ M, about $10^{-13}$ M, about $10^{-14}$ M, about $10^{-15}$ M, and about $10^{-16}$ M. The series of concentrations can include at least six concentrations of about $10^{-11}$ M, about $10^{-12}$ M, about $10^{-13}$ M, about $10^{-14}$ M, about $10^{-15}$ M, and about $10^{-16}$ M. The first or said second relationship can be obtained with use of microfluidic capillary electrophoresis, an oligonucleotide array, mass spectrometry, or chromatography. In some embodiments of the method the first or said second relationship does not involve taking real-time measurements nor generation of a standard curve. The standardized mixtures can control for sources of variation such as cDNA loading, intra-nucleic acid amplification efficiency, inter-nucleic acid amplification efficiency, inter-specimen amplification efficiency, inter-sample amplification efficiency, and intra-sample amplification efficiency. The standardized mixtures of said series can enumerate less than about 1,000 molecules of said first nucleic acid in one of said samples, less than about 100 molecules of said first nucleic acid in one of said samples, less than about 10 molecules of said first nucleic acid in one of said samples, or about 1 molecule of said first nucleic acid in one of said samples. The standardized mixtures of said series can provide a coefficient of variation of less than about 25%, less than about 15%, or less than about 10% between 2 of said samples comprising said first nucleic acid. The method can be performed on samples obtained from different subjects, different laboratories, or at different times. The method can reduce or eliminate false negatives to an insignificant number, such as to a statistically insignificant number. The method can be computer implemented, the computer implementation comprises instructing a robotic handler to select said first one of said serially-diluted standardized mixtures for combining The computer implementation can comprise obtaining said first relationship, such as determining an area under a curve. The computer implementation can comprise instructing said robotic handler to select said second one of said serially-diluted standardized mixtures based on said first relationship. The nucleic acid assessed can be an RNA molecule or a DNA molecule.

Another aspect of the invention is a method for preparing a standardized mixture of reagents, said reagents comprising sufficient competitive template for assessing amounts of a number of nucleic acids in more than about $10^6$ samples wherein said standardized mixture allows direct comparison of said amounts between 2 of said samples. The number can be two nucleic acids, is at least about 96 nucleic acids, at least about 100 nucleic acids, or at least about 1,000 nucleic acids. The method can involve the use of reagents that are sufficient to assess said amounts in more than about $10^8$ samples, more than about $10^{10}$ samples, more than about $10^{11}$ samples, or more than about $10^{12}$ samples. The method can employ reagents which further comprise a forward primer and/or a reverse primer for priming amplification of said competitive template for said number of nucleic acid(s). The competitive template, said forward primer and/or said reverse primer can comprise a sequence referenced in Table 4. The forward primer and/or said reverse primer can have substantially the same annealing temperature as another forward primer and/or reverse primer in said standardized mixture. The forward primer and/or said reverse primer can allow for detection of about 600 molecules or less of said nucleic acid(s), about 60 molecules or less of said nucleic acid(s), or about 6 molecules or less of said nucleic acid(s). At least one of said nucleic acids can comprise a sequence referenced in Table 1 or 2. One of said number of nucleic acids can serve as a first reference nucleic acid. The first reference nucleic acid can be a control for loading and can be GADP, ACTB, or β-actin. Also, another one of said number of nucleic acids serves as a second reference nucleic acid. The second reference nucleic acid can be a gene selected from GADP, ACTB, and β-actin. The assessing can be performed with use of microfluidic capillary electrophoresis, an oligonucleotide array, mass spectrometry, or chromatography. In some embodiments, the does not involve taking real-time measurements nor generation of a standard curve. The standardized mixtures can control for sources of variation such as cDNA loading, intra-nucleic acid amplification efficiency, inter-nucleic acid amplification efficiency, inter-specimen amplification efficiency, inter-sample amplification efficiency, and intra-sample amplification efficiency. The standardized mixtures of said series can enumerate less than about 1,000 molecules of said first nucleic acid in one of said samples, less than about 100 molecules of said first nucleic acid in one of said samples, less than about 10 molecules of said first nucleic acid in one of said samples, or about 1 molecule of said first nucleic acid in one of said samples. The standardized mixtures of said series can provide a coefficient of variation of less than about 25%, less than about 15%, or less than about 10% between 2 of said samples comprising said first nucleic acid. The method can be performed on samples obtained from different subjects, different laboratories, or at different times. The method can reduce or eliminate false negatives to an insignificant number, such as to a statistically insignificant number. The nucleic acid assessed can be an RNA molecule or a DNA molecule.

Another aspect of the invention is a method comprising preparing a series of serially-diluted standardized mixtures of reagents, said reagent comprising sufficient competitive template for assessing amounts of a number of nucleic acids in more than about $10^6$ samples wherein said standardized mixtures allow direct comparison of said amounts between 2 of said samples. The number can be two nucleic acids, is at least about 96 nucleic acids, at least about 100 nucleic acids, or at least about 1,000 nucleic acids. The method can involve the use of reagents that are sufficient to assess said amounts in more than about $10^8$ samples, more than about $10^{10}$ samples, more than about $10^{11}$ samples, or more than about $10^{12}$ samples. In some methods, the amounts can vary over a range of more than about 2 orders of magnitude, over a range of about 3 or more orders of magnitude, over a range of about 4 or more orders of magnitude, over a range of about 6 or more orders of magnitude, or over a range of about 7 or more orders of magnitude. The series can allow for detection of less than about a two-fold difference over said range, of less than about a 50% difference over said range, of less than about a 20% difference over said range.

Also, about 8 or more orders of magnitude, about 9 or more orders of magnitude, about 10 or more orders of magnitude, or about 15 or more orders of magnitude are encompassed herein. The about 7 orders of magnitude can span about a 7-log range of gene expression and can include about $10^{-3}$, about $10^{-2}$, about 0.1, about 1, about 10, about $10^2$, about $10^3$, and about $10^4$ copies/cell. The method can employ reagents which further comprise a forward primer and/or a reverse primer for priming amplification of said competitive template for said number of nucleic acid(s). The competitive template, said forward primer and/or said reverse primer can comprise a sequence referenced in Table 4. The forward primer and/or said reverse primer can have substantially the same annealing temperature as another forward primer and/or reverse primer in said standardized mixture. The forward primer and/or said reverse primer can allow for detection of about 600 molecules or less of said nucleic acid(s), about 60 molecules or less of said nucleic acid(s), or about 6 molecules or less of said nucleic acid(s). At least one of said nucleic acids can comprise a sequence referenced in Table 1 or 2. The competitive templates can comprise a first competitive template for a first one of said nucleic acids and a second competitive template for a second one of said nucleic acids wherein said first competitive template is at a series of concentrations relative to said second competitive template. The second nucleic acid can serve as a first reference nucleic acid, such as a control for loading and be GADP, ACTB, or β-actin. In the method the series of concentrations can provide 10-fold serial dilutions of said first competitive template relative to said second competitive template. At least two of said series of concentrations span about one order of magnitude, about three orders of magnitude, or about 6 orders of magnitude. The series of concentrations can include concentrations selected from about $10^{-11}$ M, about $10^{-12}$ M, about $10^{-13}$ M, about $10^{-14}$ M, about $10^{-15}$ M, and about $10^{-16}$ M. The assessing can be performed with use of microfluidic capillary electrophoresis, an oligonucleotide array, mass spectrometry, or chromatography. In some embodiments, the does not involve taking real-time measurements nor generation of a standard curve. The standardized mixtures can control for sources of variation such as cDNA loading, intra-nucleic acid amplification efficiency, inter-nucleic acid amplification efficiency, inter-specimen amplification efficiency, inter-sample amplification efficiency, and intra-sample amplification efficiency. The standardized mixtures of said series can enumerate less than about 1,000 molecules of said first nucleic acid in one of said samples, less than about 100 molecules of said first nucleic acid in one of said samples, less than about 10 molecules of said first nucleic acid in one of said samples, or about 1 molecule of said first nucleic acid in one of said samples. The standardized mixtures of said series can provide a coefficient of variation of less than about 25%, less than about 15%, or less than about 10% between 2 of said samples comprising said first nucleic acid. The method can be performed on samples obtained from different subjects, different laboratories, or at different times. The method can reduce or eliminate false negatives to an insignificant number, such as to a statistically insignificant number. The nucleic acid assessed can be an RNA molecule or a DNA molecule.

Another aspect of the invention is compositions for use in the methods described herein. One embodiment is a composition comprising a standardized mixture of reagents, said reagents comprising sufficient competitive template for assessing amounts of a number of nucleic acids in more than about $10^6$ samples wherein said standardized mixture allows direct comparison of said amounts between 2 of said samples. Another embodiment is a composition comprising a series of serially-diluted standardized mixtures of reagents, said reagent comprising sufficient competitive template for assessing amounts of a number of nucleic acids in more than about $10^6$ samples wherein said standardized mixtures allow direct comparison of said amounts between 2 of said samples.

Another aspect of the invention is a database comprising numerical values corresponding to amounts of a first nucleic acid in a number of samples wherein said numerical values are directly comparable between about 5 of said samples. In the database the number can be at least about 10 samples, at least about 100 samples, at least about 1,000 samples, at least about 5,000 samples, or at least about 10,000 samples. The samples can be obtained from different subjects, from different species, from different laboratories, or at different times. In the database the amounts can show a coefficient of variation of less than about 25%, less than about 20%, less than about 15%, less than about 10%, or less than about 5% between said 2 samples. The database can further comprise numerical values corresponding to amounts of a number of other nucleic acid(s) in said number of samples. The number can be at least about 100 other nucleic acids, at least about 1,000 other nucleic acids, or at least about 10,000 other nucleic acids. The amounts can be obtained using microfluidic capillary electrophoresis, an oligonucleotide array, mass spectrometry, or chromatography. In some embodiments, the amounts are not obtained using real-time measurements nor generation of a standard curve. The numerical values can be corrected for sources of variation such as cDNA loading, intra-nucleic acid amplification efficiency, inter-nucleic acid amplification efficiency, inter-specimen amplification efficiency, inter-sample amplification efficiency, and intra-sample amplification efficiency. The numerical values typically correspond to numbers of molecules of said first nucleic acid in said number of samples. In the database, at least one of said numerical values can correspond to less than about 1,000 molecules, less than about 100 molecules, less than about 10 molecules, or to about 1 molecule of said first nucleic acid in at least one of said samples. The numerical values can correspond to less than about a two-fold difference or less than about a one-fold difference in said first nucleic acid between 2 of said samples. The numerical values can correspond to less than about an 80% difference, less than about a 50% difference, less than about a 30% difference, or less than about a 20% difference in said first nucleic acid between 2 of said samples. The numerical values can vary over a range of more than about 2 orders of magnitude, over a range of about 4 or more orders of magnitude, over a range of about 6 or more orders of magnitude, or over a range of about 7 or more orders of magnitude. The about 7 orders of magnitude can span about a 7-log range of gene expression to magnitude include about $10^{-3}$, about $10^{-2}$, about 0.1, about 1, about 10, about $10^2$, about $10^3$, and about $10^4$ copies/cell. The numerical values typically do not comprise a statistically significant number of false positives. The numerical values can be used in at least one stage of drug development selected from drug target screening, lead identification, pre-clinical validation, clinical trial and patient treatment. The pre-clinical validation can be a bioassay and/or an animal study. In some embodiments, the direct comparison in the database does not use a bioinformatics resource. The nucleic acid comprises an RNA molecule or a DNA molecule. The database can indicate a gene expression level corresponding to a biological state, such as a normal state or a disease state.

In some embodiments, the database comprises numerical indices, said numerical indices obtained by mathematical computation of 2 numerical values, said 2 numerical values corresponding to amounts of 2 nucleic acids in a number of samples wherein said numerical indices are directly comparable between 5 of said samples. The numerical indices can indicate a biological state. In some embodiments, at least one numerical index is a balanced numerical index. The numerical index can be calculated by dividing a numerator by a denominator, said numerator corresponding to said amount of one of said 2 nucleic acids and said denominator corresponding to said amount of the other of said 2 nucleic acids. The numerator can correspond to a gene positively associated with said biological state and said denominator corresponds to a gene negatively associated with said biological state. In the database, said biological state can be a disease state, a predisposition to a disease state, a therapeutic drug response, a predisposition to a therapeutic drug response, an adverse drug response, a predisposition to an adverse drug response, a drug toxicity, or a predisposition to a drug toxicity.

Yet another aspect of the invention is a method for obtaining a numerical index that indicates a biological state, comprising providing 2 samples corresponding to each of a first biological state and a second biological state; assessing an amount of each of 2 nucleic acids in each of said 2 samples wherein said assessing can enumerate less than about 1,000 molecules of each of said 2 nucleic acids; providing said amounts as numerical values wherein said numerical values are directly comparable between a number of samples; mathematically computing said numerical values corresponding to each of said first and said second biological states; and determining a mathematical computation that discriminates said first and said second biological states, thereby obtaining said numerical index. The method of determining said mathematic computation can involve a use of software. The 2 nucleic acids can be associated with said first biological state and not with said second biological state. The 2 nucleic acids can be positively associated with said first biological state and the other of said 2 nucleic acids is negatively associated with said first biological state. The mathematical computation can comprise dividing a numerator by a denominator, said numerator corresponding to said nucleic acid positively associated with said first biological state and said denominator corresponding to said nucleic acid negatively associated with said first biological state. The first biological state can be a disease state and said second biological state is a non-disease state. The can be an angiogenesis-related condition, an antioxidant-related condition, an apoptosis-related condition, a cardiovascular-related condition, a cell cycle-related condition, a cell structure-related condition, a cytokine-related condition, a defense response-related condition, a development-related condition, a diabetes-related condition, a differentiation-related condition, a DNA replication and/or repair-related condition, an endothelial cell-related condition, an folate receptor-related condition, an hormone receptor-related condition, an inflammation-related condition, an intermediary metabolism-related condition, a membrane transport-related condition, an oxidative metabolism-related condition, neurotransmission-related condition, a cancer-related condition, a protein maturation-related condition, a signal transduction-related condition, a stress response-related condition, a tissue structure-related condition, a transcription factor-related condition, a transport-related condition, or a xenobiotic metabolism-related condition. In some embodiments, direct comparison does not use a bioinformatics resource.

Another embodiment is a method comprising state and not with a second biological state; providing 2 samples corresponding to each of said first biological state and said second biological state; assessing an amount of each of said 2 nucleic acids in each of said 2 samples wherein said assessing can enumerate less than about 1,000 molecules of each of said 2 nucleic acids; and mathematically computing said amounts corresponding to each of said first and said second biological states to determine a numerical index, said numerical index discriminating said first and said second biological states.

Yet another embodiment is a method of identifying a biological state comprising assessing an amount each of 2 nucleic acids in a first sample, wherein said assessing can enumerate less than about 1,000 molecules of each of said 2 nucleic acids in said first sample; providing said amounts as numerical values wherein said numerical values are directly comparable between a number of samples; and using said numerical values to provide a numerical index, whereby said numerical index indicates said biological state.

Yet another embodiment is a method of identifying a biological state comprising assessing an amount a nucleic acid in a first sample, wherein said assessing can enumerate less than about 1,000 molecules of said nucleic acid in said first sample; and providing said amount as a numerical value wherein said numerical value is directly comparable between a number of other samples.

Other aspects of the invention include business methods. One embodiment is a business method comprising collecting a first specimen comprising a first nucleic acid; measuring an amount of said first nucleic acid in a first sample of said first specimen wherein said measuring can enumerate less than about 1,000 molecules of said first nucleic acid in said first sample; and providing said amount as a numerical value wherein said numerical value allows direct comparison to an amount of said first nucleic acid in a second sample. The first and said second samples can be measured at different times or in different laboratories. The second sample can be obtained from said first specimen or a second specimen. The first and said second specimens can be collected from different subjects or from different species. The measuring step can be performed at least about 100 times per day, at least about 1,000 times per day, or at least about 4,000 times per day. The first specimen can comprise at least about 1,000 cells. The first specimen can comprise a human specimen, which can be collected without identifying information. The collecting information can comprise attesting to compliance with investigative protocol. The identifying information can be collected at a later time than said collection of said first specimen. The information can be collected via a website. The method can further comprise identifying which of said selected nucleic acids electrophorese together. The amounts of said identified nucleic acids can be electrophoresed simultaneously. The numerical value can be provided via e-mail. The assessing can comprise providing a standardized mixture comprising a competitive template for said first nucleic acid and a competitive template for a second nucleic acid in said first specimen wherein said competitive templates are at known concentrations relative to each other; combining said standardized mixture with a first sample of said specimen; co-amplifying said first nucleic acid and said competitive template for said first nucleic acid to produce first amplified product thereof, diluting said first amplified product; further co-amplifying said diluted first amplified product of said first nucleic acid and of said competitive template for said first nucleic acid, to produce second amplified product thereof, and co-amplifying said second nucleic and said competitive template for said second nucleic acid to produce first amplified product thereof. The first nucleic acid and said competitive template for said first nucleic acid can be co-amplified in a first vessel and said second nucleic acid and said competitive template for said second nucleic acid are co-amplified in a second vessel. The method can further comprise obtaining a first relationship, said first relationship comparing said second amplified product of said first nucleic acid and said second amplified product of said competitive template for said first nucleic acid; obtaining a second relationship, said second relationship comparing said first amplified product of said second nucleic acid and said first amplified product of said competitive template for said second nucleic acid; and comparing said first and said second relationships. The second nucleic acid can serve as a reference nucleic acid. The standardized mixture can further comprise sufficient amounts of said competitive templates for assessing said first nucleic acid in more than about $10^6$ samples.

Business methods for drug development are also provided herein. One embodiments is a business method of improving drug development, comprising collecting a first specimen comprising a nucleic acid from a first biological entity administered a candidate drug at first stage of drug development; collecting a second specimen comprising said nucleic acid from a second biological entity at a second stage of drug development; assessing an amount of said nucleic acid in each of said first and said second specimen; directly comparing said amounts; and altering a step of said drug development based on said comparison. Another embodiment is a business method of improving drug development, comprising providing a database comprising numerical values corresponding to amounts of a first nucleic acid in a number of samples wherein said numerical values are directly comparable between 5 of said samples; collecting a first specimen comprising said first nucleic acid from a biological entity administered a candidate drug at a stage of drug development; assessing an amount of said first nucleic acid in a first sample of said first specimen; directly comparing said amount to at least one of said numerical values in said database; and altering a step of said drug development based on said comparison. The first or said second biological entity is typically at least one entity selected from a virus, a cell, a tissue, an in vitro culture, a plant, an animal, and a subject participating in a clinical trial. The first or said second stage of drug development can be drug target screening, lead identification, pre-clinical validation, clinical trial and/or patient treatment. The pre-clinical validation can be a bioassay and/or an animal study. The altering can comprise a stratification of a clinical trial. The stratification can involve identifying subjects to have a reduced side effect. The altering can reduce the time for said drug development.

Yet another embodiment is a business method of improving drug development, comprising providing a database comprising numerical indices, said numerical indices obtained by mathematical computation of 2 numerical values corresponding to amounts of 2 nucleic acids in a number of samples wherein said numerical indices are directly comparable between 5 of said samples; collecting a first specimen comprising said 2 nucleic acids from a biological entity administered a candidate drug at a stage of drug development; assessing an amount of each of said 2 nucleic acids in a first sample of said first specimen; using said 2 amounts to mathematically compute a first numerical index; directly comparing said first numerical index to at least one of said numerical indices in said database; and altering a step of said drug development based on said comparison.

BRIEF DESCRIPTION OF THE FIGURES

The novel features of the invention are set forth with particularity in the appended claims. A better understanding of the objects, features and advantages of the present invention will be obtained by reference to the following detailed description that sets forth illustrative embodiments, in which the principles of the invention are utilized, and the accompanying drawings of which:

FIG. 1 illustrates a table showing numerical values for a number of nucleic acids corresponding to expression measurements for some candidate carboplatin chemoresistant genes in primary non-small cell lung cancer (NSCLC).

FIG. 2 illustrates a table showing numerical values for a number of nucleic acids corresponding to expression measurements for a number of genes in lung donor airway epithelial cells.

FIGS. 4A-4B illustrate a table providing numerical values for a number of nucleic acids corresponding to expression measurements for a number of genes derived from Stratagene Human Reference RNA, measured using embodiments of both two-step and non-two step approaches. Corresponding sequences used as a forward primer (F), a reverse primer (R) and a competitive template (CT) for each of the genes are also provided (Sequence ID Nos. 1-282).

FIG. 22 tabulates a number of sources of variation and control methods

FIG. 25 illustrates use of numerical indices in identifying a biological state

FIG. 29 illustrates experiments comparing a non-two step with a two-step approach, according to some embodiments of the instant invention.

FIG. 35 illustrates a calculation based on densitometry values.

FIG. 37 illustrate results from experiments comparing some embodiments of the instant invention with oligonucleotide microarray analysis.

Figure 3:
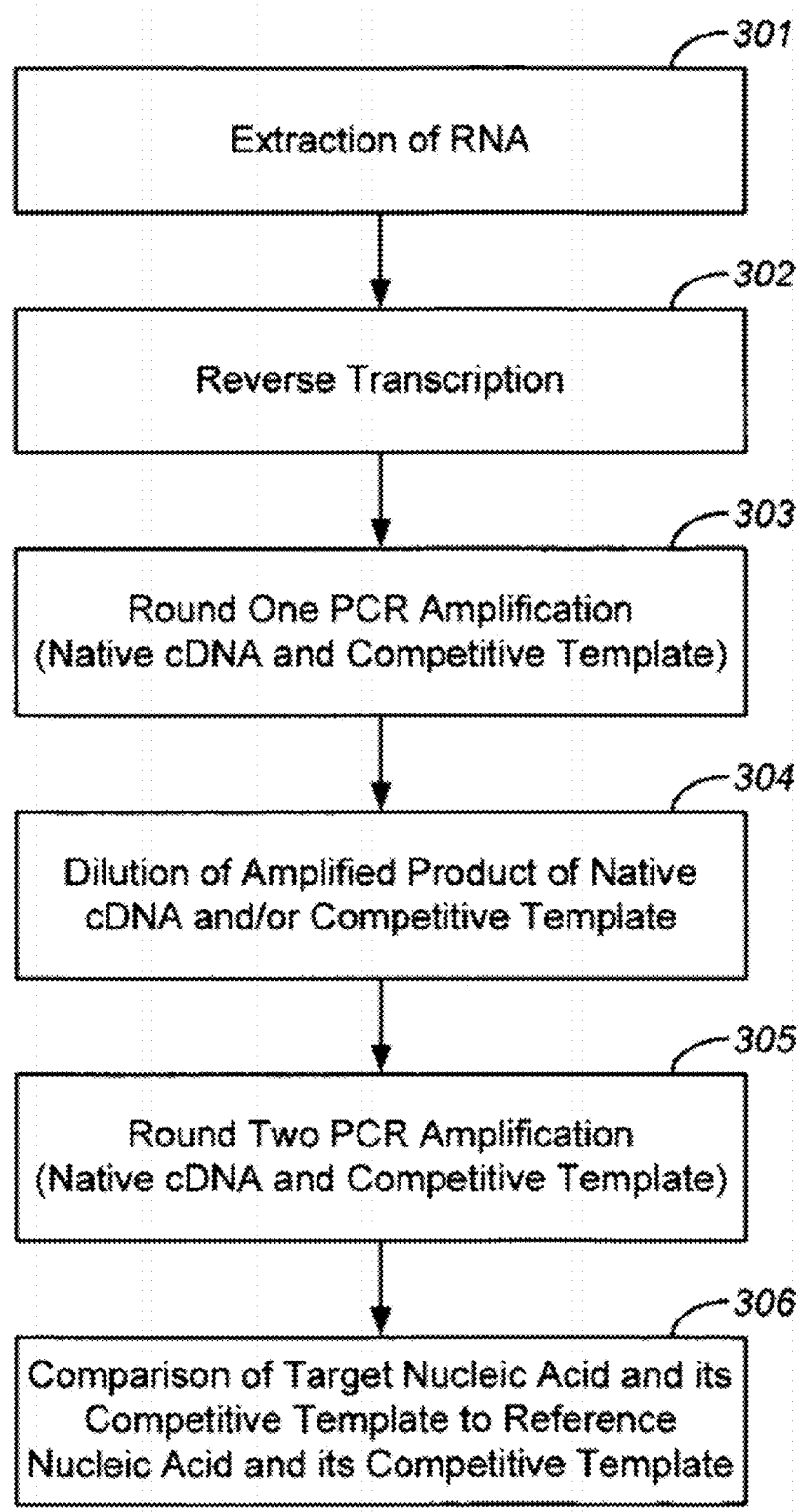
FIG. 3 illustrates an overall "two-step" process for evaluating nucleic acids in some embodiments.

Each of these figures provides an illustration only, and is in no way intended to be limiting with respect to the present invention. For example, those skilled in the art will readily appreciate variations and modifications of the schemes illustrated based on the teachings provided herein.

DETAILED DESCRIPTION OF THE INVENTION

The present invention is directed to methods and compositions for evaluating nucleic acids, methods of preparing such compositions, and applications and business methods employing such compositions and methods. Some aspects of the present invention relate to improvements upon the Willey and Willey et al. U.S. Pat. Nos. 5,043,390; 5,639,606; and 5,876,978.

I. Methods for Assessing a Nucleic Acid

One aspect of the present invention relates to methods for assessing amounts of a nucleic acid in a sample. In some embodiments, the invention allows measurement of small amounts of a nucleic acid, for example, where the nucleic acid is expressed in low amounts in a specimen, where small amounts of the nucleic acid remain intact and/or where small amounts of a specimen are provided. For example, in some embodiments, practice of the invention assesses gene expression in small samples of biological specimens.

"Specimen" as used herein can refer to material collected for analysis, e.g., a swab of culture, a pinch of tissue, a biopsy extraction, a vial of a bodily fluid e.g., saliva, blood and/or urine, etc. that is taken for research, diagnostic or other purposes from any biological entity. "Biological entity" as used herein can refer to any entity capable of harboring a nucleic acid, including any species, e.g., a virus, a cell, a tissue, an in vitro culture, a plant, an animal, and/or a subject participating in a clinical trial. "Sample" as used herein can refer to specimen material used for a given assay, reaction, run, trial, and/or experiment. For example, a sample may comprise an aliquot of the specimen material collected, up to and including all of the specimen. As used herein the terms assay, reaction, run, trial and/or experiment can be used interchangeably. Some embodiments of the present invention can be practiced using small starting amount of nucleic acid to yield quantifiable amounts.

In some embodiments, the specimen collected may comprise less than about 100,000 cells, less than about 10,000 cells, less than about 5,000 cells, less than about 1,000 cells, less than about 500 cells, less than about 100 cells, less than about 50 cells, or less than about 10 cells. In some embodiments, methods of the present invention are capable of assessing the amount of a nucleic acid present in a sample comprising less than about 100,000 cells. For example, a sample from a biopsy may comprise less than about 100,000 cells. In some embodiments, the method is capable of assessing the amount of a nucleic acid in less than about 10,000 cells, less than about 5,000 cells, less than about 1,000 cells, less than about 500 cells, less than about 100 cells, less than about 50 cells, or less than about 10 cells Small biological specimen can also refer to amounts typically collected in biopsies, e.g., endoscopic biopsies (using brush and/or forceps), needle aspirate biopsies (including fine needle aspirate biopsies), as well as amounts provided in sorted cell populations (e.g., flow-sorted cell populations) and/or micro-dissected materials (e.g., laser captured micro-dissected tissues). For example, biopsies of suspected cancerous lesions in the lung, breast, prostate, thyroid, and pancreas, commonly are done by fine needle aspirate (FNA) biopsy, bone marrow is also obtained by biopsy, and tissues of the brain, developing embryo, and animal models may be obtained by laser captured micro-dissected samples.

In some embodiments, assessing, evaluating and/or measuring a nucleic acid can refer to providing a measure of the amount of a nucleic acid in a specimen and/or sample, e.g., to determine the level of expression of a gene. In some embodiments, providing a measure of an amount refers to detecting a presence or absence of the nucleic acid of interest. In some embodiments, providing a measure of an amount can refer to quantifying an amount of a nucleic acid can, e.g., providing a measure of concentration or degree of the amount of the nucleic acid present. In some embodiments, providing a measure of the amount of nucleic acid refer to enumerating the amount of the nucleic acid, e.g., indicating a number of molecules of the nucleic acid present in a sample. The nucleic acid of interest may be referred to as a target nucleic acid, and a gene of interest, e.g., a gene being evaluated, mat be referred to as a target gene.

In some embodiments, methods of the present invention are capable of enumerating less than about 1,000 molecules of a nucleic acid in a sample, e.g., about 800, about 600, or about 400 molecules of the nucleic acid. In some embodiments, less than about 100 molecules, e.g., about 60 molecules, preferably less than about 10 molecules, e.g., about 6 molecules, or more preferably less than about 1 molecule of a nucleic acid can be enumerated in a sample. For example, in preferred embodiments, a single molecule of nucleic acid template can give rise to detectable amplified product. In some embodiments, methods of the instant invention can measure less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of a nucleic acid in a sample. The number of molecules of a nucleic acid can also be referred to as the number of copies of the nucleic acid found in a sample and/or specimen.

The practice of some embodiments of the present invention permits rare transcripts to be measured with statistical significance. For example, in some embodiments, the number of copies of a nucleic acid corresponding to a gene transcript can be determined, e.g., the number of copies/cell, where the gene is expressed in low copy number. Enumerating less than about 1,000 molecules can allow measurement of less than about 10 copies/cell of at least 100 different gene transcripts in a small biological specimen, e.g., from the amount of material typically used to obtain one gene measurement, e.g., to measure that few copies of a nucleic acid corresponding to one gene. In some embodiments, methods of the instant invention are capable of measuring and/or enumerating less than about 10 copies/cell of at least 100 different gene transcripts in a small biological specimen, from the amount of material typically used to obtain one gene measurement. In some embodiments, enumerating less than about 10,000 molecules can allow measurement of less than about 10 copies/cell of at least 100 different gene transcripts in a small biological specimen, e.g., from the amount of material typically used to obtain one gene measurement, e.g., to measure that few copies of a nucleic acid corresponding to one gene.

In still some embodiments, more measurements can be obtained from a given specimen and/or sample, e.g., of the size typically used to measure that few copies of a nucleic acid corresponding to one gene. For example, practice of some embodiments of the invention disclosed herein can measure and/or enumerate less than about 100, less than about 50, less than about 20, less than about 10, less than about 8, or less than about 5 copies/cell of at least about 20, at least about 50, at least about 80, at least about 100, at least about 120, at least about 150, or at least about 200 different nucleic acids in a sample, e.g., corresponding to different gene transcripts.

The expressed material may be endogenous to the biological entity, e.g., transcripts of a gene naturally expressed in a given cell type, or the expressed material to be measured may be of an exogenous nature. For example, in some embodiments, methods of the present invention can be used to quantify transfected genes following gene therapy and/or a reporter gene in transient transfection assays, e.g., to determine the efficiency of transfection (Morales, M. J., and Gottlieb, D. I., A polymerase chain reaction-based method for detection and quantification of reporter gene expression in transient transfection assays, Analytical Biochemistry, 210, 188-194 (1993)).

As used herein, "nucleic acid" can refer to a polymeric form of nucleotides and/or nucleotide-like molecules of any length. In preferred embodiments, the nucleic acid can serve as a template for synthesis of a complementary nucleic acid, e.g., by base-complementary incorporation of nucleotide units. For example, a nucleic acid can comprise naturally occurring DNA, e.g., genomic DNA; RNA, e.g., mRNA, and/or can comprise a synthetic molecule, including but not limited to cDNA and recombinant molecules generated in any manner. For example the nucleic acid can be generated from chemical synthesis, reverse transcription, DNA replication or a combination of these generating methods. The linkage between the subunits can be provided by phosphates, phosphonates, phosphoramidates, phosphorothioates, or the like, or by nonphosphate groups as are known in the art, such as peptide-type linkages utilized in peptide nucleic acids (PNAs). The linking groups can be chiral or achiral. The polynucleotides can have any three-dimensional structure, encompassing single-stranded, double-stranded, and triple helical molecules that can be, e.g., DNA, RNA, or hybrid DNA/RNA molecules. A nucleotide-like molecule can refer to a structural moiety that can act substantially like a nucleotide, for example exhibiting base complementarity with one or more of the bases that occur in DNA or RNA and/or being capable of base-complementary incorporation. The terms "polynucleotide," "polynucleotide molecule," "nucleic acid molecule," "polynucleotide sequence" and "nucleic acid sequence," can be used interchangeably with "nucleic acid" herein. In some specific embodiments, the nucleic acid to be measured may comprise a sequence corresponding to a gene referenced in Table 1 or 2, in FIG. 1 or 2, respectively.

In some embodiments the specimen collected comprises RNA to be measured, e.g., mRNA expressed in a tissue culture. In some embodiments the specimen collected comprises DNA to be measured, e.g., cDNA reverse transcribed from transcripts. In some embodiments, the nucleic acid to be measured is provided in a heterogeneous mixture of other nucleic acid molecules.

A. Two-Step Approach

In some embodiments, the present invention provides a method of assessing a nucleic acid provided in a sample, comprising co-amplifying the nucleic acid, a number of other nucleic acid(s), a competitive template for the nucleic acid and a competitive template(s) for the other nucleic acid(s), e.g., to produce first amplified product thereof. In some embodiments, first amplified product can be diluted and then further co-amplified, e.g., to produce second amplified product thereof. Amplifying and then further amplifying nucleic acid and competitive template for the nucleic acid may be considered as two rounds of amplification and a process employing two rounds of amplification may be referred to as a "two-step" process or "two-step" approach.

FIG. 3 schematically illustrates some embodiments of the overall "two-step" process described herein, e.g., where the amplified nucleic acid is cDNA. Experimental details comparing a two-step approach to a non-two-step approach can be found in Example I below.

At step 301 of FIG. 3, for example, RNA can be extracted from specimen cells or tissues.

At step 302 of FIG. 3, extracted RNA can be reverse transcribed to provide cDNA. In some embodiments, the amplified nucleic acid is a nucleic acid other than cDNA, as described above. In some embodiments, although reverse transcription efficiency may be variable, the representation of one nucleic acid in comparison to another in the resultant cDNA product may not be affected. That is, in some embodiments, the amount of cDNA of target nucleic acid compared with the amount of cDNA of a second nucleic acid (e.g., a second nucleic acid serving as a reference nucleic acid) can remain equivalent or substantially equivalent to amount of mRNA of target nucleic acid compared with the amount of mRNA of the second nucleic acid.

At step 303 of FIG. 3, native cDNA and its competitive template are co-amplified in a first round of amplification. Native cDNA may comprise both the target nucleic acid and one or more other nucleic acids, which can be co-amplified with a competitive template for the target nucleic acid and a competitive template for one or more of the other nucleic acids. For example, the cDNA may be serially diluted and one or more serial dilutions then amplified.

In preferred embodiments, the competitive templates of at least two nucleic acids are at known concentrations relative to one another. "Competitive template" as used herein can refer to a nucleic acid that competes with a target nucleic acid during an amplification reaction. That is, when present in a reaction mixture for amplifying the target nucleic acid, the competitive template competes to serve as the template for such amplification. In some embodiments, for example, the competitive template for a given nucleic acid has a structure allowing its amplification to the same or substantially the same extent as the given nucleic acid. In preferred embodiments, a competitive template for a given nucleic acid can be amplified using one or more of the same primers as that of the given nucleic acid and/or amplifies with the same or substantially the same efficiency as the given nucleic acid. In preferred embodiment a competitive template for a given nucleic acid is amplified using the same primers, shares sequence homology, and/or amplifies with the same or substantially similar efficiency as the given nucleic acid. In some embodiments, competitive templates are referred to as internal standards or as a competitive template internal standard.

The term "native template" as used herein can refer to nucleic acid obtained directly or indirectly from a specimen that can serve as a template for amplification. For example, it may refer to cDNA molecules, corresponding to a gene whose expression is to be measured, where the cDNA is amplified and quantified. In some specific embodiments, at least one competitive template used comprises a sequence referenced in Table 4 of FIGS. 4A-4B.

The term "primer" generally refers to a nucleic acid capable of acting as a point of initiation of synthesis along a complementary strand when conditions are suitable for synthesis of a primer extension product. In some specific embodiments, at least one primer used comprises a sequence referenced in Table 4 of FIGS. 4A-4B. Also, the table in FIGS. 4A-4B shows the primer sequence and position for several genes whose expression can be measured.

Preferably, the competitive template has a distinguishing feature from the target nucleic acid, allowing its amplified product to be distinguished from the amplified product of the target nucleic acid. For example, the competitive template can comprise mutants of nucleic acid to be evaluated. Mutations can be point mutations, insertions, inversions, deletions or the like. For example, in some embodiments, a competitive template comprises at least one nucleotide that is different from the corresponding nucleotide in the nucleic acid to be evaluated. In some embodiments, the competitive template comprises at least about two, at least about three, at least about 5, at least about 10, at least about 15, or at least about 20 nucleotides that are different. Longer deletions, insertions, inversions, substitutions and/or other alterations are provided in some embodiments. For example, artificially shortened competitive templates may be generated according to the method described by Celi et al., Nucleic Acids Res. 21:1047 (1993).

In some preferred embodiments, the competitive template comprises an alteration that causes a loss and/or a gain of one or more cleavage sites in the competitive template compared to its corresponding nucleic acid. For example, a base may be substituted in a competitive template sequence to result in the gain and/or loss of a restriction endonuclease recognition site, chemical cleavage site, or other specific cleavage site. Various programs may be used to identify and match one or two or more base mismatch sequences for known recognition sites. For example, the Map program within Genetics Computer Group software package (Devereux et al., supra, 1984) may be used. In this program, cDNA sequences are obtained for a given nucleic acid, and then the sequence is evaluated for the presence of one or two base pair mismatches for known restriction endonucleases.

In some embodiments, the competitive template comprises an alteration that causes a loss and/or a gain of one or more specific recognition sites in the competitive template compared to its corresponding nucleic acid. For example, a base may be substituted in a competitive template sequence to result in the gain and/or loss of a protein binding site such as a transcription factor binding site. Other structural changes for distinguishing amplified product of a competitive template from amplified product of its corresponding nucleic acid will be apparent to those of skill in the art and are also within the scope of the instant invention.

Amplification can be achieved by any methods known in the art and/or disclosed herein for amplifying nucleic acid molecules. When polymerase chain reaction (PCR) amplification is used, conditions can include the presence of ribonucleotide and/or deoxyribo-nucleotide di-, tri-, tetra-, penta- and/or higher order phosphates; primers for PCR amplification for at least one nucleic acid and its corresponding competitive template; and at least one polymerization-inducing agent, such as reverse transcriptase, RNA polymerase and/or DNA polymerase. Examples of DNA polymerases include, but are not limited to, E. coli DNA polymerase, Sequenase 2.0®, T4 DNA polymerase or the Klenow fragment of DNA polymerase 1, T3, SP6 RNA polymerase, AMV, M-MLV, and/or Vent polymerase, as well as ThermoSequenase™ (Amersham) or Taquenase™ (ScienTech, St Louis, Mo.). Further examples include thermostable polymerases isolated from *Thermus aquaticus*, *Thermus thermophilus*, *Pyrococcus woesei*, *Pyrococcus furiosus*, *Thermococcus litoralis*, and *Thermotoga maritima*. The polymerization-inducing agent and nucleotides may be present in a suitable buffer, which may include constituents which are co-factors or which affect conditions such as pH and the like at various suitable temperatures. PCR primers used are preferably single stranded, but double-, triple- and/or higher order stranded nucleotide molecules can be practiced with the present invention. As used herein "amplified product" can refer to any nucleic acid synthesized at least partly by base-complementary incorporation using another nucleic acid as template. An amplified product may also be referred to an amplicon and/or amplimer herein. Amplification may be carried out for a number of cycles of PCR, e.g., at least about 10, at least about 20, at least about 30, at least about 35, at least about 40, or at least about 50 cycles in some embodiments.

In some embodiments, more than one nucleic acid (and its corresponding competitive template) are co-amplified. In preferred embodiments, the number of other nucleic acids is at least one. In some embodiments, the number is at least about 50 other nucleic acid, at least 100 other nucleic acids, at least about 200, at least about 300 other nucleic acids, at least about 500 other nucleic acids, at least about 800 other nucleic acids, at least about 1,000 other nucleic acids, at least about 5,000 other nucleic acids, at least about 10,000 other nucleic acids, at least about 50,000 other nucleic acids, or at least about 100,000 other nucleic acids. A competitive template can be used for each additional nucleic acid to be evaluated and, in preferred embodiments, a plurality of nucleic acids in a sample can be measured simultaneously.

At least one of the other nucleic acids can serve as a reference nucleic acid. "Reference nucleic acid" as used herein can refer to a nucleic acid that is amplified as well as the nucleic acid to be evaluated. The nucleic acid can be "normalized" to a reference nucleic acid. In some embodiments, the reference nucleic acid serves as a control for loading, e.g., to control for cDNA loaded into the reaction. For example, in some preferred embodiments, the reference nucleic acid comprises a nucleic acid that is not expected to vary (or to vary significantly) among given biological specimen and/or in response to certain stimuli. For example, mRNA from a constitutively expressed gene may provide the reference nucleic acid. In some embodiments, known or potential housekeeping genes may provide the reference nucleic acid, including but not limited to human, mouse and/or rat glyceraldehydes-3-phospate dehydrogenase (GAPD or GAPDH), β actin, 28S RNA, 18S RNA, and/or other ribonuclear protein genes. Other housekeeping genes that have been used as internal standards in Northern analyses of gene expression may also be used. See, e.g., Devereux et al., Nucleic Acids Res. 12:387 (1984); Barbu et al., Nucleic Acids Res. 17:7115 (1989). In some embodiments, a competitive template for a reference nucleic acid may comprise a nucleic acid having a sequence similar to either strand of cDNA of a housekeeping gene, but having a distinguishable feature as described above.

Many different genes can provide reference nucleic acids. The choice of reference nucleic acid may depend on the tissues to be assayed and/or the biological states being studied. For example, β-actin varies little among different normal bronchial epithelial cell samples (see, e.g., Crawford, E. L., Khuder, S. A., Durham, S. J., et al. (2000)

Normal bronchial epithelial cell expression of glutathione transferase P1, glutathione transferase M3, and glutathione peroxidase is low in subjects with bronchogenic carcinoma. Cancer Res. 60, 1609-1618), but it may vary over about 100-fold in samples from different tissues, such as bronchial epithelial cells compared to lymphocytes.

At step 304 of FIG. 3, amplified product of native cDNA and competitive template (obtained in round one) are diluted before further amplification in round two. In some embodiments, amplified product of target nucleic acid and its corresponding competitive template may be diluted. In some embodiments, amplified product of a reference nucleic acid and its corresponding competitive template may be diluted. Diluting amplified product may be achieved by any techniques known in the art and/or described herein. For example, diluting may involve removal of an aliquot of a mixture comprising first amplified product, and transfer to a vessel containing additional buffer. In some embodiments, diluting produces at least about a 1,000,000-fold dilution, at least about a 500.000-fold dilution, at least about a 100.000-fold dilution, at least about a 50.000-fold dilution, at least about a 10.000-fold dilution, at least about a 5.000-fold dilution, at least about a 1.000-fold dilution, at least about a 500-fold dilution, or at least about a 100-fold dilution.

At step 305 of FIG. 3, diluted amplified product of native cDNA and competitive template (obtained in round one) are further amplified in round two. In some embodiments, diluted amplified product of a target nucleic acid and its corresponding competitive template may be further co-amplified in a second round of amplification. In some embodiments, diluted amplified product of a reference nucleic acid and its corresponding competitive template may be further co-amplified in a second round of amplification. As mentioned above, the use of two rounds may be referred to as a "two-step" approach. In some embodiments, target nucleic acid and/or the reference nucleic acid can be subjected to more than two rounds of amplification. For example, second amplified product of the target nucleic acid and its corresponding competitive template may be again diluted and further amplified and/or second amplified product of the reference nucleic acid and its corresponding competitive template may be again diluted and further amplified.

Various nucleic acids and corresponding competitive templates may be amplified in a given vessel during round one and/or round two of a two-step process. For example, in some embodiments, more than one nucleic acid (each with its corresponding competitive template) are co-amplified in a given vessel. In some embodiment, repeat amplifications are carried out with fewer different nucleic acids (each with its corresponding competitive template) in a given vessel. For example, in some preferred embodiments, amplified products are further amplified with primers for a nucleic acid corresponding to one gene. For example, co-amplifying diluted first amplified product of a nucleic acid and of the competitive template for the nucleic acid can be achieved by using a primer pair for co-amplifying the particular nucleic acid and its corresponding competitive template dried onto the vessel used in round two. For example, primers for individual genes can be aliquotted into individual reaction vessels and dried down, e.g., on 384-well plates. Multiple plates loaded with primers (e.g., about 10, about 100, about 500 plates) can be prepared in advance. For example, in some embodiments, primers prepared this way are stable at 4° C. for months.

At step 306 of FIG. 3, amounts of amplified products can be compared. In some embodiments, the amount of amplified product of a target nucleic acid is compared to the amount of amplified product of its competitive template. In some embodiments, e.g., comparison involves obtaining a relationship, e.g., a first relationship reflecting the amplified amounts of target nucleic acid compared with the amplified amounts of its competitive template. In preferred embodiments, this relationship is provided as a ratio, e.g., a first ratio of the amount of amplified product of a nucleic acid to the amount of amplified product of its competitive template, e.g., where the nucleic acid and its competitive template are co-amplified.

In some embodiments, the amount of amplified product of a target nucleic acid is compared to a reference nucleic acid. In preferred embodiments, the reference nucleic acid is itself compared to a competitive template for the reference nucleic acid. For example, in some embodiments, the amount of amplified product of a reference nucleic acid is compared to the amount of amplified product of its competitive template. In some embodiments, e.g., this comparison involves obtaining a relationship, e.g., a second relationship reflecting the amplified amount of reference nucleic acid compared with the amplified amount of its competitive template. In preferred embodiments, this relationship is provided as a ratio, e.g., a second ratio of the amount of amplified product of reference nucleic acid to the amount of amplified product of its competitive template, e.g., where the reference nucleic acid and its competitive template are co-amplified.

In preferred embodiments, comparison of the target nucleic acid to a reference nucleic acid involves comparing the first and second relationships described above. For example a relationship reflecting how the first relationship compares with the second relationship can be obtained. In some embodiments, this relationship compares the first ratio to the second ratio, e.g., as a ratio of the first and second ratios.

The adjectives "first," "second," "third" and so forth, as used herein, do not necessarily indicate any order of preference, importance, chronology, or degree of a quality, concentration, and/or amount. Rather the terms are used to differentiate nouns qualified by the adjectives, e.g., a first and a second ratio can mean two different ratios; a second nucleic acid can mean a different nucleic acid to that referred to as the first nucleic acid.

In a two-step process, amplified product obtained after the first or second (or higher) round for target nucleic acid (and its corresponding competitive template); and amplified product obtained after the first or second (or higher round) for reference nucleic acid (and its corresponding competitive template) may be used in the comparisons described above. For example, in preferred embodiments, a first relationship is obtained comparing second amplified product of the target nucleic acid to second amplified product of the competitive template for the target nucleic acid; a second relationship is obtained comparing first amplified product of reference nucleic acid to first amplified product of competitive template for the reference nucleic acid; and the first and second relationships are compared. In more preferred embodiments, the relationship obtained by comparing the first and second relationships remains substantially constant beyond the exponential phase of amplification of the nucleic acid. Substantially constant can refer to variations of +/− about 1%, about 5, about 10%, about 15%, or about 20% of an absolute constant number.

In some embodiments, another one of the nucleic acids amplified can serve as a second reference nucleic acid. In such embodiments, measuring the amount of target nucleic acid can comprise obtaining a third relationship that compares the first amplified product of this second reference nucleic acid to the first amplified product of competitive template for the second reference nucleic acid; and comparing the first and third relationships. Also, in some embodiments, data calculated using a first reference nucleic acid can be re-calculated relative to that of another reference nucleic acid.

In some embodiments, using two or more reference nucleic acids can provide an understanding of inter-specimen and/or inter-sample variation among the reference nucleic acids. In some embodiments, for example, 43-actin and GAPD can be used as first and second reference nucleic acids. For example, there is a significant correlation between the ratio of β-actin/GAPD expression and cell size (Willey, J. C., Crawford, E. L., and Jackson, C. M. (1998) Expression measurement of many genes simultaneously by quantitative RT-PCR using standardized mixtures of competitive templates. Am. J. Respir. Cell Mol. Biol. 19, 6-17), which may make use of these 2 reference nucleic acids preferred in some embodiments. In some embodiments, any measured nucleic acid or combination of nucleic acids, including all measured nucleic acids, can be used as a reference. The number of genes that must be quantitated for normalization to any of the nucleic acids measured to result in adequate normalization may vary depending on the samples being studied.

As mentioned above, in some embodiments, a two-step method may comprise two step amplification of the nucleic acid serving as a reference nucleic acid. In some such embodiments, a fourth relationship may be obtained comparing second amplified product of the reference nucleic acid to second amplified product of its competitive template. In some embodiments, the first and fourth relationships are compared, e.g., by obtaining a ratio of the first and fourth ratios. In still some embodiments, where the nucleic acid serving as a reference nucleic acid is amplified in two rounds, first amplified product of the target nucleic and first amplified product of its competitive template can be used to obtain the first relationship, e.g., the first ratio.

Where the "two-step" approach is extended for more than two rounds of amplification, second amplified product of a nucleic acid and of a competitive template for the nucleic acid can be diluted and still further amplified, e.g., to produce third amplified product thereof. The steps of diluting and further amplifying may be repeated at least about once, at least about twice, at least about 3 times, at least about 5 times, at least about 10 times, at least about 20 times, at least about 50 times, at least about 100 or more.

In some embodiments, comparing the first and second and/or first and third and/or first and fourth relationships can provide a "ratio of ratios" corresponding to a numerical value. In some embodiments, numerical values for various measured nucleic acids, e.g., for various gene expression measurements, are provided as a database, as described in more detail below. For example, such a database can be used with gene expression data in clinical diagnostic testing.

In some embodiments, obtaining the comparisons, e.g., the first, second, third and/or fourth ratios, involves measuring the amounts of amplified product of each of the nucleic acid, the competitive template for nucleic acid, the reference nucleic acid(s) and the competitive template(s) for the reference nucleic acid. Any method capable of quantifying nucleic acids having a distinguishable feature (e.g., having different sizes and/or sequences) can be used. Quantifying methods may involve separating and/or isolating the amplified product, for example, by use of electrophoresis, solid phase hybridization such as arrays, mass spectrometry, chromatography, HPLC and/or other methods known in the art for separating different nucleic acid molecules.

The electrophoresis used may be one or more of gel electrophoresis (e.g., agarose and/or polyacrylamide gel electrophoresis), capillary electrophoresis (e.g., using a capillary electrophoresis device like PE 310 or a microfluidic CE device like Agilent 2100 or Calipertech AMS 90 high-throughput system), and/or other types of electrophoresis devices known in the art. See, e.g., (G. Gilliland, S. Perrin, K. Blanchard and H. F. Bunn, Proc Natl. Acad. Sci. USA 87, 2725-2729 (1990); M. J. Apostolakos, W. H. Schuermann, M. W. Frampton et al., Analytical Biochemistry 213, 277-284 (1993)). Further, capillary electrophoresis (CE), in particular, microfluidic CE technology can allow measurement of nucleic acid in very small volumes. See, e.g., T. S. Kanigan et al., in Advances in Nucleic Acid and Protein Analyses, Manipulation, and Sequencing, P. A. Limbach, J. C. Owicki, R. Raghavachari, W. Tan, Eds. Proc. SPIE 3926: 172, (2000). Other electrophoresis devices that may be used include, for example, Agilent or AB1 310. In some embodiments, separation of amplified product on agarose gel, a PerkinElmer 310 CE (ABI Prism 310 Genetic Analyzer), and a 2100 Bioanalyzer microfluidic CE (Agilent, Santa Clara, Calif., USA) were shown to provide statistically similar and reproducible results. E. L. Crawford, L A. Warner, D. A. Weaver and J. C. Willey, Quantitative endpoint RT-PCR expression measurement using the Agilent 2100 Bioanalyzer and standardized RT-PCR. Agilent Application September 2001, 1-8.

Where amplified products are to be separated by electrophoresis, the size of the competitive templates and/or reference nucleic acid(s) can be selected to differ from that of the target nucleic acid. For example, in some embodiments, amplified product generated from the reference nucleic acid and the target nucleic acid are of sufficiently different sizes to be separated by electrophoresis. Further, in some embodiments, amplified product generated from the competitive template for a given nucleic acid and the given nucleic acid are of sufficiently different sizes to be separated by electrophoresis.

In some embodiments, a size difference is achieved by using a competitive template for a given nucleic acid that is longer or shorter that the given nucleic acid. In some embodiments, this size differential can be achieved by restriction endonuclease digestion of the amplified product where the competitive template differs from its corresponding nucleic acid by the addition or lack of a restriction endonuclease site. For example, in a specific embodiment, GAPD competitive templates were prepared that separate from native GAPD on the basis of EcoRI or BamHI digestion. Separation on the basis of other restriction endonuclease digestion may also be used. Further, in some embodiments, the same recognition site can be used for both the reference nucleic acid and the nucleic acid to be measured.

In addition, in some embodiments, the length of the amplified product after restriction endonuclease digestion is a factor to be considered. For example, in certain embodiments, greater nucleic acid size differences are preferred for adequate separation on agarose gels, e.g., preferably about 40, about 50, about 80, about 100 or about 120 base pair differences.

Separated products may be quantified by any methods known in the art and/or described herein, including, for example, use of radiolabled probes, autoradiography, and preferably by spectrophotometry and/or densitometry, e.g., densitometry of ethidium bromide stained gels. Other methods that may be used to quantify amplified product include chromatography, e.g., high-performance liquid chromatography (HPLC); gas chromatography; and/or mass spectrometry, e.g., matrix-assisted laser desorption ionization-time-of-flight mass spectrometry (MALDI-TOF-MS) (An economic forecast for the gene expression market researchandmarkets.com/reports/5545).

In some embodiments, amplified products are measured using solid-phase hybridizations. Some embodiments, for example, comprise use of an array, including microbeads and/or microarrays. Arrays can include, for example, oligonucleotide arrays, including cDNA, DNA, and/or RNA oligonucleotide arrays. Such arrays may comprise a macroarray, a microarray (e.g., a microfluidic array), and/or a nanoarray. In some embodiments, the amplified product and/or the oligonucleotide hybridizing thereto may be labeled, e.g., with a detectable moiety. For example, one or more of the nucleotides in the amplification reaction may be labeled with a detectable moiety. Detectable moieties that can be used include fluorescent moieties, radioactive moieties, quantum dots, and/or luminescent systems.

In some embodiments, arrays for use in the practice of the present invention comprise oligonucleotides immobilized on a solid support where a first set of the immobilized oligonucleotides can bind to a sequence of the amplified product of the nucleic acid that is not common to the amplified product of the competitive template for the nucleic acid and where a second set of the immobilized oligonucleotides can bind to a sequence of the amplified product of the competitive template of the nucleic acid that is not common to the amplified product of the nucleic acid, for example, sequences that span the juncture between the 5' end of the competitive template and the truncated, mis-aligned 3' end of the competitive template (e.g., that can be prepared according to the method of Celi). Amplified product of the nucleic acid and of the competitive template for the nucleic acid can be allowed to bind to the array and a ratio obtained from the two sets. In still some embodiments, the two-step approach can be practiced without the use of solid phase hybridizations, e.g., without the use of arrays.

The use of two rounds in preferred embodiments of a two-step process can lower the threshold amount of nucleic acid that can be measured in a sample. The lower threshold of detection can be defined as the minimum amount of analyte that can be reliably detected above background. The detection limit can be defined as the lowest concentration or quantity of analyte that can be detected with reasonable certainty. Without being limited to a particular hypothesis and/or theory, there may be a minimum amount of cDNA that can be used to achieve a statistically significant measurement. Lower threshold of detection in gene expression measurements may be considered in terms the minimal number of molecules of cDNA in a reaction for amplification or the minimal number of cells.

Figure 5:
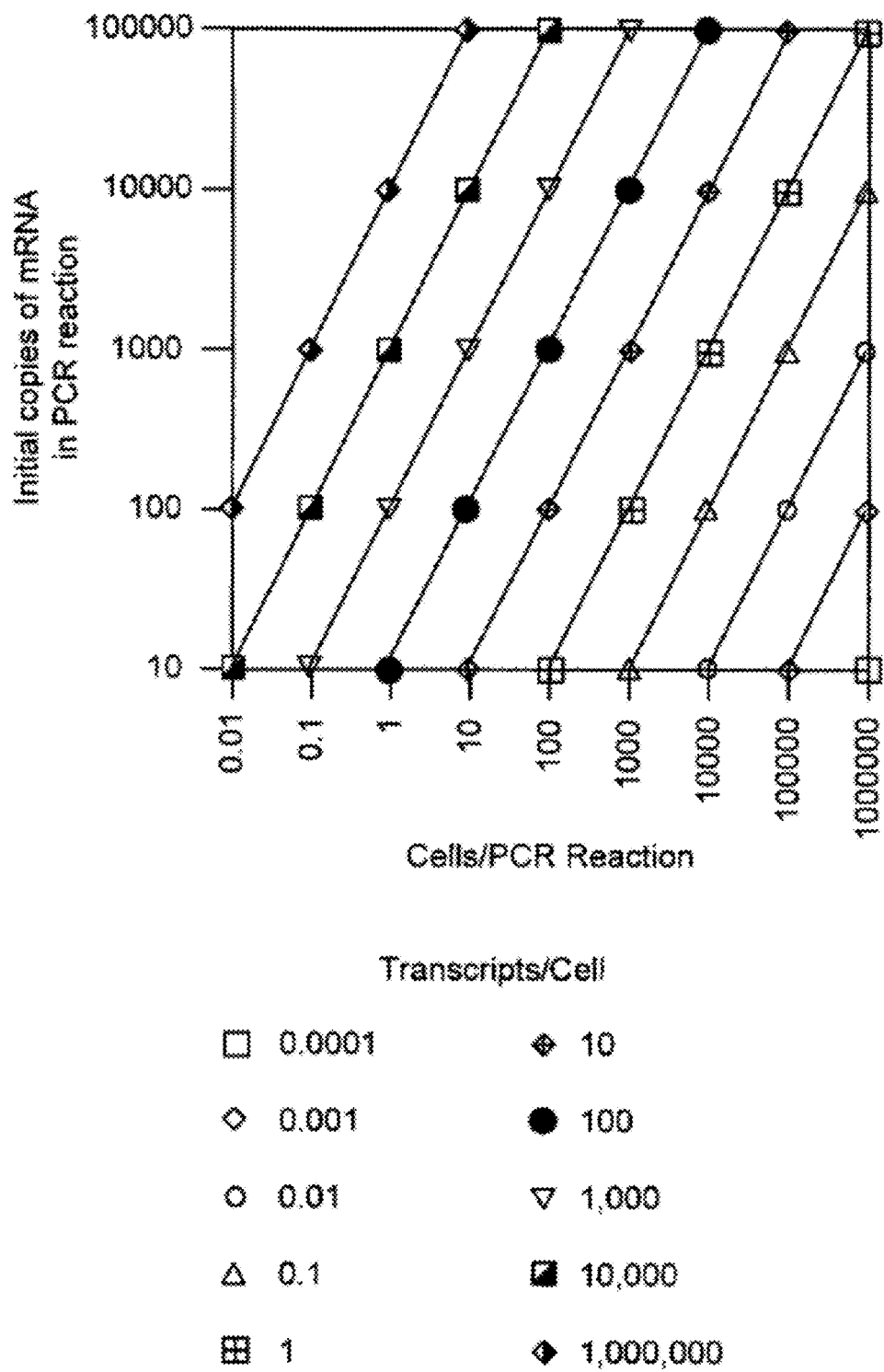
FIG. 5 illustrates a relationship between the amount of nucleic acid used in a PCR reaction and the number of copies of mRNA transcripts/cell that can be measured for a given number of cells/PCR reaction.

FIG. 5 schematically illustrates how the amount of cDNA used in a PCR reaction has a direct relationship to the number of copies of mRNA transcripts/cell that can be measured for a given number of cells used. The minimal number of cells then depends on mRNA copies/cell in a sample, as well as the efficiency of RNA extraction and/or reverse transcription. For example, consider the number of cells to provide RNA sufficient to result in at least 10 molecules of cDNA for a particular gene. It generally is assumed that RNA extraction is close to about 100% whereas reverse transcription is about 10% efficient. Thus, if a homogeneous population of cells is studied and each cell contains 10 copies of mRNA for a gene, 1 copy per cell will remain after reverse transcription. Due to stoichiometric considerations, cDNA samples included in a PCR reaction that contain less than about 10 molecules of a transcript is questionable, in some types of PCR. In such embodiments, cDNA representing about 10 cells is preferably present in the PCR reaction, as illustrated in FIG. 5. If a heterogeneous cell population is studied in which 1 cell out of 10 expresses a particular transcript, cDNA representing about 1,000 cells is preferably present in the PCR reaction.

In certain embodiments, the use of two rounds can overcome some of the limitations illustrated in FIG. 5. Consider a typical about 10 µl cDNA sample representing about 1,000 cells and comprising about $6 \times 10^5$ molecules of β-actin nucleic acid. Genes expressed at the mean level (100-fold lower than β-actin), are represented by about 6,000 molecules in the sample. A number of genes that may be important functionally are expressed 10,000-fold lower than β-actin, and for such genes there would be about 60 molecules represented in the sample. In a 100-fold smaller sample of about 100 nanoliters, genes expressed 10,000-fold lower than β-actin would be represented by about 0.6 copies or fewer.

In certain embodiments of the instant invention, about 10 nanoliters of an about 10 µl round one amplified product may be used in around two reaction volume of about 100 nanoliters. Because more than about 1,000,000-fold amplification is routinely achieved in the round one reaction, about 10 nanoliters of the about 10 µl round one reaction will contain ample amplified product of nucleic acid and competitive template to be measured with statistical confidence after round two.

Further, in some preferred embodiments, the use of two rounds can increase the number of measurements obtainable from a small sample of nucleic acid. For example, in some embodiments, at least about 10,000, at least about 50,000, at least at about 80,000, at least about 100,000, at least about 150,000 nucleic acid measurements can be obtained from the same amount of starting nucleic acid typically used to obtain one measurement using the processes provided in Willey and Willey et al. '390, '606, and '978. In some embodiments, at least about 200,000, at least about 500,000, at least at about 800,000, at least about 1,000,000, or at least about 1,500,000 nucleic acid measurements can be obtained from the same amount of starting nucleic acid typically used to obtain one measurement using the processes provided in Willey and Willey et al. '390, '606, and '978, preferably without loss of sensitivity to detect rare transcripts. For example, in some embodiments, sufficient amplified product can be generated to measure nucleic acids corresponding to several genes in about 100 to about 1,000 cell samples. Using the processes provided in Willey and Willey et al. '390, '606, and '978, cDNA representing about 100 to about 1,000 cells is typically used to measure one nucleic acid in one PCR reaction. Referring again to FIG. 5, using this amount allows detection of transcripts that are expressed at about 0.1 to about 1 copy per cell (or about 1 to about 10 copies per 10 cells) with statistical significance. The same amount of cDNA can be used in a first round of amplification in certain embodiments of the instant invention. Since this cDNA is co-amplified with a competitive template for the nucleic acid to be measured, and since the relationship of endogenous cDNA to its competitive template remains constant or substantially constant, amplified product from round one can be diluted and further amplified in a second round with primers specific to a given nucleic acid without significantly changing the relative amounts of amplified product.

Further, in some embodiments, use of two rounds can increase the number of nucleic acid that can be measured in a given sample. Some embodiments, for example, allow replicate measurement of many genes in small amounts of specimen material.

In some embodiments, methods of the instant invention reduce false positives to a statistically insignificant number. In some embodiments, false negatives are reduced to a statistically insignificant number, and in some embodiments, eliminated. For example, where a competitive template is used in a number of nucleic acid measurements, there may be no false negatives and a statistically insignificant number of false positives.

B. Use of a Standardized Mixture

In some embodiments, the two-step approach of assessing a nucleic acid in a sample can comprise use of a standardized mixture "Standardized mixture" as used herein can refer to a mixture comprising a number of internal standards, e.g., a number of competitive templates, at known concentrations. In preferred embodiments, the standardized mixture comprises a competitive template for at least one target nucleic acid and a competitive template for at least one reference nucleic acid in a sample, where the competitive templates are at known concentrations relative to each other. In more preferred embodiments, the competitive templates are at fixed concentrations relative to other, up to and including all other, competitive templates in the mixture.

Figure 6:
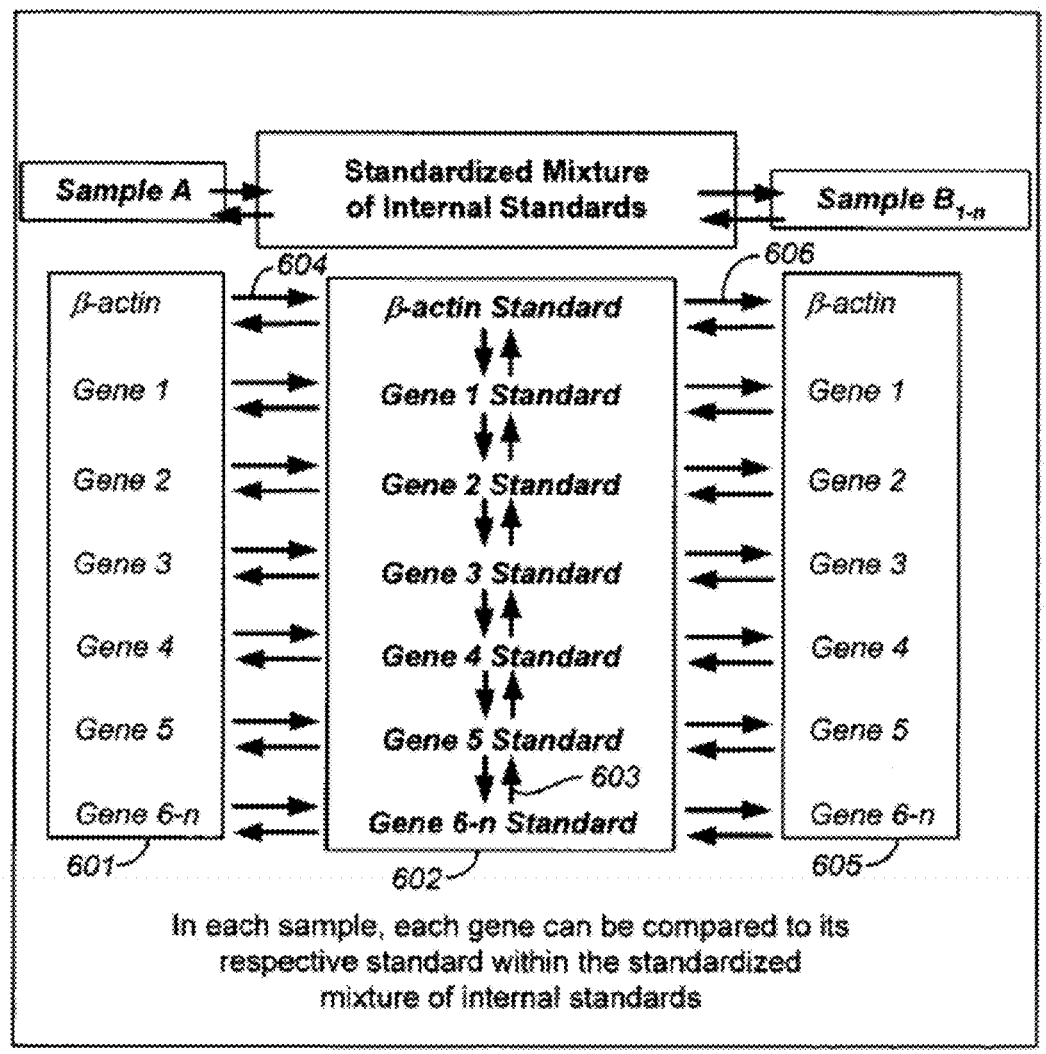
FIG. 6 illustrates a standardized mixture used in some embodiments of the present invention.

FIG. 6 illustrates a standardized mixture used in some embodiments of the present invention. Feature 601 illustrates a sample, Sample A, which comprises a number of nucleic acids to be measured, corresponding to Genes 1-6-n, as well as a nucleic acid to serve as a reference, corresponding to βactin in this illustration.

Feature 602 illustrates a standardized mixture of internal standards comprising competitive templates for the reference nucleic acid (β-actin standard) as well as competitive templates for target nucleic acids (Genes 1 to 6-n standards). In some embodiments, the number of competitive template(s) can be at least one other competitive template in addition to a target nucleic acid, at least about 100, at least about 200, at least about 500, at least about 1,000, at least about 5,000, at least about 10,000, at least about 50,000, or at least about 100,000 other competitive templates. For example, competitive templates for several genes to be measured can be included in a given standardized mixture, as illustrated in feature 602.

Feature 603 (vertical two-way arrows) illustrates a relationship among internal standards within a standardized mixture. A competitive template for each of a number of genes can be at a fixed concentration relative to other competitive templates within a standardized mixture. Accordingly, in some embodiments, when a cDNA sample is combined with a standardized mixture, the concentration of each competitive template is fixed relative to the cDNA representing its corresponding gene.

Feature 604 (horizontal two-way arrows) illustrate a relationship between an internal standard and its corresponding cDNA from a sample and how each target nucleic acid is measured relative to its respective competitive template in the standardized mixture. Because the competitive template for each of these nucleic acids is present at a fixed concentration relative to other competitive templates, the standardized mixture can allow a target nucleic acid to be assessed relative other nucleic acids being measured with the standardized mixture 602. For example, Sample A 601 can be combined with standardized mixture 602, e.g., to form a master mixture used for further co-amplifications. For example, the master mixture can be used in co-amplifying nucleic acid corresponding to Gene 1 and its competitive template (Gene 1 standard), as well as co-amplifying nucleic acid corresponding to Gene 2 and its competitive template (Gene 2 Standard).

In a two-step approach using standardized mixture 602, a target nucleic acid and its respective competitive template can be co-amplified to produce first amplified product thereof. The amplified products can be diluted and further co-amplified one or more times, as described in more detail above. In some embodiments, first amplified product of the reference nucleic acid can be diluted and further amplified one or more times, also as described above.

Feature 606 illustrates a number of other samples, Samples $B_{1-n}$ 605, which also comprise nucleic acids, corresponding to Genes 1 to 6-n, and a reference nucleic acid, corresponding to β-actin. In some embodiments, the number of β-actin mRNA molecules obtained from a cell may vary from about 100 to about 1000, e.g., depending on efficiency of RNA extraction, the size and/or other characteristics of the cell.

In some embodiments, another nucleic acid can serve as a second reference nucleic acid. For example, in some embodiments, gene expression measured in reference to β-actin mRNA can be re-calculated relative to that of another reference nucleic acid, if so desired. For example, if another nucleic acid, e.g. GAPDH or any other of Genes 1 to 6-n 602, appears to vary less than β-actin across the samples $B_1$-n 605, the data may be re-calculated ("normalized") to that reference without altering the relative expression measurement, e.g., the relative expression measurement within a sample. When nucleic acid measurement data are re-calculated, the relative measured amounts among nucleic acids can remain the same or substantially the same.

Figure 7:
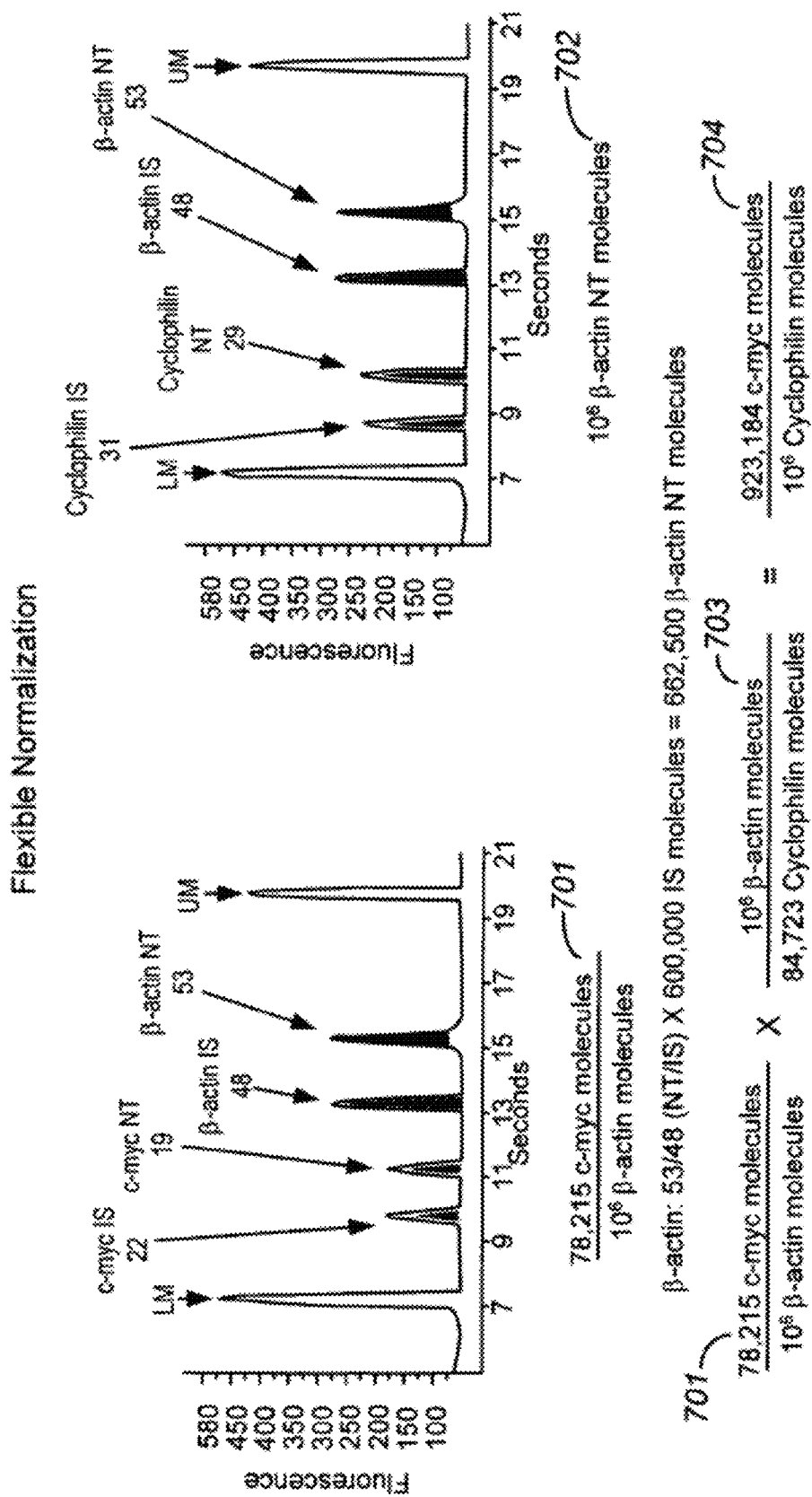
FIG. 7 illustrates re-calculating numerical values based on a first reference nucleic acid (β-actin) to numerical values based on a second reference nucleic acid (cyclophilin)

FIG. 7 illustrates a re-calculation using cyclophilin as a second reference gene, where gene expression is provided as a ratio of (target gene NT molecules)/($10^6$ β-actin NT molecules). In FIG. 7, NT refers to native template, and the target gene is c-myc.

Ratio 701 illustrates a gene expression value for the target gene as the ratio of (c-myc NT molecules)/($10^6$ β-actin NT molecules). Ratio 702 illustrates a gene expression value for a first reference gene as the ratio of (cyclophilin NT molecules)/($10^6$ β-actin NT molecules). Ratio 703 illustrates a conversion factor for re-calculating relative to cyclophilin Ratio 703 provides the inverse of ratio 702, namely of ($10^6$ β-actin NT molecules)/(cyclophilin NT molecules). Conversion can be achieved by multiplying ratio 701 by the ratio 703 to provide ratio 704. Ratio 704 illustrates the ratio (c-myc NT molecules)/(cyclophilin NT molecules), a gene expression value for the target gene relative to the new reference gene.

In other embodiments, conversion from (molecules of target nucleic acid)/(molecules of a first reference nucleic acid) to (molecules of target nucleic acid)/(molecules of a second reference nucleic acid) can be achieved, e.g., by inverting a gene expression value of the second reference, e.g., to (molecules of first reference nucleic acid)/(molecules of second reference gene) and multiplying this factor by the data. The value for molecules of the first reference nucleic acid can cancel out, leaving the second reference gene in the denominator.

Re-calculation may be accomplished using a spreadsheet, in some embodiments. In some cases, re-calculating relative to a new reference can alter the numerical value of a measured amount of a given nucleic acid without altering the numerical values of nucleic acids relative to each other.

Without being limited to a particular hypothesis and/or theory, this may be explained in that measured amounts of a nucleic acid can be said to be linked through use of a common standardized mixture of competitive templates 602. Thus, the ratio between two nucleic acids within a sample would be the same or substantially the same using β-actin, cyclophilin, or a combination of nucleic acids as the reference nucleic acid.

Feature 605 (two way arrows) illustrates how each of these nucleic acids in additional samples can be measured relative to its respective competitive template in the standardized mixture 602. As with Sample A 601, each of these nucleic acids can be assessed relative other nucleic acids measured with the standardized mixture 602. Further, it is possible to compare data from analysis of Sample A 601 to data from analysis of samples $B_{1-n}$ 604. For example, because the number of molecules for each competitive template is known within the standardized mixture, it is possible to calculate all data in the form of molecules/reference nucleic acid molecules. In some embodiments, the standardized mixture 602 comprises sufficient amounts of competitive templates for assessing one or more of the target nucleic acids in a large number of samples $B^{1-n}$604, e.g., in more than about $10^4$ samples, in more than about $10^5$ samples, in more than about $10^6$ samples, in more than about $10^7$ samples, in more than about $10^8$ samples; in more than about $10^9$ samples, in more than about $10^{10}$ samples, in more than about $10^{11}$ samples, in more than about $10^{12}$ samples, in more than about $10^{13}$ samples, in more than about $10^{14}$ samples, or in more than about $10^{15}$ samples. In some preferred embodiments, use of a common standardized mixture for multiple samples can reduce time to obtain nucleic acid measurements. For example, re-preparing reagents for PCR reactions can be time consuming and can also lead to sources of error.

A nucleic acid and its competitive template may be co-amplified (and/or further co-amplified) in the same or different vessels as one or more other nucleic acid and corresponding competitive template. See, e.g., Apostolakos, M. J., Schuermann, W. I I., Frampton, M., Utell, M. J., and Willey, J. C. (1993) Measurement of gene expression by multiplex competitive polymerase chain reaction. Anal. Biochem. 213, 277-284; Willey, J. C., Crawford, E. L., and Jackson, C. M. (1998) Expression measurement of many genes simultaneously by quantitative RT-PCR using standardized mixtures of competitive templates. Am. J. Respir. Cell Mol. Biol. 19, 6-17. The vessel used may be any object capable of allowing a reaction mixture to exist therein and/or thereon. For example, the vessel may comprise a well, tube, nano and/or microfluidic reservoir and/or channel, capillary, groove, surface, and/or other container.

In some preferred embodiments, use of a standardized mixture 602 allows different nucleic acids amplified in separate vessels to be directly compared. In some embodiments, for example, one nucleic acid and its competitive template are co-amplified in one vessel, while another nucleic acid and its competitive template are co-amplified in a different vessel. In either case, as feature 603 illustrates, nucleic acid can be measured relative to its respective internal standard competitive template within the standardized mixture and the other nucleic acid can serve as a reference nucleic acid. That is, in preferred embodiments, the use of a standardized mixture allows the concentration of internal standard for a nucleic acid relative to others to remain fixed across different measurements.

As feature 603 illustrates, use of a common standardized mixture allows direct comparisons to be made among Samples $B_{1-n}$ 604. The different samples may be amplified at different times, e.g., on different days; in the same or different experiments in the same laboratory; and/or in different laboratories. Crawford, E. L., Peters, G. J., Noordhuis, P., et al. (2001) Reproducible gene expression measurement among multiple laboratories obtained in a blinded study using standardized RT (StaRT)-PCR. Mol. Diagn. 6, 217-225; Crawford, E. L., Warner, K. A., Khuder, S. A., et al. (2002) Multiplex standardized RT-PCR for expression analysis of many genes in small samples. Biochem, Biophys. Res. Commun 293, 509-516; Crawford, E. L., Khuder, S. A., Durham, S. J., et al. (2000) Normal bronchial epithelial cell expression of glutathione transferase P1, glutathione transferase M3, and glutathione peroxidase is low in subjects with bronchogenic carcinoma. Cancer Res. 60, 1609-1618; DeMuth, J. P., Jackson, C. M., Weaver, D. A., et al. 1998). The gene expression index c-myc x E2F1/p21 is highly predictive of malignant phenotype in human bronchial epithelial cells. Am. J. Respir. Cell Mol. Biol. 19, 18-24; Mollerup, S., Ryberg, D., Hewer, A., Phillips, D. H., and Haugen, A. (1999) Sex differences in lung CYP1A1 expression and DNA adduct levels among lung cancer patients. Cancer Res. 59, 3317-3320; Rots, M. G., Willey, J. C., Jansen, G., et al. (2000) mRNA expression levels of methotrexate resistance-related proteins in childhood leukemia as determined by a standardized competitive template-based RT-PCR method. Leukemia 14, 2166-2175; Rots, M. G., Pieters, R., Peters, G. J., et al. (1999) Circumvention of methotrexate resistance in childhood leukemia subtypes by rationally designed antifolates. Blood 94, 3121-3128; Allen, J. T., Knight, R. A., Bloor, C. ., and Spiteri, M. A. (1999) Enhanced insulin-like growth factor binding protein-related protein 2 (connective tissue growth factor) expression in patients with idiopathic pulmonary fibrosis and pulmonary sarcoidosis. Am. J. Respir. Cell Mol. Biol. 21, 693-700; Loitsch, S. M., Kippenberger, S., Dauletbaev, N., Wagner, T. 0., and Bargon, J. (1999) Reverse transcription-competitive multiplex PCR improves quantification of mRNA in clinical samples-application to the low abundance CFTR mRNA. Clin. Chem. 45, 619-624; Vondracek, M. T., Weaver, D. A., Sarang, Z., et al. (2002) Transcript profiling of enzymes involved in detoxification of xenobiotics and reactive oxygen in human normal and Simian virus 40 T antigen-immortalized oral keratinocytes. In. J. Cancer 99, 776-782. In preferred embodiments, measurements are made using the same standardized mixture and dilution of internal standard competitive templates.

Further, in some embodiments, measurements obtained using various quantifying approaches are directly comparable where a common standardized mixture is used. For example, statistically similar results were obtained using a common standardized mixture and quantifying amplified product by various types of electrophoresis, or by either a Caliper AMS 90 SE30 electrophoretic separation or by hybridizing them to microarrays in accordance with some embodiments of the instant invention. In another example, reproducible gene expression measurements were obtained when amplified product was quantitated using MALDI-TOF MS instead of using electrophoresis. Ding C. and Cantor, C. R. (2003) A high-throughput gene expression analysis technique using competitive PCR and matrix-assisted laser desorption ionization time-of-flight MS. Proc. Natl. Acad. Sci. SA 100, 3059-3064.

The use of the standardized mixtures may also be applied to other methods for measuring nucleic acids, e.g., in real-time RT-PCR. For example, in some embodiments, obtaining a ratio of amplified product of a nucleic acid to amplified product of a competitive template for the nucleic acid can comprise a use of real-time RT-PCR analyses. As another example, a standardized mixture may be used in accordance with some embodiments of the instant invention in combination with competitive template techniques described, e.g., in Siebert, P. D., et al., Nature 359:557-558 (1992); Siebert, P. D., et al., BioTechniques 14:244-249 (1993), and Clontech Brochure, 1993, Reverse Transcriptase-PCR (RT-PCR). For example, fluorescent probes for using a standardized mixture with real-time RT-PCR may be developed.

C. Use of Serially-Diluted Standardized Mixtures

In some embodiments, a series of serially-diluted standardized mixtures is used to assess amounts of nucleic acid. "Serially-diluted standardized mixtures" can refer to two or more standardized mixtures in which one or more of the reagents in the standardized mixtures is serially-diluted. In some embodiments, one or more reagents in the standardized mixtures is serially-diluted relative to a different one or more of the reagents in the mixtures. For example, in preferred embodiments, a competitive template for a first nucleic acid is serially diluted relative to a competitive template for a second nucleic acid where the second nucleic acid can act as a reference nucleic acid. In some embodiments, the reference nucleic acid can be present at two different concentrations in two of the serially-diluted standardized mixtures. One of a series of serially-diluted mixtures is also referred to herein as a "Mix."

Figure 8:
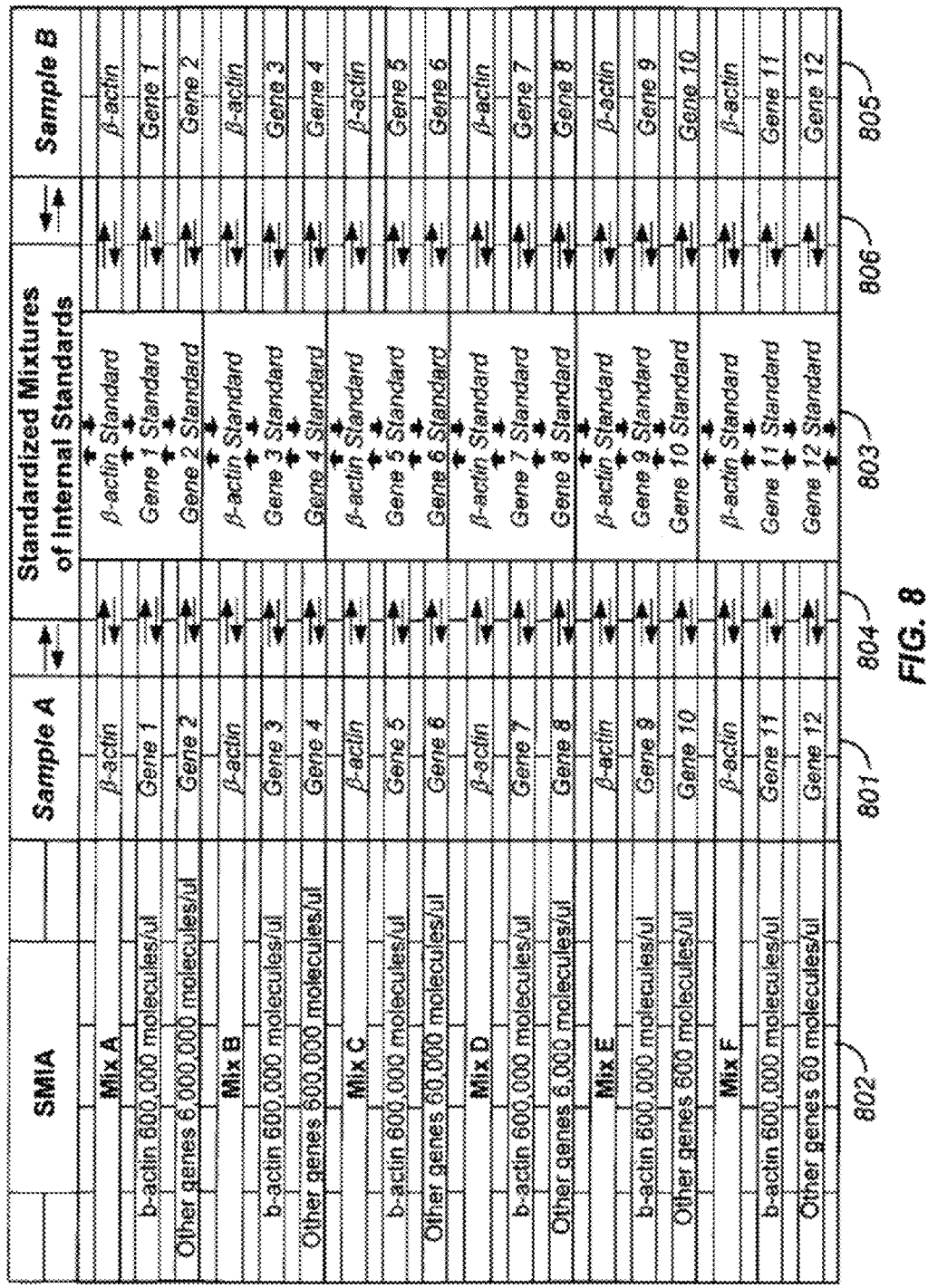
FIG. 8 illustrates use of a series of standardized mixtures, according to some embodiments of the instant invention.

FIG. 8 illustrates use of a series of standardized mixtures, according to some embodiments of the instant invention. In the figure, "SMIS" refers to a standardized mixture of internal standards, prepared in accordance with embodiments of the instant invention.

Feature 801 illustrates a sample, Sample A, which comprises a number of nucleic acids to be measured, corresponding to Genes 1-12, as well as a nucleic acid that serves as a reference, corresponding to β-actin in this illustration.

Feature 802 illustrates a series of six standardized mixtures, Mixes A-F, comprising 10-fold dilutions of competitive templates for different genes relative to competitive templates for a reference gene, β-actin in this illustration.

Feature 803 illustrates the relationship between competitive templates for the reference nucleic acid (β-actin standard) compared to competitive templates for target nucleic acids (Genes 1 to 12 standards) in the different serially-diluted mixtures. Use of the series can allow measurement of the nucleic acids corresponding to different genes expressed over a range, e.g., a range of more than six orders of magnitude.

Feature 804 (two way arrows) illustrates how these different nucleic acids in the Sample 801 are in balance with (i.e., calibrated to) different concentrations of their corresponding competitive templates in the different mixes. "Balancing" or being in balance with, as used herein, can refer to calibrating amounts of two nucleic acids. For example, Genes 9 and 10 in Sample A 801, expressed at a low level, are in balance with Mix E comprising 600 molecules/ μl of competitive template for gene 9 and Gene 10. Genes 9 and 10 are preferably measured using Mix E. Genes 6 and 7 are expressed at a higher level in Sample A 801 and are in balance with Mix C and Mix D, respectively. Gene 6 is preferably measured using Mix C and Gene 7 is preferably measured Mix D.

In some embodiments, use of a series allows measurement of nucleic acids over a range of concentrations. Where practice of the invention assesses gene expression, as in FIG. 8, some embodiments allow measurement over one or more orders of magnitude of gene expression. For example, in some embodiments, the amounts of two nucleic acids to be measured vary over a range of less than about one order of magnitude, more than about one order of magnitude, or more than about 2 orders of magnitude. In some embodiments, the amounts of two different nucleic acids to be measured, e.g., mRNA levels expressed from two or more different genes, vary over a range of about 3 or more orders of magnitude, about 4 or more orders of magnitude, about 5 or more orders of magnitude, about 6 or more orders of magnitude, or about 7 or more orders of magnitude, e.g., spanning an about 7-log range of gene expression including about $10^{-3}$, about $10^{-2}$, about 0.1, about 1, about 10, about $10^2$, about $10^3$, and about $10^4$ copies/cell. In some embodiments, the amounts of two different nucleic acids to be measured vary over a range of about 8 or more, about 9 or more, or about 10 or more orders of magnitude, e.g., spanning an about 10-log range of gene expression of about $10^{-3}$, about $10^{-2}$, about 0.1, about 1, about 10, about $10^2$, about $10^3$, about $10^4$, about $10^5$, or about $10^6$ copies/cell. Such ranges of gene expression may be important in detecting agents of biological warfare, for example.

Feature 805 illustrates a different sample, Sample B, also comprising nucleic acids corresponding to Genes 1-12 and to βactin.

Feature 806 (two way arrows) illustrates the different nucleic acids in the Sample B 805 are also in balance with different concentrations of their corresponding competitive templates in the different mixes. A given gene in a different sample can be in balance with the same Mix, allowing past experience with a measuring a given gene to inform the selection of an appropriate Mix.

In some embodiments, the series can comprise serial 10-fold dilution from a standardized mixture comprising competitive template for more or less than the 12 genes of FIG. 8. For example, a series can be prepared for a 96-nucleic acid standardized mixture or a standardized mixture comprising various numbers of nucleic acids as detailed above.

In some embodiments, the method for assessing an amount of a nucleic acid involves providing a series of serially-diluted standardized mixtures comprising a competitive template for the nucleic acid and a competitive template for another nucleic acid present in a number of samples comprising the nucleic acid, where the competitive templates are at known concentrations relative to each other; combining one of the samples comprising the nucleic acid with one of the serially-diluted standardized mixtures; co-amplifying the nucleic acid and its competitive template to produce amplified product thereof, obtaining a first relationship that compares amplified product of the nucleic acid to amplified product of its competitive template; determining whether the relationship corresponds to a ratio within about 1:10 to about 10:1; and if not, repeating combining, co-amplifying, obtaining and determining steps using a second one of the serially-diluted standardized mixtures. Further, in some embodiments, the other nucleic acid and its competitive template can be co-amplified to produce amplified product thereof, a second relationship obtained that compares amplified product of the other nucleic acid to its competitive template; and comparing first and second relationships.

In some embodiments, a "two-step" approach may be used. For example, in some embodiments, the method further comprises diluting amplified product of nucleic acid and its corresponding competitive template; and further co-amplifying the diluted amplified product to produce further amplified product thereof.

In some embodiments, different concentrations of competitive templates for reference nucleic acid may be used. For example, where the expression of a first reference nucleic acid varies in comparison to a second reference nucleic acid, use of more than one concentration can be helpful in determining inter-sample and/or inter-specimen variation in expression of corresponding reference genes. For example, some embodiments use two different concentrations of GAPD competitive templates, as the expression of GAPD relative to β-actin may vary as much as about a 100-fold from one tissue type to another. Having two different concentrations of GAPD competitive template relative to that for β-actin, can enable better comparison of GAPD to β-actin in various samples.

Figure 9:
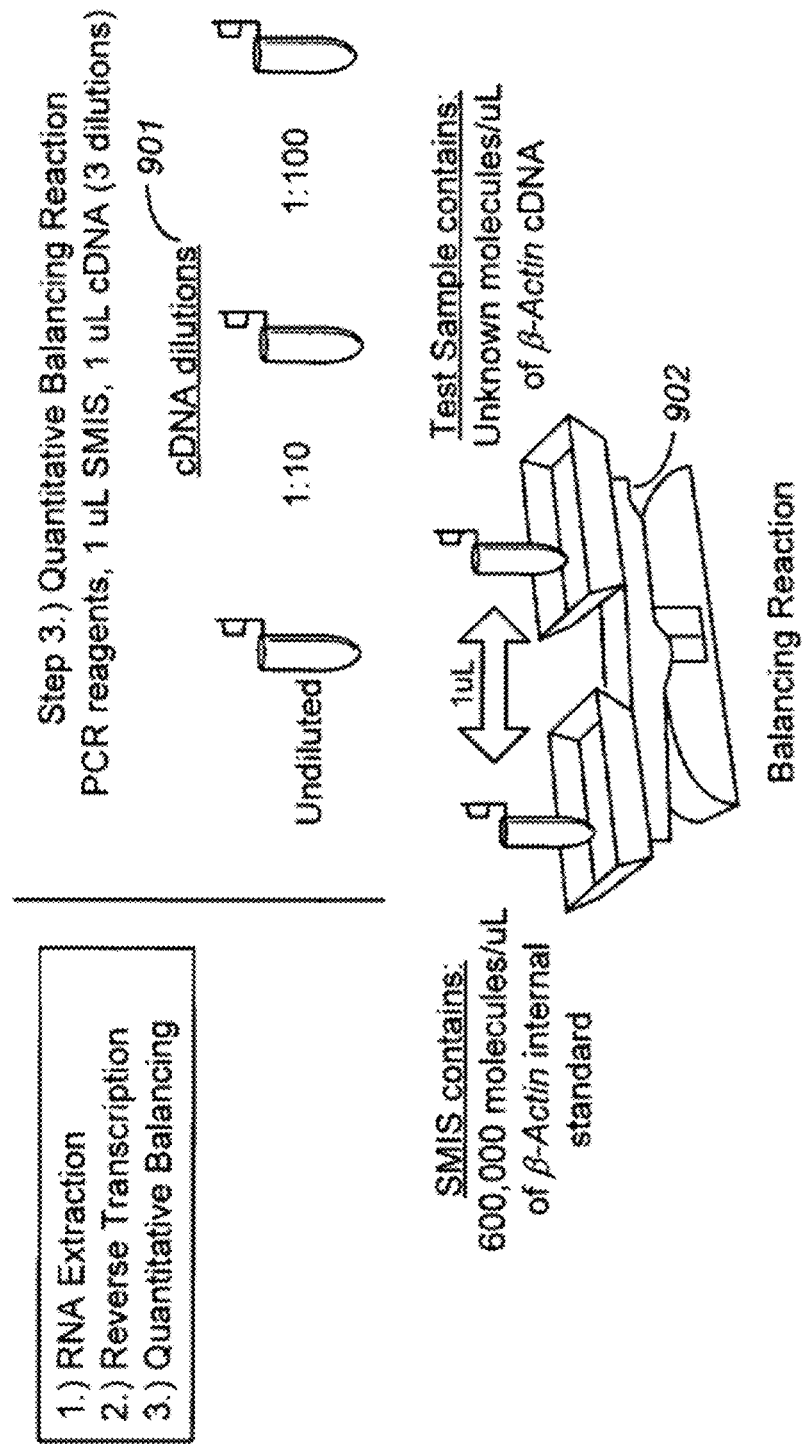
FIG. 9 illustrates using a nucleic acid serving as a reference to balance a sample with a standardized mixture of a series of serially-diluted standardized mixtures.

FIG. 9 illustrates how, in some embodiments, nucleic acid serving as a reference can be used to balance a sample with a standardized mixture of the series of serially-diluted standardized mixtures.

Step 901 illustrates quantitative balancing of a nucleic acid sample. Qualitative balancing, as used herein, can also be referred to as qualitative calibration. The nucleic acid sample can be diluted provide a series of serially-diluted samples and one of the series selected, for combining with standardized mixture, depending on the concentration of the reference nucleic acid in the dilution. For example, at step 901, cDNA material is serially-diluted to provide a series of samples having serial dilutions of β-actin nucleic acid.

Step 902 illustrates that a dilution is selected to provide about equivalent β-actin native template (NT) molecules as there are β-actin competitive template (CT) molecules in a SMIS Mix. In some embodiments, a specimen can be diluted until any one (or more) of the nucleic acids is approximately balanced with, i.e., approximately calibrated to, the amount of competitive template for that nucleic acid in the standardize mixture. Thus, in preferred embodiments, the first one of the number of samples to be combined with standardized mixture is selected to provide reference nucleic acid calibrated or approximately calibrated to its competitive template in the standardized mixture. Approximate calibration can occur when the nucleic acid is within about a 10-fold range, a 9-fold range, an 8-fold range, a 7-fold range, a 6-fold range, a 5-fold range, a 4-fold range, a 3-fold range, a 2-fold range, or a 1-fold range or less, of the concentration of the competitive template for that particular nucleic acid in the standardized mixture. In preferred embodiments, the NT/CT ratio for the reference nucleic acid is between about 1:10 and about 10:1 (e.g., for measurement to be within linear dynamic range).

Figure 10:
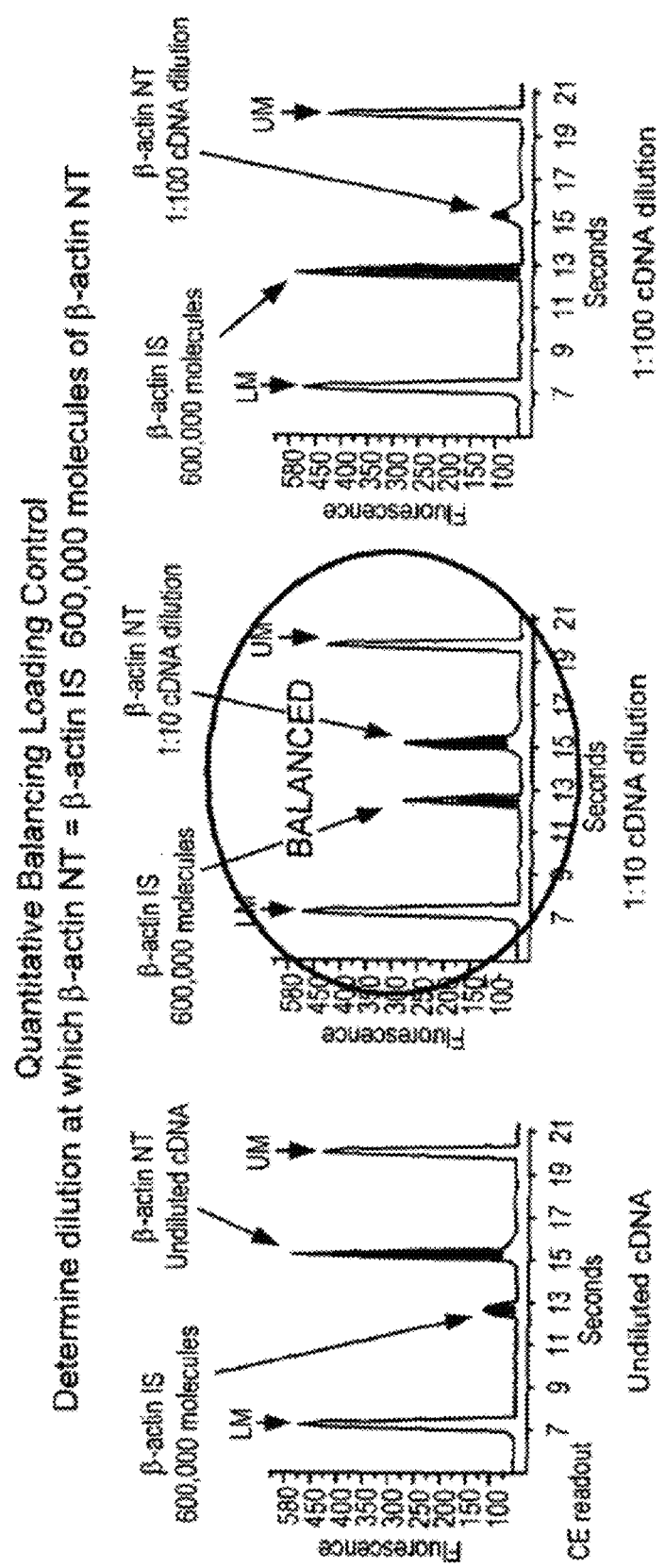
FIG. 10 illustrates a cDNA dilution that provides a reference nucleic acid (β-actin) in balance with 600,000 molecules of the reference nucleic acid competitive template in a standardized mixture.

FIG. 10 further illustrates selection of a cDNA dilution that provides a reference nucleic acid (β-actin in this illustration) in balance with 600,000 molecules of the reference nucleic acid competitive template in the standardized mixture, e.g., so the nucleic acid can compete equally (or substantially equally) with the 600,000 competitive template molecules. In preferred embodiments, all standardized mixtures in a given series contain a given number of molecules of a particular reference nucleic acid, allowing any of the standardized mixtures to be used in balancing. For example, A-F can each contain about $10^{-12}$ M β-actin competitive template so than any of Mixes A-F can be used in balancing with a cDNA sample. Typically, Mix F is used for balancing β-actin cDNA in a sample.

Figures 11, 12:
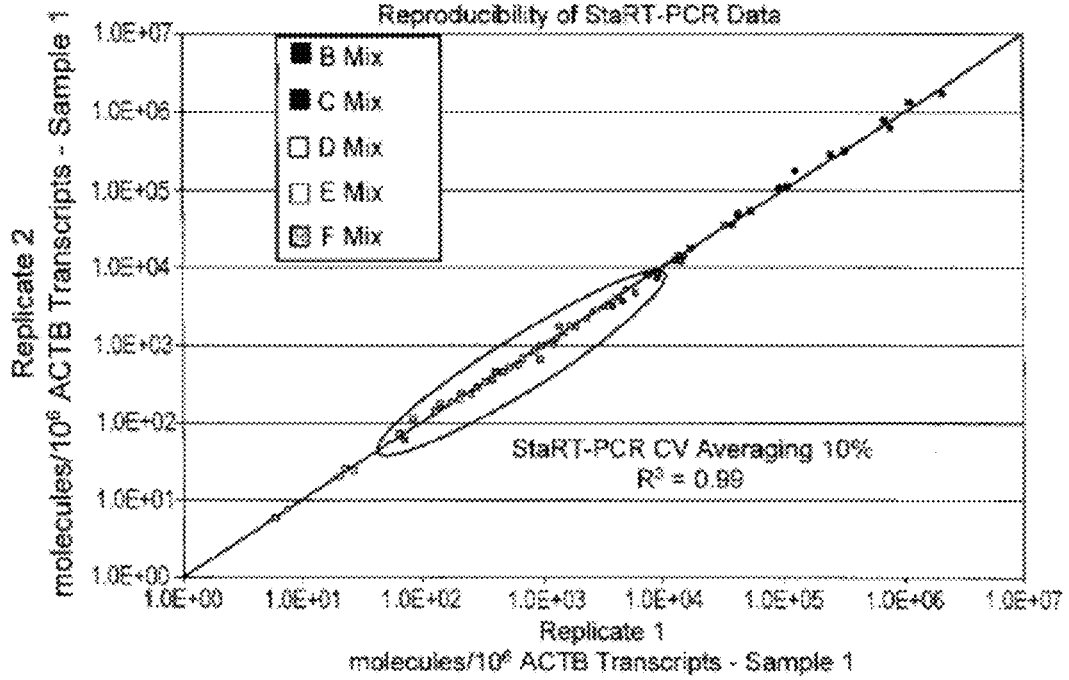
FIG. 11 illustrate a series of serially-diluted standardized mixtures A-F comprising a series of concentrations of competitive templates for target nucleic acids (6,000,000; 600,000; 60,000; 6,000; 600 and 60 molecules/ μL, respectively) relative to a given concentration of competitive template for a β actin (600,000 molecules/ μL).
FIG. 12 illustrates use of Mix E initially, based on the expression levels of most genes.

FIG. 11 illustrate a series of serially-diluted standardized mixtures comprising one or more mixes where 1 µL contains 600,000 molecules of β-actin competitive template, corresponding to 1 µL of a standardized mixture containing $10^{-12}$ M β-actin competitive template. In that case, for example, cDNA material can be diluted until 1 µL is calibrated to 600,000 molecules of β-actin competitive template. Typically, this is the amount of cDNA derived from 100 to 1,000 cells in the case of β-actin. Although the number of β-actin mRNA copies/cell varies from one cell to another, using a conservative estimate of 600 β-actin mRNA copies/cell and assuming a reverse transcription efficiency of 10%, a cDNA sample containing 600,000 molecules of β-actin cDNA can be derived from 1,000 cells.

This amount may be used to provide sufficient cDNA to quantify genes expressed at low levels, e.g., genes expressed in low copy number, e.g., at about 0.1 copy/cell, 0.05 copies/cell, and/or 0.01 copies/cell. With reference cDNA in balance with about $10^{-12}$ M β-actin in the PCR reaction, some embodiments can quantify sample nucleic acid that is in balance with about $10^{-16}$M or less of its CT. In some specific embodiments, where reference cDNA is in balance with about $10^{-12}$ M β-actin in a 10 µl PCR reaction volume, there can be about 600,000 molecules of β-actin NT and about 600,000 molecules of β-actin CT in the reaction, and the number of molecules of sample nucleic acid in balance with about $10^{-16}$ M or about $10^{-17}$ M of its CT can be about 60 or about 6 respectively. About 60 or about 6 molecules of nucleic acid can translate into about 0.1 to about 0.01 molecules/cell.

This balancing can provide at least about 10 copies present at the beginning of amplification, avoiding, e.g., stoichiometric problems. In some embodiments where less sensitivity is sought, less cDNA may be used. For example, in some embodiments, an amount of cDNA approximately in balance with 60,000 molecules of β-actin CT can be used, allowing reduced consumption of cDNA, e.g., by about 10-fold.

A first one of the serially-diluted standardized mixtures can be selected for combing with the nucleic acid sample. FIG. 12 illustrates that Mix E can be used initially, based on the expression levels of most gene. There appears to be a stoichiometric and/or stochastic distribution of expression among genes (see, e.g., Kuznetsova, et al., General Statistics of Stochastic Process of Gene Expression in Eukaryotic Cells, Genetics, Vol. 61, 1321-1332, July 2002), with a mean approximately 2 orders of magnitude lower than the expression for β-actin, e.g., in human bronchial epithelial cells. Without being limited to a given theory and/or hypothesis, the distribution of gene expression levels in cells indicates that mRNA transcripts of many genes will be balanced with Mix E, in some embodiments.

FIG. 12 further illustrates that the use of a series of serially-diluted standardized mixtures of some embodiments can allow gene expression measurement over a full spectrum observed. As FIG. 12 illustrates through color-coding, different Mixes can be used to measure genes expressed at different levels with good reproducibility. Because there are about 100 to about 1,000 β-actin copies/cell for most cell types, this level of sensitivity allows measurement of molecule per about 100 to about 1,000 cells. At the other end of the expression spectrum, a standardized mixture comprising greater concentrations of competitive templates can allow measurement of more highly expressed genes. For example, Mix A in some embodiments, can allow measurement of more than $10^7$ molecules/$10^6$ molecules of βactin (about 1,000 to about 10,000 copies/cell). Examples of genes expressed at these levels, include UGB (Genbank no. U01101) and vimentin (X56134).

In other embodiments, a different mix may be used initially based on past experience and/or prediction of the amounts of nucleic acid expected. For example, Mix A, Mix B, Mix C, Mix E, or Mix F may be used initially. In preferred embodiments, the mixture selected is one containing a concentration of competitive template likely to be approximately calibrated with (e.g., within about a 10-fold range) the gene or genes being assessed. In preferred embodiments, an appropriate standardized mixture can be selected based on data in some embodiments of standardized expression databases described herein.

After combining a sample comprising a nucleic acid to be measured with one of the series of serially-diluted standardized mixture, the nucleic acid and its competitive template can be co-amplified, e.g., as described in detail above. Also as described above, a ratio can be obtained comparing amount of amplified product of the nucleic acid to amount of amplified product of its corresponding competitive template. Although a reference nucleic acid in the sample was balanced with its competitive template in the Mix, the target nucleic acid may not be balanced. Where the amounts of amplified product of a target nucleic acid and of its competitive template differ greatly, the co-amplification may be repeated using a different Mix of the series of serially-diluted mixtures. That is, a second and/or subsequent serially-diluted standardized mixture can be selected for combing with the nucleic acid sample.

Figure 13:
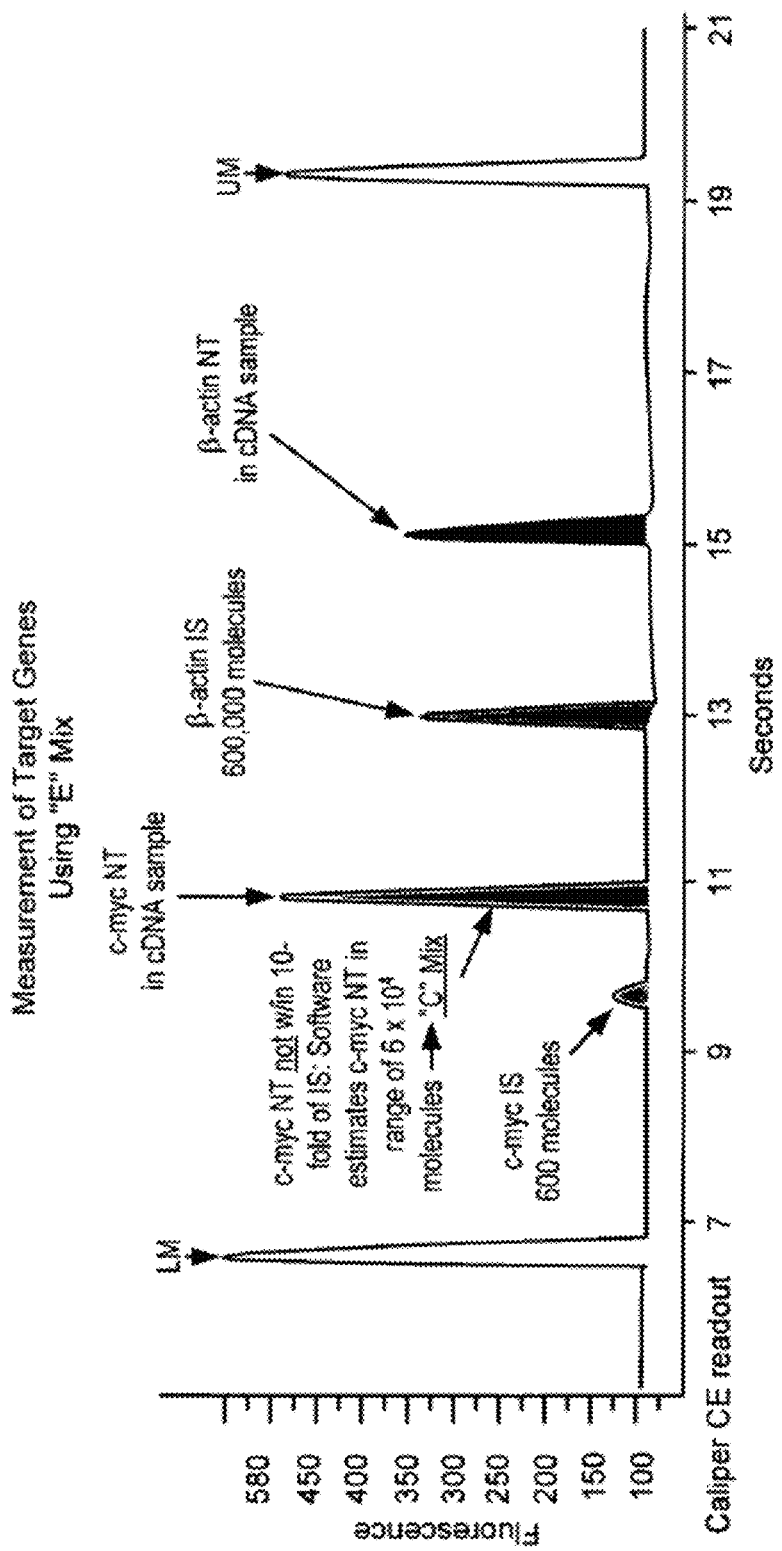
FIG. 13 illustrates a situation where the initial Mix used does not provide competitive template for the target nucleic acid (c-myc) sufficiently in balance with the amount of target nucleic acid in the cDNA dilution used.

FIG. 13 illustrates a situation where the initial Mix did not provide competitive template for target nucleic acid sufficiently in balance with the amount of target nucleic acid in the cDNA dilution. The target nucleic acid in this illustration corresponds to c-myc; IS refers to an internal standard competitive template. As FIG. 12 illustrates, amplified product of c-myc NT is not within about a 10-fold amount of amplified product of c-myc CT. In some embodiments, software determines area under curve for the NT and CT and calculates the ratio of NT/CT for the target nucleic acid.

In preferred embodiments, the next Mix selected from the series is based on the ratio obtained when amplified product of the target nucleic acid is compared to amplified product of its competitive template. For example, where the ratio is less than about 1/10, a more dilute mixture from the series will be used subsequently; where the NT/CT ratio is more than about 10/1, a more concentrated mixture from the series will be used. FIG. 12 illustrates the situation where a large ratio is obtained, indicating that a more concentrated Mix should be used next, e.g., Mix C. In some embodiments, software can be used to automatically determine which Mix should be selected next.

Figure 14:
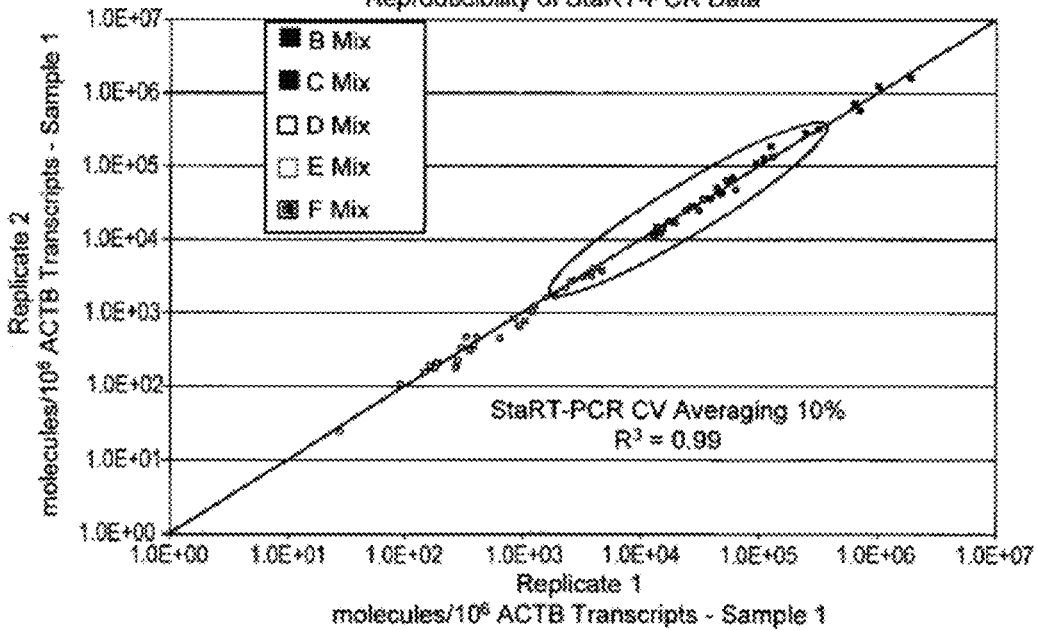
FIG. 14 illustrates selection of a subsequent mix, Mix C, based on results obtained using the first Mix.

FIG. 14 further illustrates selection of Mix C. The NT/CT ratio obtained for the target nucleic acid (c-myc in this illustration) is plotted on a graph. Position on the graph can indicate which Mix should be used for nucleic acid expressed at that level. In some embodiments, described in more detail below, software automatically communicates the correct Mix to be used to a robot.

Figure 15:
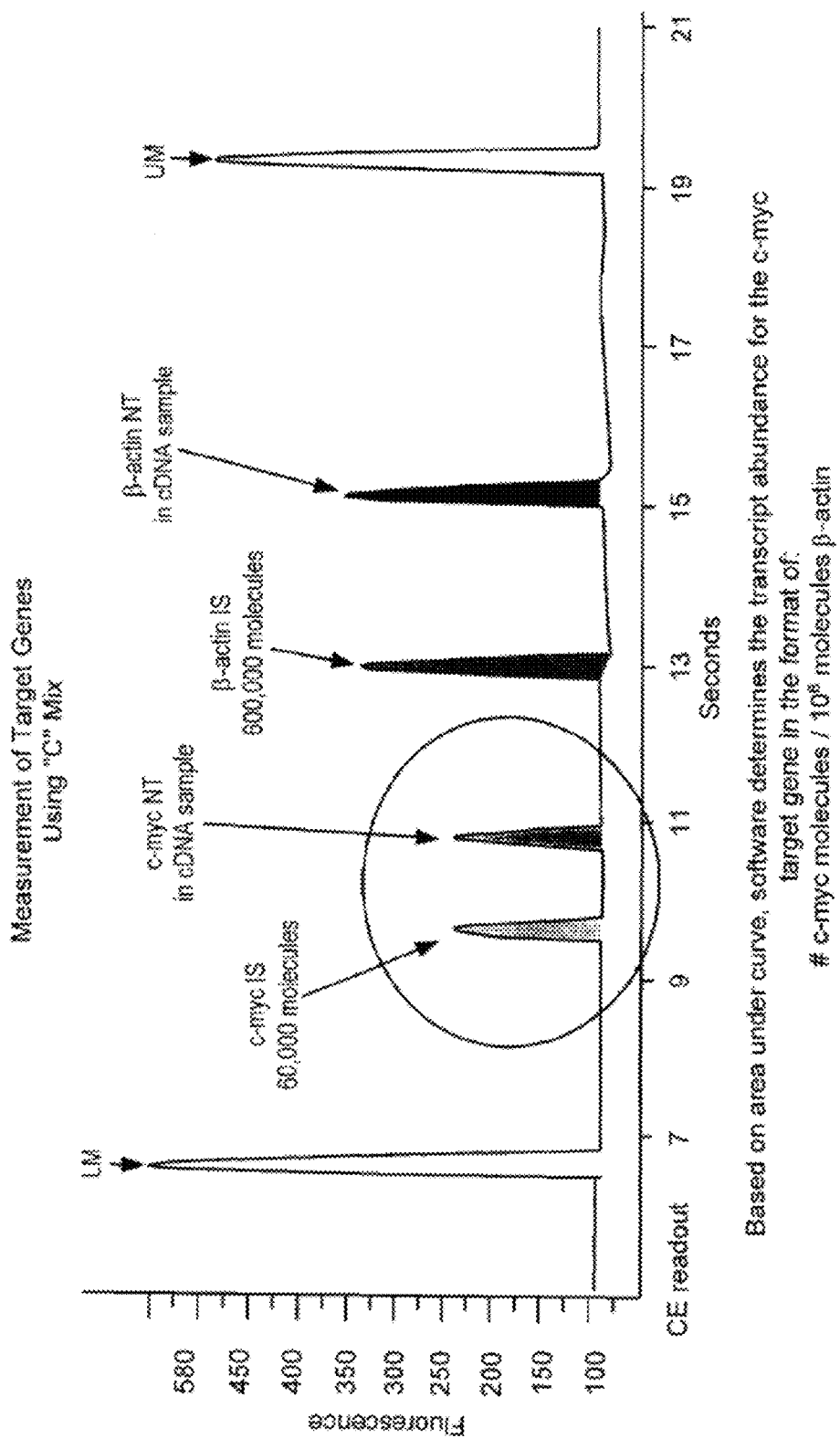
FIG. 15 illustrates the situation where the subsequent mix selected, Mix C, does provide competitive template for the target nucleic acid (c-myc) sufficiently in balance with the amount of target nucleic acid in the cDNA dilution used.

Another sample of the nucleic acid, e.g., at the same cDNA dilution, can then be combined with the subsequently-selected serially-diluted standardized mixture. After combining, the nucleic acid and its competitive template can be co-amplified, e.g., as described in detail above. Also as described above, a ratio can be obtained comparing amount of amplified product of the nucleic acid to amount of amplified product of its corresponding competitive template. FIG. 15 illustrates the situation where the next Mix selected does provide competitive template for target nucleic acid sufficiently in balance with the amount of target nucleic acid in the cDNA dilution. As FIG. 15 illustrates, amplified product of c-myc NT is within about a 10-fold amount of amplified product of c-myc CT. In some embodiments, software determines area under curve for the NT and CT and calculates the ratio of NT/CT for the target nucleic acid. In some embodiments, software can also compare this ratio with the NT/CT ratio for the nucleic acid serving as a reference.

In preferred embodiments, the amount of sample cDNA can be kept constant while a different standardized mixture is used. As another example, if Mix D were used and the amount of amplified product of the NT was more than 10-fold greater than that of the corresponding CT, the experiment can be repeated with the same starting amount of cDNA, but using Mix C, which has about a 10-fold higher concentration of the competitive template, or Mix A or Mix B. Where the amount of amplified product of the is less than 10-fold lower than that of the corresponding CT, the experiment can be repeated with the same starting amount of cDNA, but using Mix E or Mix F. The more dilute mixture and/or the more concentrated mixture selected may be next more dilute and/or more concentrated mixture in the series or a different serially-diluted mixture in the series, e.g., depending on the magnitude of the ratio obtained.

A highly preferred embodiment, in terms of cDNA consumption and reduced cost, involves using 1 µl of balanced cDNA in round one of a two-step process with each of the six (A-F) competitive template mixes; using 10 nanoliters of the round one amplified product in parallel 100 nanoliter volume round two amplifications to measure amounts of all of the 96 nucleic acids using Mix E (which contains competitive templates at a concentration that will be in balance with the majority of genes); and then repeating the above steps for nucleic acids that are not in balance with Mix E using the appropriate mix.

Figure 16:
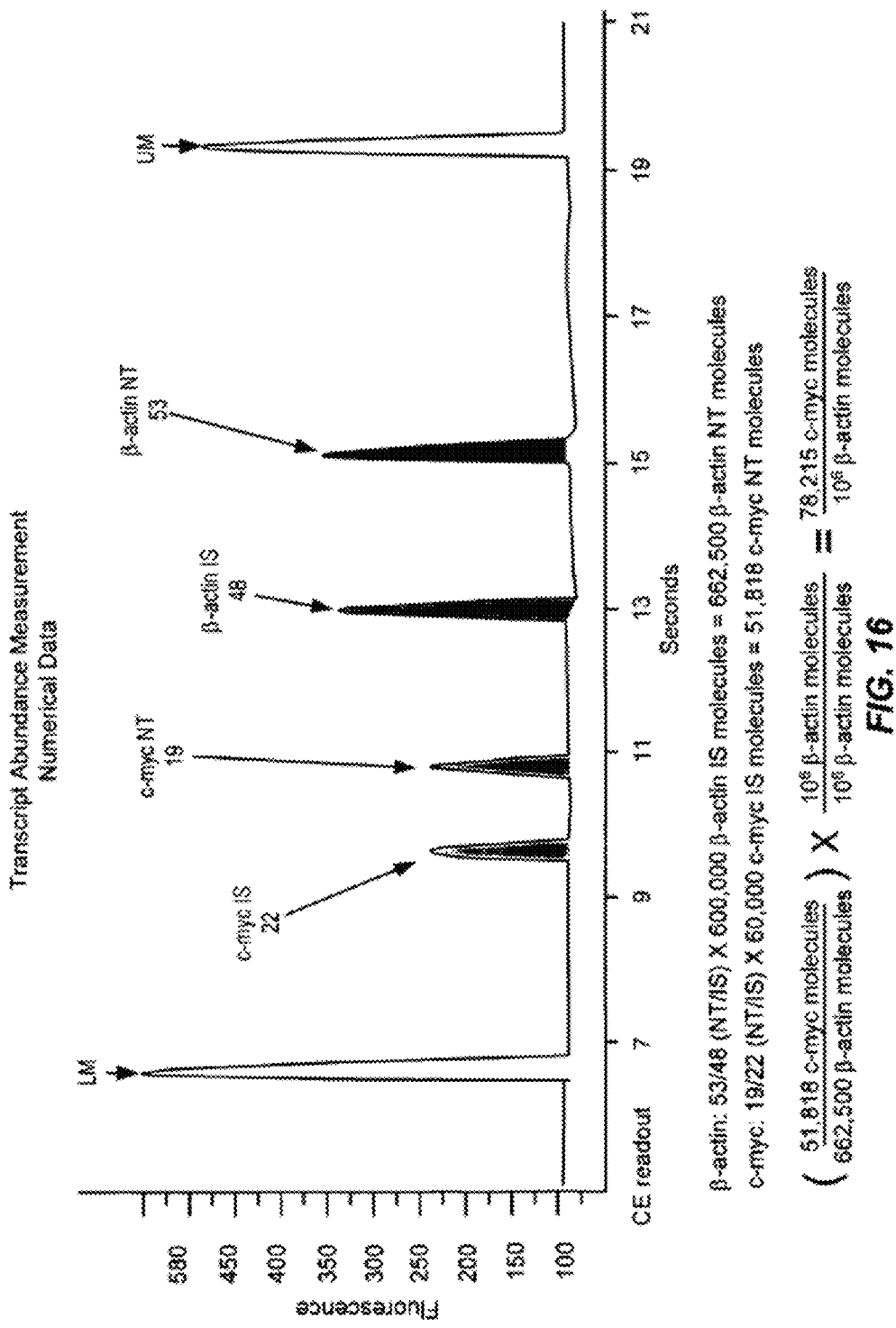
FIG. 16 illustrates calculation of a "ratio of ratios" based on data obtained using an appropriate Mix.

When an appropriate mix is used, amount of target nucleic acid can be assessed, in accordance with methods described herein. FIG. 16 illustrates calculation of a "ratio of ratios" based on data obtained using an appropriate Mix.

Figure 17:
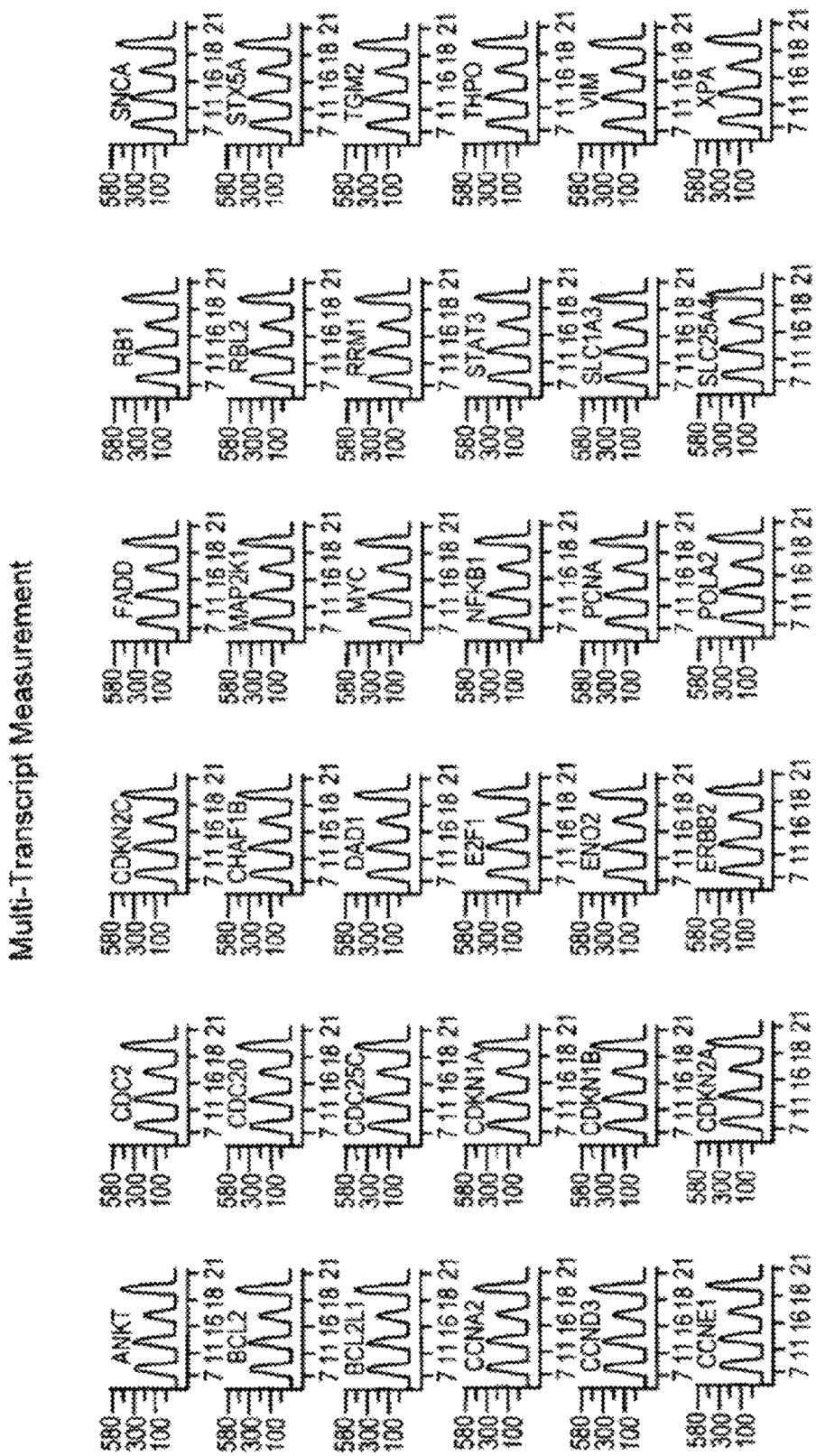
FIG. 17 illustrates a series of electropherograms for various genes.

FIG. 17 illustrates a series of electropherograms, e.g., as can be obtained in preferred embodiments where multiple nucleic acids are assessed together. Addition details regarding the practice of various steps outlines above are provided in the Example II below.

Figure 18:
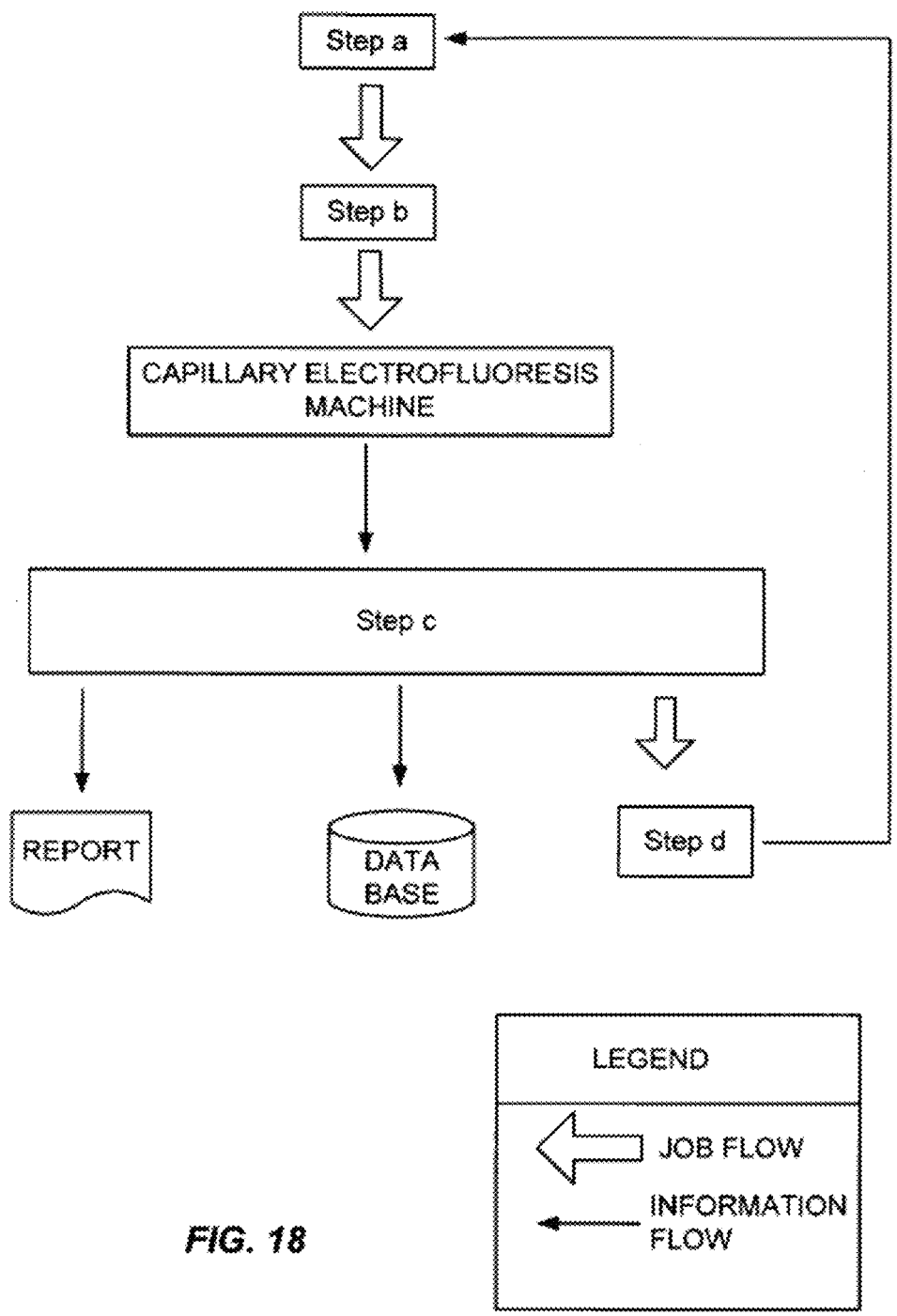
FIG. 18 illustrates an overall system for assessing nucleic acids, one or more steps of which may be computer implemented in various embodiments.

As indicated above, in some embodiments, the method for assessing nucleic acids using a series of serially-diluted standardized mixtures is computer implemented. FIG. 18 schematically illustrates an overall system for assessing nucleic acids, one or more steps of which may be computer implemented in various embodiments.

At step (a) a software program can determine a desired concentration of competitive template reagents to be used. This step can comprise selecting a sample dilution and/or selecting a Mix of a series of serially-diluted mixtures for combing. For example, computer implementation may comprise instructing a robotic handler to select a first one of the serially-diluted standardized mixtures for combining, e.g., Mix E as detailed above.

At step (b) a software program can cause at least one reagent to be dispensed into one or more vessels, in which the amplification reactions are to be conducted; and amplified product can be directed to a suitable device for separating, identifying and/or labeling, e.g., by flowing to a microfluidic capillary electrophoresis (CE) machine. In some embodiments, this step may comprise instructing a robotic handler to dispense a selected Mix and/or sample dilution in a vessel, co-amplifying nucleic acids and their corresponding competitive templates, and separating amplified product.

At step (c), information regarding the separated amplified products can be analyzed. For example, step (c) may comprise obtaining a relationship comparing amplified product of a nucleic acid to amplified product of its competitive template. For example, after sufficient gel electrophoresis, gels can be digitally imaged automatically, and the image automatically analyzed to assess amounts of amplified product, e.g., by automatically determining area under the curves. For example, software can determine area under the curves for the NT and CT of a given nucleic acid and calculate the ratio of NT/CT.

In some embodiments, calculation steps are incorporated into a spreadsheet. For example, in some embodiments, a user can enter raw values (e.g., for peak heights or area under the curve) for the NT, CT, and heterodimer PCR products for a given gene to be measured into a spreadsheet, and the expression value for the gene can be automatically calculated. In some embodiments, software can be used to automatically enter values for NT and CT amplified product for each of one or more nucleic acids to be measured into a spreadsheet to automatically calculate a numerical value, e.g., a numerical value corresponding to gene expression.

Information from step (c) can be provided in a "Report", sent to a "Database" and/or sent to step (d), which can reiterate the process for further analysis of data received. For example, if the calculated ratio is not within a desired range (for example, within about a 1:10 to about a 10:1 ratio) as described above, a new desired concentration of competitive template reagents (i.e., different from the original concentrations selected to step (a)) may be chosen and the steps (b)-(c) are repeated. In some embodiments, software can be used to automatically determine which Mix should be selected next, based on considerations described above. In some embodiments, a software program can instruct a robotic handler to combine a sample with the new Mix.

Another aspect of the present invention is directed to a computer program for implementing certain embodiments of methods of the instant invention. In certain embodiments, the computer program includes a computer readable medium and instructions, stored on the computer readable medium. In preferred embodiments, the instructions include one or more steps recited above. The computer program can further include instructions for dispensing amplified product into arrays for measurement, as well as instructions for fluorescently labeling amplified product and/or nucleic acid to which they hybridize. Amplified product may be labeled, e.g., by labeling one or more nucleotides in the amplification reaction with a detectable moiety, e.g., a fluorescent moiety. The computer program can further include instructions for measuring amounts of nucleic acid, e.g., by comparing fluorescent intensities of the arrays for the amplified product of a given nucleic acid and its competitive template.

D. Substantially Constant Relationship

Some embodiments of the present invention described above provide a relationship for assessing nucleic acid where the relationship remains constant or substantially constant beyond the exponential phase of amplification. In nucleic acid amplifications, e.g., PCR, the amount of amplified product can cease to increase exponentially after an indefinite number of cycles. For example, at some point and for uncertain reasons, the amplification reaction can become limited and the amount of amplified product can increase at an unknown and/or non-exponential rate. For example, PCR amplification rate can be low in early cycles when the concentration of the templates is low. After an unpredictable number of cycles, the reaction can enter a log-linear amplification phase. In late cycles, the rate of amplification can slow as the concentration of PCR products becomes higher, e.g., high enough to compete with primers for binding to templates. The yield of amplified product in PCR reactions, for example, has been reported to vary by as much as 6-fold between identical samples run simultaneously. Gilliland, G., et al., Proc. Natl. Acad. Sci. 87:2725-2729, 1990. PCR techniques are generally described in U.S. Pat. Nos. 4,683,195; 4,683,202; and 4,965,188. Other investigators have analyzed samples amplified for a number of cycles known to provide exponential amplification (Horikoshi, T., et al., Cancer Res. 52:108-116 (1992); Noonan, K. E., et al., Proc. Natl. Acad. Sci. 87:7160-7164 (1990); Murphy, L. D., et al., Biochemistry 29:10351-10356 (1990); Cane, P. C., et al., J. Clin. Invest. 88:1802-1810 (1991); Chelly, J., et al., Eur. J. Biochem 187:691-698 (1990); Abbs, S., et al., J. Med. Genet. 29:191-196 (1992); Feldman, A. M. et al., Circulation 83:1866-1872 (1991). Some embodiments of the instant invention allow quantification of PCR amplification at any phase in the PCR process, including the plateau phase.

Some embodiments of the present invention relate to obtaining a relationship constant (or substantially constant) beyond the exponential phase of nucleic acid amplification, thereby allowing the initial amount of a nucleic acid to be determined by extrapolation from end point amounts of amplified product. In some embodiments, the exponential phase for amplifying the nucleic acid need not be defined for each set of experimental conditions, saving time and materials. For example, some embodiments do not involve real-time measurements. Some embodiments do not involve generation of a standard curve, and/or generation of multiple standard curves, e.g., where the standard curve is used to determine an exponential range of amplification for a given nucleic acid to be measured and/or where the standard curves compare measured amounts of one nucleic acid to another.

Figure 19:
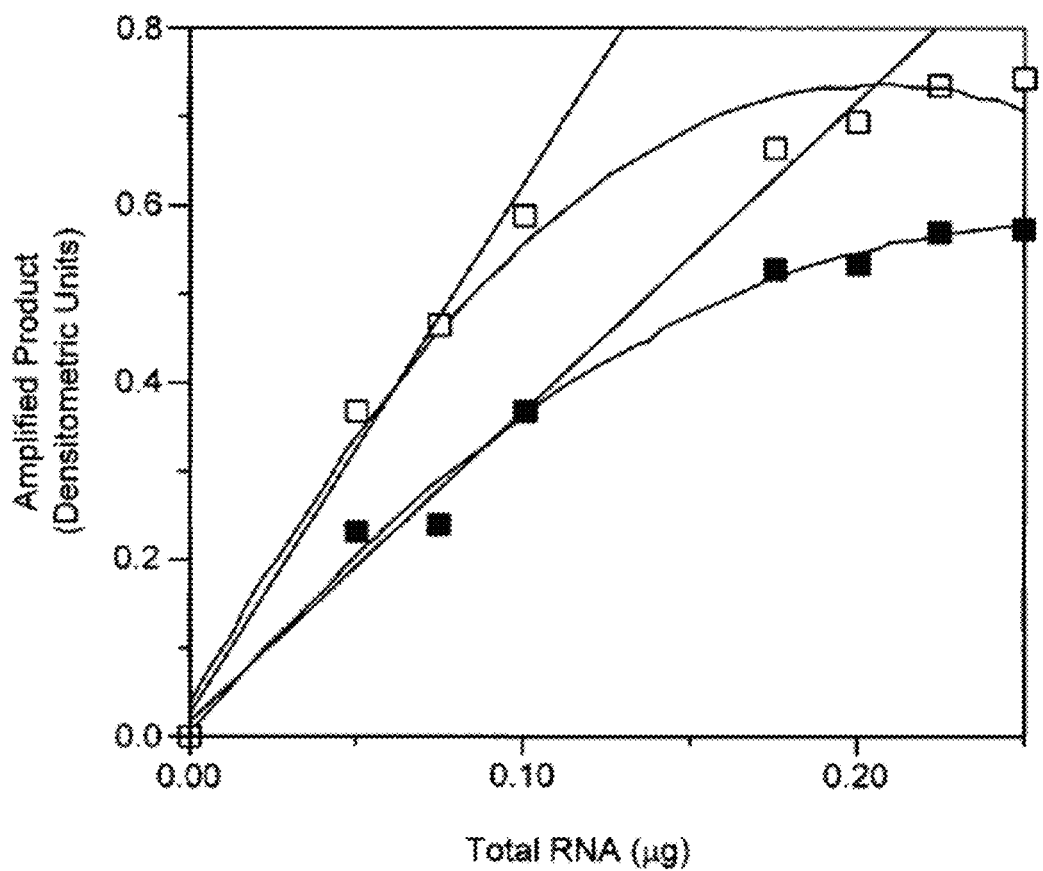
FIG. 19 illustrates a non-linear relationship between amount of amplified product of glutathione peroxidase GSH-Px (empty boxes) or of glyceraldehyde-3-phosphate dehydrogenase GAPDH (solid boxes) and total starting amount of RNA for increasing amounts of RNA, e.g., beyond the exponential phase of amplification. Straight lines represent theoretical amounts of PCR product (either GSH-Px or GAPDH) that would be obtained if amplification remained exponential throughout the amplification process.
Figure 20:
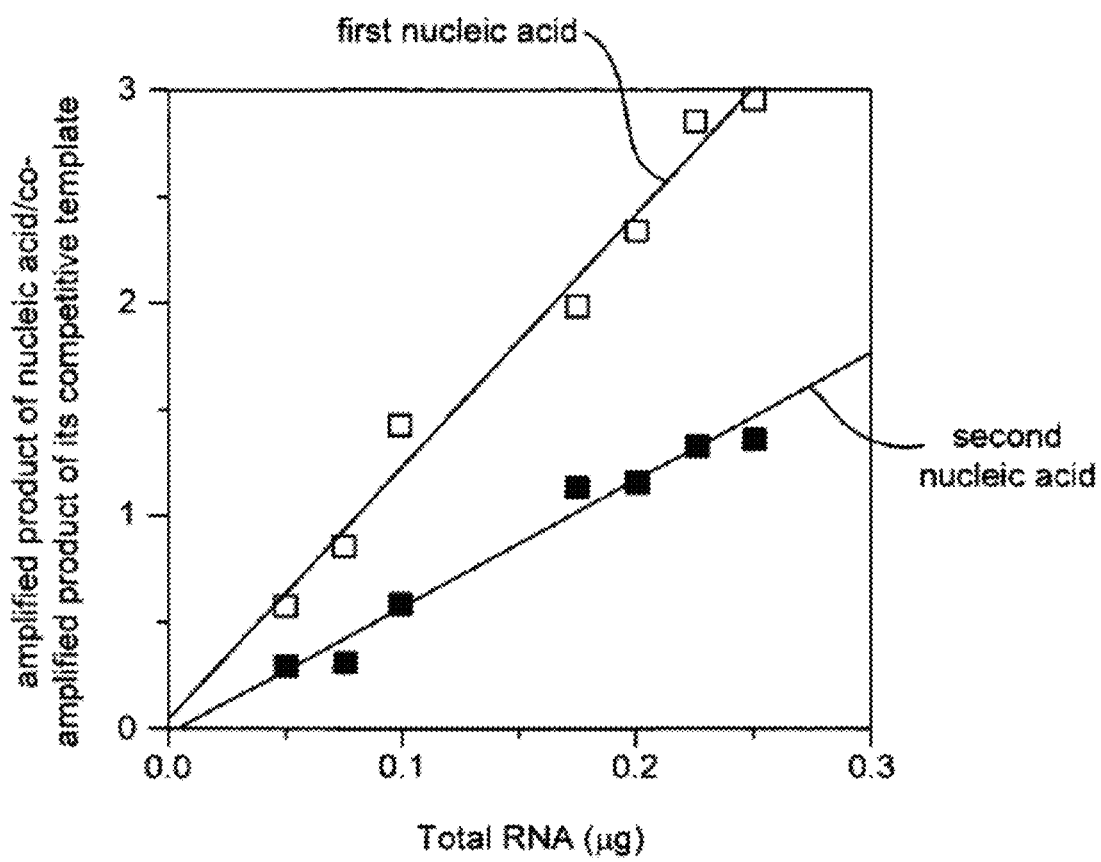
FIG. 20 illustrates a linear relationship between the ratio of (amplified product of nucleic acid/co-amplified product of its competitive template) and total starting amount of RNA for first and second nucleic acids corresponding to GSH-Px (empty boxes) and GAPDH (solid boxes), respectively.

FIG. 19 and FIG. 20 illustrate how certain embodiments of the present invention can provide a constant or substantially constant relationship using end-point measurements beyond the exponential phase of amplification. Data shown in the graphs were obtained as detailed in Example III below. FIG. 19 illustrates that the amount of amplified product vs. total starting amount of RNA does not remain linear with increasing amounts of RNA, e.g., beyond the exponential phase of amplification. That is, there is a non-linear relationship between amount of amplified product (empty boxes: glutathione peroxidase GSH-Px; solid boxes: glyceraldehyde-3-phosphate dehydrogenase GAPDH) and total starting amount of RNA for increasing amounts of RNA, e.g., beyond the exponential phase of amplification. Straight lines represent theoretical amounts of PCR product (either GSH-Px or GAPDH) that would be obtained if amplification remained exponential throughout the amplification process FIG. 20 illustrates that a linear relationship can be obtained where the ratio of (amplified product of nucleic acid/co-amplified product of its competitive template) is plotted against total starting amount of RNA for first and second nucleic acids corresponding to GSH-Px (empty boxes) and GAPDH (solid boxes), respectively. FIG. 20 illustrates two linear (or substantially linear) relationships for two different nucleic acids, each co-amplified with its respective competitive template, with $r_2$=0.982 for GSH-Px and $r_2$=0.973 for GAPDH for the range of total RNA studied.

Figure 21:
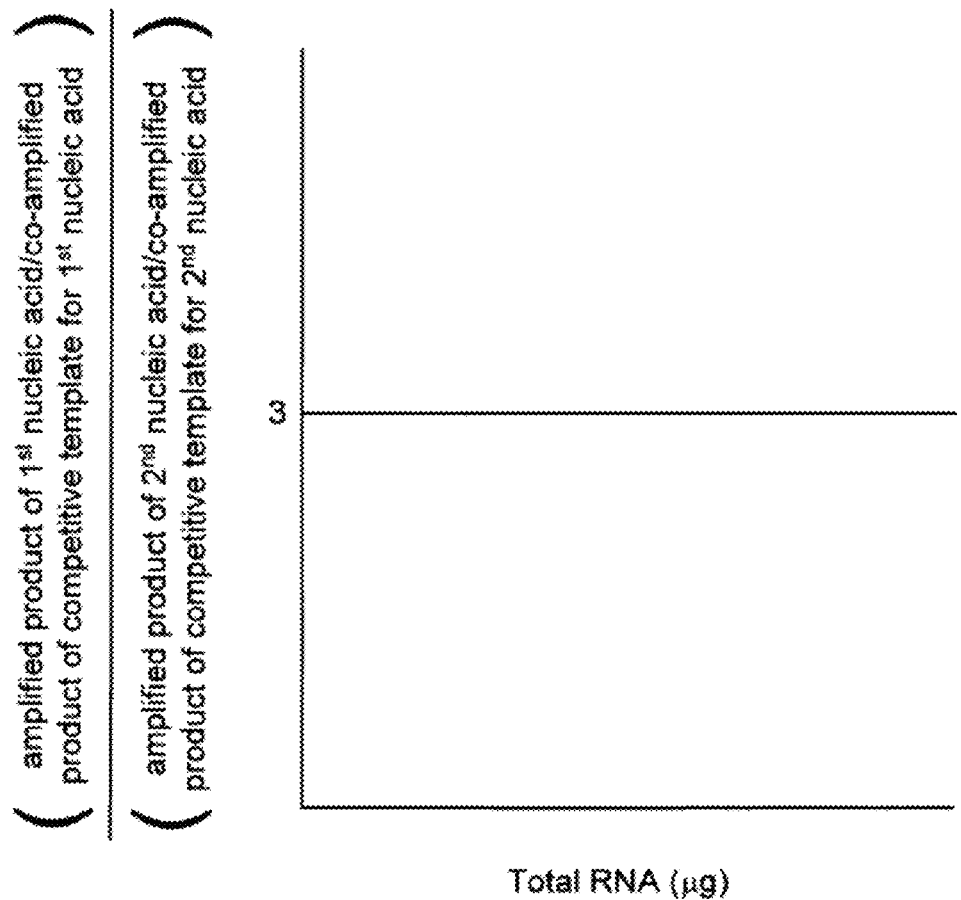
FIG. 21 illustrates that the relationship of (amplified product of first nucleic acid/co-amplified product of its competitive template)/(amplified product of second nucleic acid/co-amplified product of its competitive template) to total starting amount of RNA remains constant, or substantially constant, for the two different nucleic acids when amplified in accordance with various embodiments of the instant invention.

FIG. 21 illustrates that the relationship of (amplified product of first nucleic acid/co-amplified product of its competitive template)/(amplified product of second nucleic acid/co-amplified product of its competitive template) to total starting amount of RNA remains constant, or substantially constant, for the two different nucleic acids when amplified in accordance with various embodiments of the instant invention. Accordingly, some embodiments of the instant invention use a relationship that compares at least two relationships for at least two nucleic acids in a sample, namely, a first relationship comparing amplified product of a first nucleic acid to co-amplified product of a competitive template for the first nucleic acid, and a second relationship comparing amplified product of a second nucleic acid to co-amplified product of a competitive template for the second nucleic acid. Additional details of some of these co-amplifications are provided above. In some embodiments, the relationship sought further compares amplified product of a number of other nucleic acid(s) to co-amplified product of competitive template(s) for said number of other nucleic acid(s).

E. Sensitivity

Some embodiments of the present invention described above provide a relationship for assessing nucleic acid where the relationship with sensitivity. Sensitivity can be defined as the ability of a procedure to produce a change in signal for a defined changed in the quantity of analyte, i.e., the slope of a calibration curve. Some embodiments of the instant invention provide a slope greater than about 0.1, greater than about 0.2, greater than about 0.5, or greater than about 0.8. Some preferred embodiments of the instant invention provide a slope of about 1/1.

For example, some embodiments of the instant invention provide a relationship capable of detecting less than about a two-fold difference, less than about a one-fold difference, less than about an 80% difference, less than about a 50% difference, less than about a 30% difference, less than about a 20% difference, less than about a 10% difference, less than about a 5% difference, or less than about a 1% difference. Such sensitivities can correspond to identifying small changes in gene expression.

In some embodiments one or more of these differences can be detected in about 1,000 molecules or less of the nucleic acid in the sample, e.g., in about 800, in about 600, or in about 400 molecules. In some embodiments, one or more of these differences can be detected in about 100 molecules or less (e.g., in about 60 molecules), in about 10 molecules or less (e.g., in about 6 molecules), or in about 1 molecule or less of the nucleic acid in a sample. In some embodiments, one or more of these differences can be detected in less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of the nucleic acid in a sample.

Some embodiments, as described above, assess nucleic acids over a range of concentrations, e.g., assessing gene expression over one or more orders of magnitude of gene expression. In some such embodiments, assessing detects less than about a two-fold difference over the range. In some embodiments, assessing detects less than about a one-fold difference, less than about an 80% difference, less than about a 50% difference, less than about a 30% difference, less than about a 20% difference over said range, less than about a 10% difference, less than about a 5% difference, or less than about a 1% difference over the range.

Sensitivities described herein can be achieved by some of the embodiments of the instant invention.

F. Reproducibility

In preferred embodiments, methods of assessing a nucleic acid are reproducible. Some embodiments, for example, provide a coefficient of variation of less than about 25% between samples of a nucleic acid. In some embodiments, the coefficient of variation is less than about 50%, less than about 30%, less than about 25%, less than about 20%, less than about 15%, less than about 10%, less than about less than about 5%, or less than about 1% between 2 of more samples of the nucleic acid. Such coefficients of variation can be obtained in some embodiments where the 2 samples are amplified and/or assessed at different times, e.g., on different days; in the same or different experiments in the same laboratory; and/or in different experiments in different laboratories; and/or where the samples are obtained from different subjects and/or different species. Preferred embodiments of the present invention provide both intra- and inter-laboratory reproducibility (M. T. Vondracek, D. A. Weaver, Z. Sarang et al., Int. J. Cancer 99, 776-782 (2002)) that is sufficient to detect less than two-fold differences in gene expression. For example, in some embodiments, inter-laboratory correlation of variance was 0.48, e.g., from gene expression measurements using a A549 cDNA sample taken in different laboratories at different times, spanning nearly one year. In some embodiments, e.g., embodiments using micro-channel capillary electrophoresis, the correlation of variance was reduced to 0.26. Additional details of a study to evaluate reproducibility are provided in Example IV below.

In some embodiments, reproducibility between samples allows for the use of fewer dilution tubes. In some embodiments, a single tube may be used, simplifying procedures and permitting the evaluation of many different samples at one time.

In some embodiments, including competitive template internal standards in a common standardized mixture used in different measurements can control for one or more sources of variation. Sources of variation include, e.g., variation from cDNA loading, intra-nucleic acid amplification efficiency, inter-nucleic acid amplification efficiency, inter-specimen amplification efficiency, inter-sample amplification efficiency, and/or intra-sample amplification efficiency. For example, some embodiments using an Agilent 2100 Bioanalyzer provide reproducibility intra-lab CV of less than about 0.25 routinely, with a sensitivity comparable to slab gel electrophoresis.

FIG. 22 tabulates a number of sources of variation and control methods.

Variation in cDNA loading may result from variation in pipetting, aliquoting, quantification, and/or reverse transcription. For example, errors may occur when aliquoting RNA material into vessels for performing reverse transcription. Although reverse transcription efficiency can vary from one sample to another, the representation of one nucleic acid to another in a sample need not vary among different reverse transcriptions.

For example, the efficiency of reverse transcription can vary from about 5 to about 90% (Simmonds et al., 1990). Variation in reverse transcription efficiency, however, may affect different transcripts in the same or substantially the same manner (Willey et al., 1998; Loitsch et al., 1999). In one experiment, for example, gene expression was measured in 5 different reverse transcriptions of a given sample of RNA from the SW900 non-small cell carcinoma cell line. The mean level of expression obtained was 3,600 molecules/

$10^{-6}$ β-actin molecules with a CV of 0.26, no greater than if replicate measurements had been made on cDNA resulting from a single reverse transcription. However, if reverse transcription and amplification reactions are carried out in different vessels, errors may occur when pipetting cDNA from the reverse transcription reaction into individual PCR reaction vessels. That is, without being limited to a particular theory and/or hypothesis, the effect of variation in reverse transcription can be the same as if different levels of cDNA were loaded in a PCR reaction. Controlling for cDNA loading can then control variation in reverse transcription efficiency.

Variation in intra-nucleic acid amplification efficiency may result from, e.g., cycle-to-cycle variation, e.g., where different amplification cycles show various early slow, log-linear and/or late slow plateau phases, as described above. Where gene expression is being measured, intra-nucleic acid amplification efficiency can refer to intra-gene amplification efficiency, i.e., for example, variation in repeat amplifications of cDNA corresponding to a given gene.

Variation in inter-nucleic acid amplification efficiency can refer to inter-gene amplification efficiency, e.g., where the efficiency at which a given gene is amplified differs from that at which a different gene is amplified. Such differences may be caused by, e.g., differences in the primers used for amplifying the different genes measured in the same and/or different samples. For example, the efficiency of a pair of primers, e.g., as defined by lower detection threshold (LDT), may not be predictable, and may vary more than about 100,000-fold (from less than about 10 molecules to about $10^6$ molecules) in some embodiments.

Also, a bad lot (e.g., where degradation of primers and/or competitive templates has occurred) or inappropriate concentration of primers would cause variation in PCR amplification of one nucleic acid relative to another. In some embodiments, the concentration of competitive template is small (e.g., femptomolar range) so that any change in the number of molecules present in the reaction may introduce a large source of error. Presence of an inhibitor could alter PCR amplification efficiency of one nucleic acid, e.g., one gene, compared to another.

Variation in inter-specimen amplification efficiency may be caused by, e.g., variable presence of an inhibitor (e.g., an inhibitor of PCR) in different specimen. PCR reactions inhibitors, include, e.g., heme. Akane, A., Matsuara, K., Nakamura, H., Takahashi, S., and Kimura, K. (1994) Identification of the heme compound co purified with deoxyribonucleic acid (DNA) from blood stains, a major inhibitor of polymerase chain reaction (PCR) amplification. J. Forensic Sci. 39, 362 372; Zhu, Y. H., Lee, H. C., and Zhang, L. (2002) An examination of heme action in gene expression: Heme and heme deficiency affect the expression of diverse genes in erythroid K562 and neuronal PC12 cells. DNA Cell Biol. 21, 333 346. Further, amplification efficiency for different genes may be affected to different degrees in different samples and/or specimen. Meijerink, J., Mandigers, C., van de Locht, L., et al. (2001) A novel method to compensate for different amplification efficiencies between patient DNA samples in quantitative real-time. PCR. J. Mol. Diagn. 3, 55-61; Giulietti, A., Overbergh, L., Valckx, D., et al. (2001) An overview of real-time quantitative PCR: applications to quantify cytokine gene expression. Methods 25, 386-401. Such differences may result in variation in measuring the same or different nucleic acids (e.g., the same or different genes) in the same or different specimen and/or samples. For example, a given PCR inhibitor may have little affect on amplification of a lowly expressed gene, e.g., GSTM3. The same PCR inhibitor may have a larger effect, e.g., a significantly larger effect, on amplification of a more-highly expressed gene, e.g., ERBB2, including, e.g., preventing amplification or reducing amplification to non-detectable levels.

Variation in inter-sample amplification can refer to inter-reaction variation or well-to-well variation in repeat measurements of the same or different nucleic acids (e.g., the same or different genes) in the same or different samples and/or specimen. Variation in inter-sample amplification efficiency can result from, for example, variable presence of an inhibitor (e.g., an inhibitor of PCR) in different reaction vessels, variation in temperature cycling between different region of a themocycler block, variable quality of one or more PCR reagents or variable concentrations of one or more PCR reagent (e.g., primers).

One or more of these sources of variation can reduce PCR amplification efficiency in a well to the point where no PCR product can be observed in that well. Some embodiments of the instant invention allow this type of error to be recognized, for example, embodiments using a standardized mixture comprising about $10^{-17}$ M competitive template for the nucleic acid sought to be amplified. In a 10 μL PCR reaction volume, about $10^{-17}$ M represents about 60 molecules. With about 60 molecules of internal standard present in the PCR reaction and components of the PCR reaction functioning properly, if a nucleic acid is not present in a sample, the amplified product for the competitive template will be observed, but the amplified product for the nucleic acid will not. This may indicate that there was less than about six molecules (about 10-fold less than the number of competitive template molecules) of nucleic acid in the sample. On the other hand, if neither amplified product of neither the nucleic acid nor its competitive template is detectable, it can be determined that the PCR reaction efficiency was suboptimal.

Variation in intra-sample amplification can refer to intra-reaction variation, e.g., variable amplification efficiency in a given reaction using a given sample. Variation in intra-sample amplification efficiency may result from, e.g., variation in thermocycler efficiency at various positions within a thermocycler, and can introduce variation when measuring amounts of the same or different nucleic acids (e.g., expression of the same or different genes) in the same or different samples and/or specimen.

Some embodiments for measuring nucleic acids control for variation caused by one or more of sources of variation selected from cDNA loading, intra-nucleic acid amplification efficiency, inter-nucleic acid amplification efficiency, inter-specimen amplification efficiency, inter-sample amplification efficiency, and intra-sample amplification efficiency. For example, in some embodiments, use of a standardized mixture and/or a series of serially-diluted standardized mixtures can provide control.

Some preferred embodiments control for one or more sources of variation without the use of real-time measurements obtained using kinetic analysis (e.g., real-time PRC measurements). For example, obtaining a "ratio of ratios" in some embodiments does not involve taking real-time measurements. Some preferred embodiments control for one or more of sources of variation without generating one or more standard curve(s). For example, obtaining a "ratio of ratios" in some embodiments does not involve generating a standard curve. In more preferred embodiments, one or more sources of error are controlled for using methods that do not involve real-time measurements nor generation of a standard curve. In even more preferred embodiments, two or more, three or more, four or more, five or more or six sources of variation are controlled for without real-time measurements nor generation of a standard curve.

Figure 23:
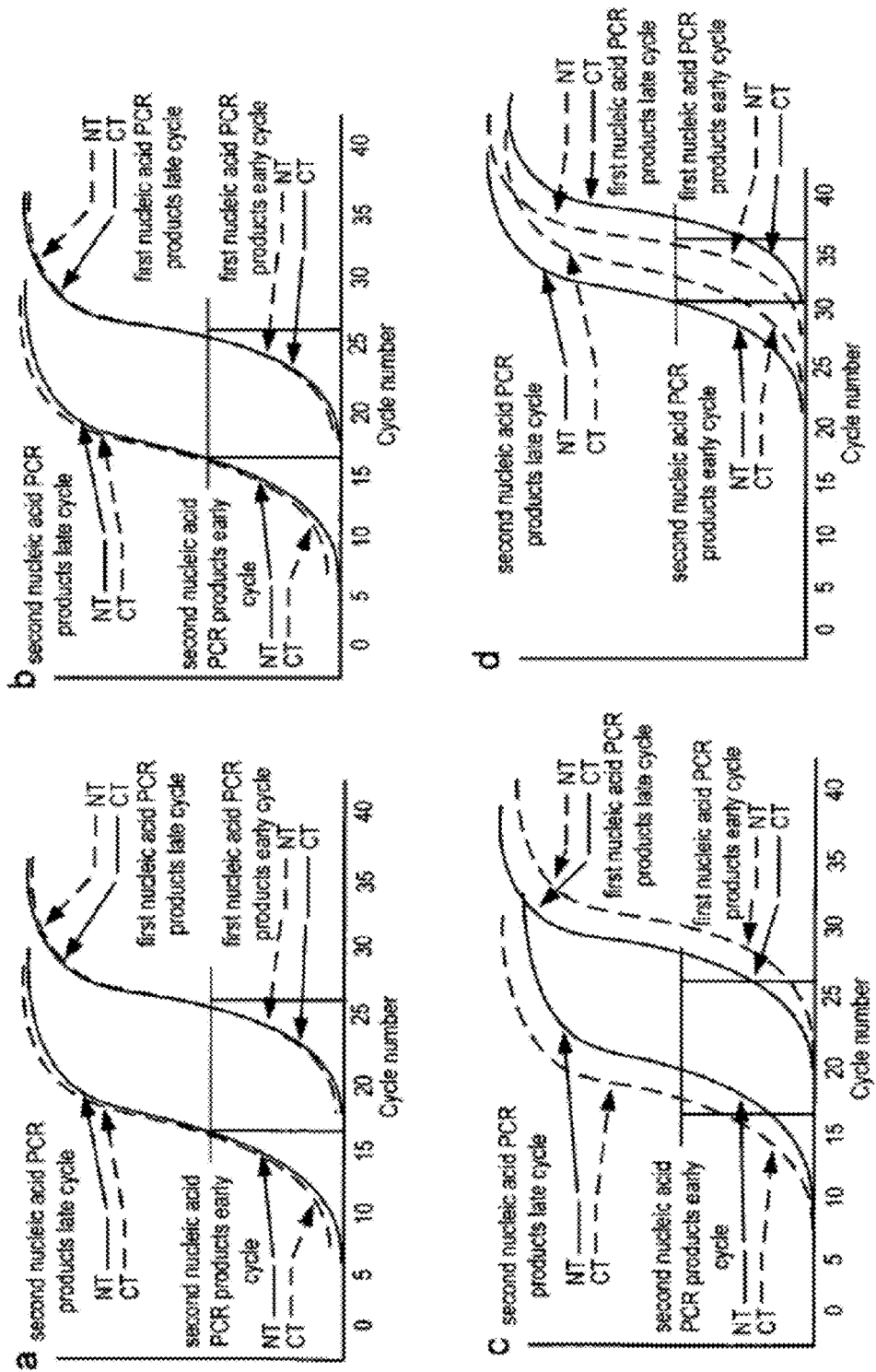
FIG. 23 illustrates the control of one or more of sources of error in some embodiments compared to real-time RT-PCR in two different specimen in four different experiments.

FIG. 23 illustrates the control of one or more of these sources of error in some embodiments compared to real-time RT-PCR in two different specimen in four different experiments. In FIG. 23, the nucleic acids being measured are referred to as native template (NT), the competitive template for each is referred to as CT, and the second nucleic acid serves as the reference nucleic acid.

FIG. 23 illustrates amplified product of native template and competitive template for a first and a second nucleic acid that are PCR-amplified simultaneously for indicated number of cycles. The amplified products at endpoint are electrophoretically separated, e.g., in the presence of fluorescent intercalating dye, and quantified densitometrically. In the illustrated embodiment, the shorter CT PCR product migrates faster than the NT PCR product, and is represented by a CT band below the NT band. As one of skill in the art will understand, if there is more NT product than CT product, the NT band will emit more fluorescent light; if there is more CT product than NT product, the CT band will emit more fluorescent light. In real-time, the fluorescent PCR product is measured at each of the 35 to 40 cycles. FIG. 23 illustrates how the reactions would look if measured at each cycle in real time and the $C_T$ for the real-time curve is represented by the perpendicular black line.

In FIG. 23, graph "a" illustrates that the ratio of NT/CT present at the beginning of PCR remains (substantially) constant throughout PCR to endpoint. As described above, it is not necessary to monitor the amplification reaction in real-time to ensure that the reaction is in log-linear phase in some embodiments of the instant invention.

In FIG. 23, graph "a" illustrates an experiment using a first sample of a first specimen. In the first sample, there are about equivalent number of molecules of the second nucleic acid NT and CT present at the beginning of the PCR reaction (e.g., as described above, where a balanced cDNA dilution is used). Thus, following electrophoresis of the amplified product of the second nucleic acid, the NT and CT bands are about equivalent, and during real-time measurement, the fluorescent intensity for the NT will be about the same as for the CT. The NT/CT ratio is the same at an early cycle as it is at a late cycle (endpoint), even though the band intensity for both NT and CT is low at early cycle compared to late cycle. Similarly, the first nucleic acid NT band and CT band are about equivalent, and the real-time value for the NT is about the same as for the CT. The .DELTA.$C_T$ between the second and the first nucleic acid in real-time measurements is about 10.

In FIG. 23, graph "b" further illustrates controls for loading from one sample to another. In FIG. 23, graph "b," the first specimen is re-analyzed using a lower starting amount of nucleic acid, e.g., less cDNA loaded, due to a variation in pipetting, e.g., in aliquoting a second sample of the first specimen into a different vessel. The NT/CT ratio for the second nucleic acid is lower. However, because the relative concentration of competitive templates is fixed and the relative representation of each nucleic acid is fixed, the NT/CT ratio for the first nucleic acid goes down commensurately. Accordingly, the "ratio of ratios" (odds ratio) of the first nucleic acid NT/CT divided by second nucleic acid NT/CT remains the same as in FIG. 23, graph "a." In this case, the .DELTA.$C_T$ in real-time analysis is also unchanged.

In FIG. 23, graph "c" illustrates controls for loading and variation in amplification efficiency. In FIG. 23, graph "c," the first specimen is again re-analyzed, but with both (1) a larger amount of cDNA loaded due to variation in pipetting (leading to variation in starting amount of native template) and (2) lowered amplification efficiency of the second nucleic acid, as might be caused by inhibitor in the well that affects amplification of this nucleic acid more than the other, or inappropriate concentrations of primers for the second nucleic acid.

In FIG. 23, graph "c" illustrates that with real-time measurements, this reduces the .DELTA.$C_T$ from 10 to 6, and the value for the first nucleic acid is inappropriately high. In real-time measurements, the gene selective inhibition is associated with a decreased .DELTA.$C_T$ and erroneous measurement.

In contrast, using certain embodiments described herein, because the amplification efficiency of the NTs for each of the two nucleic acids is affected the same way as its corresponding CT, the NT/CT ratio is unchanged in FIG. 23, graph "a" and graph "c" for either first or second nucleic acid. Also, with the larger amount of cDNA loaded, the first nucleic acid NT/CT ratio and the second nucleic acid NT/CT ratio increase commensurately. Accordingly, the "ratio of ratios" (odds ratio) of first nucleic acid NT/CT divided by the second nucleic acid NT/CT stays the same between FIG. graph "a and graph "23."

In FIG. 23, graph "d" further illustrates controls for loading a sample of a second specimen, where the first nucleic acid is more highly expressed. Although, the first nucleic acid is expressed at a higher level compared to the second nucleic acid, real-time measurements give a .DELTA.$C_T$ of about 7.

In contrast, using certain embodiments of described herein, the ratio of ratios indicates the higher level of expression. As less cDNA is loaded into the PCR reaction, there are fewer copies of the second nucleic acid NT than CT copies present at the beginning of the PCR reaction compared with FIG. 23, graph "a." Throughout real-time measurement, the fluorescence value of the NT is less than that of the CT and at the end of PCR, the second nucleic acid NT band is still less than the CT band. However, even though less cDNA was loaded into the PCR reaction compared to the first sample, the first nucleic acid NT band is more dense than the first nucleic acid CT band due to its higher expression, and the first nucleic acid NT fluorescence value during real-time measurement is higher throughout PCR. Accordingly, the "ratio of ratios" (odds ratio) of first nucleic acid NT/CT divided by the second nucleic acid NT/CT provides a higher value in FIG. 23, graph "d" than in FIG. 23, graph "a."

Thus real-time RT-PCR may control for loading by measuring the first and second nucleic acids in the same PCR reaction (FIG. graph "a", graph "b", graph "d"). The CT (for each nucleic acid represented by a black line intersecting with the X axis) for the first and second nucleic acids both could vary from one experiment to another, but the .DELTA.$C_T$ do not vary. However, real-time does not control for variation in the presence of inhibitors, or the quality of PCR reagents.

II. Methods of Preparing Compositions for Assessing Nucleic Acid

Another aspect of the instant invention relates to methods for preparing compositions for assessing a nucleic acid in a sample.

A. Preparation of Standardized Mixtures

Some embodiments of the invention provide a method for preparing a standardized mixture of reagents. As used herein, "reagent" can refer to a component used in a mixture, including solvent and/or solute. For example, reagents include nucleic acids and/or water, e.g., in the case of aqueous mixtures. In some embodiments, the standardized mixture of reagents comprises sufficient amounts of competitive template for assessing amounts of a number of nucleic acids in a number of samples, e.g., more than about $10^6$ samples. In preferred embodiments, the standardized mixture allows direct comparison of the amounts between at least 2 of the samples. More preferred embodiments allow direct comparison of amounts assessed in at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some specific embodiments, the standardized mixture allows direct comparison of amounts assessed in up to an unlimited number of samples.

In some embodiments, the standardized mixture comprises sufficient reagents for assessing amounts of one nucleic acid. In some embodiments, the standardized mixture comprises sufficient reagents for assessing amounts of more than one nucleic acid, e.g., at least about 50, at least about 96, at least about 100, at least about 200, at least about 300, at least about 500, at least about 800, at least about 1,000, or at least about 5,000, at least about 10,000, at least about 50,000, or at least about 100,000 nucleic acids. In some embodiments, the standardized mixture comprises sufficient reagents for assessing amounts of less than about 100,000, less than about 500,000, or less than about 1,000,000 nucleic acids. In preferred embodiments, different nucleic acids correspond to different gene transcripts.

In some embodiments, the reagents include at least one forward primer and/or a reverse primer capable of priming amplification of a competitive template in the mixture. In some embodiments, at least one competitive template, forward primer and/or reverse primer comprises a sequence referenced in Table 4, illustrated in FIGS. 4A-4B.

In some embodiments, a forward primer and/or a reverse primer are designed to have substantially the same annealing temperature as another forward primer and/or reverse primer in the standardized mixture. Designing primers with the same or substantially the same annealing temperature can allow amplification reactions to achieve approximately the same amplification efficiency under identical or substantially identical conditions. In such embodiments, if there is variation in amplification efficiency, amplification efficiency of a nucleic acid and its competitive template can be affected identically (or substantially identically), so that the ratio of amplified product of the nucleic acid and its corresponding competitive template may not vary or may not substantially vary. In some specific embodiments, a forward and reverse primer have the same or substantially the same annealing temperature as each of the other forward and reverse primers in a given standardized mixture. For example, the annealing temperature may be about 40° C., about 40° C., about 44° C., about 50° C., about 55° C., about 57° C., about 58° C., about 59° C., about 60° C., about 65° C., about 70° C., about 75° C., or about 85° C.

In some embodiments, an internal standard competitive template can be prepared for a number of nucleic acids to be evaluated, including nucleic acids that can serve as one or more reference nucleic acids. The competitive templates can then be cloned to generate enough to assess amounts of a nucleic acid in more than about $10^4$ samples, in more than about $10^5$ samples, in more than about $10^6$ samples, in more than about $10^7$ samples, in more than about $10^8$ samples; in more than about $10^9$ samples, in more than about $10^{10}$ samples, in more than about $10^{11}$ samples, in more than about $10^{12}$ samples, in more than about $10^{13}$ samples, in more than about $10^{14}$ samples, or in more than about $10^{15}$ samples.

The competitive templates can be carefully quantified and then mixed together to form a standardized mixture. In some embodiments, the forward primer and/or reverse primer can be selected to allow for detection of about $10^{-10}$, about $10^{-11}$, about $10^{-12}$, about $10^{-13}$, about $10^{-14}$, about $10^{-15}$, about $10^{-16}$, about $10^{-17}$, about $10^{-18}$ M or less of the nucleic acid to be measured. For example, the forward and/or reverse primer can allow for the detection of about 600 molecules, about 60 molecules or about 6 molecules of the nucleic acid in some embodiments.

In some embodiments, a standardized mixture of the instant invention can measure and/or enumerate less than about 1,000 molecules of nucleic acid in a sample, e.g., about 800, about 600, or about 400 molecules. In some embodiments, less than about 100 molecules (e.g., about 60 molecules), preferably less than about 10 molecules (e.g., about 6 molecules), or more preferably less than about 1 molecule of a nucleic acid can be measured and/or enumerated in a sample. In some embodiments, a standardized mixture of the instant invention can measure and/or enumerate less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of a nucleic acid in a sample.

In some embodiments, the reagents for measuring amounts of nucleic acids are stable. For example, the primers and/or competitive templates of a standardized mixture may comprise stable nucleic acid molecules, such as DNA. Reagents may be stable for at least about 20 years, at least about 50 years, at least about 100 years, at least about 500 years, or at least about 1,000 years. In preferred embodiments, a standardized mixture of the present invention can provide reagents to measure sufficient nucleic acids corresponding to gene expression measurements expected to be made for at least about 20 years, at least about 50 years, at least about 100 years, at least about 500 years, or at least about 1,000 years, e.g., at the current rate of gene expression measurement (estimated to be about one billion assays a year (An economic forecast for the gene expression market http://www.researchandmarkets.com/reports/5545)).

In some embodiments, long term storage of reagents and/or samples comprising DNA can be achieved at −20° C. In some embodiments, reagents and/or samples comprising RNA are stable for years frozen as an EtOH precipitate and/or in RnASE free water. In some embodiments, competitive templates are stably frozen for more than six years. In some embodiments, cDNA samples are stable for more than two years frozen at −20° C.

A standardized mixture according to some embodiments of the present invention can be prepared to perform one or more of the methods described herein. For example, as described above, using a standardized mixture, a nucleic acid can be assessed relative to one or more other nucleic acids (e.g., that can serve as controls for cDNA loaded into the reaction). Also as detailed above, a nucleic acid can be assessed relative to its respective competitive template provided in the standardized mixture.

In some embodiments, the standardized mixture can allow for detection with one or more of the sensitivities, one or more of the accuracies, one or more of the detection limits, and/or with more or more of the coefficients of variation taught herein. Additional features of the prepared standardized mixture will be apparent to one of skill in the art, based on the disclosure herein.

B. Preparation of Series of Serially-Diluted Standardized Mixtures

Some embodiments of the invention provide a method for preparing a series of serially-diluted standardized mixtures. In some embodiments, the one or more of the series of standardized mixtures comprises sufficient amounts of competitive templates for assessing amounts of a number of nucleic acids in a number of samples, e.g., more than about $10^6$ samples. In preferred embodiments, the standardized mixture allows direct comparison of the amounts between at least 2 of the samples. More preferred embodiments allow direct comparison of amounts assessed in at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some specific embodiments, the standardized mixture allows direct comparison of amounts assessed in up to an unlimited number of samples.

The series of serially-diluted standardized mixtures may be obtained by serially diluting a standardized mixture, e.g., a standardized mixture described above. For example, in some embodiments, one or more of the series may contain sufficient reagents for assessing various numbers of nucleic acids and/or for assessing various numbers of samples, e.g., as detailed above. Similarly, in some embodiments, one or more of the series of serially-diluted standardized mixtures can comprise any of the reagents of some embodiments of the standardized mixtures described above.

In preferred embodiments, a standardized mixture is diluted so that the competitive template for a first nucleic acid is at a series of concentrations relative to the competitive template for a second nucleic acid. In some embodiments, a standardized mixture is serially diluted 10-fold, providing 10-fold serial dilutions of the competitive template for the first nucleic acid relative to the competitive template for the second nucleic acid. In some embodiments, at least two of the series of concentrations span about one order of magnitude, about 2 orders of magnitude, about 3 orders of magnitude, about 4 orders of magnitude, about 5 orders of magnitude, about 6 orders of magnitude, about 7 orders of magnitude, or more. In some embodiments, the series of concentrations includes at least two, at least 3, at least 4, at least 5, or six concentrations selected from about $10^{-10}$ M, about $10^{-11}$ M, about $10^{-12}$ M, about $10^{-13}$ M, about $10^{-14}$ M, about $10^{-15}$ M, and about $10^{-16}$ M.

In some embodiments, one or more of the series of standardized mixtures can allow for detection with one or more of the sensitivities, one or more of the accuracies, one of more of the detection limits, and/or with more or more of the coefficients of variation taught herein, over various ranges of orders of magnitude, e.g., any of the orders of magnitude discussed herein.

III. Compositions for Assessing Nucleic Acid

Another aspect of the instant invention relates to compositions for assessing a nucleic acid in a sample, for example, compositions comprising a standardized mixture or a series of serially-diluted standardized mixtures, e.g., as described above. Other aspects of the instant invention relate to databases, e.g., databases comprising data obtained using some embodiments of the methods and/or compositions of the present invention.

A. Database of Numerical Values

Another aspect of the instant invention is directed to a database. For example, some embodiments provide a database of numerical values corresponding to amounts of a first nucleic acid in a number of samples.

In preferred embodiments, the numerical values are directly comparable between the number of samples. For example, in some embodiments, the numerical values are directly comparable between at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some embodiments, direct comparison involves comparing the numerical values to one another without using a bioinformatics resource. In some embodiments, a bioinformatics resource, e.g., a simple bioinformatics resource, can be used.

Figure 24:
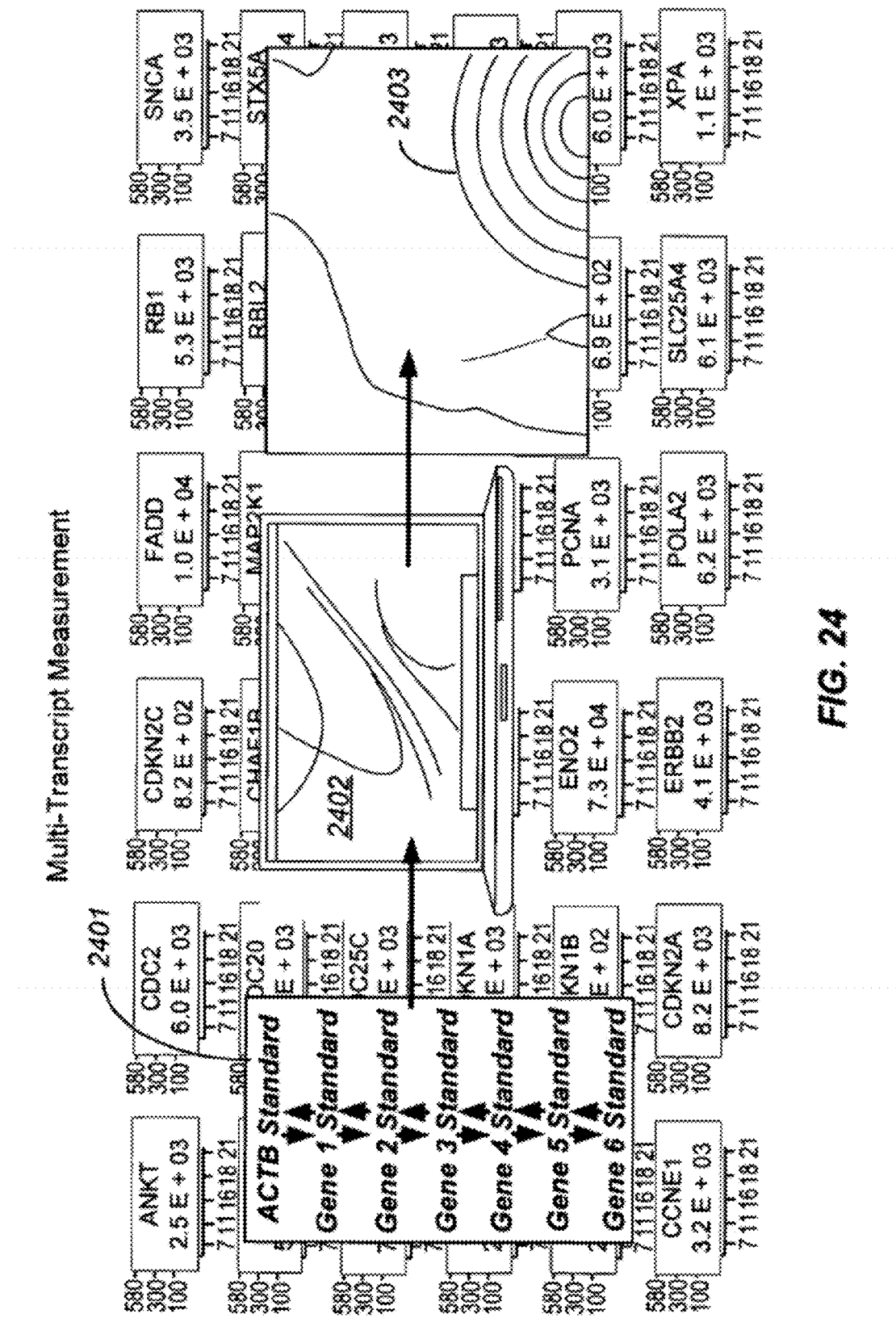
FIG. 24 illustrates development and use of a database of numerical values of some embodiments described herein.

FIG. 24 illustrates development and use of a database of numerical values of some embodiments described herein. At step 2401, measured amounts are obtained by any methods of various embodiment of the instant invention described herein to provide numerical values. For example, as step 2401 illustrates, a nucleic acid can be assessed relative to a known number of competitive template molecules for the nucleic acid that have been combined into a standardized mixture. Such embodiments can facilitate the reporting of nucleic acid measurement as a numerical value. For example, the numerical value can be obtained by calculating a "ratio of ratios" as described above. In some specific embodiments, each value in the database has been made relative to an internal standard within a standardized mixture of internal standards.

In preferred embodiments, numerical values correspond to numbers of molecules of a given nucleic acid in a sample. In some embodiments, numerical values can be provided in units of (molecules of a first nuclei acid)/(molecules of a second nucleic acid), e.g., where the second nucleic acid serves as a reference nucleic acid. In a specific embodiment, measurements are provided in units of (cDNA molecules of a first nucleic acid)/($10^6$ cDNA molecules of a second nucleic acid). Numerical values in some embodiments, for example, may correspond to less than about 1,000 molecules of a nucleic acid in a sample, e.g., to about 800, at to about 600, or to about 400 molecules. In some embodiments, numerical values may correspond to less than about 100 molecules (e.g., to about 60 molecules), less than about 10 molecules (e.g., to about 6 molecules), or less than about 1 molecule of a nucleic acid in a sample. In some embodiments, numerical values may correspond to less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of a nucleic acid in a sample.

The database of the instant invention can comprise numerical values varying over a range. For example, in some embodiments, numerical values can vary over a range of less than about one order of magnitude, more than about one order of magnitude, or more than about 2 orders of magnitude. In some embodiments, numerical values of measured amounts of different nucleic acids, e.g., mRNA levels expressed from two or more different genes, can vary over a range of about 3 or more orders of magnitude, about 4 or more orders of magnitude, about 5 or more orders of magnitude, about 6 or more orders of magnitude, or about 7 or more orders of magnitude, e.g., spanning the about 7-log range of gene expression of about $10^{-3}$, about $10^{-2}$, about 0.1, about 1, about 10, about $10^2$, about $10^3$, and about $10^4$ copies/cell. In some embodiments, numerical values of measured amounts of different nucleic acids can vary over a range of about 8 or more, about 9 or more, or about 10 or more orders of magnitude, e.g., spanning an about 10-log range of gene expression of about $10^{-3}$, about $10^{-2}$, about 0.1, about 1, about 10, about $10^2$, about $10^3$, about $10^4$, about $10^5$, or about $10^6$ copies/cell. Such ranges of gene expression may be important in detecting agents of biological warfare, for example.

In some embodiments, numerical values of the database correspond to less than about a two-fold difference in a nucleic acid between 2 of the samples. In some embodiments, the numerical values correspond less than about a one-fold difference, less than about an 80% difference, less than about a 50% difference, less than about a 30% difference, less than about a 20% difference, less than about a 10% difference, less than about a 5% difference, or less than about a 1% difference.

Without being limited to a given hypothesis and/or theory, since the data in some embodiments is standardized against a common mixture of internal standard competitive templates, direct comparisons are possible. For example, as discussed above, in some embodiments, the numerical values are directly comparable between a number of samples, e.g., samples obtained from different subjects and/or from different species. In some embodiments the numerical values are directly comparable between a number of samples measured in different laboratories and/or at different times. In preferred embodiments, such comparisons are possible without the use of a calibrator sample (e.g., a non-renewable calibrator sample).

Two values can be described as being "directly comparable" where, e.g., the numerical values of each describe the amounts relative to a common standard. As a readily understandable analogy, 10° C. is directly comparable to 50° C. as both values are provided relative to the boiling point of water (100° C.). Using some embodiments provided herein, the number of cDNA molecules representing a gene in a given sample is measured relative to its corresponding competitive template in a standardized mixture, rather than by comparing it to another sample. Use of a common standardized mixture can provide the common standard and can facilitate direct comparisons.

In contrast, using techniques such as real-time RT-PCR and/or microarray analysis (other than in combination with some embodiments of the instant invention), nucleic acids being measured scale differently. For example, differences in hybridization melting temperatures between cDNA with bound polynucleotides (microarrays) or fluorescent probes (real-time RT-PCR) cause measurements to scale differently. Consequently, relative amounts of different nucleic acids in a specimen and/or between specimen may not be directly comparable, e.g., it may not be possible to compare difference in expression among many genes in a sample. Further, real-time PT-PCR and/or microarray analysis measurements may not provide direct information as to the number of molecules of a nucleic acid present in a sample.

Assessed amounts may also be corrected for one or more sources of variation, e.g., in accordance with various embodiments of the teachings provided herein. In some embodiments, the values in the database show a coefficient of variation of less than about 50%, less than about 30%, less than about 25%, less than about 20%, less than about 15%, less than about 10%, less than about 5%, or less than about 1% between 2 of more samples. In some preferred embodiments, numerical values do not comprise a statistically significant number of false positives. In some preferred embodiments, numerical values do not comprise a statistically significant number of false negatives. In more preferred embodiments, numerical values do not comprise false negatives.

In some embodiments, the database further comprises numerical values corresponding to amounts of a number of other nucleic acid(s) in the samples, where said amounts are directly comparable. The number of other nucleic acids for which data is included in the database can be at least about 5, at least about 10, at least about 50, at least about 100, at least about 500, at least about 1,000, at least about 5,000, at least about 10,000, at least about 50,000, at least about 100,000, at least about 500,000, at least about 1,000,000, at least about 5,000,000 or at least about 10,000,000 other nucleic acids.

In some embodiments, the database of the instant invention can serve as a common databank, where measured amounts of nucleic acids (e.g., gene expression measurements) are reported as numerical values that allow for direct inter-experiment comparison. Step 2402 illustrates such a database. In preferred embodiments, the database establishes a continuously expanding virtual multiplex experiment (i.e., data from an ever-expanding number of nucleic acids, samples and/or specimens can be entered into a given database and compared directly to other data within the database). This can lead to synergistic increases in knowledge, e.g., knowledge regarding the relationship between gene expression patterns and phenotype.

More preferred embodiments of the instant invention can be used to provide a common language for gene expression. Gene expression may be measured at the mRNA, protein, or functional level, preferably at the mRNA level. For example, mRNA expression is regulated primarily by the number of transcripts available for translation. Because mRNA expression is related primarily to copy number, one is able to develop an internal standard for each gene and/or to establish a common unit for gene expression measurement. For example, in a multi-institutional study, data generated by methods discussed herein were sufficiently sensitive and reproducible to support development of a meaningful gene expression database, serving as a common language for gene expression.

Some embodiments provide a common language for gene expression across species. For example, primers can be identified that PCR amplify nucleic acids corresponding to both human and mouse genes, e.g., for at least about 20%, for at least about 30%, for at least about 50%, for at least about 80%, or for at least about 90% of genes common to human and mice. Primers can also be developed to obtain wider cross-species application, e.g., for amplifying nucleic acids corresponding to two or more different species. For example, in some embodiments, primers can identified that amplify nucleic acids corresponding to two or more of human, rat, pig, horse, sheep, monkey, plant, fruit fly, fish, yeast, bacterial and/or viral genes.

In some embodiments, the database is web-based. In some embodiments, the database invention finds use in experimental research, clinical diagnoses and/or drug development. Step 2403 illustrates this use. For example, in some embodiments, the database can be used to advance studies on pathways of transcriptional control, and/or serve as a basis for mechanistic investigation. For example, bivariate analysis of individual gene expression numerical values for transcription factor genes and genes controlled by these transcription factors can improve understanding of gene expression regulation. In some embodiments, this can increase insight into control of gene expression, e.g., in normal and malignant cells.

In some embodiments, the numerical values of a database described herein can be used in one, two, or more stages of drug development. Stages of drug development may include, e.g., drug target screening, lead identification, pre-clinical evaluation (e.g., bioassay and/or animal study), clinical trial and patient treatment. Such applications are described in more detail below.

B. Database of Numerical Indices

Some embodiments of the instant invention provide a database comprising numerical indices. The numerical indices can be obtained by mathematical computation of 2 or more numerical values, where the numerical values correspond to amounts of nucleic acids in a number of samples. In some embodiments, the database of the instant invention includes one or more numerical indices provided in FIGS. 1, 2 and/or 4.

In preferred embodiments, the numerical indices are directly comparable between the samples. For example, in some embodiments, the numerical indices are directly comparable between at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some embodiments, direct comparison involves comparing the numerical indices to one another without a bioinformatics resource. In some embodiments, a bioinformatics resource, e.g., a simple bioinformatics resource, can be used. In some specific embodiments, each measurement in the database has been made relative to an internal standard within a standardized mixture of internal standards.

As discussed above, nucleic acid measurements can be reported as numerical values. The numerical values can be combined into numerical indices by mathematical computation to provide a numerical index, e.g., allowing mathematical interaction among the numerical values. For example, in some embodiments, a numerical index is calculated by dividing a numerator by a denominator, the numerator corresponding to the amount of one of 2 nucleic acids and the denominator corresponding to the amount the other of the 2 nucleic acids. In some embodiments, a numerical index is calculated by a series of one or more mathematical functions. For example, a numerical index may be calculated by a formula (gene 1+gene 2)/(gene 3-gene4). A numerical index can be described as balanced e.g., where it is computed by a formula having equal numbers of numerical values in the numerator as in the denominator. Methods for obtaining numerical indices that indicate a biological state, e.g., that can act as biomarkers by correlating with a phenotype of interest, are detailed below.

In some embodiments, the numerical indices are directly comparable between a number of samples, e.g., samples obtained from different subjects and/or from different species. In some embodiments the numerical indices are directly comparable between a number of samples measured and/or enumerated in different laboratories and/or at different times.

In some embodiments, the database of the instant invention can serve as a common databank, where measured amounts of nucleic acids (e.g., gene expression measurements) are mathematically combined to provide numerical indices that allow for direct inter-experiment comparison. In preferred embodiments, the database establishes a continuously expanding multiplex experiment (i.e., data from an ever-expanding number of nucleic acids, samples and/or specimens can be used to calculate numerical indices that are entered into a given database and compared directly to other data within the database).

As discussed above, in some embodiments, any measured nucleic acid or combination of nucleic acids, including all measured nucleic acids, can be used as the reference gene and data calculated using a first reference nucleic acid can be re-calculated relative to that of another reference nucleic acid. In the case of numerical indices, the difference in value obtained after converting from one reference nucleic acid to another can depend on how many numerical values are in the numerator and how many are in the denominator. For example, in some embodiments, each numerical value in a numerical index may be converted to the new reference in calculating the index. In some embodiments, for example, where there are equal numbers of numerical values in the numerator and denominator, conversion to a new reference may have no effect on the relative numerical index between samples and/or specimen.

In the case of balanced numerical indices where numerical values correspond to gene expression measurements, the effect of a reference nucleic acid that varies in expression from one sample and/or specimen to another can be neutralized. This can also occur in doing bivariate analysis. In other embodiments, for example, where there are non-equal numbers of numerical values in the numerator and denominator, the relative numerical index between samples and/or specimen may change in accordance with a difference in relative numerical values for the reference nucleic acids between the samples and/or specimen.

In some embodiments, the database is web-based. In some embodiments, the database invention finds use in experimental research, clinical diagnoses and/or drug development. For example, in some embodiments, the database can be used to advance studies on pathways of transcriptional control, and/or serve as a basis for mechanistic investigation. For example, in some embodiments, at least one numerical index indicates a biological state. Numerical indices may correlate better with a given biological state, e.g., a given phenotype, than a numerical value corresponding to an individual nucleic acid (e.g., to an individual gene). For example, in some embodiments, the numerical indices of a database described herein can be used in one, two, or more stages of drug development. Such applications are described in more detail below.

IV. Applications

Another aspect of the instant invention relates to methods of using numerical values and/or indices in research, diagnostic and/or other applications.

A. Identification of Biomarkers

In some embodiments, methods for obtaining numerical indices are provided. In preferred embodiments, the numerical index obtained indicates a biological state. A "biological state" as used herein can refer to a phenotypic state, for e.g., a clinically relevant phenotype or other metabolic condition of interest. Biological states can include, e.g., a disease phenotype, a predisposition to a disease state or a non-disease state; a therapeutic drug response or predisposition to such a response, an adverse drug response (e.g., drug toxicity) or a predisposition to such a response, a resistance to a drug, or a predisposition to showing such a resistance, etc. In preferred embodiments, the numerical index obtained can act as a biomarker, e.g., by correlating with a phenotype of interest. In some embodiments, the drug may be and anti-tumor drug. In preferred embodiments, use of embodiments of the instant invention described herein can provide personalized medicine.

In some embodiments, a method for obtaining a numerical index that indicates a biological state comprises providing 2 samples corresponding to each of a first biological state and a second biological state; measuring and/or enumerating an amount of each of 2 nucleic acids in each of the 2 samples; providing the amounts as numerical values that are directly comparable between a number of samples; mathematically computing the numerical values corresponding to each of the first and second biological states; and determining a mathematical computation that discriminates the two biological states.

First and second biological states as used herein correspond to two biological states of to be compared, such as two phenotypic states to be distinguished. Examples include, e.g., non-disease (normal) tissue vs. disease tissue; a culture showing a therapeutic drug response vs. a culture showing less of the therapeutic drug response; a subject showing an adverse drug response vs. a subject showing a less adverse response; a treated group of subjects vs. a non-treated group of subjects, etc.

A numerical index that discriminates a particular biological state, e.g., a disease or metabolic condition, can be used as a biomarker for the given condition and/or conditions related thereto. For example, in some embodiments, the biological state indicated can be at least one of an angiogenesis-related condition, an antioxidant-related condition, an apotosis-related condition, a cardiovascular-related condition, a cell cycle-related condition, a cell structure-related condition, a cytokine-related condition, a defense response-related condition, a development-related condition, a diabetes-related condition, a differentiation-related condition, a DNA replication and/or repair-related condition, an endothelial cell-related condition, a hormone receptor-related condition, a folate receptor-related condition, an inflammation-related condition, an intermediary metabolism-related condition, a membrane transport-related condition, a neurotransmission-related condition, a cancer-related condition, an oxidative metabolism-related condition, a protein maturation-related condition, a signal transduction-related condition, a stress response-related condition, a tissue structure-related condition, a transcription factor-related condition, a transport-related condition, and a xenobiotic metabolism-related condition.

For example, in specific embodiments, numerical indices that indicate lung cancer (E. L. Crawford, K. A. Warner, S. A. Khuder et al., Biochem. Bioph. Res. Co. 293, 509-516 (2002); E. L. Crawford, S. A. Khuder, S. J. Durham et al., Cancer Res. 60, 1609-161 8 (2000); J. P. DeMuth, C. M. Jackson, D. A. Weaver et al., Am. J. Respir. Cell Mol. Biol. 19, 18-24 (1998)), pulmonary sarcoidosis (M. G. Rots, R. Pieters. G. J. Peters et al., Blood 94, 3121-3128 (1999)) cystic fibrosis (J. T. Allen, R. A. Knight, C. A. Bloor and M. A. Spiteri, Am. J. Respir. Cell. Mol. Biol. 21, 693-700 (1999)) and chemo-resistance in childhood leukemias (S. Mollerup, D. Ryberg, A. Hewer et al., A. Cancer Res. 9, 3317-3320 (1999)) have been identified. In other specific embodiments, antioxidant and xenobiotic metabolism enzyme genes have been evaluated in human buccal epithelial cells; micro-vascular endothelial cell gene expression has been associated with scleroderma progression; membrane transport genes expression has been studied in rat congestive heart failure models; immune resistance has been studied in primary human tissues; transcription control of hormone receptor expression has been studied; and gene expression patterns have been associated with carboplatin and/or taxol resistance in ovarian carcinoma and with gemcitabine resistance in multiple human tumors. Other specific examples include, e.g., identification of numerical indices for predicting responsiveness of colon cancer to 5-FU and for indicating one or more different stages of bladder carcinoma. Embodiments of inventions described herein can accelerate discovery of associations between gene expression patterns and biological states of interest, leading to better methods for preventing, diagnosing and treating various conditions.

FIG. 25 illustrates use of numerical indices in identifying a biological state.

Measuring nucleic acid amounts may be performed by any methods known in the art and/or described herein. Preferably, the method used can measure and/or enumerate less than about 10,000 molecules, less than about 8,000, less than about 6,000, or less than about 4,000, preferably less than about 1,000, less than about 800, less than about 600, or less than about 400 molecules, of a given nucleic acid in a given sample. In some embodiments, the measurements correspond to gene expression measurements, e.g., levels of mRNA transcripts can be measured. In preferred embodiments, transcript levels, in particular, transcript levels of 2 or more genes, can be used to indicate a biological state. For example, microarray analysis has identified gene sets that are associated with disease states and/or drug responses (D. A. Wigle, I. Jurisica, N. Radulovich et al., Cancer Res. 62, 3005-3008 (2002); M. E. Garber, 0. G. Troyanskaya. K. Schluens et al., Proc. Natl. Acad. Sci. USA 98, 13784-13789 (2001); A. Bhattacharjee, W. G. Richards, J. Staunton et al., Proc. Natl. Acad. Sci. USA 98, 13790-13795 (2001); I. Hedenfalk, D. Duggan, Y. Chen et al., New Engl. J. Med. 344, 539-548 (2001); T. Sorlie, C. M. Perou, R. Tibshirani et al., Proc. Natl. Acad. Sci. USA 98, 10869-10874 (2001); C. M. Perou, S. S. Jeffrey, M. van de Rijn et al., Proc. Natl. Acad. Sci. USA 96, 9212-9217 (1999)). Providing the measured and/or enumerated amounts as numerical values is preferably accomplished by methods described herein, where the numerical values are directly comparable for a number of samples used.

In some embodiments, one or more of the nucleic acids to be measured are associated with one of the biological states to a greater degree than the other(s). For example, in some preferred embodiments, one or more of the nucleic acids to be evaluated is associated with a first biological state and not with a second biological state. A nucleic acid may be said to be "associated with" a particular biological state where the nucleic acid is either positively or negatively associated with the biological state. For example, a nucleic acid may be said to be "positively associated" with a first biological state where the nucleic acid occurs in higher amounts in a first biological state compared to a second biological state. As an illustration, genes highly expressed in cancer cells compared to non-cancer cells can be said to be positively associated with cancer. On the other hand, a nucleic acid present in lower amounts in a first biological state compared to a second biological state can be said to be negatively associated with the first biological state.

The nucleic acid to be measured and/or enumerated may correspond to a gene associated with a particular phenotype. The sequence of the nucleic acid may correspond to the transcribed, expressed, and/or regulatory regions of the gene (e.g., a regulatory region of a transcription factor, e.g., a transcription factor for co-regulation).

In some embodiments, expressed amounts of more than 2 genes are measured and used in to provide a numerical index indicative of a biological state. For example, in some cases, expression patterns of about 50 to about 100 genes are used to characterize a given phenotypic state, e.g., a clinically relevant phenotype. See, e.g., Heldenfalk, I. et al. NEJM 344: 539, 2000. In some embodiments of the instant invention, expressed amounts of at least about 5 genes, at least about 10 genes, at least about 20 genes, at least about 50 genes, or at least about 70 genes may be measured and used to provide a numerical index indicative of a biological state. In some embodiments of the instant invention, expressed amounts of less than about 90 genes, less than about 100 genes, less than about 120 genes, less than about 150 genes, or less than about 200 genes may be measured and used to provide a numerical index indicative of a biological state. Specific examples of several of these embodiments include, e.g., identification of gene expression patterns associated with lung cancer (Crawford, E. L. et al. normal bronchial epithelial cell expression of glutathione transferase P1, glutathione transferase M3, and glutathione peroxidase is low in subjects with bronchogenic carcinoma. Cancer Res., 60: 1609-1618, 2000; DeMuth, et al., The gene expression index c-myc x E2F-1/p21 is highly predictive of malignant phenotype in human bronchial epithelial cells. Am. J. Respir. Cell Mol. Biol., 19: 18-24, 1998); pulmonary sarcoidosis (Allen, J. T., et al., Enhanced insulin-like growth factor binding protein-related protein 2 (connective tissue growth factor) expression in patients with idiopathic pulmonary fibrosis and pulmonary sarcoidosis. Am. J. Respir. Cell Mol. Biol., 21: 693-700, 1999); cystic fibrosis (Allen, et al., supra); and chemoresistance in childhood leukemias (Rots, M. G., et al., Circumvention of methotrexate resistance in childhood leukemia subtypes by rationally designed antifolates. Blood, 94(9): 3121-3128, 1999; Rots, M. G., et al., mRNA expression levels of methotrexate resistance-related proteins in childhood leukemia as determined by a competitive template-based RT-PCR method. Leukemia, 14:2166-2175 (2000)).

Mathematically computing numerical values can refer to using any equation, operation, formula and/or rule for interacting numerical values, e.g., a sum, difference, product, quotient, log power and/or other mathematical computation. As described above, in some embodiments, a numerical index is calculated by dividing a numerator by a denominator, where the numerator corresponds to an amount of one nucleic acid and the denominator corresponds to an amount the another nucleic acid. In preferred embodiments, the numerator corresponds to a gene positively associated with a given biological state and the denominator corresponds to a gene negatively associated with the biological state. In some embodiments, more than one gene positively associated with the biological state being evaluated and more than one gene negatively associated with the biological state being evaluated can be used. For example, in some embodiments, a numerical index can be derived comprising numerical values for the positively associated genes in the numerator and numerical values for an equivalent number of the negatively associated genes in the denominator. As mentioned above, in such balanced numerical indices, the reference nucleic acid numerical values cancel out. An example of a balanced numerical index include a numerical index for predicting anti-folate resistance among childhood leukemias. Rots, M. G., Willey, J. C., Jansen, G., et al. (2000) mRNA expression levels of methotrexate resistance-related proteins in childhood leukemia as determined by a standardized competitive template-based RT-PCR method. Leukemia 14, 2166-2175. In some embodiments, balanced numerical values can neutralize effects of variation in the expression of the gene(s) providing the reference nucleic acid(s). In some embodiments, a numerical index is calculated by a series of one or more mathematical functions.

Determining which mathematic computation to use to provide a numerical index indicative of a biological state may be achieved by any methods known in the arts, e.g., in the mathematical, statistical, and/or computational arts. In some embodiments, determining the mathematical computation involves a use of software. For example, in some embodiments, a machine learning software can be used.

In some embodiments, more than one sample corresponding to each biological state can be provided. For example, at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples may be provided.

In some embodiments, more than 2 biological states can be compared, e.g., distinguished. For example, in some embodiments, samples may be provided from a range of biological states, e.g., corresponding to different stages of disease progression, e.g., different stages of cancer. Cells in different stages of cancer, for example, include a non-cancerous cell vs. a non-metastasizing cancerous cell vs. a metastasizing cell from a given patient at various times over the disease course. Cancer cells of various types of cancer may be used, including, for example, a bladder cancer, a bone cancer, a brain tumor, a breast cancer, a colon cancer, an endocrine system cancer, a gastrointestinal cancer, a gynecological cancer, a head and neck cancer, a leukemia, a lung cancer, a lymphoma, a metastases, a myeloma, neoplastic tissue, a pediatric cancer, a penile cancer, a prostate cancer, a sarcoma, a skin cancer, a testicular cancer, a thyroid cancer, and a urinary tract cancer. In preferred embodiments, biomarkers can be developed to predict which chemotherapeutic agent can work best for a given type of cancer, e.g., in a particular patient.

A non-cancerous cell may include a cell of hematoma and/or scar tissue, as well as morphologically normal parenchyma from non-cancer patients, e.g., non-cancer patients related or not related to a cancer patient. Non-cancerous cells may also include morphologically normal parenchyma from cancer patients, e.g., from a site close to the site of the cancer in the same tissue and/or same organ; from a site further away from the site of the cancer, e.g., in a different tissue and/or organ in the same organ-system, or from a site still further away e.g., in a different organ and/or a different organ-system.

Numerical indices obtained can be provided as a database. Numerical indices and/or databases thereof can find use in diagnoses, e.g., in the development and application of clinical tests, as described below.

B. Micro-Array Screening

Another application of some embodiments of the instant invention relates to use with screening techniques, e.g., screening techniques using solid-phase hybridization such as microarray analyses. For example, in specific embodiments, relevant gene expression patterns can be identified through microarray gene expression screening, and assays suitable for analysis of subset of genes can follow this.

Figure 26:
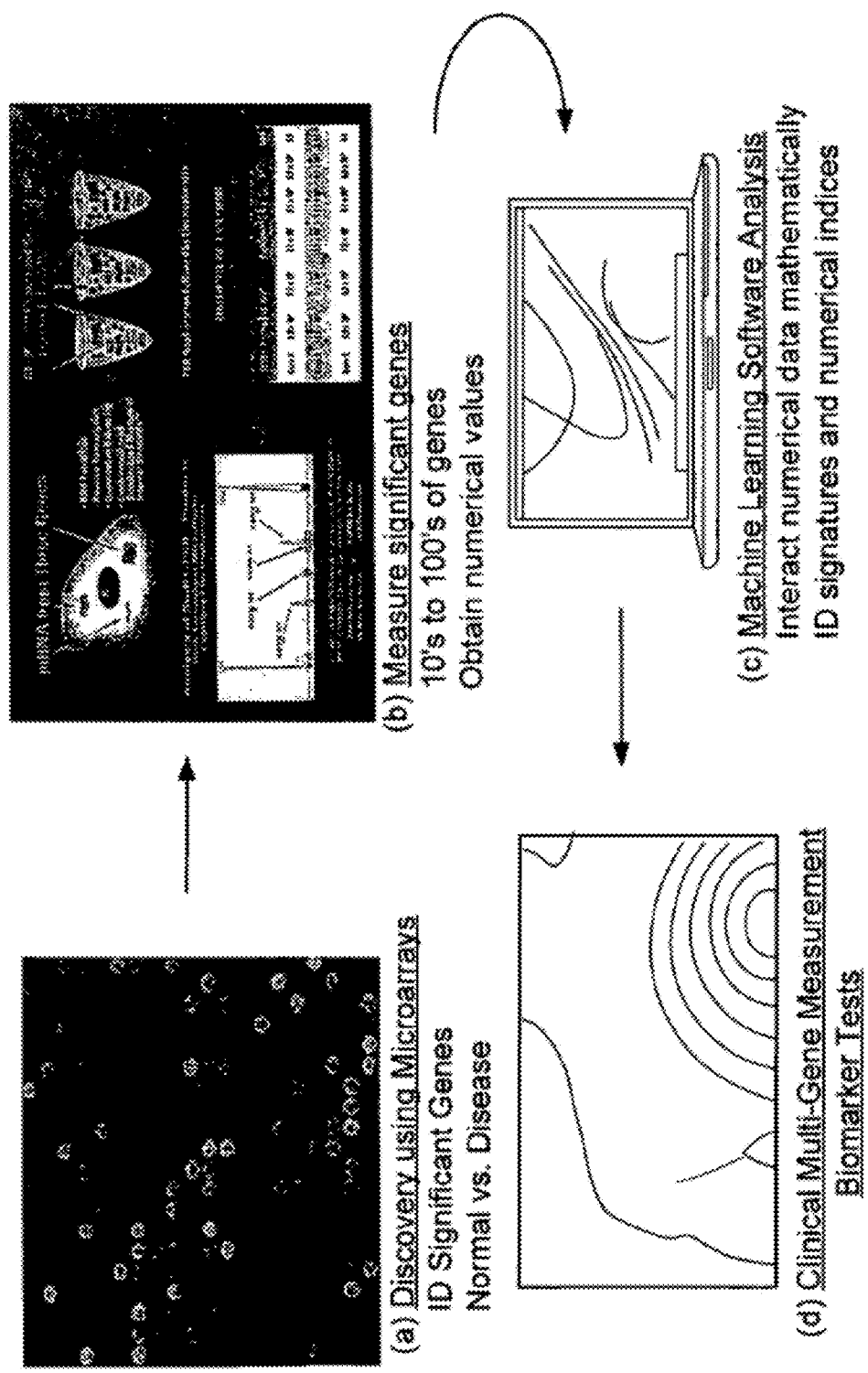
FIG. 26 illustrates the overall process relating to using micro-array screens with embodiments of the instant invention.

FIG. 26 illustrates the overall process relating to using micro-array screens with embodiments of the instant invention. FIG. 26(a) schematically illustrates discovery of genes of interest using micro-arrays. In some embodiments a population of genes may be screened to determine a subset of genes of interest, e.g., genes corresponding to nucleic acids associated with a first biological state but not with a second biological state. In some embodiments, for example a subset comprising about 30, about 50, about 80, about 100, about 120, about 150, about 200, about 250, or about 300 genes may be found to be associated with a clinically relevant phenotype, e.g., disease vs. non-disease states, or any other biological states to be distinguished, as discussed above. The microarray analysis used may use any microarrays and microarray techniques known in the art and/or described herein. One or more of the nucleic acids so identified may then be evaluated in accordance with some embodiments described herein.

FIG. 26(b) schematically illustrates evaluations of genes of interest, according to some embodiments described here. Briefly, as FIG. 26(b) illustrates, mRNA corresponding to one or more genes (e.g., 3 genes) can be extracted and reverse transcribed, e.g., as discussed in detail above. Again as discussed above, a cDNA sample may be quantitatively balanced and combined with an appropriate standardized mixture, e.g., comprising competitive templates for each of the genes to be evaluated. Native templates for each of the 3 genes may be co-amplified with its corresponding competitive template in a given vessel. PCR amplification can be followed by electrophoresis to provide an electropheregram. Areas under the cure can be used to obtain a "ratio of ratios" as detailed above. Expression measurements for each of the 3 genes are provided as a numerical value.

Any other embodiments and or variations of these methods, e.g., as disclosed herein, can be used, e.g., to allow for detection with one or more of the sensitivities, one or more of the accuracies, one or more of the detection limits, and/or with more or more of the coefficients of variation taught herein. In preferred embodiments, methods employed can improve the threshold of detection, sensitivity and/or coefficient of variation compared to micro-arrays. For example, analysis using some embodiments of the instant invention can avoid, reduce and/or control differences in melting temperatures between cDNA for each gene and the oligonucleotide or cDNA spotted on the array; differences in amount of sample loaded; time of hybridization; stringency of wash; and/or parameters used to calibrate fluorescence intensity. Details of experiments comparing with methods of the instant invention with microarray analysis are provided in Example V below.

In some embodiments, nucleic acids corresponding to genes of interest are evaluated in samples corresponding to one or more biological states. For example, a sample corresponding to a first biological state and a sample corresponding to a second biological state may be used. In some embodiments, amounts of nucleic acids corresponding to each of said two biological states may be evaluated and/or enumerated, e.g., to provide data representative of the two biological states.

FIG. 26(c) schematically illustrates mathematical computation of numerical values obtained for the genes of interest. Numerical values obtained for 2 or more nucleic acids can be used to determine one or more numerical indices. For example, again as detailed above, numerical values corresponding to each of a first and a second biological state can be mathematically combined. A mathematical computation can be determined that indicates the biological state of interest, e.g., by discriminating the first and second biological states. FIG. 26(c) illustrates using software to perform the mathematical computations, again as provided in detail above.

FIG. 26(d) schematically illustrates use of such numerical indices in a clinical setting, e.g., as a biomarker for diagnoses and/or prognoses, as discussed in more detail below. When analyzing clinical samples that are size limited, it is likely to be more cost effective to measure only those genes that contribute information on expression profiles that define the biological state of interest. Accordingly, rather than measuring expression of a large population of genes, e.g., about 40,000 to about 80,000 genes, a smaller subset can be evaluated in clinical samples. Using some embodiments for evaluating nucleic acids herein provided, multi-gene measurements can be made on the smaller subset and data used in biomarker tests, e.g., as numerical indices indicative of the biological state.

C. Diagnostic Applications

In some embodiments of the instant invention, a method of identifying a biological state is provided. In some embodiments, the method comprises measuring and/or enumerating an amount of each of 2 nucleic acids in a sample, providing the amounts as numerical values; and using the numerical values to provide a numerical index, whereby the numerical index indicates the biological state. In some embodiments, the numerical index comprises a numerical index provided in FIGS. 1, 2 and/or 4

A numerical index that indicates a biological state can be determined as described above in accordance with various embodiments of the instant invention. The sample may be obtained from a specimen, e.g., a specimen collected from a subject to be treated. The subject may be in a clinical setting, including, e.g., a hospital, office of a health care provider, clinic, and/or other health care and/or research facility. Amounts of nucleic acid(s) of interests in the sample can then be measured and/or enumerated.

Assessing nucleic acid amounts may be performed by any methods described herein. Preferably, the method used can measure and/or enumerate less than about 10,000 molecules, less than about 8,000, less than about 6,000, or less than about 4,000, preferably less than about 1,000, less than about 800, less than about 600, or less than about 400 molecules, of a given nucleic acid in a given sample. In cases where several genes are to be measured in a sample and/or specimen, preferred embodiments can be practiced using small amounts of starting cellular material, e.g., using the amounts of material obtained from a diagnostic biopsy sample, e.g., by the methods described in more detail above and/or as known in the art. In more preferred embodiments, more than one gene can be evaluated at the same time, and in highly preferred embodiments, where a given number of genes are to be evaluated, expression data for that given number of genes can be obtained simultaneously. For example, in some embodiments, data obtained from primary lung cancer tissue can be assayed. By comparing the expression pattern of certain genes to those in a database, a chemotherapeutic agent that a tumor with that gene expression pattern would most likely respond to can be determined In some embodiments, methods of the invention can be used to evaluate simultaneously both an exogenous reporter gene and an endogenous housekeeping gene, such as GAPDH RNA in a transfected cell, either in vitro or in vivo.

In some embodiments, for example, relative amounts of exogenous cystic fibrosis transmembrane conductance regulator (CFTR) gene per cell can be measured. Although numerous different mutations in the CFTR gene have been reported to be associated with disease, the most common disease-associated mutation is a 3 base deletion at position 508. It is possible to prepare primers that result in amplification of one or other of the abnormal 508 deleted gene or the normal CP IR gene using described methods, e.g., Cha, R. S., Zarbl, H., Keohavong, P., Thilly, W. G., match amplification mutation assay (MAMA): application to the c-Ha ras gene, PCR methods and applications, 2:14-20 (1992). These can be used with certain embodiments of the present invention to measure amounts of exogenous normal CP IR nuclei acid and/or amounts of endogenous mutant CP IR gene.

Similarly, in some embodiments, methods of the invention can be used to quantify exogenous normal dystrophin gene in the presence of mutated endogenous gene. In the case of dystrophin, the disease results from relatively large deletions. Using primers that span the deleted region, one can selectively amplify and quantitate expression from a transfected normal gene and/or a constitutive abnormal gene for dystrophin. As will be appreciated by those in the art, other genes associated with other diseases and/or conditions can also be evaluated in similar manner.

In some embodiments, methods described herein can be used to determine normal expression levels, e.g., providing numerical values corresponding to normal gene transcript expression levels. Such embodiments may be used to indicate a normal biological state, at least with respect to expression of the evaluated gene.

Normal expression levels can refer to the expression level of a transcript under conditions not normally associated with a disease, trauma, and/or other cellular insult. In some embodiments, normal expression levels may be provided as a number, or preferably as a range of numerical values corresponding to a range of normal expression of a particular gene, e.g., within +/− a percentage for experimental error. Comparison of a numerical value obtained for a given nucleic acid in a sample, e.g., a nucleic acid corresponding to a particular gene, can be compared to established-normal numerical values, e.g., by comparison to data in a database provided herein. As numerical values can indicate numbers of molecules of the nucleic acid in the sample, this comparison can indicate whether the gene is being expressed within normal levels or not.

In some embodiments, for example, provide a method for identifying a biological state comprising assessing an amount a nucleic acid in a first sample, and providing said amount as a numerical value wherein said numerical value is directly comparable between a number of other samples. In some embodiments, the numerical value is directly comparable to at least about 5, at least about 10, at least about 100, at least about 1,000, at least about 5,000, or at least about 10,000 other samples. In some embodiments, the numerical value is potentially directly comparable to an unlimited number of other samples. Samples may be evaluated at different times, e.g., on different days; in the same or different experiments in the same laboratory; and/or in different experiments in different laboratories, In preferred embodiments, the biological state corresponds to a normal expression level of a gene. Where the biological state does not correspond to normal levels, for example falling outside of a desired range, a non-normal, e.g., disease condition may be indicated, as discussed above.

V. Business Methods

Another aspect of the present invention relates to business methods, including business methods for providing gene expression measurement services and for improving research and development.

A. Nuclei Acid Evaluation Services

Figure 27:
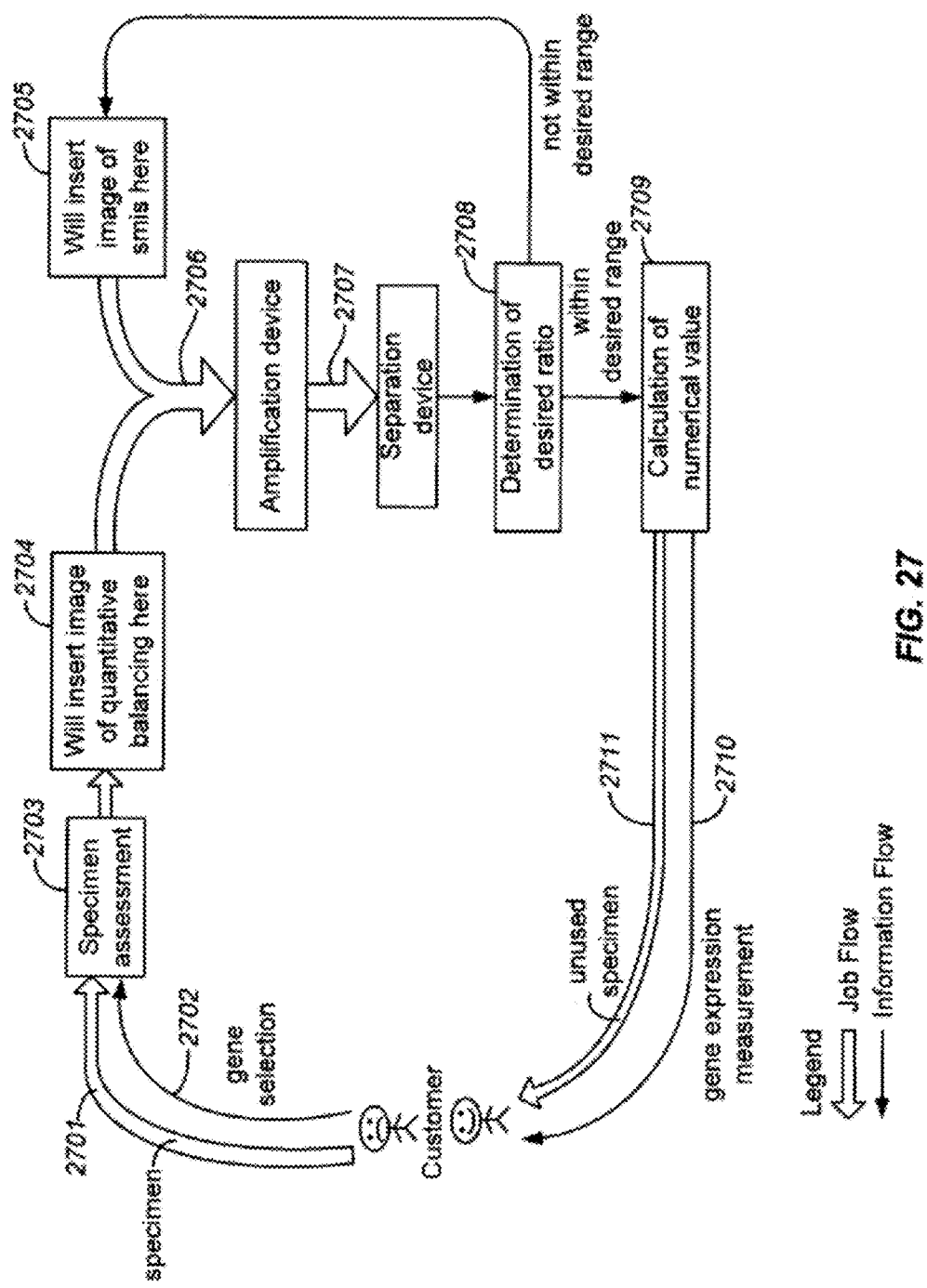
FIG. 27 illustrates the overall process of some embodiments of a business method for evaluating nucleic acids.

FIG. 27 illustrates the overall process of some embodiments of a business method for evaluating nucleic acids. In preferred embodiments, the business provides gene expression measurements. The amounts and/or concentrations of other nucleic acids can also be evaluated in some embodiments, e.g., as described by the methods herein.

Preferred embodiments measure an amount of a nucleic acid to provide standardized, reproducible gene expression measurements as a service. "Measuring an amount of a nucleic acid" can refer to running a given assay for evaluating the nucleic acid. Measuring nucleic acid amounts may be performed by any methods known in the art and/or described herein. Preferably, the method used can measure and/or enumerate less than about 10,000 molecules, less than about 8,000, less than about 6,000, or less than about 4,000, preferably less than about 1,000, less than about 800, less than about 600, or less than about 400 molecules, of a given nucleic acid in a given sample.

Step 2701 illustrates collecting specimen comprising nucleic acid, e.g., from a customer. The nucleic acid material may be mRNA, cDNA, genomic DNA and/or any other nucleic acid material, as provided for herein. Customers may include pharmaceutical companies, universities and/or other research organizations, government agencies, as well as clinicians, medical practitioners and/or other health care providers, as well as any entity desiring information regarding nucleic acid concentration in a sample.

The specimen collected may be a specimen from any biological entity comprising a nucleic acid. For example, specimen may be collected from different subjects and/or different species. In some embodiments, the specimen comprises a human specimen. In some embodiments, the specimen is collected with or without identifying information. For example, in some embodiments, customers may send human specimen without annotating information to preserve anonymousness.

Step 2702 illustrates collecting information selecting which nucleic acids in the specimen are to be measured. For example, in some embodiments, customers select a set of genes whose expression levels are to be evaluated, and send a request listing the selected genes along with the specimen for analysis. In some embodiments, nucleic acids and/or genes available for analysis are listed on a website. An example of such a list, e.g., may be found at www.geneexpressinc.com/assays_list.asp. In some embodiments, the information may be collected via a website.

In some embodiments, the business method further comprises collecting information attesting to compliance with investigative protocol. For example, a request for gene expression measurement may include an attestation that any primary human samples and/or specimen were obtained under approved and/or active investigative review board (IRB) protocol. In cases where no or negligible potentially identifying information is provided, there may be no need to obtain an IRB protocol for the specimen to be analyzed. Identifying information can include any information that would identify the subjects that provided the specimen and/or samples being assessed.

In some embodiments, upon receipt of a specimen to be tested, a number is assigned comprising basic information, such as, e.g., the date, the number received that day and/or other preliminary organizing information. In some embodiments, a label with some or all of such information can be attached to the material. In preferred embodiments, a duplicate label can be provided to the customer, e.g., for their records. In some embodiments, the basic information can be entered into a log, e.g., with the customer's name and/or account number, e.g., for billing purposes.

Step 2703 illustrates assessment of the collected specimen. For example, in some embodiments, RNA specimen may be assessed for quality. An Agilent 2100 RNA chip may be used for this purpose. In some embodiments, an approximate measurement of the amount of RNA provided and/or cDNA provided and/or obtained may be made. If there is insufficient quality and/or quantity, the customer can be notified, e.g., asked to prioritize genes to be evaluated and/or asked to send more RNA and/or cDNA material.

In preferred embodiments, measurements can be obtained rapidly. To obtain data rapidly, several nucleic acids may be assayed at the same time or during overlapping time periods, e.g., to accommodate numerous steps of measuring the amounts of nucleic acids in a given time period. In some embodiments, for example, an assay is performed at least about 10 times per day, at least about 50 times per day, at least about 100 times per day, at least about 500 times per day, at least about 1,000 times per day, at least about 2,000 times per day, at least about 4,000 times per day, at least about 5,000 times per day, at least about 10,000 times per day, at least about 50,000 times per day, at least about 100,000 times per day, at least about 500,000 times per day, at least about 1,000,000 times per day, at least about 5,000,000 times per day, at least about 10,000,000 times per day, at least about 50,000,000 times per day, or at least about 100,000,000 times per day.

In preferred embodiments, one or more steps of the business model are automated, e.g., to increase speed. For example, in some embodiments, one or more embodiments of the computer implemented methods described above may be used.

Step 2704 illustrates quantitative balancing of a cDNA sample, e.g., as described herein, and which may be automated. In some embodiments, the business method further comprises identifying which of the selected nucleic acids electrophorese together. For example, some embodiments use software to identify which nucleic acids, e.g., cDNAs corresponding to various genes, can be electrophoretically separated if run together, e.g., to be separated simultaneously.

Software can be used to identify which genes may be electrophoresed together for the set of genes selected by a customer. As discussed in more detail above, factors considered include length in base-pairs of the nucleic acid and its respective competitive template, as well as the relative lengths of various selected nucleic acids and the nucleic acid serving as a reference. For example, in some embodiments, primers and competitive templates can be designed to produce suitably-sized amplified PCR products of the one or more of the various selected nucleic acids and/or their respective competitive templates. In preferred embodiments, nucleic acid identified as electrophoresing together can be run together and/or enumerated at the same time or about the same time.

Step 2705 illustrates the selection of one of a series of standardized mixtures for combining with a selected cDNA dilution, again as described herein. The Mix can be selected to provide competitive templates for each of the genes to be evaluated, e.g., genes selected by the customer and/or genes identified as electrophoresing together. In some embodiments, many nucleic acids are amplified in a given PCR reaction to speed measuring. In more preferred embodiments, all the genes selected to be measured by a given customer in a particular specimen and/or sample are measured simultaneously.

Step 2706 illustrates combining a Mix and a cDNA dilution along with transfer to vessels for PCR amplification. In preferred embodiments, a sufficient volume of PCR mixture for the anticipated number of nucleic acid measurements can be prepared. In some specific embodiments, for example, a PCR mixture can contain reagents for performing selective amplification of the nucleic acids to be evaluation and the corresponding competitive template, including, e.g., buffer, one or more thermostable polymerases, NTPs and/or dNTPs, cDNA and competitive templates.

In some embodiments, reaction preparation and/or transfer is automated. For example, an automated means to prepare and load chips can be used. For example, automated means comprising one or more steps of pressurizing, loading markers, vortexing, and loading chip into a Agilent 2100 can be used in some embodiments. For example, a robotic liquid handler can be programmed to assess different reagent reservoirs, assemble PCR reaction mixtures, and distribute into various vessels, e.g., 96- and/or 384-well microplates. For example, in preferred embodiments, the robotic liquid handler can transfer a 1 µL aliquot to wells of Agilent 2100 DNA 1000 chips, e.g., automatically dispensing a solution or combination of solutions into individual wells and/or varying the spacing between sample probes (Varispan). In some embodiments, a liquid handler can be programmed to distribute a given volume of primers for the nucleic acid(s) to be measured into reaction vessels. In preferred embodiments, one pair of primers can be present in a given vessel, allowing amplification of a given nucleic acid its respective competitive template in that vessel. In preferred embodiments, the robotic liquid handler is able to communicate with one or more other devices used in the process, e.g., as detailed below.

Amplification can take place in an amplification device. The amplification device may comprise any of the systems described herein and/or known in the art for amplifying nucleic acids. Some embodiments of the instant business method use one or more thermocyclers. In some preferred embodiments, thermocyclers having motorized and/or heated lids are used, e.g., to allow oil-free thermocycling and/or automation. For example, some specific embodiments use two MJ 384-well block thermocyclers in the MJ PTC-225 DNA Engine Tetrad System, which can further be expanded to four 384-well microplate block thermocyclers.

In preferred embodiments, the thermocycler used is compatible with the robotic liquid handler used. For example, a Multiprobe II HT EX robotic liquid handler can communicate with one or more thermocyclers, e.g., to coordinate lid-opening and/or closing with microplate insertion and/or removal. In preferred embodiments, the robotic liquid handler can avoid cross-contamination of reaction vessels, can position filled vessels in block thermocyclers for amplification, and/or can remove aliquots from the vessels following amplification.

Step 2707 illustrates transfer of the contents of reaction vessels to a separation device, i.e., a device for separating amplified product of the nucleic acid being measured and its respective competitive template, e.g., in accordance with methods known in the art and/or detailed herein. Some embodiments use a microfluidic chip with a sipper that moves from well to well, aspirating and then electrophoretically separating amplified product at a rate of, e.g., at least about every 10 seconds, at least about every 20 seconds, at least about every 30 seconds, at least about every 40 seconds, or at least about every 50 seconds. Some embodiments allow analysis of a 384-well plate in approximately three hours. In some embodiments, a combined throughput of 4,608 measurements/24 hours can be achieved.

As described above, where amplified products are to be separated by electrophoresis, the size of the competitive templates and/or reference nucleic acid(s) can be selected to differ from that of the target nucleic acid. In some embodiments, primers are designed to amplify a nucleic acid and its respective competitive template to give amplified product of suitable sizes, e.g., sizes that facilitate obtaining data rapidly. For example, designing primers that amplify different sized products for different target nucleic acids can support automation and high-throughput applications, including capillary gel and microchannel CE. Other embodiments may use microarrays, microbeads, MALDI-TOF MS and/or real-time RT-PCR as detailed above.

For example, in some embodiments competitive templates and/or amplified products are at least about 20, at least about 25, at least about 30, at least about 50, at least about 75, at least about 100, at least about 150, at least about 200, at least about 250, at least about 300, at least about 350, or at least about 400 base pairs. In some embodiments, amplified product are less than about 500, less than about 600, less than about 700, less than about 800, less than about 850, less than about 900, less than about 1,000, less than about 1,500, less than about 1,800, less than about 2,000, less than about 2,200, or less than about 2,500 base pairs. In some embodiments, amplified product corresponding to 1 gene, 2 genes, 3 genes, 4 genes, about 5 genes, about 10 genes, about 15 genes, about 20 genes or more can be separated and quantified in a given channel, e.g., using microchannel CE where different PCR NT and CT products have different sizes.

In a specific embodiment where amplified product are between about 200 to about 800 base pairs, more than about 100 genes can be amplified and/or separated in a given CE channel. It can be appreciated that a 96-channel CE device, for example, may be converted to automated, high throughput (>300,000 standardized gene expression assays/24 hours) device using some embodiments of the instant invention Similarly, use of a Caliper AMS90 SE30 device can provide more than about 1,000 nucleic acid measurements in about eight hours. Another specific embodiment uses amplified product between about 20 and bout 2,000 base pairs.

The Agilent 2100 Lab-on-a-chip 1000, for example, can separate bands with approximately 10% difference in size. For example, in an about 150 to about 850 base pair span, about 15 differently sized PCR products, (e.g. about 150, about 170, about 190, about 210, about 230, about 260, about 290, about 320, about 350, about 400, about 440, about 490, about 540, about 600, about 660, about 730, about 800 base pairs) can be separated in some embodiments. Using of an Agilent 2100 Bioanalyzer, electrophoresis can take at least about 1 minute, at least about 1.5 minutes, or at least about 2 minutes. Running multiple channels on an Agilent 2100 chip can take at least about 5 minutes, or at least about 10 minutes, or at least about 15 minutes. In some embodiments, running multiple channels can take less than about 15 minutes, less than about 20 minutes, less than about 25 minutes, or less than about 30 minutes, e.g., using an Agilent 2100 Bioanalyzer. As a specific example, using 12 channels and running two chips/hour, an 8 hour day of continuous use would allow 12 channels/chip×1 chip/30 minutes×two 30 minute segments/hour×1 PCR product/channel×8 hours=about 192 expression measurements/day. Some such embodiments provide throughput capabilities that of more than 4,000 gene expression measurements/24 hours.

In some embodiments, a higher throughput may be achieved by increasing the number of channels/device, genes/channel and/or the number of electrophoresis devices used. As another specific example, using two Agilent 2100's, and electrophoresing 4 genes/channel, the throughput capacity in eight hours can be about 1,056 (2 Agilent 2100×12 channels/chip×4 genes/channel×2 chips/hour×8 hours=1056). Using four Agilent 2100's, in some embodiments, for example, can double throughput to about 2,112 measurements/eight hours. Other preferred embodiments may have 96 channels instead of 12, further increasing the number of genes that may be measured/run. Other preferred embodiments can triple throughput potential to about 6,336 measurements/eight hours.

Preferably, the separation device used in the practice of the present business method allows for miniaturization. Automation combined with miniaturization can lead to high throughput and further increase speed, as well as using only small amounts of nucleic acid (e.g., small amounts of cDNA) and/or other reagents For example, in some embodiments, throughput capacity for gene expression measurement is increased with the use of microfluidic separation devices. Some highly preferred embodiments can use capillary electrophoreses (CE) devices, more preferably, microfluidic CE devices, such as an AMS 90 SE30 microfluidic device (Caliper/Zymar, Hopkinton, Mass., USA). For example, a highly preferred embodiment in the instant business method involves electrophoretically separating and quantifying end-point PCR products using an AMS90 SE30 device. In some embodiments, amplified product of the at least 2, at least 3, or at least about 4 nucleic acids and corresponding competitive template can be electrophoresed (separated and quantified) in a given microfluidic channel of an AMS 90 SE30 device. In a specific embodiment, for example, a combined automated system of multiblock thermal cyclers and CE devices allows over about 4,000 gene expression assays/24 hours.

In some embodiment, PRC reaction mixtures can be dispensed into microarrays. In some embodiments, nanoarrays and/or nanofluidic techniques may be used. The use of nanotechnology methods for manipulating small liquid volumes can further decrease PCR reaction volumes, e.g., to about 200 nL, about 150 nL, about 100 nL, about 80 nL, about 50 nL, about 20 nL, about 10 nL, about 5 nL, or about 1 nL. See, e.g., Crawford, E. L., Warner, K. A., Khuder, S. A., et al. (2002) Multiplex standardized RT-PCR for expression analysis of many genes in small samples. Biochem, Biophys. Res. Commun. 293, 509-516.

Step 2708 illustrates determining a ratio of amplified product to nucleic acid and its competitive template, e.g., as described in detail herein. Where the ratio is not within a desired ratio, software can be used to instruct a robotic liquid handler on how to set up the next experiment, as also described herein.

Step 2709 illustrates calculation of a numerical value, e.g., as described herein, where a ratio within the desired range is obtained. In preferred embodiments, quantification is automated. For example, in some embodiments densitometric measurement of amplified product takes place automatically, e.g., as bands migrate past a laser/photomultiplier unit. For example, in some embodiments, the relative amounts of NT and CT can be determined by densitometric quantification of intercalator dye stained bands, using peak areas. Use an Agilent 2100 electrophoresis device, e.g., can facilitate automated quantification.

Step 2710 illustrates providing data obtained back to the customer. Data may be communicated by any suitable means. For example, the information can be provided via e-mail and/or hard copy. Other communicative means include, e.g., a CD ROM, floppy disc, paper, or telephonic communication.

Step 2711 illustrates any remaining material being returned to the customer, as may be done in some embodiments. In certain embodiments, customers may be encouraged to provide some annotating information, e.g., upon acceptance of a manuscript containing the data for publication, publication of the data, and/or public disclosure of the data. Identifying information may then be collected at a time later than that of collecting the specimen. In some embodiments, annotated standardized gene expression measurements can be entered into a database, e.g., databases comprising numerical values and/or numerical indices, as also described herein.

Additional details for operating a business providing gene expression services are provided in Example VI.

Some embodiments further comprise a step of charging a fee, e.g., charging a fee for a given nucleic acid measurement. In some embodiments, a fee of less than about U.S. $2 per measurement, less than about U.S. $1 per measurement, or less than about U.S. $0.5 per measurement is charged. In some embodiments, a fee of less than about U.S. $10,000, less than about U.S. $1,000, less than about U.S. $100, less than about U.S. $50, less than about U.S. $20, or less than about U.S. $5 per nucleic acid measurement may be charged. In some embodiments, the fees charged customers may be used, at least in part, towards funding developments of other aspects of the instant invention, e.g., funding determination of new biomarkers, numerical values and/or indices indicating a biological state.

In preferred embodiments, the business method further comprises quality control features. For example, any embodiments of the methods and/or compositions described herein can be used to accomplish quality control. For example, use of some embodiments of the database and the use of internal standard can simplify quality control, including quality control sought by regulatory agencies, such as the FDA (FDA guidance paper on acceptable use of multigene expression measurement in drug development fda.gov/cdrh/oivd/guidance/1210.pdf) and/or Centers for Disease Control (CDC, Atlanta, Ga., USA), e.g., the Clinical Laboratory Improvement Amendment (CLIA) standards. In some embodiments, the business method provides measurements with one or more of the sensitivities, one or more of the accuracies, one or more of the detection limits, and/or with one or more of the coefficients of variation taught herein. In preferred embodiments, the coefficient of variation is less than about 15% for all or nearly all genes, and less than about 10% for most genes whose expression is measured. Samples may be measured at different times, e.g., on different days; in the same or different experiments in the same laboratory; and/or in different experiments in different laboratories, e.g., allowing comparisons in bivariate and/or multivariate analyses.

As a specific embodiment of the business method described herein, a Standardized Expression Measurement (SEM) Center has been established at the Medical College of Ohio (Toledo, Ohio, USA). The SEM center uses robotic systems to conduct high throughout gene expression measurements, in accordance with some of the methods described herein, and is available for use at geneexpressinc.com.

B. Business Method for R&D Improvement

Some embodiments of the present invention provide a business method of improving drug development. For example, use of a standardized mixture of internal standards, a database of numerical values and/or a database of numerical indices may be used to improve drug development.

Figure 28:
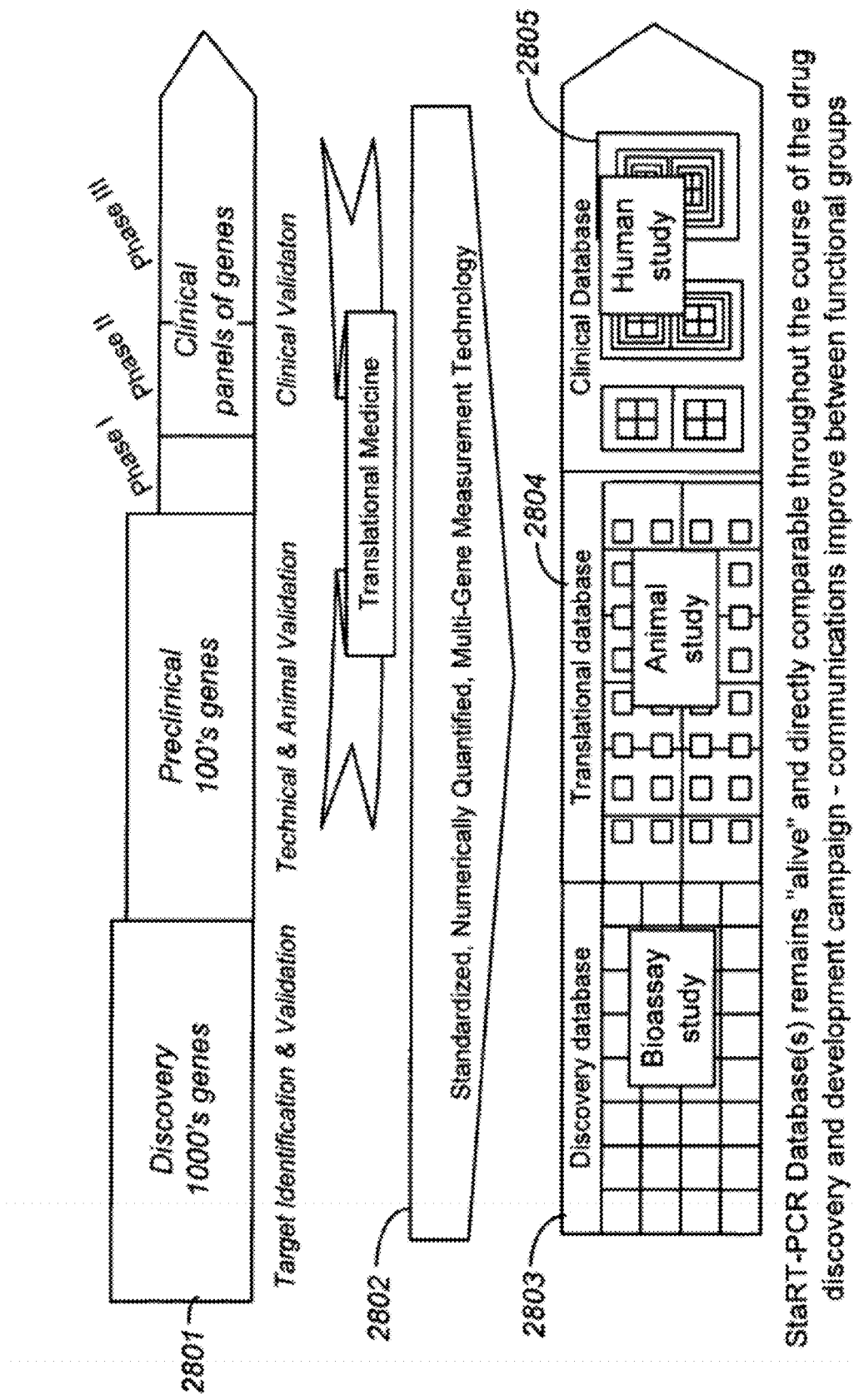
FIG. 28 illustrates the overall process of some embodiments of a business method for improving drug development.

FIG. 28 illustrates the overall process of some embodiments of a business method for improving drug development. Feature 2801 illustrates various stages of drug development. For example, stages can include drug target screening, lead identification, pre-clinical evaluation (e.g., bioassay and/or animal studies), clinical trials and patient treatment.

In some embodiments, modulation of gene expression is measured and/or enumerated at one or more of these stages, e.g., to determine effect a candidate drug. For example, a candidate drug (e.g., identified at a given stage) can be administered to a biological entity. The biological entity can be any entity capable of harboring a nucleic acid, as described above, and can be selected appropriately based on the stage of drug development. For example, at the lead identification stage, the biological entity may be an in vitro culture. At the stage of a clinical trial, the biological entity can be a human patient.

The effect of the candidate drug on gene expression may then be evaluated, e.g., using various embodiments of the instant invention. For example, a nucleic acid sample may be collected from the biological entity and amounts of nucleic acids of interest can be measured and/or enumerated. Preferably, methods are used that allow direct comparison of the amount of nucleic acid in the sample to other nucleic acid measurements, e.g., as described herein. For example, amounts can be provided as numerical value and/or numerical indices.

An amount then may be compared to another amount of that nucleic acid at a different stage of drug development, and/or to a numerical values and/or indices in a database. This comparison can provide information for altering the drug development process in one or more ways.

Altering a step of drug development may refer to making one or more changes in the process of developing a drug, preferably so as to reduce the time and/or expense for drug development. For example, altering may comprise stratifying a clinical trial. Stratification of a clinical trial can refer to, e.g., segmenting a patient population within a clinical trial and/or determining whether or not a particular individual may enter into the clinical trial and/or continue to a subsequent phase of the clinical trial. For example, patients may be segmented based on one or more features of their genetic makeup determined using various embodiments of the instant invention.

For example, consider a numerical value obtained at a pre-clinical stage, e.g., from an in vitro culture that is found to correspond to a lack of a response to a candidate drug. At the clinical trial stage, subjects showing the same or similar numerical value can be exempted from participation in the trial. The drug development process has accordingly be altered, saving time, and costs.

Feature 2802 illustrates the development of databases of numerical data from one or more biological entities at various stages of drug development. Using methods of the instant invention, e.g., a common standardized mixture of competitive templates, data from various specimen, evaluated in different laboratories and/or at different time, can be entered in a database and compared directly.

Feature 2803, for example, illustrates a discovery database, e.g., a database comprising gene expression measurement made during bioassays. Feature 2804 illustrates a translational database, e.g., a database comprising gene expression measurements made during animal studies. Feature 2805 illustrates a clinical database, e.g., a database made during clinical trials. Such databases can facilitate communication between various research groups and/or departments and co-ordination of their efforts, increasing synergy along the various steps of drug development.

Some embodiments of the present invention provide a business method of improving drug development using a database comprising numerical values and/or numerical indices, e.g., as described herein.

In some embodiments, a business method is provided that comprises providing a database of numerical values corresponding to measured amounts of a nucleic acid in a number of samples where the numerical values are directly comparable between the number of samples; collecting a specimen of the nucleic acid from a biological entity administered a candidate drug at a stage of drug development; measuring an amount of the nucleic acid in a first sample of the specimen; directly comparing the measured amount to at least one of the numerical values in the database; and altering a step of drug development based on the comparison.

In some embodiments, a business method is provided that comprises providing a database of numerical indices obtained by mathematical computation of 2 numerical values corresponding to measured amounts of 2 nucleic acids in a number of samples where the numerical indices are directly comparable between the number of samples; collecting a specimen of the 2 nucleic acids from a biological entity administered a candidate drug at a stage of drug development; measuring amounts of each of the 2 nucleic acids in a first sample of the specimen; using the 2 measured amounts to mathematically compute a first numerical index; directly comparing the first numerical index to at least one of the numerical indices in the database; and altering a step of drug development based on the comparison.

Such databases can further improve the process of drug development, e.g., by facilitating comparison of a numerical index and/or value with different biological states and altering a step of drug development accordingly. For example, a numerical index and/or numerical value obtained from potential subjects can used to segment a population and/or to determine whether a given patient is allowed to enter a trial or a subsequent phase. Such numerical values and/or indices may indicate a biological state, e.g., the biological state identifying subjects having a reduced side effect to a given drug.

EXAMPLES

Example I

The following example compares a non-"two-Step" with a "two-step approach, in accordance with some embodiments of the instant invention.

Reagents

10× PCR buffer for the Rapidcycler (500 mM Tris, pH 8.3, 2.5 mg/ μl BSA, 30 mM $MgCl_2$ was obtained from Idaho Technology, Inc. (Idaho Falls, Id.). Thermo 10× buffer (500 mM KCl, 100 mM Tris-HCl, pH 9.0, 1.0% Triton X-100), taq polymerase (5 U/μ), oligo dT primers, RNasin (25 U/ μl), pGEM size marker, and dNTPs were obtained from Promega (Madison, Wis.). M-MLV reverse transcriptase (200 U/ μl) and 5× first strand buffer (250 mM Tris-HCl, pH 8.3, 375 mM KCl, 15 mM $MgCl_2$, 50 mM DTT) were obtained from GibcoBRL (Gaithersburg, Md.). NuSieve and SeaKem LE agarose were obtained from FMC BioProducts (Rockland, Me.). TriReagent was obtained from Molecular Research Center (Cincinnati, Ohio). RNase-free water was obtained from Research Genetics (Huntsville, Ala.). DNA 7500 Assay kit containing dye, matrix and standards was obtained from Agilent Technologies (Palo Alto, Calif.). The lung adenocarcinoma cell line, A549, was purchased from American Type Culture Collection (Rockville, Md.). RPMI-1640 cell culture medium was obtained from Sigma (St. Louis, Mo.). Universal Human Reference RNA was obtained from Stratagene (La Jolla, Calif.). Oligonucleotide primers were custom synthesized by Biosource International (Menlo Park, Calif.). G.E.N.E. system 1 and system 1a gene expression kits were kindly provided by Gene Express National Enterprises, Inc. (Huntsville, Ala.). All other chemicals and reagents were molecular biology grade.

RNA Extraction and Reverse Transcription

Total RNA from cells grown in monolayer was extracted according to the TriReagent Manufacturer Protocol. Universal Human Reference RNA was precipitated according to the manufacturer protocol. Approximately 1 μg total RNA was reverse transcribed using M-MLV reverse transcriptase and an oligo dT primer.

Non-Two-Step Approach

Gene expression measurements were performed using previously published (non-two-step) methods (see, e.g., Willey, J. C. et al., Am. J. Respir. Cell Mol. Biol. 19: 6-17, 1998; Gene Express System1 Instruction Manual, Gene Express National Enterprises, Inc. genexnat.com 2000) with G.E.N.E. system 1 or system 1a gene expression kit (Gene Express National Enterprises, Inc.). Briefly, a master mixture containing buffer, $MgCl_2$, dNTPs, cDNA, competitive template (CT) mixture from G.E.N.E. system 1 or system 1a kit and taq polymerase was prepared and aliquotted into tubes, e.g., 384-well microplate, containing gene-specific primers and cycled either in a Rapidcycler (Idaho Technology, Inc.) or Primus HT Multiblock thermal cycler (MWG-BIOTECH, Inc., High Point, N.C.) or a PTC-100 block thermocycler with heated lid for 35 cycles.

In each protocol of this example, the denaturation temperature was 94° C., the annealing temperature was 58° C., and the elongation temperature was 72° C. for the Rapidcyler, the denaturation time was 5 seconds, the annealing time was 10 seconds, the elongation time was 15 seconds and the slope was 9.9. For the Primus HT Multiblock, the denaturation, annealing and elongation times were each 1 minute, the lid temperature was 110° C. and the lid pressure was 150 Newtons. PCR products were evaluated on an agarose gel or in the Agilent 2100 Bioanalyzer (Agilent Technologies, Inc.) as described below.

Two-Step Approach

In this example, gene expression measurements were obtained for 9 genes. PCR reactions were amplified in two rounds. In the first round, one reaction was set up containing buffer, $MgCl_2$, dNTPs, a previously prepared mixture of cDNA and competitive template mixture (1:1 cDNA from A549 p85 and one of the competitive template mixes from G.E.N.E. system 1a mix D), taq polymerase and primer pairs for the 9 genes. This reaction was cycled for 5, 8, 10 or 35 cycles. Mix D from G.E.N.E. system 1 contained $10^{-12}$M β-actin CT and $10^{-15}$M of CTs for the other genes. The concentration of each primer in the primer mix was 0.05 μg/

µl. Following this amplification, this PCR product was diluted with water for use as a template in round two.

In round two, a standardized mixture containing buffer, $MgCl_2$, taq polymerase and a primer pair specific for a given gene was aliquotted into tubes containing 1 µl of each of the following dilutions of PCR product from the first round: undiluted, 1/5, 1/10, 1/50, 1/100, 1/1,000, 1/10,000, 1/100,000 and 1/1,000,000. These reactions were cycled 35 times and detected on an agarose gel or in the Agilent 2100 Bioanalyzer as described below. Primer pairs used in this round were selected from among the primer pairs used in round one. No additional cDNA or competitive template mixture was added into the PCR reaction in round two, in this example.

For control non-two-step reactions, the mixture of cDNA and competitive template mixture prepared for use in round one of the nine genes was serially diluted prior to amplification: undiluted, 1/5, 1/10, 1/50, 1/100, 1/1,000, and 1/10,000. A 1 µl aliquot of each of these dilutions was combined with a 9 µl aliquot of a standardized mixture containing buffer, $MgCl_2$, Taq polymerase and a primer pair specific for a given gene (0.05 µg/ µl of each primer). These reactions were amplified with only one round of 35 cycles.

Gene expression measurements were also obtained for another 96 Genes using a two-step approach of some embodiments. Samples of cDNA derived from Stratagene Universal Human Reference RNA and competitive template mixes from G.E.N.E. system 1 (which contain CTs for 96 genes) were used in these experiments. A solution containing primers for each of the 96 genes represented by CTs in G.E.N.E. System 1 was included in the first round reactions. This 96 gene primer mix was diluted so that the concentration of each primer was 0.005 µg/ µl . Every round one reaction was cycled 35 times. Round one PCR products then were diluted 100-fold (1 µl of round one product was diluted into 99 µl water). One microliter of diluted round one PCR product was used in each round two reaction along with primers for a given gene selected from among those amplified in round one, and cycled 35 times.

Control non-two-step reactions were conducted using samples of cDNA derived from Stratagene Universal Human Reference RNA and competitive template mixes from G.E.N.E., system 1 as described above. For these experiments, no dilution of the cDNA or competitive template mix was done prior to amplification.

Electrophoresis and Quantitation
Agarose Gel Electrophoresis:

Following amplification, PCR products were loaded directly on to 4% agarose gels (3:1 NuSieve:SeaKem) containing 0.5 µg/ml ethidium bromide. Gels were electrophoresed for approximately one hour at 225V. Electrophoresis buffer was cooled and recirculated during electrophoresis. Gels were visualized with a Foto/Eclipse image analysis system (Fotodyne, Hartland, Wis.). Digital images were saved on a Power Mac 7100/66 computer and Collage software (Fotodyne) was employed for densitometric analysis (or were analyzed using Agilent 2100 Bioanalyzer (as discussed below)).

Quantification of gene expression was determined First, the native template/competitive template (NT/CT) ratio of a reference gene βactin was calculated, as well as and the NT/CT ratios for each of the genes to be measured. Because the initial concentration of competitive template added into the PCR reaction was known, the initial NT concentration could be determined. Since each NT/CT ratio was based on an intercalating dye (ethidium bromide) staining of the PCR products and staining intensity is affected by both the number of molecules present and the length of the molecules in base pairs, NTs were arbitrarily corrected to the size of the competitive template product prior to taking the NT/CT ratio. Heterodimers (HD), when measurable, were corrected to the size of the competitive template and divided by two. One half of the HD value was added to the NT and one half was added to the competitive template prior to taking the NT/CT ratio since one strand of the HD comes from the NT and the other comes from the CT. Second, the calculated number of NT molecules for a given gene was divided by the calculated number of β-actin NT molecules to correct for loading differences.

For embodiments using the two-step approach, genes detected under each condition (varying dilution and/or round one cycle number) were measured against β-actin detected under the same condition. For example, round one of a two-step process contained primers for nine genes including β-actin and c-myc that can be used as reference nucleic acids. A 1/100,000 dilution of the PCR reaction from round one was made and used in round two. An aliquot of this dilution was used in round two to amplify both β-actin and c-myc. Under these conditions, c-myc was measured as $3.40 \times 10^4$ molecules/β-actin molecules when cycled 35 times in round one and 35 times in round two.

FIG. 29 illustrates the results for these experiments. Briefly, PCR reactions were amplified in the Rapidcycler. In round one, a 10 µl reaction mixture was prepared containing buffer, $MgCl_2$, dNTPs, a previously prepared mixture of cDNA and competitive template mixture (1:1 cDNA from A549 p85 and G.E.N.E. system 1 mix D), Taq polymerase and 1 µl of a 10×stock solution of 9 primer pairs (concentration of 0.05 µ/ µl). This reaction was cycled 5, 8, or 35 cycles. Following round one amplification, the PCR products were diluted for use as templates in round two. In round two, 10 µl of PCR reaction were prepared by placing 9 µl of a master mixture containing buffer, $MgCl_2$, Taq polymerase and a primer pair specific for one gene into tubes containing 1 µl of each of the following dilutions of PCR product from the round one: undiluted, 1/5, 1/10, 1/50, 1/100, 1/1,000, 1/10,000, 1/100,000, and 1/1,000,000. These reactions were cycled 35 times. Primer pairs used in round two were selected from among the primer pairs used in round one. No additional cDNA or competitive template mixture was added into the PCR reaction in round two. For non-two-step reactions, the mixture of cDNA and competitive template mixtures prepared for use in round one was serially diluted prior to amplification: undiluted, 1/5, 1/10, 1/50, 1/100, 1/1,000, and 1/10,000. These reactions were amplified in only one round of 35 cycles. A 1 µl aliquot of each dilution was combined with an aliquot of a mixture containing buffer, $MgCl_2$, Taq polymerase and a primer pair specific for one gene (0.05 µg/ µl of each primer). Quantification of gene expression was determined.

Agilent 2100 Bioanalyzer Microcapillary Electrophoresis:

Following amplification, 1 µl of each 10 µl PCR reaction was loaded into a well of a chip prepared according to the manufacturer's protocol for the DNA 7500 Assay. Briefly, 9 µl gel-dye matrix was loaded into the chip in one well and the chips were pressurized for 30 seconds. Two additional wells were filled with gel-dye matrix and the remaining wells each were loaded with 5 µl of molecular weight marker. One microliter of DNA ladder was loaded into a ladder well and 1 µl of PCR product was loaded into each sample well. The chip was vortexed and placed into the Agilent 2100 Bioanalyzer. The DNA 7500 Assay program which was run applies a current sequentially to each sample to separate products. DNA was detected by fluorescence of the intercalating dye in the gel-dye matrix. NT/CT ratios were calculated from the area under the curve for each PCR product and a size correction was made since, as with ethidium bromide stained agarose gel electrophoresis, an intercalating dye was used to detect DNA.

All statistical analyses were conducted using SPSS version 9.0 for Windows. A two-tailed Pearson Correlation test was conducted on logarithmically transformed data to compare gene expression values obtained by using a non-two-step with those obtained by using a "two-step approach, in accordance with some embodiments of the instant invention. The correlation was considered statistically significant if the p value was less than 0.05.

Results: Non-Two Step Approach Amplifying Nine Genes

Figure 30:
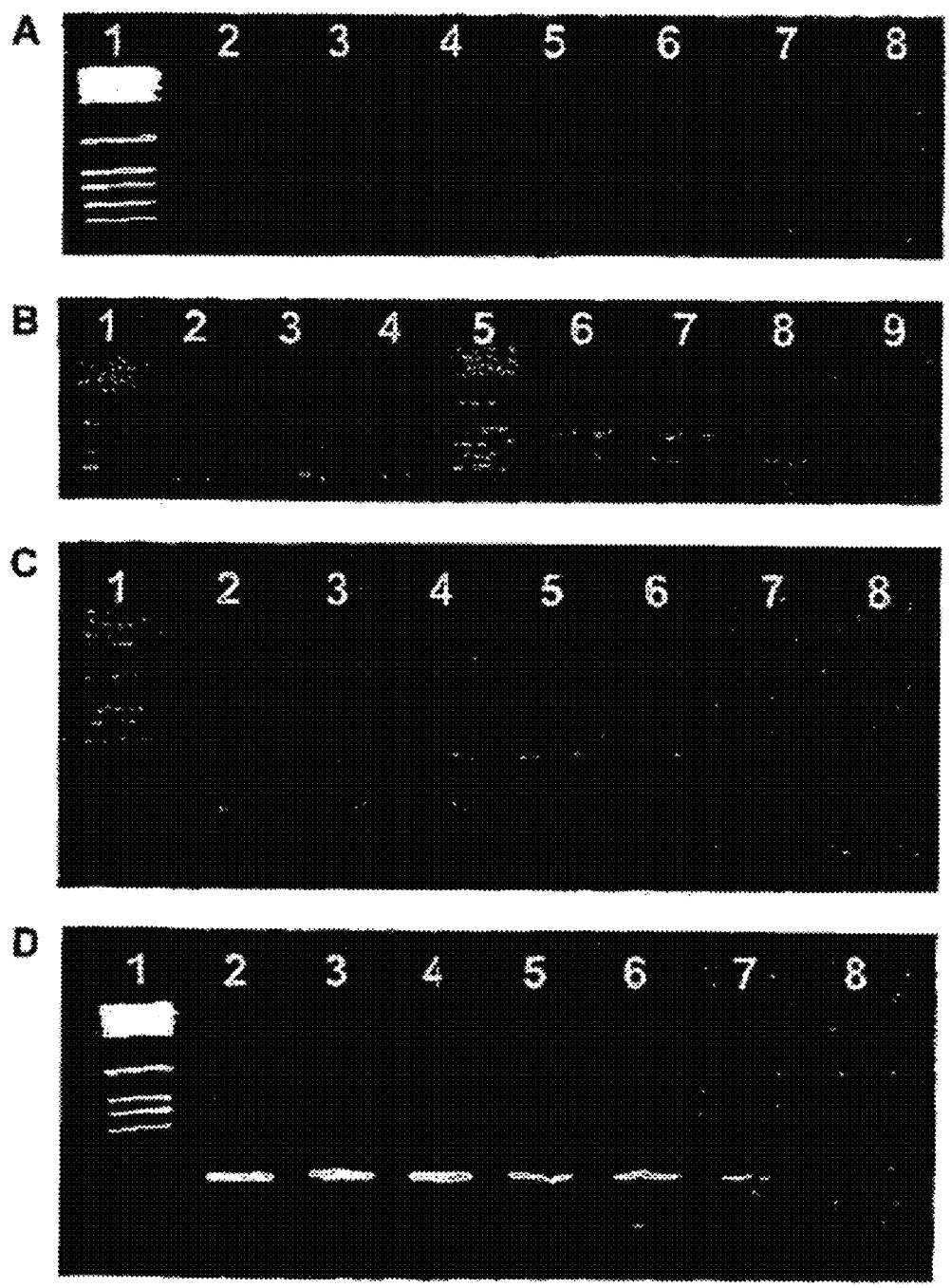
FIG. 30 illustrates the results of experiments comparing a non-two step with a two-step approach, according to some embodiments of the instant invention.

FIG. 30 illustrates the results of experiments comparing non-two step (30A and 30C) with two-step approaches (30B and 30D), according to some embodiments of the instant invention. FIGS. 30A-D illustrate representative results of using a two-step vs. a non-two step process. FIG. 30A illustrates that, in a non-two step reaction using β-actin primers, a dilution of the un-amplified PCR reaction mixture from round one by more than 100, followed by one 35 cycle round of PCR-amplification with one primer pair did not yield any detectable product. Lanes are as follows: Lane 1, pGEM size marker; lane 2, PCR reaction contained undiluted cDNA in which β-actin NT equivalent to 300,000 molecules initial molecules of β-actin CT; lane 3, PCR reactions containing 1:5 diluted cDNA/CT mix, 60,000 molecules; lane 4, 1:10 diluted cDNA/CT mix, 30,000 molecules; lane 5, 1:50 diluted cDNA/CT mix, 6,000 molecules; lane 6, 1:100 diluted cDNA/CT mix, 3,000 molecules; lane 7, 1:1,000 diluted cDNA/CT mix, 300 molecules; lane 8, 1:10,000 diluted cDNA/CT mix, 30 molecules.

FIG. 30B illustrates PCR products obtained from a two-step approach, using an aliquot of round one PCR product and β-actin primers. Lane 1, pGEM size marker; lane 2, 1/500th of the round one 10 µl PCR product (1 pi of a 1:50 dilution), equivalent to 600 initial molecules of β-actin CT; lane 3, 1/1,000th round one PCR product, 300 molecules; lane 4, 1/10,000th round one PCR product, 30 molecules; lane 5, pGEM size marker, lane 6, 1/10,000 round one PCR product, 30 molecules; lane 7, 1/100,000th round one PCR product, 3 molecules; lane 8, 1/1,000,000round one PCR product, 0.3 molecules; lane 9, 1/10,000,000th round one PCR product, 0.003 molecules.

FIG. 30C illustrates a non-two step reaction using catalase primers, where a dilution of the un-amplified PCR reaction mixture from round one by more than 100, followed by one 35 cycle round of PCR-amplification with one primer pair did not yield any detectable product. That is, diluting unamplified PCR reaction mixture by more than 1,000 followed by one 35 cycle round of PCR did not yield product, as was the case with β-actin (FIG. 30A) Lanes are as follows: Lane 1, pGEM size marker; lane 2, PCR reaction contained undiluted cDNA and competitive template mix, equivalent to 3,000 molecules of catalase CT; lane 3, 1:5 diluted cDNA/CT mix, 600 molecules; lane 4, 1:10 diluted cDNA/CT mix, 300 molecules; lane 5, 1:50 diluted cDNA/CT mix, 60 molecules; lane 6, 1:100 diluted cDNA/CT mix, 30 molecules; lane 7, 1:1,000 diluted cDNA/CT mix, 3 molecules; lane 8, 1:10,000 diluted cDNA/CT mix, 0.3 molecules.

FIG. 30D PCR products obtained from a two-step approach, using an aliquot of round one PCR product and catalase primers PCR products for the second round. Lanes are as follows: Lane 1, pGEM size marker; lane 2, 1/100th of the 10 µl round one PCR product (1 µl of a 1:10 dilution), equivalent to 30 molecules catalase CT; lane 3, 1/500th round one PCR product, 6 molecules; lane 4, 1/1,000th round one PCR product, 3 molecules; lane 5, 1/10,000th round one PCR product, 0.3 molecules; lane 6, 1/100,000th round one PCR product, 0.03 molecules; lane 7, 1/1,000,000th round one PCR product, 0.003 molecules; lane 8, 1/10,000,000th round one PCR product, 0.0003 molecules.

Two-Step Approach Amplifying Nine Genes

After 35 cycles of amplification in round one with primer pairs for nine genes, aliquots of the PCR products were diluted and amplified with primers for one of the nine genes. Bright, distinct bands were observed for each gene. Thus, the same amount of cDNA and competitive template mix that is used in a typical non-two-step reaction to measure one gene in one round of amplification was used to obtain nine gene expression measurements in two-step approaches.

Further, the round one PCR product can be diluted more than 100,000-fold for c-myc, 1,000,000-fold β-actin, or 10,000,000-fold for catalase or and still be quantified following amplification with primer pairs for one gene in round two (FIG. 29). In contrast, when the cDNA and competitive template mix used in round one was diluted more than 1,000-fold prior to amplification (or more than 100-fold for β-actin) and then amplified with a single primer pair for any one of these genes in a single round of 35 cycles, no detectable product was observed. The amount of amplified product that could be diluted prior to round two and still yield detectable product after round two was directly related to the number of round one cycles.

Increasing the number of cycles used in round one increased the amount the PCR product that could be diluted prior to round two and still be detectable after round two amplification. Therefore, more gene expression measurements can be made using a sample when it is amplified in the two-step approach (e.g., with 35 cycles used in each round) than when fewer cycles (e.g., 5, 8 and 10 cycles) are used in round one, or when no second round is used. Details for each gene and each condition are shown in FIG. 29. Representative gels of control non-two step reactions and two-step reactions are shown in FIG. 30.

Two-Step Approach Amplifying 96 Genes

Gene expression values obtained by non-two-step and 96 gene two-step reaction using cDNA derived from Stratagene Universal Human Reference RNA are shown in FIGS. 4A-4B. Although 96 primer pairs were included in the two-step reactions, gene expression values for only 93 genes are reported because 1) each gene expression value is reported as molecules of a given gene/$10^6$ molecules of β-actin so β-actin values are not reported, 2) although two sets of reagents to measure GAPD gene expression (GAPD CT 1 and GAPD CT2) are included in the G.E.N.E. system 1 kit, only GAPD CT1 was measured in this sample and, 3) reagents for one gene, BAX a, provided in the kit did not pass quality control testing done by G.E.N.E., Inc. so this gene was not assessed in this study. Bivariate analysis of gene expression values using the two approaches revealed a highly significant (p=0.001) positive correlation (r=0.993). The two approaches were reproducible showing not significant differences in measurements for more than 90% of genes assayed. (FIG. 29).

Figure 31:
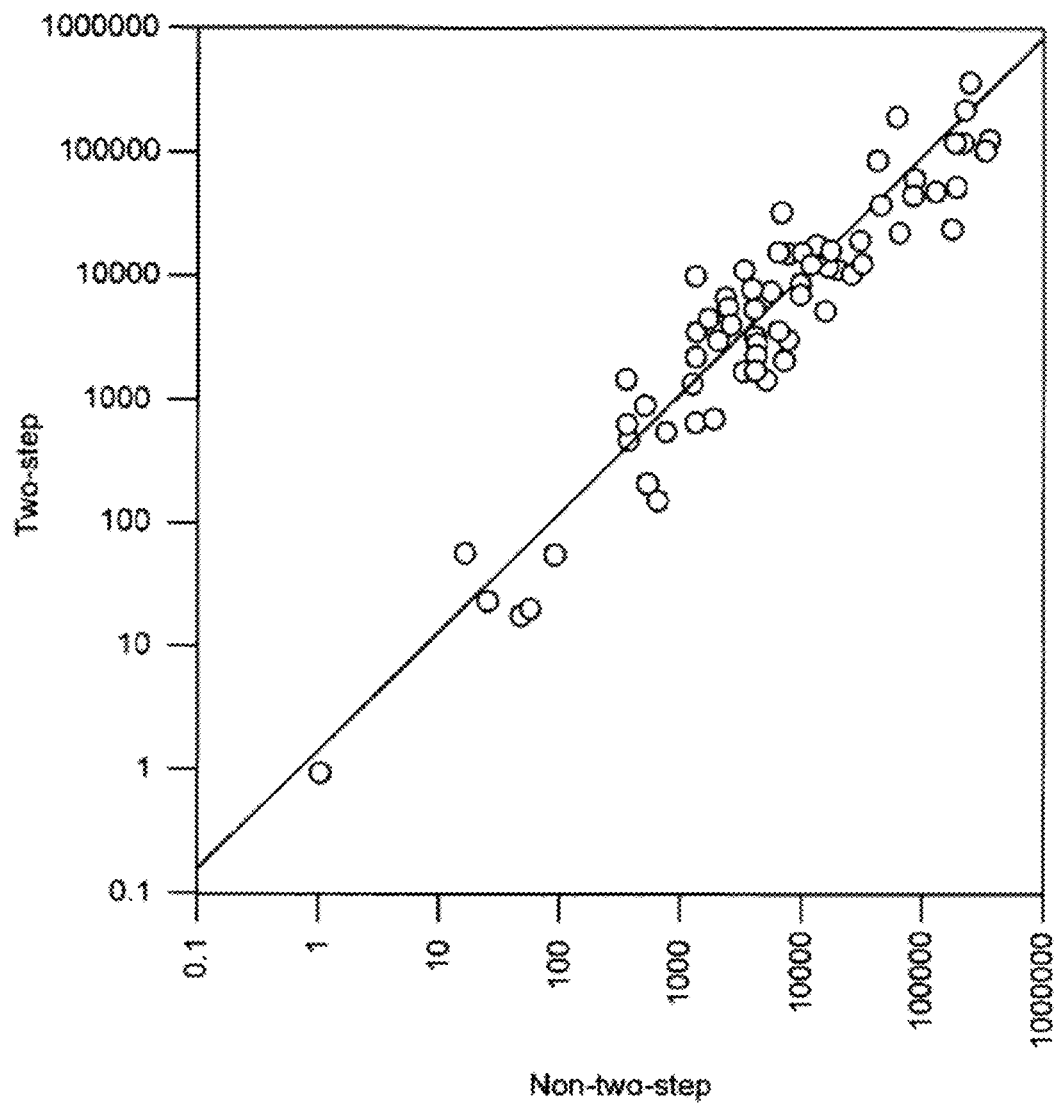
FIG. 31 is a graph showing the correlation of gene expression values obtained by either 96 gene two-step or non-two-step approaches.

FIG. 31 is a graph showing the correlation of gene expression values obtained by either 96 gene two-step or non-two-step approaches. Samples of cDNA derived from Stratagene Universal Human Reference RNA were combined with CT mix (mixes B, C, D, E and F from G.E.N.E.

system 1 were used) and amplified either by uniplex StaRT-PCR or by 96 gene multiplex StaRT-PCR with primer pairs for all genes in G.E.N.E. system 1. Mean values are presented in FIGS. 4A-4B for the 93 genes that could be evaluated. Of these, 79 were measured by both non-two-step and two-step approaches and could be compared. Gene expression values are presented as molecules of mRNA per $10^{-6}$ β-actin mRNA molecules. Values obtained by non-two step methods are plotted along the X axis and values obtained by two-step methods are plotted along the Y axis.

Two-Step Approach Measurements on Small Samples

FIGS. 1 and 2 indicate gene expression data obtained from small amounts of materials. FIG. 1 shows data collected from a fine needle aspiration biopsy of non-small cell lung-cancer (NSCLC) primary tissues cells. All data was measured using the competitive template mixtures from the GENE System 1 by 18 multiplex PCR.

FIG. 2 shows data collected from primary tissue cells from a lung donor who had no disease of the lung. The gene expression was also collected using 96 gene multiplex PCR with the competitive template mixes from the GENE System 1.

Example II

The following example provides additional details of an overall process of evaluating gene expression measurements according to some embodiments of the instant invention Materials 1. Standardized RT-PCR reagents, including primers and standardized mixtures are purchased from Gene Express, Inc. (GEI, Toledo, Ohio).

2. Buffer for Idaho Rapidcycler air thermocycler: 500 mM Tris-HCl, pH 8.3, 2.5 μg/μ, BSA, 30 mM MgCl$_2$ (Idaho Technology, Inc., Idaho Falls, Id.).

3. Buffer for block thermocyclers, Thermo 10×, 500 mM KCl, 100 mM Tris-HCl, pH 9.0, 1.0% Triton X-100 (Promega, Madison, Wis.).

4. Taq polymerase (5 U/μL), Moloney Murine Leukemia Virus (MMLV) reverse transcriptase, MMLV RT 5× first strand buffer: 250 mM Tris-HCl, pH 8.3, 375 mM KCl, 15 mM MgCl$_2$, 50 mM dithiothreitol, oligo dT primers, Rnasin, pGEM size marker, and deoxynucleotide triphosphates (dNTPs) also are obtained from Promega.

5. TriReagent is obtained from Molecular Research Center, Inc. (Cincinnati, Ohio).

6. Ribonuclease (Rnase)-free water and TOPO TA cloning kits are obtained from Invitrogen (Carlsbad, Calif.). The quality of the RNase-free water can be important for the efficient extraction of intact RNA. For example, inadequate DEPC treatment and/or inadequate removal of DEPC after treatment can inhibit reverse transcription and PCR.

7. GigaPrep plasmid preparation kits are purchased from Qiagen (Texas).

8. Caliper AMS 90SE chips are obtained from Caliper Technologies, Inc. (Mountain View, Calif.).

9. DNA purification columns are obtained from QiaQuick (Qiagen, Valencia, Calif.).

RNA Extraction and Reverse Transcription

RNA Extraction: Cell suspensions can be pelleted, the supernatant poured off, and the pellet dissolved in TriReagent and extract (according to manufacturer's instructions and previously described methods, see, e.g., Bustin, S. A. (2000) Absolute quantification of mRNA using real-time reverse transcription polymerase chain reaction assays. J. Mol. Endocrinol. 5, 169-193. The RNA pellet can be stored under ethanol at −80° C., or suspended in RNAse free water and frozen at −80° C. It may be stored in this condition for years. The quality of the RNA can be evaluated on an Agilent 2100 using the RNA chip, according to manufacturer's instructions.

Reverse Transcription: 1 μg total RNA can be reverse transcribed using MMLV RT and an oligo dT primer as previously described. See, e.g., Willey, J. C., Coy, E. L., Frampton, M. W., et al. 1997) Quantitative RT-PCR measurement of cytochromes p450 1A1, 1B1, and 2B7, microsomal epoxide hydrolase, and NADPH oxidoreductase expression in lung cells of smokers and non-smokers. Am. J. Respir. Cell Mol. Biol. 17, 114-124. For small amounts of RNA (e.g., less than about 100 ng), the efficiency of reverse transcription may be improved with using Sensicript™ rather than MMLV reverse transcriptase, e.g., efficient reverse transcription may be obtained about 50 ng of RNA with Sensiscript.™. The reaction can be incubated at 37° C. for 1 h.

Synthesis and Cloning of Competitive Templates

Internal standard competitive templates (CTs) can be constructed based on previously described methods. See, e.g., Willey, J. C., Crawford, E. L., and Jackson, C. M. (1998) Expression measurement of many genes simultaneously by quantitative RT-PCR using standardized mixtures of competitive templates. Am. J. Respir. Cell Mol. Biol. 19, 6-17; Crawford, E. L., Peters, G. J., Noordhuis, P., et al. (2001) Reproducible gene expression measurement among multiple laboratories obtained in a blinded study using standardized RT (StaRT)-PCR. Mol. Diagn. 6, 217-225; and/or Celi, F. S., Zenilman, M. E., and Shuldiner, A. R. (1993) A rapid and versatile method to synthesize internal standards for competitive PCR. Nucleic Acids Res. 21, 1047.

Native Template Primer Design

Before a CT for a gene is constructed, a primer pair can be designed that amplifies (preferably, efficiently amplifies) native cDNA corresponding to the expressed gene. For example, primers can be designed with one or more of the following characteristics: (1) an ability to amplify from about 200 to about 850 bases of the coding region of genes of interest; (2) an annealing temperature of about 58° C. (tolerance of +/−1° C.). Primer 3.1 software (Steve Rozen, Helen J. Skaletsky, 1996, 1997) Primer 3 can be used to design the primers (code available at genome.wi.netedu/genome_software/other/primer3.html) in some embodiments. Primers were initially designed using Primer 3.1 software to amplify from about 200 to about 800 bases of the coding region of targeted genes with an annealing temperature of about 58° C. (tolerance of +/−about 1° C.). This allowed the PCR reactions in this example to be run under identical or nearly identical conditions and further allows for automation and high throughput applications, including microfluidic capillary gel electrophoresis. For example, primer sequences and Genbank accession numbers for genes certain genes are available at www.geneexpressinc.com. Primers can also be designed to amplify from about 20 to about 2,000 bases, in other examples.

Native Template Primer Testing

Designed primers can be synthesized and used to amplify native template of cDNA corresponding to the gene(s) of interest. The presence of a single strong band after 35 cycles of PCR can verify that the primers are sufficiently efficient and/or specific for some embodiments. For example, primers can be tested using reverse transcribed RNA from a variety of tissues and/or cDNA clones known to represent the gene(s) of interest. In some embodiments, primer pairs that fail to amplify the target gene in any tissue or individual cDNA clone, e.g., less than about 10% of the time, can be redesigned and the process repeated.

Competitive Template Primer Design

Figure 32:
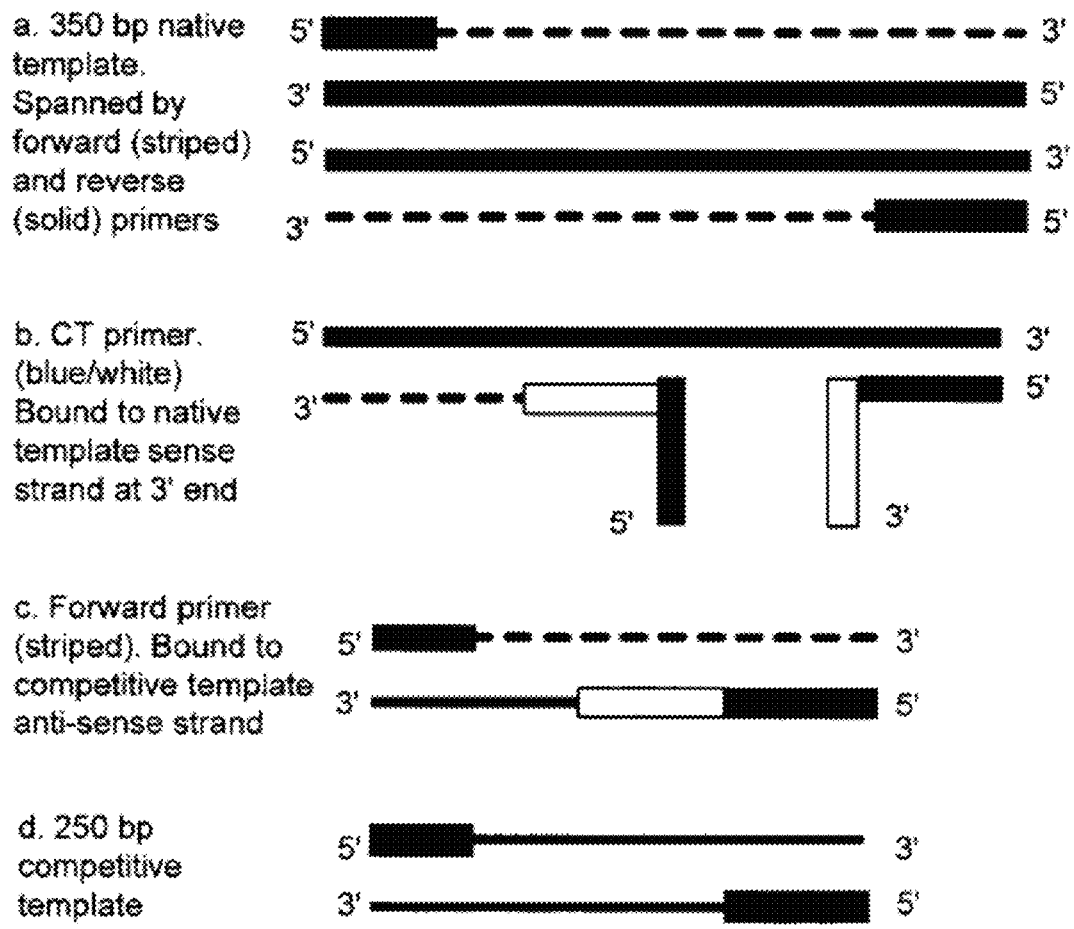
FIG. 32 illustrates a method for designing competitive template for use in some embodiments of the instant invention.

A CT primer can be prepared according to previously described methods and/or as illustrated in FIG. 3. FIG. 32a illustrates Forward (striped bar) and reverse (black bar) primers (approx 20 bp in length) that span a 150-850 bp region can be used to amplify the native template (NT) from cDNA. Taq polymerase can synthesize DNA from these primers (dashed lines) using the NT.

FIG. 32b illustrate that after testing that native template primers work, a CT primer can be designed to be about 40 bp primer with the sequence for the reverse primer (black bar) at the 5' end, and a 20 bp sequence homologous to an internal native template sequence (white bar) at the 3' end, collinear with the reverse primer sequence. The 3' end of this 40 bp primer can be designed to be homologous to a region about 50 to about 100 bp internal to the reverse primer. The 5' end of this about 40 bp primer can hybridize to the region homologous to the reverse primer, while the 3' end can hybridize to the internal sequence. Furthermore, Taq polymerase can synthesize DNA using the primers bound at the 3' end (dashed line) and not the primer bound at the 5' end.

FIG. 32c illustrates that in the next PCR cycle, the DNA newly synthesized using the about 40 bp primer hybridized to the internal sequence can be bound to forward primer (striped bar), and a homologous strand can be synthesized. FIG. 32d illustrates that this can generate a double stranded CT with the reverse primer sequence about 100 bp closer to the forward primer than occurs naturally in the NT. See, e.g., Chomczynski, P. and Sacchi, N. (1993) Single-step method of RNA isolation by acid guanidinium thiocyanate-phenol-chloroform extraction. Anal. Biochem. 62, 156-159; Celi, F. S., Zenilman, M., and Shuldiner, A. R. (1993) A rapid and versatile method to synthesize internal standards for competitive PCR. Nucleic Acids Res. 1, 1047).

Competitive Template Primer Testing

The prepared CT may be tested. For example, the CT primer can be paired with the designed forward primed and used to amplify CT from native cDNA. Before each competitive template in this example was constructed, each primer pair in this example was tested using reverse transcribed RNA from a variety of tissues or individual cDNA clones known to represent the gene of interest as a quality control. For primer pairs that failed (about 10% of the time), new ones were designed and the process repeated. For each gene, a competitive template primer (a fusion oligo of about 40 bp) then was prepared. The 3' end of each fusion primer consisted of an about 20 base sequence homologous to a region about 50 to about 100 bases 3' to the reverse primer. The 5' end was the 20 bp reverse primer.

Competitive Template-Internal Standard Production

For each of a number of genes to be assay, five 10 μL PCR reactions can be set up, using the designed NT forward primer and the CT primer, and amplified for 35 cycles. The products of the five PCR reactions can be combined, electrophoresed on a 3% NuSieve gel in 1× TAE, and the band of correct size cut from the gel and extracted using a QiaQuick method (Qiagen, Valencia, Calif.). The purified PCR products can be cloned into PCR 2.1 vector using TOPO TA cloning kits (Invitrogen, Carlsbad, Calif.) then can be transformed into HS996 (a T1-phage resistant variant of DH10B). After cloning, transformation, and colonies can be plating on LB plates containing X-Gal, IPTG, and carbenicillin and 3 isolated white colonies selected. Plasmid minipreps can be prepared, EcoRI digestion performed and the digested products electrophoresed on 3% SeaKem agarose. For those clones showing an insert based on EcoRI digestion, it can be confirmed that the insert is the desired one by sequencing the same undigested plasmid preparation using vector specific primers. The clones with homology to the correct gene sequence and having 100% match for the primer sequences can be used in large-scale CT preparation and can be included in standardized mixtures. For example, those that pass this quality control assessment can be used in the following steps.

Plasmids from each quality-assured clone then were prepared in quantities large enough (about 1.5 L) to allow for about 1 billion assays (approximately 2.6 mg). The plasmids were purified from the resultant harvested cells using the Qiagen GigaPrep kit. Plasmid yields were assessed using a Hoeffer DyNAQuant 210 fluorometer.

In this example, an aliquot of each plasmid preparation was again sequenced as a quality control. For each competitive template that passed the quality control steps outlined in this example, the sensitivity of the cloned CT and primers was assessed by performing PCR reactions on serial dilutions and determining the limiting concentration that still yielded a PCR product. In this example, only those preparations and primers that allow for detection of 60 molecules or less (e.g., a product obtained with $10^{-16}$ CT in 10 μl PCR reaction volume) were allowed to be included into standardized competitive template mixtures. In this example, most of the assays that were developed had a sensitivity of about 6 molecules or less (e.g., more than 80% of the CTs that were developed had a sensitivity of 6 molecules or less or $10^{-17}$ M CT).

Preparation of Standardized Mixtures

Plasmids from quality-assured preparations were mixed into competitive template mixtures representing either 24 or 96 genes. The concentration of the competitive templates in the 24 gene standardized mixtures were $4 \times 10^{-9}$ M for β-actin CT, $4 \times 10^{-10}$ M for GAPD (CT1), $4 \times 10^{-11}$ M for GAPD (CT2), and $4 \times 10^{-8}$ M for each of the other CTs in this example.

The 24 gene competitive template mixes can be linearized by NotI digestion prior to preparation of a series of serially-diluted standardized mixtures described below. For example, the mixes can be incubated with NotI enzyme at a concentration of 1 unit/μg of plasmid DNA in about 15 mL of buffer at 37° C. for 12-16 hours. Four linearized 24-gene competitive template mixes were combined in equal amounts to yield 96-gene competitive template mixes having concentrations of $10^{-9}$ M for β-actin, $10^{-10}$ M GAPD (CT1), $10^{-11}$ M GAPD (CT2), and $10^{-8}$ M for the other CTs. These mixes then can be serially diluted with a reference gene CT mix, e.g., comprising the $10^{-9}$ M β-actin, $10^{-10}$ M GAPDH (CT1), $10^{-11}$ M GAPDH(CT2) mix, yielding a stock series at concentrations of $10^{-9}$ M for β-actin, $10^{-10}$ M for GAPD CT1, $10^{-11}$ M for GAPD CT2, and $10^{-8}$, $10^{-9}$, $10^{-10}$, $10^{-11}$, $10^{-12}$, and $10^{-13}$ M for the other CTs used in this example.

These stock concentrations can be diluted 1,000-fold to provide working dilutions, e.g., to yield a series of six serially-diluted standardized mixtures (A-F) at concentrations of $10^{-12}$ M for β-actin, $10^{-13}$ M for GAPD CT1, $10^{-14}$ M for GAPD CT2, and $10^{-11}$(A), $10^{-12}$(B), $10^{-13}$(C), $10^{-14}$(D), $10^{-15}$(E), and $10^{-16}$ M (F) for the other CTs used in this example.

The following illustrates use of a series of serially-diluted standardized mixtures, in accordance with some embodiments of the instant invention. In this example, "SMIS"

refers to a standardized mixture of internal standards, prepared in accordance with embodiments of the instant invention.

A volume of cDNA sample (diluted to a level in balance with the amount of (β-actin CT molecules in 1 µL of SMIS ($6\times10^5$) molecules) can be combined and mixed with an equal volume of the appropriate SMIS A-F, such that the NT/CT ratio for a nucleic acid being measured will be greater than about 1/10 and less than about 10/1. For example, if among previous samples, a gene has been expressed within a range of $10^1$-$10^3$ molecules/$10^6$ β-actin molecules, the gene will be measured using SMIS E. In contrast, if among previous samples, a gene has been expressed within a range of $10^5$-$10^7$ molecules/$10^6$ β-actin molecules, the gene will be measured using SMIS B. If the appropriate SMIS is not known for a particular gene in a sample from a particular type of tissue, expression can be measured using both SMIS C and E. This allows measurement over four orders of magnitude. For the rare samples that express the gene outside of the expected ranges, a follow-up analysis with the appropriate CT mix can be performed. For example, for the few genes expressed at very high or low level, analysis can be repeated with SMIS A or F.

A 1 µL volume of the cDNA/SMIS mixture can be used for each gene expression assay to be performed and can be combined with other components of the PCR reaction mixture (e.g., buffer, dNTPs, Mg++, Taq polymerase, $H_2O$). Tubes or wells can be prepared with a primer pair for a single gene to be measured. If products are to be analyzed by PE 310 device, the primers can be labeled with appropriate fluor. Aliquots of this PCR reaction mixture can be placed into individual tubes each containing primers for a single gene. Using this approach, the ratio of CT for every gene in the mixture relative to its corresponding NT in the cDNA is fixed simultaneously. When aliquots of this mixture are transferred to PCR reaction vessels, although there may be variations in loading volumes resulting from pipetting, variation is controlled in the NT/CT ratio for any gene relative to the NT/CT ratio for a reference gene. This approach also enables standardized expression measurement.

PCR Amplification

Each reaction mixture can be cycled either in an air thermocycler (e.g., Rapidcycler (Idaho Technology, Inc., Idaho Falls, Id.) or block thermocycler (e.g., PTC-100 block thermal cycler with heated lid, MJ Research, Inc., Incline Village, Nev.) for 35 cycles. In either thermocycler, the denaturation temperature is 94° C., the annealing temperature is 58° C., and the elongation temperature is 72° C.

Separation and Quantification of NT and CT PCR Products a. Agarose gel. Following amplification, the entire volume of PCR product (typically 10 µL) can be into wells of 4% agarose gels (3/1 NuSieve: Sea Kem) containing 0.5 µg/mL ethidium bromide. Gels can be electrophoresed for approx 1 h at 225 V in continuously chilled buffer, and then visualized and quantifying with an image analyzer (products available from Fotodyne, BioRad). Following electrophoresis, the relative amount of NT and CT can be determined by densitometric quantification of bands that have been stained by an intercalating dye (e.g., ethidium bromide).

b. PE Prism 310 Genetic Analyzer CE Device. PCR products can be amplified with fluor-labeled primers. One microliter of each PCR reaction can be combined with 9 µL of formamide and 0.5-0.1 µL of ROX size marker. Samples can be heated to 94° C. for 5 min and flash cooled in an ice slurry. Samples can be loaded onto the machine and electrophoresed at 15 kV, 60° C. for 35-45 min using POP4 polymer and filter set D. The injection parameters can be 15 kV, 5 sec. Fragment analysis software, GeneScan (Applied Biosystems, Inc., Foster City, Calif.) can be used to quantify peak heights that are used to calculate NT/CT ratios. No size correction need be performed where each DNA molecule was tagged with one fluorescent marker from one labeled primer.

c. Agilent 2100 Bioanalyzer Microfluidic CE Device. The DNA 7500 or DNA 1000 LabChip kit may be used. Following amplification, 1 µL of each 10 µL PCR reaction can be loaded into a well of a chip prepared according to protocol supplied by manufacturer. DNA assay can be run, which applies a current to each sample sequentially to separate NT from CT. DNA can be detected by fluorescence of an intercalating dye in the gel-dye matrix. NT/CT ratios can be calculated from area under curve (AUC) and one or more size corrections can be made.

d. Caliper AMS 90 Microfluidic CE Device. The PCR reactions can be set up in wells of a 96- or 384-well microplate. Following amplification, the microplate can be placed in a Caliper AMS 90 and protocol recommended by the manufacturer followed. The AMS 90 can remove and electrophorese a sample from each well sequentially every 30 sec. The NT and CT PCR products can be separated and quantified. Where detection is through fluorescent intercalating dye, size correction need not be necessary.

e. MALDI-TOF separation. A method for separating PCR products recently was described. Ding, C. and Cantor, C. R. (2003) A high-throughput gene expression analysis technique using competitive PCR and matrix-assisted laser desorption ionization time-of-flight MS. Proc. Natl. Acad. Sci. USA 100, 3059-3064. This method may be used to quantify products resulting from amplification of cDNA in the presence of SMIS.

Figure 33:
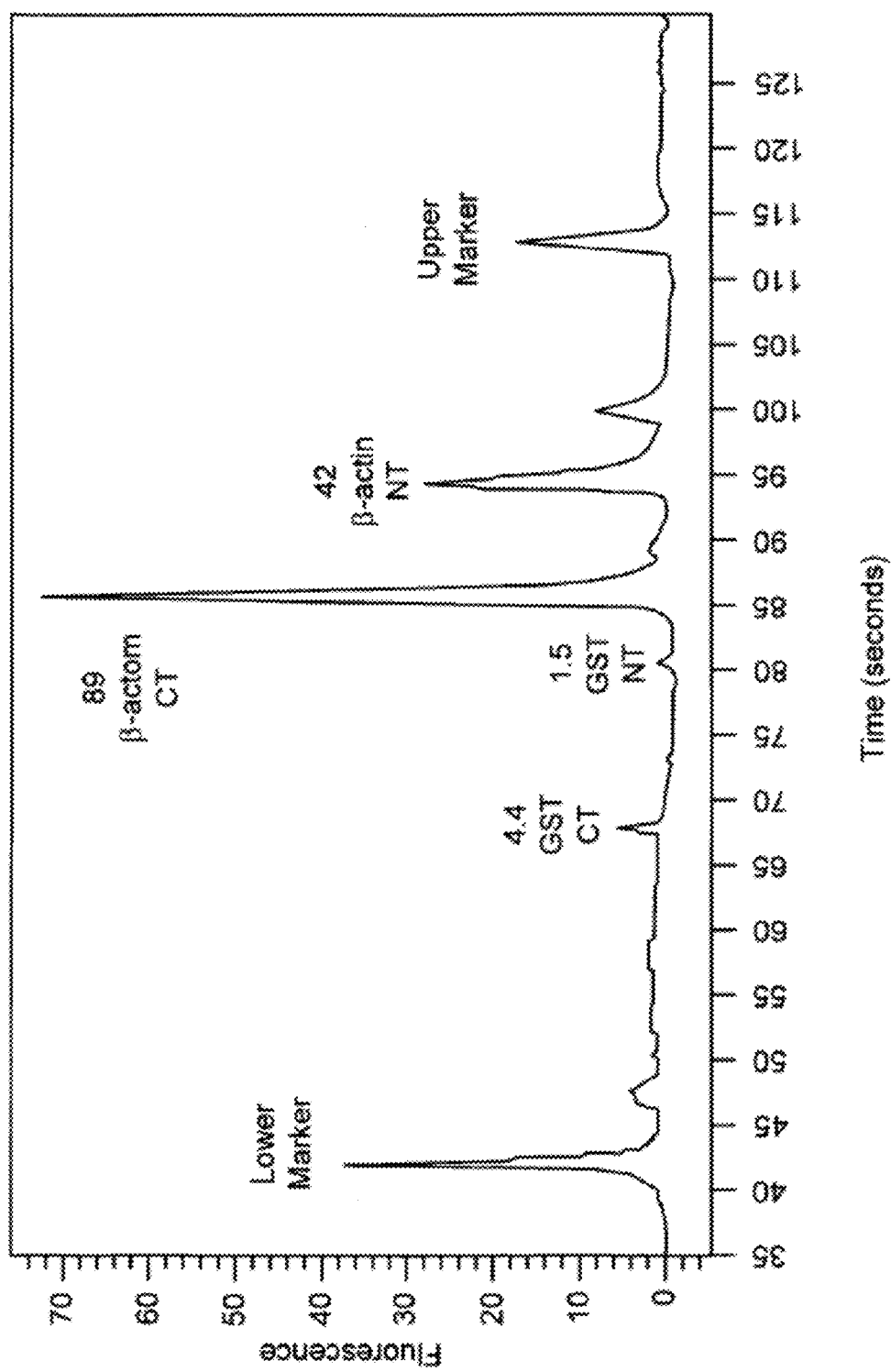
FIG. 33 illustrates a calculation of gene expression based on densitometric values for electrophoretically separated amplified product of GST NT and CT.

Calculation of Gene Expression—Calculating the Number of NT Molecules Present at the Beginning of PCR for Each Gene The steps taken to calculate gene expression can be based on densitometric measurement values for electrophoretically separated NT and CT PCR products such as those presented in FIG. 33. The calculations below are based on the example in FIG. 3, measuring GST gene expression relative to β-actin in an actual bronchial epithelial cell (BEC) sample. A volume of SMIS containing 600,000 competitive template molecules for β-actin and 6000 competitive template molecules for GST was included at the beginning of the PCR reaction. For each gene, the NT and competitive template amplify with the same efficiency. Thus, the β-actin gene NT/CT PCR product ratio allows determination of the number of βactin NT copies at the beginning of PCR and the target gene NT/CT ratio allows determination of the number of target gene copies of the beginning of PCR, as detailed in the steps below:

1. Correct NT PCR product area under the peak (AUP) to length of CT DNA.
2. Determine ratio of corrected NT AUP relative to CT AUP.
3. Multiply NT/CT value x number of CT molecules at beginning of PCR.

A calculation of β-actin molecules using above protocol is outlined below:

1. 416/532β-actin CT bp/NT bp)×42 (NT AUP)=33 (corrected NT value).
2. Correct β-actin NT AUP divided by β-actin CT AUP=0.37.

3. 0.37 β-actin NT/CT)×600,000 (number of (β-actin CT molecules at beginning of PCR)=222,000 NT molecules at beginning of PCR.

A calculation of GST molecules using above protocol is outlined below:
1. 227/359 (GST CT bp/NT bp)×1.5 (NT AUP)=0.95 (corrected NT AUP).
2. 0.95 (GST corrected NT AUP) divided by 4.4 (GST CT AUP)=0.22.
3. 0.22 (GST NT/CT)×6000 (number of GST CT molecules at beginning of PCR)=1290 GST NT molecules at beginning of PCR.

Calculation of molecules of GST/$10^6$ β-actin molecules is 1290 GST NT molecules/222,000 β-actin NT molecules=580 GST molecules/$10^6$ β-actin molecules.

Example III

The following example provides additional details of a non-two-step approach for evaluating gene expression according to some embodiments of the instant invention RNA extraction Purified deoxyribonucleotides obtained from Pharmacia (Piscataway, N.J.) were diluted to a stock solution of 10 mM. Recombinant *Thermus aquaticus* DNA polymerase (Taq polymerase), Avian myeloblastosis virus (AMV) reverse transcriptase, and ribonuclease inhibitor (RNasin) were obtained from Promega (Madison, Wis.). EcoRI enzyme was obtained from USB (Cleveland, Ohio). Primers were prepared on an Applied Biosystems model 391 PCR-Mate EP™ synthesizer. PCR was performed in a Perkins, Elmer, Cetus DNA Thermal Cycler 480. The other buffers and solutions used were from various sources and were molecular biology grade.

Studies were performed on a human papillomavirus-immortalized human bronchial epithelial cell line (BEP2D) (Willey et al., Cancer Res. 5 1:5370-5377, 1990). The isolation of RNA was as follows: RNA was isolated based on the method described by Chomczynski and Sacchi (Analytical Biochemistry 1 6 2:156-159, 1987) Culture medium was removed from flasks containing the BEP2D cell line. Immediately GIT (4.0 M guanidinium thiocyanate, 0.1M Tris Cl pH=7.5, 1% β-mercaptoethanol) buffer was placed on the cells (approximately 500 μL, per 5-10 million BEP2D cells). Each 500 μL, of GIT buffer containing the lysed cells was then transferred to a 1.5 mL microfuge tube. To each microfuge tube was added sequentially 50 .μL of 2M Na acetate pH=4, 500 mL, of water saturated phenol and 100 mL of chloroform-isoamyl alcohol mixture (49:1). The tubes then were shaken thoroughly, placed on ice for 15 min, and microcentrifuged for 20 min at 14,000 RPM and 4° C. The aqueous phase of each tube was transferred to a fresh tube and the above extraction was repeated. Again, the aqueous phase of each tube was transferred to a fresh tube with isopropanol (500 μL), and placed at −70° C. for 15 min. The tubes were then microcentrifuged for 20 min at 14,000 RPM and 4° C. The RNA was washed twice with 70% ethanol and vacuum dried. RNA was taken up in 0.1% diethyl pyrocarbonate (DEPC) treated $H_2O$ and quantified by spectrophotometry (Gilford Instrument Spectrophotometer 260).

Reverse Transcription

The reverse transcription was conducted as follows: the extracted RNA was placed in a sterile microfuge tube. For each 1 μg of RNA, 0.2 mg oligo dT was added. This was heated at 65° C. for 5 min and placed on ice for one min. To this was added 2 μL 1-mM dNTP's, 2 μL reverse transcriptase (RT) buffer (500 mM Tris, 400 mM KCl, and 80 mM $MgCl_2$), 0.5 μL RNasin, and 1 μL AMV reverse transcriptase (9.500 units/ml). This was incubated at 42° C. for one hour and heated to 80° C. for 10 min to halt the reaction. Resultant cDNA was stored at −20° C.

Preparation of Primers and CTs, PCR Amplification and Gel Electrophoresis

The preparation of primers and competitive templates was as follows: suitable sequences were identified using the Oligo™ Primer Analysis Software (National Biosciences, Hamel, Minn.) The primers were made using an Applied Biosystems Model 391 PCR-Mate DNA Synthesizer. The primer sequences are described below.

Glutathione Peroxidase (GSH-Px) (Chada et al., *Genomics* 6:268-271, 1990)

The "outer" primers were used to amplify both the nucleic acid to be measured and its competitive template and result in a product length of 354 base pairs. The "outer" primers are Sequence I.D. No. 1 (Chada et al., Genomics 6:268-271, 1990) Pos. 241 5'-GGGCCTGGTGGTGCTTCGGCT-3' (coding sense) which corresponds to bases 241-261 of the cloned sequence, and Sequence I.D. No. 2(Chada et al., Genomics 6:268-271, 1990) Pos. 74 5'-CAATGGTCTG-GAAGCGGCGGC-3' (anti-coding sense) which anneals to bases 574-594.

The "inner" primers used to synthesize the mutated competitive template remove an EcoRI restriction endonuclease recognition site (GAATTC) by changing a native cDNA base pair (bold bases). The "inner" primers are Sequence I.D. No. 3 (Chada et al., Genomics 6:268-271, 1990) Pos. 309 5'-ATTCT GATTTC CCTCAAGTACGTC-CGGCCT-3' (coding sense)

Sequence I.D. No. (Chada et al., Genomics 6:268-271, 1990) Pos. 309 3'-TAAGA CTAAAG GGAGTTCATGCA-GGCCGGA-5' (anti-coding sense).

Both primers correspond to bases 309-338 of the cloned sequence. The mutation results from the substitution of a T for the native A at position 316 of the sense strand. Restriction endonuclease digestion of the native GSH-Px yields products of 280 and 74 base pairs.

Glyceraldehyde-3-Phosphate Dehydrogenase (GAPDH) (Tso et al., *Nucleic Acids Res.* 13:2485-2502, 1985)

The "outer" primers used to amplify both the native and mutated templates result in a product length of 788 or 790 base pairs. The "outer" primers are:

Sequence I.D. No. 5 (Tso et al., Nucleic Acids Res. 13:2485-2502, 1985) Pos. 46 5'-GGTCGGAGTCAACG-GATTTGGTCG-3' (coding sense) corresponding to bases 9-32 of the cloned sequence, and Sequence I.D. No. 6 (Tso et al., Nucleic Acids Res. 13:2485-2502, 1985) Pos. 812 5'-CCTCCGACGCCTGCTTCACCAC-3' (anti-coding sense) which anneals bases 777-798.

The "inner" primers used to synthesize the mutated template create an EcoRI restriction endonuclease recognition site (GAATTC) by changing one native cDNA base pair (bold bases). The "inner" primers are:

Sequence I.D. No. 7 (Tso et al., Nucleic Acids Res. 13:2485-2502, 1985) Pos. 234 5'-TGATCAATG GAATTC CCATCACCA-3' (coding sense)

Sequence I.D. No. 8 (Tso et al., Nucleic Acids Res. 13:2485-2502, 1985) Pos. 234 3'-ACTAGTTAC CTTAAG GGTAGTGGT-5' (anti-coding sense)

Both primers correspond to bases 199-222 of the cloned sequence. The mutation results from the substitution of a T for the native A at position 211 of the sense strand. Restriction endonuclease digestion of the mutated GAPDH yields products of 588 and 200 base pairs.

Several experiments were performed using a different mutated GAPDH template. This template had a novel BamHI restriction site introduced.

The "outer" primers used to amplify both the native and mutated templates result in a product length of 634 base pairs. The "outer" primers are:

Sequence I.D. No. 9 (Tso et al., Nucleic Acids Res. 13:2485-2502, 1985) Pos. 200 5'-CATGGCACCGT-CAAGGCTGAGAAC-3' (coding sense) corresponding to bases 165-188 of the cloned sequences, and Sequence I.D. No. 10 (Tso et al., Nucleic Acids Res. 13:2485-2502, 1985) Pos. 813 5'-CCTCCGACGCCTGCTTCACCAC-3' (anti-coding sense) which anneals to bases 777-798.

The "inner" primers used to synthesize the mutated template create a BamHI restriction endonuclease recognition site (GGATCC) by changing one native cDNA base pair (bold bases). The "inner" primers are:

Sequence I.D. No. 11 (Tso et al., Nucleic Acids Res. 13:2485-2502, 1985) Pos. 368 5'-CAGGGG GGATCC AAAAGGGTCATCAT-3' (coding sense)

Sequence I.D. No. 12 (Tso et al., Nucleic Acids Res. 13:2485-2502, 1985) Pos. 368 3'-GTCCCC CCTAGG TTTTCCCAGTAGTA-5' (anti-coding sense)

Both primers correspond to bases 333-358 of the cloned sequence. The mutation results from the substitution of a T for the native G at position 342 of the sense strand. Restriction endonuclease digestion of this mutated GAPDH yields products of 460 base pairs and 174 base pairs.

The mutated internal standard competitive templates were prepared by site directed mutagenesis as described by Higuchi et al., Nucleic Acids Res. 16:7351-7367, 1988. These single base mutations resulted in either the gain (GAPDH) or loss (GSH-Px) of an EcoRI restriction endonuclease recognition site. (Experiments were also conducted using a muted GAPDH with a BamHI site introduced). For each mutated product, two initial polymerase chain reactions using an "outer" primer and an "inner" single base mismatched primer produce two overlapping DNA fragments. (Primers 1 and 4, 2 and 3 for GSH-Px; Primers 5 and 8, 6 and 7 for GAPDH). These overlapping DNA fragments were electrophoresed on a 3% Nusieve, 1% LE agarose ethidium bromide stained gel. Bands were excised and purified using Millipore Ultrafree-MC 0.45 µM filter (Nihon Millipore Kogyo K. K., Yonezawa, Japan). The purified DNA was ethanol precipitated, washed, vacuum-dried and taken up in 100 µL sterile dH$_2$O. 1 µL of each of the two overlapping DNA fragments were PCR amplified using the outer primers only. The first PCR cycle was performed without primers to allow for heterodimer formation. The entire mutated product was thus formed and amplified. The mutated PCR product was gel purified as described above and re-amplified to form bulk product. The bulk product was gel purified and measured spectrophotometrically. The mutated products were diluted to the attomolar range for use as competitive templates. Herring sperm DNA (Lofstrand, Bethesda, Md.) 1 µg/ml was used as a carrier. Restriction endonuclease digestion was performed on samples of each mutated template to assure lack of contamination.

The PCR conditions were as follows: The PCR conditions were standardized for each experiment by using a master mixture containing 1× PCR buffer (50 mM KCl, 10 mM Tris-HCl, pH 9.0, 1.5 mM MgCl$_2$), 25 pmoles of primers coding for GSH-Px and GAPDH, 0.2 mM dNTP's (A, T, C, G), and constant amounts of both internal standards per 100 µL reaction mixture. Taq DNA polymerase (2.5 units) was added to each 100 µL reaction prior to amplification. cDNA obtained from the BEP2D cell line was serially diluted and added to the sample PCR tubes. In all experiments, control tubes containing no template, native cDNA only, or mutated competitive templates only were amplified to check for contamination or complete enzyme digestion.

PCR amplification was carried out for 35 cycles at 94° C. for one min, 60° C. for one min, and 72° C. for one min After amplification, PCR products were heated for 10 min in order to maximize heterodimer formation.

The quantification of products was as follows: Samples (40 µL) for each PCR tube were EcoRI restriction endonuclease digested for 12-16 hours (Experiments conducted using mutated GAPDH with the novel BamHI restriction site were also BamHI restriction endonuclease digested for 4-5 hours). These products were isolated by electrophoresing on a 3% Nusieve, 1% LE agarose ethidium bromide stained gel for 2-3 hours at 60 V. A negative photograph was taken of the gel using Polaroid 665 positive/negative instant film.

The negative photograph was subjected to densitometry (Zeineh Soft Laser Scanning Densitometer Model SLR 2D/1D using Zeineh 1D Autostepover Videophoresis Program Software, Biomed Instruments, Fullerton, Calif.). Alternatively, the stained gel is evaluated densitometrically directly using a digital camera, or evaluated on an automated sequencing gel (such as that offered by Applied Biosystems, Inc.). Areas under each curve were calculated and used for quantification. Corrections were made for relative band sizes and heterodimer formation. Data were expressed GSH-Px to GAPDH relative ratios.

In a second set of experiments, multiplex competitive reverse transcriptase polymerase chain reaction (MC RT-PCR) with competitive templates were prepared by the Celi method to evaluate the cytochrome p450 (CYP) IAI gene in β-napthoflavone-exposed BEP2D cells. The induction of CYPIAI gene expression was evaluated using both MC RT-PCR with Celi competitive templates, and Northern analysis. Competitive templates were prepared for both the CYPIAI and GAPDH genes. The primers used to prepare the competitive template for GAPDH were:

Sequence I.D. No. 13 (Tokunaga et al., Cancer Res. 7:5616-5619, 1990) Pos. 75 5'-GGT CGG AGT CAA CGG ATT TGG TCG-3'Pos. 94 and Sequence I.D. No. 14 (Tokunaga et al., Cancer Res. 7:5616-5619, 1990) [0438] Pos. 822.backslash./Pos. 636

Pos. 842 5'-CCT CCG ACG CCT GCT TCA CCC CAT CAC GCC ACA GTT TCC C-3' Pos. 616

The lower outer primer used in conjunction with Sequence I.D. No. 13 to amplify both the competitive and native templates was Sequence I.D. No. 15 (Tokunaga et al., Cancer Res. 7:5616-5619, 1990) Pos. 842 5'-CCT CCG ACG CCT GCT TCA CC-3' Pos. 822. The primers used to prepare the competitive template for CYPIAI were:

Sequence I.D. No. 16 (Jaiswal et al., Science 228:80-83, 1989) Pos. 12415'-CAT CCC CCA CAG CAC AAC AAG-3' Pos. 1262 and:

Sequence I.D. No. 17 (Jaiswal et al., Science 228:80-83, 1989) [0444] Pos. 1555.backslash./Pos. 1428

Pos. 1575 5'-ACA GCA GGC ATG CTT CAT GGG TCT CAC CGA TAC ACT TCC G-3' Pos. 1448

The lower outer primer used in conjunction with Sequence I.D. No. 18 to amplify both the competitive and native templates was Sequence I.D. No. 18 (Jaiswal et al., Science 228:80-83, 1989) Pos. 1575 5'-ACA GCA GGC ATG CTT CAT GG-3' Pos. 1555

The PCR amplification conditions were the same as described for experiments using the competitive templates prepared for GAPDH and GSHPx by the Higuchi method except the annealing temperature was 55° C. and the amplification was carried out for 38 cycles.

Because the native and competitive templates separate without prior restriction endonuclease digestion, samples were taken directly from the PCR reaction tube and applied to ethidium bromide stained 3% Nusieve, 1% LE agarose gels. It was then possible to quantify the products by taking a negative photograph of the gel using Polaroid 665 positive/negative instant film, subjecting the negative photograph to densitometry.

RNA from BEP2D cells incubated for varying times with β3-napthoflavone (10 μM) was either electrophoresed on a 1% LE formaldehyde denaturing gel for Northern analysis or MC RT-PCR amplified, as described above. For Northern analysis, following transfer of the RNA to GeneScreen, the filters were hybridized with $^{32}$P-labeled CYPIAI cDNA.

The procedure used for PCR quantitation is as follows: Serial dilutions of BEP2D cDNA (representing 0.25 μg to 0.05 μg total RNA) were co-amplified with constant amounts of each single base mutated internal standard competitive template (10 attamoles each), then analyzed as described above.

FIGS. 4A-4B illustrates negative photographs of the gels analyzed by densitometry in order to quantify each band. Starting with the area under each curve obtained by the densitometric evaluation of the bands, the ratios of native/competitive template amplified product were calculated as follows. Corrections were made for relative band sizes. (Competitive template for GAPDH was multiplied by 788/588 when compared to native nucleic acid for GAPDH and native GSH-Px was multiplied by 354/280 when compared to competitive template for GSH-Px).

During PCR, under conditions in which primer is limiting, heterologous single strands of DNA with sequence homology may anneal to form heterodimers (Gilliland, G., Perrin, S., Blanchard, K. and Bunn, H. . 1990) Proc. Natl. Acad. Sci. 87:2725-2729). When the heterologous strands differ by only one base pair, as in this particular example, the heterologous strands can re-anneal randomly (Gilliland et al., supra; Thompson, J. D., Brodsky, I., and Yunis, J. J. (1992) Blood 79:1629-1635), as shown in the Punnett square below:

|   | N  | M  |
|---|----|----|
| N | NN | NM |
| M | NM | MM | where N=the proportion of single-stranded native products prior to re-annealing, M=the proportion of single-stranded mutated products prior to re-annealing, NN (or $N^2$)=the proportion of double-stranded native products after re-annealing, 2NM=the proportion of heterodimer formed after re-annealing, and MM (or $M^2$)=the proportion of double-stranded mutated products after re-annealing.

Heterodimers were accounted for indirectly because they were not cut, in this example, by the restriction enzyme and had the same electrophoretic mobility as the undigested homodimer. Therefore, heterodimers were read densitometrically along with the undigested homodimer. In order to quantitate products, based on the Punnett square distribution, random heterodimer formation was promoted following PCR. This was done (according to the methods described in Gilliland et al., supra, and Thompson et al., supra), by heating the products to 100° C. for 10 min followed by slow cooling. Following promoted formation of heterodimers, the quantity of each product was determined by analysis of the densitometric data using the quadratic formula as the formation of heteroduplexes follows a binomial distribution under these conditions (Gilliland et al., Proc. et al., Acad. Sci. 7:2725-2729 (1990), Becker-Andre et al., Nucleic Acids Res. 17:9437-9446 1989).

Figure 34:
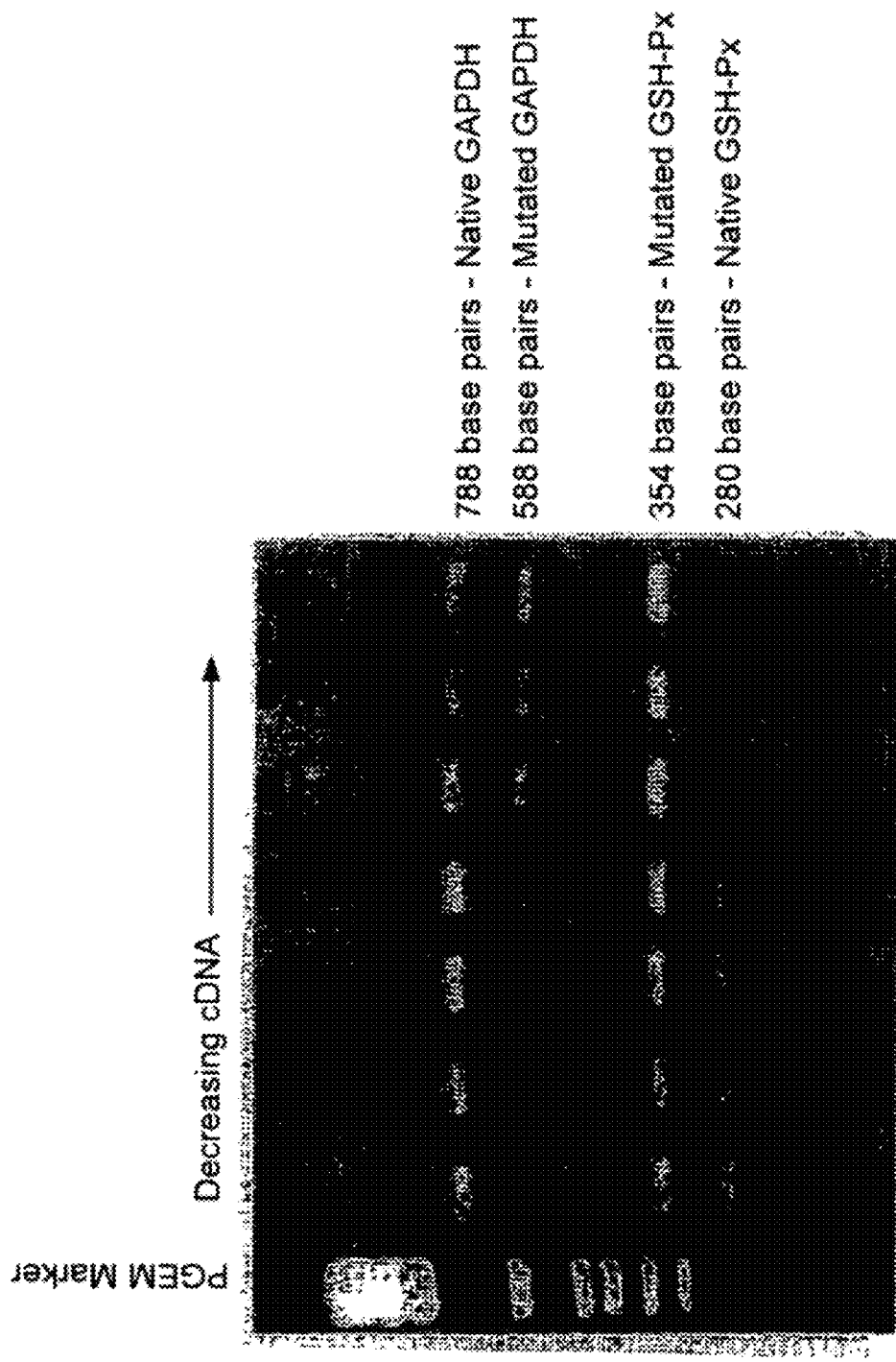
FIG. 34 illustrates negative photographs of the gels analyzed by densitometry.

For GAPDH, in this example, neither the native product (NN) nor the heterodimer (NM) were cleaved by EcoRI. Therefore, the larger band represented both native GAPDH homodimer (NN) and the NM heterodimer. This band was presented arithmetically by $N^2+2NM$, according to the Punnett square, while the proportion in the band resulting from EcoRI cleavage was represented by the value $M^2$. Therefore, when the amount of native (N) and mutated (M) template are equal (1:1) prior to PCR, after heterodimer formation is randomized, the apparent ratio will be 3:1 [$N^2+2NM$]: $M^2$]. To illustrate this further, the raw densitometric data from the first sample lane (shown in FIG. 34) are shown in FIG. 35 and are mathematically processed to final ratios below:

The value of $M^2$ is known (2,214), as is the value of $N^2+2NM$ (10,095). From this information, M is calculated (47.05) and solving for N results in quadratic equation $(aX^2+bX+c=0)$: $N^2+2N(47.05)-10,095=0$ The quadratic formula $(N=-b+/-[(b^2-4ac)/2a]$ is used to solve for N. In this case, a=1, b=94.1, c=10,095, and thus N=63.89. The information sought is the ratio N/M which is 63.89/47.10 or 1.36/1. (Although proportions of single-stranded DNA present after PCR are solved for, they will be identical to those of the corresponding double-stranded DNA present prior to the PCR, in this example.)

Since densitometric values are relative, it is possible to avoid the inconvenience of using the quadratic formula by assigning the bands proportionate densitometric values that when added=1 or $(N^2+2NM)+M^2=1$. Solving for this equation: $(N^2+2NM)+M^2=(N+M)^2=1$ and therefore N+M=1

The relative fractions of 1 assigned to each of the bands is determined by their respective densitometric values (FIG. 35). Since the total densitometric value of both bands is 12,309 (10,095+2,214), the relative proportion of the larger band ($N^2+2NM$) is 0.82 (10,095/12,309) and the relative proportion of the smaller band ($M^2$) is 0.18 (2,214/12,309). Thus, the proportion of mutated GAPDH homodimer ($M^2$) is 0.18, and the proportion of single-stranded mutated GAPDH (M) is 0.424. Since N+M=1, the proportion of single-stranded native GAPDH (N) is 1-0.424 or 0.576, and the ratio of native to mutated product is 0.576/0.424 or as calculated above 1.36/1.

Next, in this example, the same calculations are carried out using the densitometric values for native and mutated GSH-Px from the same lane as the GAPDH values above (Table 1):

$N^2$=0.558, N=0.747, and M=1-0.747=0.253

Native/mutated ratios are obtained:

GSH-Px native/mutated=0.747/0.253=2.95/1

GAPDH native/mutated=0.576/0.424=1.36/1

Final values were expressed as an odds ratio (e.g., a "ratio of ratios"):

GSH-Px native/mutated: GAPDH native/mutated=2.95/1.36=2.17/1

As FIG. 19 illustrates, the relationship between the amount of native product (in arbitrary densitometric units) and total starting RNA did not remain linear throughout PCR amplification for either GSH-Px or GAPDH.

As FIG. 20 illustrates, however, the relationship of the ratios GSH-Px native/competitive template and GAPDH native/competitive template to total starting RNA was linear for both genes. By averaging the ratio of GSH-Px native/ competitive template to GAPDH native/competitive template obtained from sample tubes (2.17:1, 2.14:1, 2.00:1, 1.76:1, 2.46:1, 2.71:1, and 1.92:1), a mean value of 2.17:1 with a S.D. of 0.33 was obtained. In this example, no value varied more than 25% from the mean.

To assess the variability of this technique, the experiment was repeated using different dilutions of mutated (competitive template) standards and master mixture. By averaging the ratio of GSH-Px native/competitive template to GAPDH native/competitive template obtained from each sample tube in this example (1:9.09, 1:8.13, 1:9.43, 1:8.13, 1:6.62, 1:8.77, 1:7.69, 1:10.00, 1:7.58, and 1:7.04), a mean value of 1:8.25 with a S.D. of 1.07 was obtained. In this example, no value varied more than 22% from the mean.

To assess the variability between samples using the same master mixture and dilutions of mutated standards (using mutated GAPDH with novel BamHI restriction site), BEP2D RNA was independently extracted from three separate flasks and reverse transcribed to cDNA. Five fold dilutions of cDNA were performed. Four PCR tubes were run for each study. The obtained ratios of GSH-Px native/ competitive template to GAPDH native/competitive template were 15.01:1, 17.69:1, and 21.76:1. (mean=18.15, S.D.=3.40). In this example, all of the 3 values were within 20% of the mean.

Figure 36A:
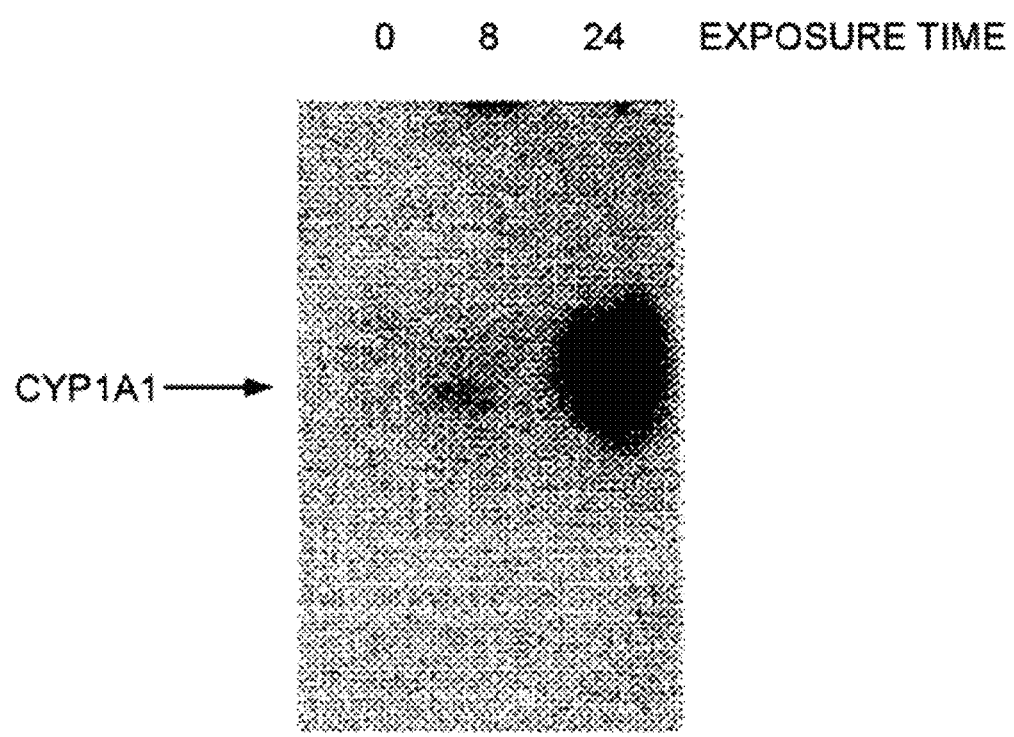
FIG. 36A-36B illustrates that a similar increase in expression of the CYPIAI gene was observed in both Northern analysis and some embodiments of methods disclosed herein.
Figure 36B:
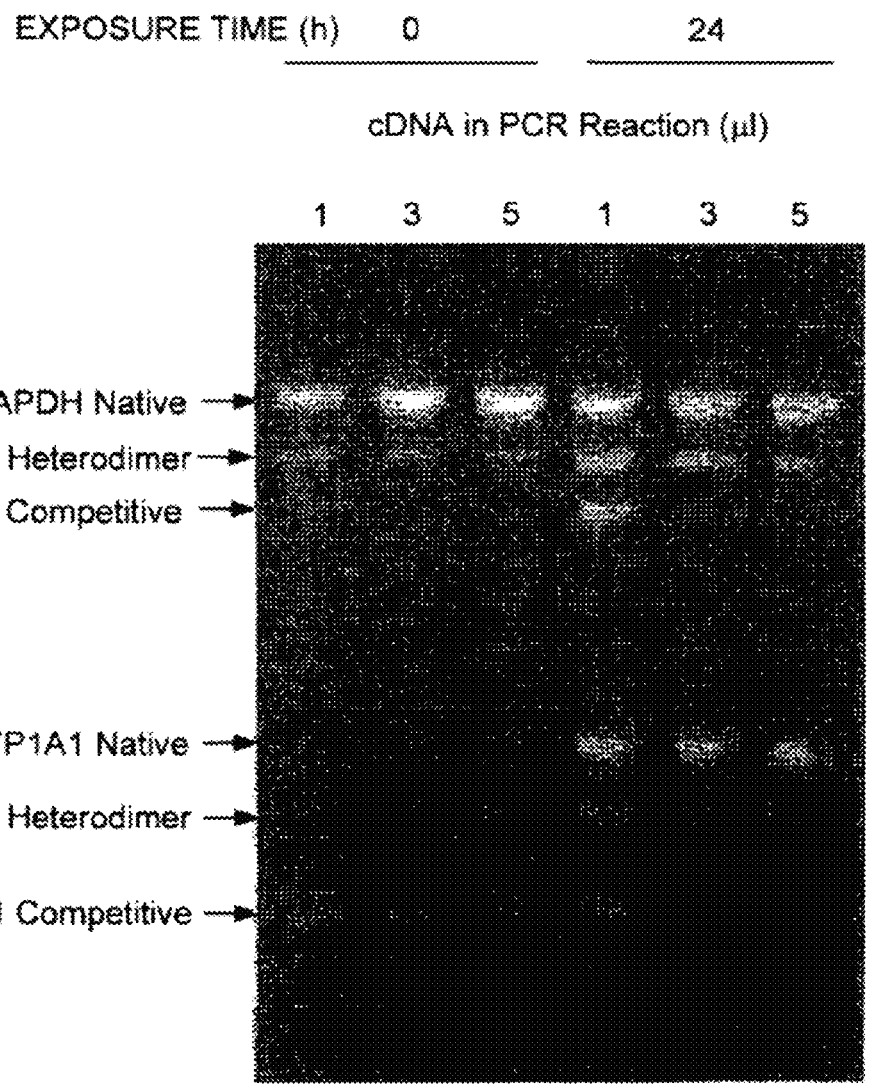

As FIG. 36 illustrates, similar increase in gene expression of the CYPIAI gene was observed in both Northern analysis and some embodiments of methods disclosed herein. FIG. 36A illustrates Northern analysis of RNA obtained from BEP2D cells that were treated with 0.1% DMSO as a control, or, β-napthoflavone in an effort to induce cytochrome p450 IA1 (CYPIA1). FIG. 36B illustrates DNA PCR-amplified from serial dilutions of cDNA from the same cells used in FIG. 36A. The cDNA was co-amplified in the presence of competitive templates for GAPDH and CYPIAI, according to some embodiments of the instant invention.

Comparing the bands of the GAPDH reference gene representing native and competitive template cDNA indicates that approximately the same amount of cDNA was loaded in the lane with 1 µl of specimen from control cells and the lane with 3 µl of specimen from β-napthoflavone exposed cells. Hence, the band representing the native CYPIAI gene is much more strongly represented in the lane containing cDNA from β-napthoflavone exposed cells compared to control cells.

To assess the variability of this technique, a repeat of the above experiment was performed using different dilutions of competitive templates and master mixture. By averaging the ratio obtained from each sample tube (1:9.09, 1:8.13, 1:9.43, 1:8.13, 1:6.62, 1:8.77, 1:7.69, 1:10.00, 1:7.58, and 1:7.04), a mean value of the ratio of GSH-Px native/competitive template to GAPDH native/competitive template of 1:8.25 with a S.D. of 1.07 was obtained. In this example, no value varied more than 22% from the mean, indicating the precision of this technique and the variability introduced by new master mixtures containing new dilutions of competitive standards.

To assess the variability between samples using the same master mixture and dilutions of competitive templates, BEP2D RNA was independently extracted from three separate flasks and reverse transcribed to cDNA. Only coarse (5 fold) dilutions of cDNA were performed. Four PCR tubes were run for each study. The obtained ratios of GSH-Px native/competitive template to GAPDH native/competitive template were 15.01, 17.69:1, and 21.76:1 (mean=18.15, S.D.=3.40). In this example, the 3 values were all within 20% of the mean, indicating the precision of this technique when comparing samples that have been independently reverse transcribed but amplified with the same master mixture and internal standard dilutions. Northern analysis of BEP2D RNA reveals a ratio of GSHPx/GAPDH mRNA of approximately 1:8.

Example IV

Blinded Inter-Laboratory Study to Evaluate Reproducibility

In a first study, six laboratories participated in triplicate measurement of five genes in cDNA derived from a bronchogenic carcinoma tissue sample 16009T. A variety of electrophoresis methods and imaging software programs were used in different laboratories to analyze amplified product. Study 1 Laboratory 2 used an Agilent 2100 Bioanalyzer. The intra-laboratory average CV for all gene expression measurements was 0.36, which is comparable to that previously reported (Willey et al., 1998; Rots et al., 1999; Rots et al;. 2000; Mollerup et al., 1999; Loitsch et al., 1999). The inter-laboratory variation showed an average CV of 0.71.

In a second study, slab gel electrophoresis and NIH Image software was used to measure expression of 10 genes (the 5 previously measured plus 5 additional genes) in A549 cDNA. Four of the original laboratories were able to participate in the second study. The combined average CV for all nine genes that could be measured was 0.27 and 0.48 for intra-lab and inter-lab comparison, respectively. For TNF a, each laboratory determined that the expression was too low to be quantified. Of the four laboratories, three laboratories were able to quantify HNF3a while the fourth lab was not. The lower limit of detection of a PCR product above background was established for the second study as an NIH image arbitrary densitometric value of 5 above background. Although the fourth laboratory observed NT and CT PCR products for HNF3a, they were below the cut-off level of 5 and therefore not included in the analysis. A CT mix that contributed 60 molecules of nucleic acid CT (F mix) was used to detect HNF3a.

Example V

Comparison to Oligonucleotide Microarray

In a first study, Affymetrix oligonucleotide arrays and an embodiment of the two-step approach of the instant invention each were used to measure expression of a total of 22 xenobiotic metabolism enzyme or antioxidant genes in Human Oral Epithelial (HOE) cells. Expression in normal HOE cells was compared to expression in immortalized buccal epithelial cell line SVpgC2a. The difference in expression between HOE and SVpgC2a was compared for each gene. Then, the differences detected by microarray were compared to the differences detected by StaRT-PCR.

The cRNA chip method gives results based on relative signals that rely on perfect matches and mismatches from chip hybridizations, in combination with image software analysis, to derive results from hybridization intensities. The technique allows for the analysis of up to 12,000 genes simultaneously and is semi-quantitative in terms of signal intensities from one hybridization experiment compared with other hybridizations. In this study three sets of hybridizations utilizing samples from normal HOE cells or SVpgC2a cells were performed, then data from each measured in SVpgC2a cells were compared to corresponding data HOE cells. The first of the three hybridizations were performed with the HuFL 6800 chip.

Gene expression measurements were in close agreement and demonstrated that the expression levels of several phase I and II metabolism transcripts were similar in normal and immortalized keratinocytes. Of the CYP genes analyzed, most were expressed at low levels, i.e., below 20 mRNA molecules/10 β-actin mRNA molecules. In this study, cDNA concentration allowed for the quantification of mRNA levels of 4 molecules/10 β-actin molecules.

Methods comprising embodiments of the instant invention were more sensitive. For example, transcripts that were found expressed at low levels were not detected with the chip method, i.e., transcripts expressed at levels below a few hundred molecules/$10^6$ copies of β-actin were not detectable with the chip hybridization method. Using methods of the instant invention, a gene expression value was obtained in both the normal and immortalized cells for 14 genes of the 22 genes evaluated (for the remaining seven genes, expression was too low to be quantified in either the normal or immortalized cells). Of these 14 genes, a gene expression value also was obtained by microarray analysis in both normal and immortalized cells for only five of them. The difference in expression of these five genes in normal compared immortalized cells were compared. The results are presented in FIG. 37.

In a second study, gene expression was measured for the Stratagene Human RNA Reference. The Stratagene Human RNA Reference comprises RNA from 10 cell lines mixed together, to represent transcription levels of a large fraction of genes in the human genome. Genes were evaluated using Oligonucleotide microarray (Affymetrix U95 version2 and HuGenFL genechips) and using embodiments of the instant invention.

Using embodiments of the instant invention, data for 163 of the 192 genes represented in G.E.N.E. Systems 1 and 2 CT mixes were obtained from the Stratagene Human RNA Reference. The remaining genes represented in Systems 1 and 2 were expressed at a value too low to be quantified (less than 6 molecules/$10^6$ β-actin molecules). Of the 163 genes measured, 85 were represented on the HuGenFL gene chip. Of these 85 genes, it was possible to assign an expression value to all of the genes measured in accordance with embodiments of the instant invention, but only 41 genes based on microarray analysis.

Figure 38:
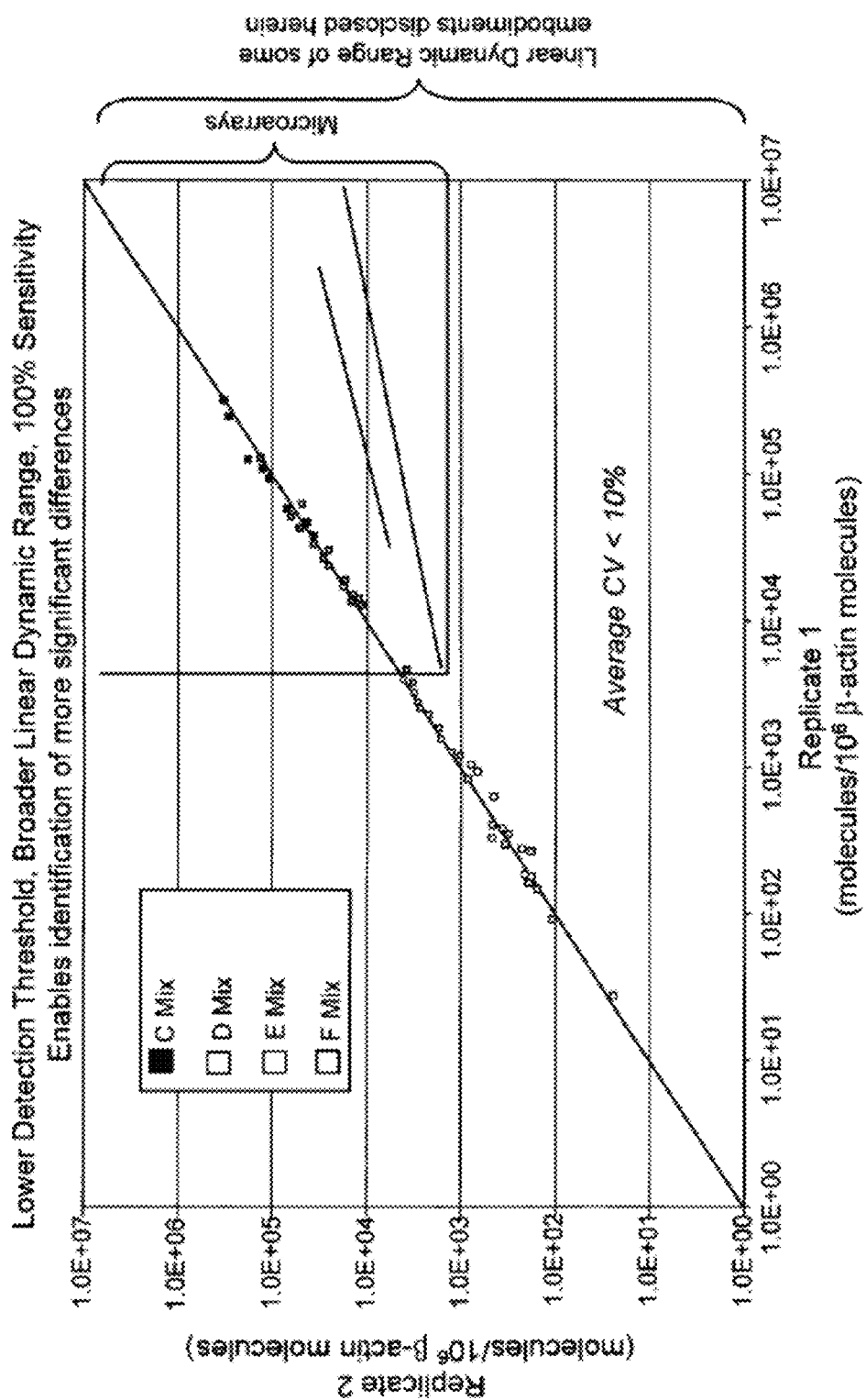
FIG. 38 illustrates a greater linear dynamic range obtained using some two step embodiments vs. microarray analysis.

Bivariate Correlation Analysis: FIG. 38 shows the Pearson correlation for some two step embodiments vs. microarray values. The Pearson correlation had an $r^2$ value of 0.373, which was highly significant ($P<0.001$).

Sensitivity: FIG. 3 also compares sensitivity between some two-step embodiments and microarrays. Among the 41 genes for which expression values were obtained by both, values ranged over about two logs in microarray analysis and about three logs by some embodiments of two-step analysis. FIG. 38. Some embodiments of two-step analysis were about 10-fold more sensitive than microarray analysis Example VI The following example entails gene expression measurement in the business method provided as a service.

Automated preparation of reactions: A PerkinElmer (Boston, Mass., USA) robotic liquid handler is used to prepare 10 µL PCR reactions in 96- or 384-well microplates. First, the liquid handler is programmed to distribute 1 µL of primers for genes to be measured into wells of the microplates. Second, for each cDNA, a sufficient volume of PCR mixture for the anticipated number of gene expression measurement is prepared, containing buffer, Taq polymerase, dNTPs, cDNA and internal standards. The robot then distributes 9 µL, of this PCR reaction mixture into each well. Thus, in each well, the internal standard competitive templates for each gene and cDNA are present in the same ratio. However, because only one pair of primers is present in each well, only one gene and its respective internal standard competitive template are amplified in each well. Following 35 cycles of PCR, each microplate is transferred to a AMS 90 SE30 high-throughput microfluidic device (Caliper/Zymar, Hopkinton, Mass., USA) for analysis.

Design of High Throughput Gene Expression Measurement

Step 1 amplification of 96 genes: Competitive templates can be combined into groups of 96 and named as sequential "Systems". Thus, the first mix of CTs representing 96 genes was called System 1 and so on. A mix of primer pairs specific for each of the 96 genes in a System can be combined and diluted to a concentration of 0.05 µg. Thus, for each of the Systems 1-4 CT mixes representing 96 genes, there can be a mix of primers corresponding to the same 96 genes.

The cDNA sample can be diluted so that it is in balance with, i.e., calibrated to, approximately 600,000 molecules of β-actin from Mix D from each System. The appropriate amount of cDNA then will be PCR-amplified in the presence of the primer mix from one of the Systems, and Mix B, C, D, E, or F from the corresponding system. In this way, PCR products can be generated in each of 20 separate 10µ PCR reactions, namely System 1, Mixes B, C, D, E, and F; System 2, Mixes B, C, D, E, and F; System 3, Mixes B, C, D, E, and F; and System 4, Mixes B, C, D, E, and F.

Thus far, the amount of cDNA and CT mix for 20 reactions has been consumed. Next, the PCR products included in these 20 PCR reactions can be used to measure all 384 genes included in Systems 1-4.

Step 2: Initial Single gene PCR Amplification from Mix D PCR Products: The PCR products generated above in round one may be diluted up to 10,000-fold and still yield quantifiable PCR products in a second round of PCR amplification. Because an internal standard CT was included in each PCR reaction, and because the amplification efficiency of the internal standard CT is the same as the NT, a gene expression value obtained after a second 35-cycle round of PCR amplification can be the same as that obtained after the first 35 cycles. For example, 2 µl from the first round of amplification can be diluted 100-fold for use in the second round. Because there were 10 µl in the first round PCR reaction volume, this constitutes a 1000-fold dilution. One half of this diluted round one PCR reaction from Mix D for each System (100 µ) then can be mixed with appropriate amount of dNTPs, taq, and $dH_2O$ and aliquotted into each of 96 wells, with each well containing a different pair of primers (representing a gene from the corresponding System) dried on the bottom. The remaining 100 µ can be saved for step 3. Thus, a Step 2 PCR reaction mixture containing diluted Step 1 Mix D PCR product can be prepared for each of the four Systems, and distributed in 10 µl aliquots into each of 96 wells on the 384 well microplate.

Following PCR amplification, 1µ of PCR product from each PCR reaction can be transferred into a well of a DNA 1000 chip mounted in an Agilent 2100. Each sample can be electrophoresed. The remaining PCR product can be retrieved into microfuge tubes to provide back-up material in the event of trouble with the electrophoresis.

Step 3: Selection of the most appropriate CT Mix Step 1 product for quantifying each of the 96 genes, based on the results of Step Two: Only about 50% of the NT and CT for various genes are expected to be in balance. Genes not in balance can be re-evaluated using a Mix containing different concentrations of CTs for those genes relative to β-actin CT. In round 3, expression of each gene can be evaluated using a Step 1 PCR reaction that contained an appropriate concentration of CTs for those genes relative to β-actin CT. A 3,900 µl PCR reaction mixture can be prepared, containing 3.9 µl of the Step 1 PCR product, and appropriate volume of taq polymerase, dNTPs and distilled $H_2O$.

384-well microplates with primers for different single genes dried to the bottom of each well can be prepared ahead of time. Such plates may be stored at 4 ° C. for months without loss or decrease in primer function. Nonetheless, a decrease in primer efficiency over time would not be expected to change gene expression measurement numerical values, because each PCR reaction contains an internal standard CT. However, it could decrease amount of amplified product for both NT and CT, reducing the signal to be quantified an Agilent 2100.

Cost Analysis of providing business method embodiments as a Service

Using two 384-well microplate thermocyclers, two cDNA samples can be screened in eight different 96-gene Step 1 reactions. Four of these reactions can contain cDNA from Sample 1 and Mix D from Systems 1-4 respectively, and four reactions can contain cDNA from Sample 2 and Mix D from Systems 1-4 respectively. PCR products from each of these reactions can be diluted 100-fold. Eight PCR reaction mixtures, each sufficient for 96 PCR reactions can be prepared with 10% volume represented by one of the eight Step 1 PCR products. The PCR reaction mixtures including Sample 1 then can be dispensed into the appropriate 96 wells of one of the 384-well microplates, and the PCR reaction mixtures including Sample 2 can be dispensed into the appropriate 96 wells of the other 384-well plate. Alternatively, when Systems 5-8 are used, both 384-well microplates can be used to screen 768 genes in Sample 1 with Mix D.

Preparing the eight different 96-gene PCR reactions can require a total of 8 µl of cDNA, and 8 µl of CT Mix D. The primary cost can be taq polymerase and primers for 768 PCR reactions, approximately $25.00 and $30.00 respectively. The primary cost of analysis may be the Agilent chips, costing $12/chip. By applying 4 PCR products/channel, 48 genes/chip can be analyzed. Thus, the cost of materials per assay can be approximately $0.32. Labor costs can include one day of work at approximately $14.00/hour=$112.00, adding about $0.15/assay to make about $0.47/assay. There can be about two more days of data input and analysis, bringing the total cost to $0.77/assay. Based on these calculations, the fee can be approximately $1.00/gene expression measurement.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and compositions within the scope of these claims and their equivalents be covered thereby.

All publications, patents, and patent applications mentioned in this specification are herein incorporated by reference to the same extent as if each individual publication, patent or patent application was specifically and individually indicated as being incorporated by reference.

What is claimed is:

1. A standardized mixture for assessing amounts of at least one target nucleic acid in a sample, comprising:
    a first competitive template for a first target nucleic acid in a sample, the first competitive template comprising a first competitive template nucleic acid at a first concentration; and,
    a second competitive template for a second target nucleic acid in the sample, the second competitive template comprising a second competitive template nucleic acid at a second concentration that is different from the first concentration;
    the first and second competitive templates being at known different concentrations relative to each other;
    the competitive templates for each target nucleic acid comprising a competitive template nucleic acid that can be amplified using identical primers, shares sequence homology, and amplified with substantially similar efficiency as the target nucleic acid while having one or more features that allow the competitive template to be distinguished from the target nucleic acid selected from the group consisting of: one or more point mutations; one or more insert mutations, one or more inversion mutations; and one or more deletion mutations.

2. The standardized mixture of claim 1, further comprising a forward primer and/or a reverse primer for priming amplification of at least one of the first and second competitive templates.

3. The standardized mixture of claim 1, wherein the first competitive template nucleic acid is present at a ratio greater than, or about 1/10 to the second competitive template.

4. The standardized mixture of claim 1, wherein the first competitive template nucleic acid has at least, or about, two nucleotides that are different from the first target nucleic acid.

5. The standardized mixture of claim 1, wherein the second competitive template nucleic acid has at least, or about, two nucleotides that are different from the second target nucleic acid.

6. The standardized mixture of claim 1, wherein at least one of the first and second target nucleic acids comprise cDNA.

7. A serially-diluted standardized mixture of reagents for assessing amounts of at least one target nucleic acid in a sample, comprising:
    a first competitive template for a first target nucleic acid in the sample, the first competitive template comprising a first competitive template nucleic acid at a first series of dilution concentrations; and,
    a second competitive template for a second target nucleic acid in the sample, the second competitive template comprising a second competitive template nucleic acid at a second series of dilution concentrations that are different from the first series of dilution concentrations in a first sample;
    the first and second competitive templates being at known different and serially diluted concentrations relative to each other;
    the competitive templates for each target nucleic acid comprising a competitive template nucleic acid that can be amplified using identical primers, shares sequence homology, and amplifies with substantially similar efficiency as the target nucleic acid while having one or more features that allow the competitive template to be distinguished from the target nucleic acid selected from the group consisting of: one or more point mutations; one or more insert mutations; one or more inversion mutations; and one or more deletion mutations;
    wherein, when combined, the first series of concentrations of the first competitive template and the second series of concentrations of the second competitive template form the standardized mixtures for assessing amounts at least one nucleic acid and for allowing direct comparison of said amounts between the first and second nucleic acids in the sample.

8. The serially-diluted standardized mixture of claim 7, wherein the serial diluted concentrations of the first competitive template, relative to a concentration of the second competitive template comprises one or more of: mixture A $=10^6$ molecules/ µL; mixture B $=10^5$ molecules/ µL; mixture C $=10^4$ molecules/ µL; mixture D $=10^3$ molecules/ µL; mixture E $=10^2$ molecules/ µL; and, mixture F $=10^1$ molecules/ µL.

9. The serially-diluted standardized mixture of claim 8, wherein the serial diluted concentrations comprise mixtures A, B, C, D, E and F.

10. The serially-diluted standardized mixture of claim 7, wherein the first competitive template nucleic acid is present at a ratio of less than, or about 10/1, to the second competitive template nucleic acid.

11. The standardized mixture of claim 7, wherein the first competitive template nucleic acid has at least, or about, two nucleotides that are different from the first target nucleic acid.

12. The standardized mixture of claim 7, wherein the second competitive template nucleic acid has at least, or about, two nucleotides that are different from the second target nucleic acid.

13. The standardized mixture of claim 7, wherein at least one of the first and second target nucleic acids comprise cDNA.

14. A kit for preparing a standardized mixture for assessing amounts of at least one target nucleic acid in a sample, comprising:
the standardized mixture of claim 1; and
instructions for combining the first competitive template and second competitive template in the sample.

15. The kit of claim 14, further including instructions for:
combining the first sample with the standardized mixture;
co-amplifying the first nucleic acid and the competitive template for the first nucleic acid to produce first amplified product thereof;
diluting the first amplified product;
further co-amplifying the diluted first amplified product of the first nucleic acid and of the competitive template for the first nucleic acid, to produce second amplified product thereof; and,
co-amplifying the second nucleic acid and the competitive template for the second nucleic acid to produce first amplified product thereof.

16. The kit of claim 14, further including instructions for: i) co-amplifying the first nucleic acid and the competitive template for the first nucleic acid in a first vessel; and, ii) co-amplifying the second nucleic acid and the competitive template for the second nucleic acid co-amplified in a second vessel.

17. The kit of claim 14, wherein the instructions include:
obtaining a first relationship by comparing the second amplified product of the first nucleic acid to the second amplified product of the competitive template for the first nucleic acid;
obtaining a second relationship by comparing the first amplified product of the first reference nucleic acid to the first amplified product of the competitive template for the first reference nucleic acid; and,
comparing the first and the second relationships.

18. The kit of claim 14, wherein the instructions include:
co-amplifying the second reference nucleic acid and the competitive template for the second reference nucleic acid to produce first amplified product thereof;
assessing by: obtaining a first relationship by comparing the second amplified product of the first nucleic acid to the second amplified product of the competitive template for the first nucleic acid;
obtaining a third relationship by comparing the first amplified product of the second reference nucleic acid to the first amplified product of the competitive template for the second reference nucleic acid; and,
comparing the first and the third relationships.

19. The standardized mixture of claim 1, further comprising sufficient amounts of the competitive templates for assessing the first nucleic acid in more than, or about, $10^6$ other samples, more than, or about, $10^8$ other samples, more than, or about, $10^{10}$ other samples, more than, or about, $10^{11}$ other samples, or more than, or about, $10^{12}$ other samples.

20. The standardized mixture of claim 1, further comprising at least one additional competitive template for at least one other nucleic acid, the additional competitive template being at known a concentration relative to the other competitive template sufficient to allow assessment of the at least one other nucleic acid in the first sample.

21. The standardized mixture of claim 1, wherein the second nucleic acid serves as a first reference nucleic acid to control for loading.

22. The standardized mixture of claim 1, wherein the at least one of the first or second competitive template nucleic acid corresponds to at least one gene selected from GADP, ACTB, and β-actin.

23. The standardized mixture of claim 1, wherein the first or second competitive template comprises at least one gene selected from the list in FIG. 4A and FIG. 4B.

24. The standardized mixture of claim 7, wherein the competitive template nucleic acid is present at two different concentrations in two of the serially-diluted standardized mixtures.

25. The standardized mixture of claim 9, further comprising:
1 µl of a balanced cDNA for use in round one of a two-step process with each of the six (A-F) competitive template mixes; and,
10 nanoliters of the round one amplified product for use in parallel 100 nanoliter volume round two amplifications to measure amounts of all of the nucleic acids using mix E;
the mix E containing competitive templates at a concentration that is in balance with the majority of nucleic acids in mix E.

26. The kit of claim 14, wherein the instructions further include making serial diluted concentrations of the first competitive template, relative to a concentration of the second competitive template comprises one or more of: mixture A$=10^6$ molecules/ µL; mixture B$=10^5$ molecules/ µL; mixture C$=10^4$ molecules/ µL; mixture D$=10^3$ molecules/ µL; mixture E$=10^2$ molecules/ µL; and, mixture F$=10^1$ molecules/ µL.

27. The kit of claim 26, wherein the serial diluted concentrations comprise mixtures A, B, C, D, E and F.

28. The kit of claim 27, further including instructions comprising:
using 1 µl of balanced cDNA in round one of a two-step process with each of the six (A-F) competitive template mixes; and,
using 10 nanoliters of the round one amplified product in parallel 100 nanoliter volume round two amplifications to measure amounts of all of the nucleic acids using mix E;
the mix E containing competitive templates at a concentration that are in balance with the majority of nucleic acids in mix E.

29. The kit of claim 28, further including instructions comprising:
repeating the steps for nucleic acids that are not in balance with mix E.

* * * * *

SEQUENCE LISTING

```
<160> NUMBER OF SEQ ID NOS: 282

<210> SEQ ID NO 1
<211> LENGTH: 21
<212> TYPE: DNA
<213> ORGANISM: Homo sapiens

<400> SEQUENCE: 1
aatatctcct ccccattctg g                                            21

<210> SEQ ID NO 2
<211> LENGTH: 21
<212> TYPE: DNA
<213> ORGANISM: Homo sapiens

<400> SEQUENCE: 2
tgtggttgag aatgagcatg t                                            21

<210> SEQ ID NO 3
<211> LENGTH: 42
<212> TYPE: DNA
<213> ORGANISM: Homo sapiens
```

```
<400> SEQUENCE: 3
tgtggttgag aatgagcatg tggataccac cttctgtaga gt                        42

<210> SEQ ID NO 4
<211> LENGTH: 20
<212> TYPE: DNA
<213> ORGANISM: Homo sapiens

<400> SEQUENCE: 4
atgacacaga gctggtagcc                                                 20

<210> SEQ ID NO 5
<211> LENGTH: 20
<212> TYPE: DNA
<213> ORGANISM: Homo sapiens

<400> SEQUENCE: 5
aaccagaaaa tacgagccct                                                 20

<210> SEQ ID NO 6
<211> LENGTH: 40
<212> TYPE: DNA
<213> ORGANISM: Homo sapiens

<400> SEQUENCE: 6
aaccagaaaa tacgagccct tctccatcta ccacaggcac                           40

<210> SEQ ID NO 7
<211> LENGTH: 20
<212> TYPE: DNA
<213> ORGANISM: Homo sapiens

<400> SEQUENCE: 7
aaaactgcta aggccaaggt                                                 20

<210> SEQ ID NO 8
<211> LENGTH: 20
<212> TYPE: DNA
<213> ORGANISM: Homo sapiens

<400> SEQUENCE: 8
tcagcaacct ctttcctcac                                                 20

<210> SEQ ID NO 9
<211> LENGTH: 40
<212> TYPE: DNA
<213> ORGANISM: Homo sapiens

<400> SEQUENCE: 9
tcagcaacct ctttcctcac tctgattcat ctgtgctgcc                           40

<210> SEQ ID NO 10
<211> LENGTH: 20
<212> TYPE: DNA
<213> ORGANISM: Homo sapiens

<400> SEQUENCE: 10
accattgtcc agccatcagc                                                 20

<210> SEQ ID NO 11
<211> LENGTH: 20
<212> TYPE: DNA
```

<213> ORGANISM: Homo sapiens

<400> SEQUENCE: 11
accctctgct gtccgtgtct                                                   20

<210> SEQ ID NO 12
<211> LENGTH: 40
<212> TYPE: DNA
<213> ORGANISM: Homo sapiens

<400> SEQUENCE: 12
accctctgct gtccgtgtct ctgaaggagg atggagtctg                             40

<210> SEQ ID NO 13
<211> LENGTH: 20
<212> TYPE: DNA
<213> ORGANISM: Homo sapiens

<400> SEQUENCE: 13
ttttaggaga ccgaagtccg                                                   20

<210> SEQ ID NO 14
<211> LENGTH: 20
<212> TYPE: DNA
<213> ORGANISM: Homo sapiens

<400> SEQUENCE: 14
agccaacgtg ccatgtgcta                                                   20

<210> SEQ ID NO 15
<211> LENGTH: 40
<212> TYPE: DNA
<213> ORGANISM: Homo sapiens

<400> SEQUENCE: 15
agccaacgtg ccatgtgcta cctctgttcc ttccctctac                             40

<210> SEQ ID NO 16
<211> LENGTH: 20
<212> TYPE: DNA
<213> ORGANISM: Homo sapiens

<400> SEQUENCE: 16
gtaccggcgg gcattcagtg                                                   20

<210> SEQ ID NO 17
<211> LENGTH: 20
<212> TYPE: DNA
<213> ORGANISM: Homo sapiens

<400> SEQUENCE: 17
agagtgagcc cagcagaacc                                                   20

<210> SEQ ID NO 18
<211> LENGTH: 40
<212> TYPE: DNA
<213> ORGANISM: Homo sapiens

<400> SEQUENCE: 18
agagtgagcc cagcagaacc cgttctcctg gatccaaggc                             40

<210> SEQ ID NO 19
<211> LENGTH: 20

```
<212> TYPE: DNA
<213> ORGANISM: Homo sapiens

<400> SEQUENCE: 19
tacgcagcgc ctccctccac                                               20

<210> SEQ ID NO 20
<211> LENGTH: 20
<212> TYPE: DNA
<213> ORGANISM: Homo sapiens

<400> SEQUENCE: 20
ctgttctcgt cgtttccgca                                               20

<210> SEQ ID NO 21
<211> LENGTH: 40
<212> TYPE: DNA
<213> ORGANISM: Homo sapiens

<400> SEQUENCE: 21
ctgttctcgt cgtttccgca accttggggg ccttttcatt                         40

<210> SEQ ID NO 22
<211> LENGTH: 20
<212> TYPE: DNA
<213> ORGANISM: Homo sapiens

<400> SEQUENCE: 22
tacgacaagg atagaagcgg                                               20

<210> SEQ ID NO 23
<211> LENGTH: 20
<212> TYPE: DNA
<213> ORGANISM: Homo sapiens

<400> SEQUENCE: 23
aggacatgac gctctttctg                                               20

<210> SEQ ID NO 24
<211> LENGTH: 42
<212> TYPE: DNA
<213> ORGANISM: Homo sapiens

<400> SEQUENCE: 24
aggacatgac gctctttctg gatttccttt ttgtttttct cg                      42

<210> SEQ ID NO 25
<211> LENGTH: 20
<212> TYPE: DNA
<213> ORGANISM: Homo sapiens

<400> SEQUENCE: 25
ggatacaaag aagggagtgc                                               20

<210> SEQ ID NO 26
<211> LENGTH: 20
<212> TYPE: DNA
<213> ORGANISM: Homo sapiens

<400> SEQUENCE: 26
ccaactcagg acaaggtaca                                               20

<210> SEQ ID NO 27
```

```
<211> LENGTH: 40
<212> TYPE: DNA
<213> ORGANISM: Homo sapiens

<400> SEQUENCE: 27
ccaactcagg acaaggtaca tcttctgggc tcttggtggc                              40

<210> SEQ ID NO 28
<211> LENGTH: 20
<212> TYPE: DNA
<213> ORGANISM: Homo sapiens

<400> SEQUENCE: 28
ccagaagaaa gcggtcaaga                                                    20

<210> SEQ ID NO 29
<211> LENGTH: 20
<212> TYPE: DNA
<213> ORGANISM: Homo sapiens

<400> SEQUENCE: 29
aaccttcatt ttcccctggg                                                    20

<210> SEQ ID NO 30
<211> LENGTH: 40
<212> TYPE: DNA
<213> ORGANISM: Homo sapiens

<400> SEQUENCE: 30
aaccttcatt ttcccctggg ccagtgatga gcgggttaca                              40

<210> SEQ ID NO 31
<211> LENGTH: 26
<212> TYPE: DNA
<213> ORGANISM: Homo sapiens

<400> SEQUENCE: 31
ggccttgcca gagcttttgg aatacc                                             26

<210> SEQ ID NO 32
<211> LENGTH: 26
<212> TYPE: DNA
<213> ORGANISM: Homo sapiens

<400> SEQUENCE: 32
agccattttc atccaagttt ttgaca                                             26

<210> SEQ ID NO 33
<211> LENGTH: 52
<212> TYPE: DNA
<213> ORGANISM: Homo sapiens

<400> SEQUENCE: 33
agccattttc atccaagttt ttgacagttg attaatttct gaatccccat gg                52

<210> SEQ ID NO 34
<211> LENGTH: 25
<212> TYPE: DNA
<213> ORGANISM: Homo sapiens

<400> SEQUENCE: 34
ggtgtggaca tgtgggctgt tggct                                              25
```

```
<210> SEQ ID NO 35
<211> LENGTH: 25
<212> TYPE: DNA
<213> ORGANISM: Homo sapiens

<400> SEQUENCE: 35
tggtcttggc agctgacatc caggt                                    25

<210> SEQ ID NO 36
<211> LENGTH: 45
<212> TYPE: DNA
<213> ORGANISM: Homo sapiens

<400> SEQUENCE: 36
tggtcttggc agctgacatc caggttctag taagtcgtct cctgc              45

<210> SEQ ID NO 37
<211> LENGTH: 20
<212> TYPE: DNA
<213> ORGANISM: Homo sapiens

<400> SEQUENCE: 37
tgccggttgt caaatccctt                                          20

<210> SEQ ID NO 38
<211> LENGTH: 20
<212> TYPE: DNA
<213> ORGANISM: Homo sapiens

<400> SEQUENCE: 38
tccgatgcag ctcagtaccg                                          20

<210> SEQ ID NO 39
<211> LENGTH: 37
<212> TYPE: DNA
<213> ORGANISM: Homo sapiens

<400> SEQUENCE: 39
tccgatgcac agtaccgatg tggattggaa cgctgat                       37

<210> SEQ ID NO 40
<211> LENGTH: 30
<212> TYPE: DNA
<213> ORGANISM: Homo sapiens

<400> SEQUENCE: 40
agcagtcttt tggagtgacc agcaactttg                               30

<210> SEQ ID NO 41
<211> LENGTH: 30
<212> TYPE: DNA
<213> ORGANISM: Homo sapiens

<400> SEQUENCE: 41
catgcaatga agctgaacat gaccgtagtt                               30

<210> SEQ ID NO 42
<211> LENGTH: 50
<212> TYPE: DNA
<213> ORGANISM: Homo sapiens

<400> SEQUENCE: 42
catgcaatga agctgaacat gaccgtagtt tctgtgatga gttttaaaaa          50
```

```
<210> SEQ ID NO 43
<211> LENGTH: 18
<212> TYPE: DNA
<213> ORGANISM: Homo sapiens

<400> SEQUENCE: 43
gctgcaggcc ctgaagga                                                   18

<210> SEQ ID NO 44
<211> LENGTH: 18
<212> TYPE: DNA
<213> ORGANISM: Homo sapiens

<400> SEQUENCE: 44
ccccgacggt ctctcttc                                                   18

<210> SEQ ID NO 45
<211> LENGTH: 36
<212> TYPE: DNA
<213> ORGANISM: Homo sapiens

<400> SEQUENCE: 45
ccccgacggt ctctcttcag ttctgagctt tcaagg                               36

<210> SEQ ID NO 46
<211> LENGTH: 20
<212> TYPE: DNA
<213> ORGANISM: Homo sapiens

<400> SEQUENCE: 46
tgtggtacaa ccacgaacag                                                 20

<210> SEQ ID NO 47
<211> LENGTH: 20
<212> TYPE: DNA
<213> ORGANISM: Homo sapiens

<400> SEQUENCE: 47
agatatttcc gcagcaacag                                                 20

<210> SEQ ID NO 48
<211> LENGTH: 40
<212> TYPE: DNA
<213> ORGANISM: Homo sapiens

<400> SEQUENCE: 48
agatatttcc gcagcaacag atgccacagc caggactaat                           40

<210> SEQ ID NO 49
<211> LENGTH: 19
<212> TYPE: DNA
<213> ORGANISM: Homo sapiens

<400> SEQUENCE: 49
caggagctaa aggcgaaga                                                  19

<210> SEQ ID NO 50
<211> LENGTH: 19
<212> TYPE: DNA
<213> ORGANISM: Homo sapiens

<400> SEQUENCE: 50
ccaggctgac ctcggggac                                                  19
```

<210> SEQ ID NO 51
<211> LENGTH: 38
<212> TYPE: DNA
<213> ORGANISM: Homo sapiens

<400> SEQUENCE: 51
ccaggctgac ctcggggacg acctccaggg acgccatc                    38

<210> SEQ ID NO 52
<211> LENGTH: 21
<212> TYPE: DNA
<213> ORGANISM: Homo sapiens

<400> SEQUENCE: 52
tgaaggtgtg gggaagcatt a                                      21

<210> SEQ ID NO 53
<211> LENGTH: 21
<212> TYPE: DNA
<213> ORGANISM: Homo sapiens

<400> SEQUENCE: 53
ttacaccaca agccaaacga c                                      21

<210> SEQ ID NO 54
<211> LENGTH: 42
<212> TYPE: DNA
<213> ORGANISM: Homo sapiens

<400> SEQUENCE: 54
ttacaccaca agccaaacga ctgatgcaat ggtctcctga ga               42

<210> SEQ ID NO 55
<211> LENGTH: 24
<212> TYPE: DNA
<213> ORGANISM: Homo sapiens

<400> SEQUENCE: 55
ccaagaggac caggagaata tcaa                                   24

<210> SEQ ID NO 56
<211> LENGTH: 24
<212> TYPE: DNA
<213> ORGANISM: Homo sapiens

<400> SEQUENCE: 56
ggataatcaa gagggaccaa tggt                                   24

<210> SEQ ID NO 57
<211> LENGTH: 44
<212> TYPE: DNA
<213> ORGANISM: Homo sapiens

<400> SEQUENCE: 57
ggataatcaa gagggaccaa tggtgtgaac gcaggctgtt tact             44

<210> SEQ ID NO 58
<211> LENGTH: 20
<212> TYPE: DNA
<213> ORGANISM: Homo sapiens

<400> SEQUENCE: 58

```
ggcgcgtctc cggcacgatg                                         20

<210> SEQ ID NO 59
<211> LENGTH: 25
<212> TYPE: DNA
<213> ORGANISM: Homo sapiens

<400> SEQUENCE: 59
gcagccagca aaaagaaca gactc                                    25

<210> SEQ ID NO 60
<211> LENGTH: 45
<212> TYPE: DNA
<213> ORGANISM: Homo sapiens

<400> SEQUENCE: 60
gcagccagca aaaagaaca gactcaaagt ttcagtgcaa gatcc              45

<210> SEQ ID NO 61
<211> LENGTH: 29
<212> TYPE: DNA
<213> ORGANISM: Homo sapiens

<400> SEQUENCE: 61
tggaattctg ttcggtgttt aagccagca                               29

<210> SEQ ID NO 62
<211> LENGTH: 29
<212> TYPE: DNA
<213> ORGANISM: Homo sapiens

<400> SEQUENCE: 62
caatatggga tagcgggtct ttaagtcga                               29

<210> SEQ ID NO 63
<211> LENGTH: 58
<212> TYPE: DNA
<213> ORGANISM: Homo sapiens

<400> SEQUENCE: 63
caatatggga tagcgggtct ttaagtcgat ccaagaggac tctcccggag gtttccaa   58

<210> SEQ ID NO 64
<211> LENGTH: 21
<212> TYPE: DNA
<213> ORGANISM: Homo sapiens

<400> SEQUENCE: 64 catccccac agcacaacaa g                                        21

<210> SEQ ID NO 65
<211> LENGTH: 21
<212> TYPE: DNA
<213> ORGANISM: Homo sapiens

<400> SEQUENCE: 65
acagcaggca tgcttcatgg t                                       21

<210> SEQ ID NO 66
<211> LENGTH: 40
<212> TYPE: DNA
<213> ORGANISM: Homo sapiens

<400> SEQUENCE: 66
```
acagcaggca tgcttcatgg gtctcaccga tacacttccg                    40

<210> SEQ ID NO 67
<211> LENGTH: 21
<212> TYPE: DNA
<213> ORGANISM: Homo sapiens

<400> SEQUENCE: 67 accccccagtc tcaatctcaa c                                      21

<210> SEQ ID NO 68
<211> LENGTH: 21
<212> TYPE: DNA
<213> ORGANISM: Homo sapiens

<400> SEQUENCE: 68
cgttcgggct gaggctggtg c                                       21

<210> SEQ ID NO 69
<211> LENGTH: 42
<212> TYPE: DNA
<213> ORGANISM: Homo sapiens

<400> SEQUENCE: 69
cgttcgggct gaggctggtg ccgtcaacag gaacccgcag gc                 42

<210> SEQ ID NO 70
<211> LENGTH: 20
<212> TYPE: DNA
<213> ORGANISM: Homo sapiens

<400> SEQUENCE: 70
ggaacttcgg aaatccaagg                                         20

<210> SEQ ID NO 71
<211> LENGTH: 20
<212> TYPE: DNA
<213> ORGANISM: Homo sapiens

<400> SEQUENCE: 71
ccatgtggag caggtaggtg                                         20

<210> SEQ ID NO 72
<211> LENGTH: 40
<212> TYPE: DNA
<213> ORGANISM: Homo sapiens

<400> SEQUENCE: 72
ccatgtggag caggtaggtg gtgtgcccca ggaaagtatt                   40

<210> SEQ ID NO 73
<211> LENGTH: 20
<212> TYPE: DNA
<213> ORGANISM: Homo sapiens

<400> SEQUENCE: 73
ccttcctcct gctggtgtcc                                         20

<210> SEQ ID NO 74
<211> LENGTH: 20
<212> TYPE: DNA
<213> ORGANISM: Homo sapiens

```
<400> SEQUENCE: 74
gccggatgtc cttccaggta                                              20

<210> SEQ ID NO 75
<211> LENGTH: 43
<212> TYPE: DNA
<213> ORGANISM: Homo sapiens

<400> SEQUENCE: 75
gccggatgtc cttccaggta atcaccacca tgcgctgctg cga                    43

<210> SEQ ID NO 76
<211> LENGTH: 20
<212> TYPE: DNA
<213> ORGANISM: Homo sapiens

<400> SEQUENCE: 76
ggggaagaga agcattgagg                                              20

<210> SEQ ID NO 77
<211> LENGTH: 20
<212> TYPE: DNA
<213> ORGANISM: Homo sapiens

<400> SEQUENCE: 77
gcctggtggt cgtggacgct                                              20

<210> SEQ ID NO 78
<211> LENGTH: 40
<212> TYPE: DNA
<213> ORGANISM: Homo sapiens

<400> SEQUENCE: 78
gcctggtggt cgtggacgct cgggaatctg gggtctagga                        40

<210> SEQ ID NO 79
<211> LENGTH: 20
<212> TYPE: DNA
<213> ORGANISM: Homo sapiens

<400> SEQUENCE: 79
agaaagagaa cagcttcgca                                              20

<210> SEQ ID NO 80
<211> LENGTH: 20
<212> TYPE: DNA
<213> ORGANISM: Homo sapiens

<400> SEQUENCE: 80
cacattgatt cattggctga                                              20

<210> SEQ ID NO 81
<211> LENGTH: 40
<212> TYPE: DNA
<213> ORGANISM: Homo sapiens

<400> SEQUENCE: 81
cacattgatt cattggctga ttttcttcca ggattctccc                        40

<210> SEQ ID NO 82
<211> LENGTH: 21
<212> TYPE: DNA
<213> ORGANISM: Homo sapiens
```

```
<400> SEQUENCE: 82
gctggatgcc catgagagag g                                              21

<210> SEQ ID NO 83
<211> LENGTH: 21
<212> TYPE: DNA
<213> ORGANISM: Homo sapiens

<400> SEQUENCE: 83
catgggaaca gctctcgagg a                                              21

<210> SEQ ID NO 84
<211> LENGTH: 42
<212> TYPE: DNA
<213> ORGANISM: Homo sapiens

<400> SEQUENCE: 84
catgggaaca gctctcgagg aatcttgttt tctttcatgc tc                       42

<210> SEQ ID NO 85
<211> LENGTH: 20
<212> TYPE: DNA
<213> ORGANISM: Homo sapiens

<400> SEQUENCE: 85
ggggacgcag tagccgagat                                                20

<210> SEQ ID NO 86
<211> LENGTH: 20
<212> TYPE: DNA
<213> ORGANISM: Homo sapiens

<400> SEQUENCE: 86
tcacttcagc atcacctcca                                                20

<210> SEQ ID NO 87
<211> LENGTH: 40
<212> TYPE: DNA
<213> ORGANISM: Homo sapiens

<400> SEQUENCE: 87
tcacttcagc atcacctcca taaagggaag agccgagtcg                          40

<210> SEQ ID NO 88
<211> LENGTH: 20
<212> TYPE: DNA
<213> ORGANISM: Homo sapiens

<400> SEQUENCE: 88
cggatgggaa tgtcgtttgg                                                20

<210> SEQ ID NO 89
<211> LENGTH: 20
<212> TYPE: DNA
<213> ORGANISM: Homo sapiens

<400> SEQUENCE: 89
gggggtctcg cctcgggact                                                20

<210> SEQ ID NO 90
<211> LENGTH: 40
<212> TYPE: DNA
```

<213> ORGANISM: Homo sapiens

<400> SEQUENCE: 90
gggggtctcg cctcgggact acttgactgg ggtaaggtgg                           40

<210> SEQ ID NO 91
<211> LENGTH: 20
<212> TYPE: DNA
<213> ORGANISM: Homo sapiens

<400> SEQUENCE: 91
acaaaagaag atgccacagc                                                20

<210> SEQ ID NO 92
<211> LENGTH: 20
<212> TYPE: DNA
<213> ORGANISM: Homo sapiens

<400> SEQUENCE: 92
tgcagcaaca aaaacacagt                                                20

<210> SEQ ID NO 93
<211> LENGTH: 41
<212> TYPE: DNA
<213> ORGANISM: Homo sapiens

<400> SEQUENCE: 93
tgcagcaaca aaaacacagt tcctagggag ttgaataagg c                         41

<210> SEQ ID NO 94
<211> LENGTH: 20
<212> TYPE: DNA
<213> ORGANISM: Homo sapiens

<400> SEQUENCE: 94
tgatacccca actccctcta                                                20

<210> SEQ ID NO 95
<211> LENGTH: 20
<212> TYPE: DNA
<213> ORGANISM: Homo sapiens

<400> SEQUENCE: 95
aaagcaggag ggaacagagc                                                20

<210> SEQ ID NO 96
<211> LENGTH: 37
<212> TYPE: DNA
<213> ORGANISM: Homo sapiens

<400> SEQUENCE: 96
aaagcaggag ggaacagagc actgcaggga ccacagg                             37

<210> SEQ ID NO 97
<211> LENGTH: 20
<212> TYPE: DNA
<213> ORGANISM: Homo sapiens

<400> SEQUENCE: 97
tgcccagcta ctgctaccta                                                20

<210> SEQ ID NO 98
<211> LENGTH: 18

-continued

```
<212> TYPE: DNA
<213> ORGANISM: Homo sapiens

<400> SEQUENCE: 98
cccagttcag gtccagga                                                18

<210> SEQ ID NO 99
<211> LENGTH: 36
<212> TYPE: DNA
<213> ORGANISM: Homo sapiens

<400> SEQUENCE: 99
cccagttcag gtccaggatg tcataccgag tcttct                            36

<210> SEQ ID NO 100
<211> LENGTH: 20
<212> TYPE: DNA
<213> ORGANISM: Homo sapiens

<400> SEQUENCE: 100
gccctgggac tgatagcaag                                              20

<210> SEQ ID NO 101
<211> LENGTH: 20
<212> TYPE: DNA
<213> ORGANISM: Homo sapiens

<400> SEQUENCE: 101
agacgaagca gaggggcaaa                                              20

<210> SEQ ID NO 102
<211> LENGTH: 40
<212> TYPE: DNA
<213> ORGANISM: Homo sapiens

<400> SEQUENCE: 102
agacgaagca gaggggcaaa ggggagttcc aaaacacctg                        40

<210> SEQ ID NO 103
<211> LENGTH: 24
<212> TYPE: DNA
<213> ORGANISM: Homo sapiens

<400> SEQUENCE: 103
ccagaaatgg gtcagaatgg acaa                                         24

<210> SEQ ID NO 104
<211> LENGTH: 24
<212> TYPE: DNA
<213> ORGANISM: Homo sapiens

<400> SEQUENCE: 104
catctgccgg ggtaggagaa agcc                                         24

<210> SEQ ID NO 105
<211> LENGTH: 44
<212> TYPE: DNA
<213> ORGANISM: Homo sapiens

<400> SEQUENCE: 105
catctgccgg ggtaggagaa agcctgtctg ctgcagagcc tggc                   44

<210> SEQ ID NO 106
```

```
<211> LENGTH: 18
<212> TYPE: DNA
<213> ORGANISM: Homo sapiens

<400> SEQUENCE: 106
ctggagcccc gaggaagc                                                       18

<210> SEQ ID NO 107
<211> LENGTH: 18
<212> TYPE: DNA
<213> ORGANISM: Homo sapiens

<400> SEQUENCE: 107
cactgggggt ttcctttg                                                       18

<210> SEQ ID NO 108
<211> LENGTH: 36
<212> TYPE: DNA
<213> ORGANISM: Homo sapiens

<400> SEQUENCE: 108
cactgggggt ttccttggaa ggccagatct tctctt                                   36

<210> SEQ ID NO 109
<211> LENGTH: 25
<212> TYPE: DNA
<213> ORGANISM: Homo sapiens

<400> SEQUENCE: 109
agtgcatctc catgtcccgc tacta                                               25

<210> SEQ ID NO 110
<211> LENGTH: 25
<212> TYPE: DNA
<213> ORGANISM: Homo sapiens

<400> SEQUENCE: 110
cgatgttctt aacgtggtgc atcaa                                               25

<210> SEQ ID NO 111
<211> LENGTH: 45
<212> TYPE: DNA
<213> ORGANISM: Homo sapiens

<400> SEQUENCE: 111
cgatgttctt aacgtggtgc atcaacaggc tgtggcttgc tttgt                         45

<210> SEQ ID NO 112
<211> LENGTH: 21
<212> TYPE: DNA
<213> ORGANISM: Homo sapiens

<400> SEQUENCE: 112
cctcctgcag tcccagctct c                                                   21

<210> SEQ ID NO 113
<211> LENGTH: 21
<212> TYPE: DNA
<213> ORGANISM: Homo sapiens

<400> SEQUENCE: 113
ggtttctccc cgccgttctc a                                                   21
```

-continued

```
<210> SEQ ID NO 114
<211> LENGTH: 42
<212> TYPE: DNA
<213> ORGANISM: Homo sapiens

<400> SEQUENCE: 114
ggtttctccc cgccgttctc atgagcaaat aatccattct ga          42

<210> SEQ ID NO 115
<211> LENGTH: 20
<212> TYPE: DNA
<213> ORGANISM: Homo sapiens

<400> SEQUENCE: 115
ggagctcccc tgtggtcatc                                   20

<210> SEQ ID NO 116
<211> LENGTH: 20
<212> TYPE: DNA
<213> ORGANISM: Homo sapiens

<400> SEQUENCE: 116
ttttgaactg tggaaggaac                                   20

<210> SEQ ID NO 117
<211> LENGTH: 40
<212> TYPE: DNA
<213> ORGANISM: Homo sapiens

<400> SEQUENCE: 117
ttttgaactg tggaaggaac aggggctcgc tcttctgatt             40

<210> SEQ ID NO 118
<211> LENGTH: 25
<212> TYPE: DNA
<213> ORGANISM: Homo sapiens

<400> SEQUENCE: 118
aaagtacttg gagtctgcag gtgcg                             25

<210> SEQ ID NO 119
<211> LENGTH: 25
<212> TYPE: DNA
<213> ORGANISM: Homo sapiens

<400> SEQUENCE: 119
tgcaattgac ctccagtgaa gttca                             25

<210> SEQ ID NO 120
<211> LENGTH: 50
<212> TYPE: DNA
<213> ORGANISM: Homo sapiens

<400> SEQUENCE: 120
tgcaattgac ctccagtgaa gttcagtgcc ccacacagga aaatagtctc   50

<210> SEQ ID NO 121
<211> LENGTH: 18
<212> TYPE: DNA
<213> ORGANISM: Homo sapiens

<400> SEQUENCE: 121
cactgggacg aagggaa                                      18
```

<210> SEQ ID NO 122
<211> LENGTH: 18
<212> TYPE: DNA
<213> ORGANISM: Homo sapiens

<400> SEQUENCE: 122
gtcataagcc ccgccaat                                                 18

<210> SEQ ID NO 123
<211> LENGTH: 36
<212> TYPE: DNA
<213> ORGANISM: Homo sapiens

<400> SEQUENCE: 123
gtcataagcc ccgccaatag acacagctgc catcct                             36

<210> SEQ ID NO 124
<211> LENGTH: 18
<212> TYPE: DNA
<213> ORGANISM: Homo sapiens

<400> SEQUENCE: 124
aagcccaccg acccatct                                                 18

<210> SEQ ID NO 125
<211> LENGTH: 18
<212> TYPE: DNA
<213> ORGANISM: Homo sapiens

<400> SEQUENCE: 125
tcaggcgcct cacaaagc                                                 18

<210> SEQ ID NO 126
<211> LENGTH: 36
<212> TYPE: DNA
<213> ORGANISM: Homo sapiens

<400> SEQUENCE: 126
tcaggcgcct cacaaagcag tgctggggta ggtgaa                             36

<210> SEQ ID NO 127
<211> LENGTH: 21
<212> TYPE: DNA
<213> ORGANISM: Homo sapiens

<400> SEQUENCE: 127
ggtcggagtc aacggatttg g                                             21

<210> SEQ ID NO 128
<211> LENGTH: 21
<212> TYPE: DNA
<213> ORGANISM: Homo sapiens

<400> SEQUENCE: 128
cctccgacgc ctgcttcacc a                                             21

<210> SEQ ID NO 129
<211> LENGTH: 42
<212> TYPE: DNA
<213> ORGANISM: Homo sapiens

<400> SEQUENCE: 129
cctccgacgc ctgcttcacc agaggggcca tccacagtct tc                      42

<210> SEQ ID NO 130
<211> LENGTH: 21
<212> TYPE: DNA
<213> ORGANISM: Homo sapiens

<400> SEQUENCE: 130
gaggagcgag gactggagcc a                                              21

<210> SEQ ID NO 131
<211> LENGTH: 21
<212> TYPE: DNA
<213> ORGANISM: Homo sapiens

<400> SEQUENCE: 131
gcacctccat gggtcgaaat t                                              21

<210> SEQ ID NO 132
<211> LENGTH: 42
<212> TYPE: DNA
<213> ORGANISM: Homo sapiens

<400> SEQUENCE: 132
gcacctccat gggtcgaaat ttgtcagtgg gtctctaata aa                       42

<210> SEQ ID NO 133
<211> LENGTH: 20
<212> TYPE: DNA
<213> ORGANISM: Homo sapiens

<400> SEQUENCE: 133
tcgccgagga gagcaagttc                                                20

<210> SEQ ID NO 134
<211> LENGTH: 20
<212> TYPE: DNA
<213> ORGANISM: Homo sapiens

<400> SEQUENCE: 134
ggaacagcgc ggtcctgtaa                                                20

<210> SEQ ID NO 135
<211> LENGTH: 40
<212> TYPE: DNA
<213> ORGANISM: Homo sapiens

<400> SEQUENCE: 135
ggaacagcgc ggtcctgtaa gaataatcca aaagaccaga                          40

<210> SEQ ID NO 136
<211> LENGTH: 20
<212> TYPE: DNA
<213> ORGANISM: Homo sapiens

<400> SEQUENCE: 136
cgtaccctgt gccattccaa                                                20

<210> SEQ ID NO 137
<211> LENGTH: 20
<212> TYPE: DNA
<213> ORGANISM: Homo sapiens

<400> SEQUENCE: 137

```
taaacagcca gacagatgca                                               20

<210> SEQ ID NO 138
<211> LENGTH: 40
<212> TYPE: DNA
<213> ORGANISM: Homo sapiens

<400> SEQUENCE: 138
taaacagcca gacagatgca atacggggaa taaaccacgt                         40

<210> SEQ ID NO 139
<211> LENGTH: 18
<212> TYPE: DNA
<213> ORGANISM: Homo sapiens

<400> SEQUENCE: 139
gtcggtggct tctgctga                                                 18

<210> SEQ ID NO 140
<211> LENGTH: 19
<212> TYPE: DNA
<213> ORGANISM: Homo sapiens

<400> SEQUENCE: 140
aacccttgag tgtagccca                                                19

<210> SEQ ID NO 141
<211> LENGTH: 37
<212> TYPE: DNA
<213> ORGANISM: Homo sapiens

<400> SEQUENCE: 141
aacccttgag tgtagcccag atgtgcatat tcacctc                            37

<210> SEQ ID NO 142
<211> LENGTH: 20
<212> TYPE: DNA
<213> ORGANISM: Homo sapiens

<400> SEQUENCE: 142
gctgctggcc gaaaacttgc                                               20

<210> SEQ ID NO 143
<211> LENGTH: 20
<212> TYPE: DNA
<213> ORGANISM: Homo sapiens

<400> SEQUENCE: 143
gtctgccttc gttgctccca                                               20

<210> SEQ ID NO 144
<211> LENGTH: 40
<212> TYPE: DNA
<213> ORGANISM: Homo sapiens

<400> SEQUENCE: 144
gtctgccttc gttgctccca tttcttcctt gttagcacag                         40

<210> SEQ ID NO 145
<211> LENGTH: 21
<212> TYPE: DNA
<213> ORGANISM: Homo sapiens

<400> SEQUENCE: 145
```

```
gcagagccgg ggacaagaga a                                              21

<210> SEQ ID NO 146
<211> LENGTH: 21
<212> TYPE: DNA
<213> ORGANISM: Homo sapiens

<400> SEQUENCE: 146
ctgctctttc tctccattga c                                              21

<210> SEQ ID NO 147
<211> LENGTH: 42
<212> TYPE: DNA
<213> ORGANISM: Homo sapiens

<400> SEQUENCE: 147
ctgctctttc tctccattga cgctcttcct gtagtgcatt ca                       42

<210> SEQ ID NO 148
<211> LENGTH: 20
<212> TYPE: DNA
<213> ORGANISM: Homo sapiens

<400> SEQUENCE: 148
gggacgctcc tgattatgac                                                20

<210> SEQ ID NO 149
<211> LENGTH: 20
<212> TYPE: DNA
<213> ORGANISM: Homo sapiens

<400> SEQUENCE: 149
gcaaaccatg gccgcttccc                                                20

<210> SEQ ID NO 150
<211> LENGTH: 40
<212> TYPE: DNA
<213> ORGANISM: Homo sapiens

<400> SEQUENCE: 150
gcaaaccatg gccgcttccc ttctccaaaa tgtccacacg                          40

<210> SEQ ID NO 151
<211> LENGTH: 20
<212> TYPE: DNA
<213> ORGANISM: Homo sapiens

<400> SEQUENCE: 151
gtgcgagtcg tctatggttc                                                20

<210> SEQ ID NO 152
<211> LENGTH: 20
<212> TYPE: DNA
<213> ORGANISM: Homo sapiens

<400> SEQUENCE: 152
agttgtgtgc ggaaatccat                                                20

<210> SEQ ID NO 153
<211> LENGTH: 40
<212> TYPE: DNA
<213> ORGANISM: Homo sapiens
```

<400> SEQUENCE: 153
agttgtgtgc ggaaatccat tgctctgggt gatcttgttc                                  40

<210> SEQ ID NO 154
<211> LENGTH: 20
<212> TYPE: DNA
<213> ORGANISM: Homo sapiens

<400> SEQUENCE: 154
tccgctgcaa atacatctcc                                                         20

<210> SEQ ID NO 155
<211> LENGTH: 20
<212> TYPE: DNA
<213> ORGANISM: Homo sapiens

<400> SEQUENCE: 155
tgtttcccgt tgccattgat                                                         20

<210> SEQ ID NO 156
<211> LENGTH: 40
<212> TYPE: DNA
<213> ORGANISM: Homo sapiens

<400> SEQUENCE: 156
tgtttcccgt tgccattgat taggacctca tggatcagca                                  40

<210> SEQ ID NO 157
<211> LENGTH: 20
<212> TYPE: DNA
<213> ORGANISM: Homo sapiens

<400> SEQUENCE: 157
gctctacctg gacctgctgt                                                         20

<210> SEQ ID NO 158
<211> LENGTH: 20
<212> TYPE: DNA
<213> ORGANISM: Homo sapiens

<400> SEQUENCE: 158
ggaacacagg gaacatcacc                                                         20

<210> SEQ ID NO 159
<211> LENGTH: 40
<212> TYPE: DNA
<213> ORGANISM: Homo sapiens

<400> SEQUENCE: 159
ggaacacagg gaacatcacc tagagcagga tggccacact                                  40

<210> SEQ ID NO 160
<211> LENGTH: 20
<212> TYPE: DNA
<213> ORGANISM: Homo sapiens

<400> SEQUENCE: 160
atgtgaacca gccagatgtt                                                         20

<210> SEQ ID NO 161
<211> LENGTH: 20
<212> TYPE: DNA
<213> ORGANISM: Homo sapiens

```
<400> SEQUENCE: 161
ctctgggttc tctgccgtag                                           20

<210> SEQ ID NO 162
<211> LENGTH: 40
<212> TYPE: DNA
<213> ORGANISM: Homo sapiens

<400> SEQUENCE: 162
ctctgggttc tctgccgtag aggaggaggg tggggctgag                     40

<210> SEQ ID NO 163
<211> LENGTH: 23
<212> TYPE: DNA
<213> ORGANISM: Homo sapiens

<400> SEQUENCE: 163
gctctacgtt gcccgccagc ctg                                       23

<210> SEQ ID NO 164
<211> LENGTH: 23
<212> TYPE: DNA
<213> ORGANISM: Homo sapiens

<400> SEQUENCE: 164 gttgggcc gtctttgtag taa                                         23

<210> SEQ ID NO 165
<211> LENGTH: 46
<212> TYPE: DNA
<213> ORGANISM: Homo sapiens

<400> SEQUENCE: 165 gttgggcc gtctttgtag taatttatta tgctgttgac ggtttg                46

<210> SEQ ID NO 166
<211> LENGTH: 20
<212> TYPE: DNA
<213> ORGANISM: Homo sapiens

<400> SEQUENCE: 166
ttttgggagg gggttgtgcc                                           20

<210> SEQ ID NO 167
<211> LENGTH: 20
<212> TYPE: DNA
<213> ORGANISM: Homo sapiens

<400> SEQUENCE: 167
ggccacacca gcagcatcca                                           20

<210> SEQ ID NO 168
<211> LENGTH: 40
<212> TYPE: DNA
<213> ORGANISM: Homo sapiens

<400> SEQUENCE: 168
ggccacacca gcagcatcca taaccaactt ctgaggaact                     40

<210> SEQ ID NO 169
<211> LENGTH: 20
<212> TYPE: DNA
```

<213> ORGANISM: Homo sapiens

<400> SEQUENCE: 169
agttgtggcc tttacagcag                                              20

<210> SEQ ID NO 170
<211> LENGTH: 20
<212> TYPE: DNA
<213> ORGANISM: Homo sapiens

<400> SEQUENCE: 170
tgtgtgcccc aagtaatttt                                              20

<210> SEQ ID NO 171
<211> LENGTH: 40
<212> TYPE: DNA
<213> ORGANISM: Homo sapiens

<400> SEQUENCE: 171
tgtgtgcccc aagtaatttt gcacggacaa ttttaaaggg                        40

<210> SEQ ID NO 172
<211> LENGTH: 21
<212> TYPE: DNA
<213> ORGANISM: Homo sapiens

<400> SEQUENCE: 172
cctaccagct ccagaccttt g                                            21

<210> SEQ ID NO 173
<211> LENGTH: 21
<212> TYPE: DNA
<213> ORGANISM: Homo sapiens

<400> SEQUENCE: 173
tggcttcgtc agaatcacgt t                                            21

<210> SEQ ID NO 174
<211> LENGTH: 42
<212> TYPE: DNA
<213> ORGANISM: Homo sapiens

<400> SEQUENCE: 174
tggcttcgtc agaatcacgt tcccagtatt actgcacacg tc                     42

<210> SEQ ID NO 175
<211> LENGTH: 22
<212> TYPE: DNA
<213> ORGANISM: Homo sapiens

<400> SEQUENCE: 175
ccttactgtg agtctgggtt ga                                           22

<210> SEQ ID NO 176
<211> LENGTH: 22
<212> TYPE: DNA
<213> ORGANISM: Homo sapiens

<400> SEQUENCE: 176
tgggttttct gctttctgat at                                           22

<210> SEQ ID NO 177
<211> LENGTH: 44

```
<212> TYPE: DNA
<213> ORGANISM: Homo sapiens

<400> SEQUENCE: 177
tgggttttct gctttctgat atgtcccttt acagcagtca tgtg          44

<210> SEQ ID NO 178
<211> LENGTH: 19
<212> TYPE: DNA
<213> ORGANISM: Homo sapiens

<400> SEQUENCE: 178
tggcccagct caaacagaa                                       19

<210> SEQ ID NO 179
<211> LENGTH: 19
<212> TYPE: DNA
<213> ORGANISM: Homo sapiens

<400> SEQUENCE: 179
cctcttcccc tccctgtta                                       19

<210> SEQ ID NO 180
<211> LENGTH: 37
<212> TYPE: DNA
<213> ORGANISM: Homo sapiens

<400> SEQUENCE: 180
cctcttcccc tccctgttac ttgtaaacgt cgaggtg                   37

<210> SEQ ID NO 181
<211> LENGTH: 20
<212> TYPE: DNA
<213> ORGANISM: Homo sapiens

<400> SEQUENCE: 181
ctcaaggatg ccaggaacaa                                      20

<210> SEQ ID NO 182
<211> LENGTH: 20
<212> TYPE: DNA
<213> ORGANISM: Homo sapiens

<400> SEQUENCE: 182
acactgagcc caccacctag                                      20

<210> SEQ ID NO 183
<211> LENGTH: 40
<212> TYPE: DNA
<213> ORGANISM: Homo sapiens

<400> SEQUENCE: 183
acactgagcc caccacctag ccactgccat atccagagga                40

<210> SEQ ID NO 184
<211> LENGTH: 20
<212> TYPE: DNA
<213> ORGANISM: Homo sapiens

<400> SEQUENCE: 184
tgccttggac acggggttct                                      20

<210> SEQ ID NO 185
```

```
<211> LENGTH: 20
<212> TYPE: DNA
<213> ORGANISM: Homo sapiens

<400> SEQUENCE: 185
ttgcccttct gaatagtccc                                                    20

<210> SEQ ID NO 186
<211> LENGTH: 40
<212> TYPE: DNA
<213> ORGANISM: Homo sapiens

<400> SEQUENCE: 186
ttgcccttct gaatagtccc catggatgcc gtctaattgc                              40

<210> SEQ ID NO 187
<211> LENGTH: 20
<212> TYPE: DNA
<213> ORGANISM: Homo sapiens

<400> SEQUENCE: 187
ttcagcgaga gcagcgacac                                                    20

<210> SEQ ID NO 188
<211> LENGTH: 20
<212> TYPE: DNA
<213> ORGANISM: Homo sapiens

<400> SEQUENCE: 188
cagaaccaac agggagaacc                                                    20

<210> SEQ ID NO 189
<211> LENGTH: 40
<212> TYPE: DNA
<213> ORGANISM: Homo sapiens

<400> SEQUENCE: 189
cagaaccaac agggagaacc tcttgatgct ggtgctggaa                              40

<210> SEQ ID NO 190
<211> LENGTH: 20
<212> TYPE: DNA
<213> ORGANISM: Homo sapiens

<400> SEQUENCE: 190
tgacatcgag gtggagagcg                                                    20

<210> SEQ ID NO 191
<211> LENGTH: 20
<212> TYPE: DNA
<213> ORGANISM: Homo sapiens

<400> SEQUENCE: 191
cccccatcga aggcagaaat                                                    20

<210> SEQ ID NO 192
<211> LENGTH: 40
<212> TYPE: DNA
<213> ORGANISM: Homo sapiens

<400> SEQUENCE: 192
tgacatcgag gtggagagcg cacacacacc agcaagatat                              40
```

```
<210> SEQ ID NO 193
<211> LENGTH: 21
<212> TYPE: DNA
<213> ORGANISM: Homo sapiens

<400> SEQUENCE: 193
cctgctgaag tggctgccaa a                                              21

<210> SEQ ID NO 194
<211> LENGTH: 21
<212> TYPE: DNA
<213> ORGANISM: Homo sapiens

<400> SEQUENCE: 194
aacttggttt gatgctgtgc c                                              21

<210> SEQ ID NO 195
<211> LENGTH: 42
<212> TYPE: DNA
<213> ORGANISM: Homo sapiens

<400> SEQUENCE: 195
aacttggttt gatgctgtgc ctttcttcct ggagactcaa aa                       42

<210> SEQ ID NO 196
<211> LENGTH: 25
<212> TYPE: DNA
<213> ORGANISM: Homo sapiens

<400> SEQUENCE: 196
tgtccgcagt tgatggccag agaca                                          25

<210> SEQ ID NO 197
<211> LENGTH: 25
<212> TYPE: DNA
<213> ORGANISM: Homo sapiens

<400> SEQUENCE: 197
acttgattac cgcagacagt gatga                                          25

<210> SEQ ID NO 198
<211> LENGTH: 50
<212> TYPE: DNA
<213> ORGANISM: Homo sapiens

<400> SEQUENCE: 198
acttgattac cgcagacagt gatgaacaac cggttgaggt cctgataaat                50

<210> SEQ ID NO 199
<211> LENGTH: 21
<212> TYPE: DNA
<213> ORGANISM: Homo sapiens

<400> SEQUENCE: 199
tgctgaagaa cggagggatg t                                              21

<210> SEQ ID NO 200
<211> LENGTH: 21
<212> TYPE: DNA
<213> ORGANISM: Homo sapiens

<400> SEQUENCE: 200
tttgccattt tcctgctcct c                                              21
```

```
<210> SEQ ID NO 201
<211> LENGTH: 42
<212> TYPE: DNA
<213> ORGANISM: Homo sapiens

<400> SEQUENCE: 201
tttgccattt tcctgctcct ccatctccaa aaaaagtctt cg          42

<210> SEQ ID NO 202
<211> LENGTH: 20
<212> TYPE: DNA
<213> ORGANISM: Homo sapiens

<400> SEQUENCE: 202
caggagttcg cagtcaagat                                   20

<210> SEQ ID NO 203
<211> LENGTH: 20
<212> TYPE: DNA
<213> ORGANISM: Homo sapiens

<400> SEQUENCE: 203
acaggatgtt ctccggcttg                                   20

<210> SEQ ID NO 204
<211> LENGTH: 40
<212> TYPE: DNA
<213> ORGANISM: Homo sapiens

<400> SEQUENCE: 204
acaggatgtt ctccggcttg atctggcttg cttccgactc             40

<210> SEQ ID NO 205
<211> LENGTH: 20
<212> TYPE: DNA
<213> ORGANISM: Homo sapiens

<400> SEQUENCE: 205
acaattgact ctggccttcc                                   20

<210> SEQ ID NO 206
<211> LENGTH: 20
<212> TYPE: DNA
<213> ORGANISM: Homo sapiens

<400> SEQUENCE: 206
tagacaatgg ccagcgcaac                                   20

<210> SEQ ID NO 207
<211> LENGTH: 40
<212> TYPE: DNA
<213> ORGANISM: Homo sapiens

<400> SEQUENCE: 207
acaattgact ctggccttcc acgatctcag acgtcagcgt             40

<210> SEQ ID NO 208
<211> LENGTH: 20
<212> TYPE: DNA
<213> ORGANISM: Homo sapiens

<400> SEQUENCE: 208
gagagcccgg acatcaagta                                   20
```

<210> SEQ ID NO 209
<211> LENGTH: 20
<212> TYPE: DNA
<213> ORGANISM: Homo sapiens

<400> SEQUENCE: 209
acttcccttt gccctggtag                    20

<210> SEQ ID NO 210
<211> LENGTH: 40
<212> TYPE: DNA
<213> ORGANISM: Homo sapiens

<400> SEQUENCE: 210
acttcccttt gccctggtag actgagacat cttccctcca            40

<210> SEQ ID NO 211
<211> LENGTH: 21
<212> TYPE: DNA
<213> ORGANISM: Homo sapiens

<400> SEQUENCE: 211
cgctcatcgt gggtctccta a                  21

<210> SEQ ID NO 212
<211> LENGTH: 21
<212> TYPE: DNA
<213> ORGANISM: Homo sapiens

<400> SEQUENCE: 212
agaagtcctg ggcattgtcg g                  21

<210> SEQ ID NO 213
<211> LENGTH: 42
<212> TYPE: DNA
<213> ORGANISM: Homo sapiens

<400> SEQUENCE: 213
agaagtcctg ggcattgtcg gcaggtcggc caggtcatac tc          42

<210> SEQ ID NO 214
<211> LENGTH: 20
<212> TYPE: DNA
<213> ORGANISM: Homo sapiens

<400> SEQUENCE: 214
cctgctccgc tgctccttgg                    20

<210> SEQ ID NO 215
<211> LENGTH: 20
<212> TYPE: DNA
<213> ORGANISM: Homo sapiens

<400> SEQUENCE: 215
catgcccaac actcccctcc                    20

<210> SEQ ID NO 216
<211> LENGTH: 40
<212> TYPE: DNA
<213> ORGANISM: Homo sapiens

<400> SEQUENCE: 216

```
catgcccaac actcccctcc ccctctctaa cacctcagca                            40

<210> SEQ ID NO 217
<211> LENGTH: 20
<212> TYPE: DNA
<213> ORGANISM: Homo sapiens

<400> SEQUENCE: 217
aggtacagct ccccaccagc                                                  20

<210> SEQ ID NO 218
<211> LENGTH: 20
<212> TYPE: DNA
<213> ORGANISM: Homo sapiens

<400> SEQUENCE: 218
cttccagcca gggcctgagc                                                  20

<210> SEQ ID NO 219
<211> LENGTH: 40
<212> TYPE: DNA
<213> ORGANISM: Homo sapiens

<400> SEQUENCE: 219
cttccagcca gggcctgagc aggaatggtt accgtttgcc                            40

<210> SEQ ID NO 220
<211> LENGTH: 20
<212> TYPE: DNA
<213> ORGANISM: Homo sapiens

<400> SEQUENCE: 220
ggagcccaac tgcgccgacc                                                  20

<210> SEQ ID NO 221
<211> LENGTH: 22
<212> TYPE: DNA
<213> ORGANISM: Homo sapiens

<400> SEQUENCE: 221
ccttcggtga ctgatgatct aa                                               22

<210> SEQ ID NO 222
<211> LENGTH: 38
<212> TYPE: DNA
<213> ORGANISM: Homo sapiens

<400> SEQUENCE: 222
ggagcccaac tgcgccgacc cccgtggacc tggctgag                              38

<210> SEQ ID NO 223
<211> LENGTH: 21
<212> TYPE: DNA
<213> ORGANISM: Homo sapiens

<400> SEQUENCE: 223
gcgctgcagg ttatgaaact t                                                21

<210> SEQ ID NO 224
<211> LENGTH: 21
<212> TYPE: DNA
<213> ORGANISM: Homo sapiens

<400> SEQUENCE: 224
```

```
agccccgttt gcctgcatca g                                              21

<210> SEQ ID NO 225
<211> LENGTH: 42
<212> TYPE: DNA
<213> ORGANISM: Homo sapiens

<400> SEQUENCE: 225
agccccgttt gcctgcatca gacccggagg tggccttctt tg                       42

<210> SEQ ID NO 226
<211> LENGTH: 20
<212> TYPE: DNA
<213> ORGANISM: Homo sapiens

<400> SEQUENCE: 226
gcatcccgac gccctcaacc                                                20

<210> SEQ ID NO 227
<211> LENGTH: 20
<212> TYPE: DNA
<213> ORGANISM: Homo sapiens

<400> SEQUENCE: 227
gatgtccacg aggtcctgag                                                20

<210> SEQ ID NO 228
<211> LENGTH: 40
<212> TYPE: DNA
<213> ORGANISM: Homo sapiens

<400> SEQUENCE: 228
gcatcccgac gccctcaacc gatgtccacg aggtcctgag                          40

<210> SEQ ID NO 229
<211> LENGTH: 20
<212> TYPE: DNA
<213> ORGANISM: Homo sapiens

<400> SEQUENCE: 229
gctgtccctc cccttgtct                                                 20

<210> SEQ ID NO 230
<211> LENGTH: 20
<212> TYPE: DNA
<213> ORGANISM: Homo sapiens

<400> SEQUENCE: 230
tgttccgctg ctaatcaaag                                                20

<210> SEQ ID NO 231
<211> LENGTH: 40
<212> TYPE: DNA
<213> ORGANISM: Homo sapiens

<400> SEQUENCE: 231
tgttccgctg ctaatcaaag tactccccca tcatataccc                          40

<210> SEQ ID NO 232
<211> LENGTH: 20
<212> TYPE: DNA
<213> ORGANISM: Homo sapiens
```

```
<400> SEQUENCE: 232
cgggacttgg agaagcactg                                                20

<210> SEQ ID NO 233
<211> LENGTH: 20
<212> TYPE: DNA
<213> ORGANISM: Homo sapiens

<400> SEQUENCE: 233
tagaagaatc gtcggttgca                                                20

<210> SEQ ID NO 234
<211> LENGTH: 40
<212> TYPE: DNA
<213> ORGANISM: Homo sapiens

<400> SEQUENCE: 234
tagaagaatc gtcggttgca tgacatcctg gctctcctgc                          40

<210> SEQ ID NO 235
<211> LENGTH: 20
<212> TYPE: DNA
<213> ORGANISM: Homo sapiens

<400> SEQUENCE: 235
agaccggcgc acagaggaag                                                20

<210> SEQ ID NO 236
<211> LENGTH: 20
<212> TYPE: DNA
<213> ORGANISM: Homo sapiens

<400> SEQUENCE: 236 cttttttggac ttcaggtggc                                               20

<210> SEQ ID NO 237
<211> LENGTH: 40
<212> TYPE: DNA
<213> ORGANISM: Homo sapiens

<400> SEQUENCE: 237 cttttttggac ttcaggtggc cctcattcag ctctcggaac                         40

<210> SEQ ID NO 238
<211> LENGTH: 23
<212> TYPE: DNA
<213> ORGANISM: Homo sapiens

<400> SEQUENCE: 238
cgaaggctac gaaggctatt aca                                            23

<210> SEQ ID NO 239
<211> LENGTH: 23
<212> TYPE: DNA
<213> ORGANISM: Homo sapiens

<400> SEQUENCE: 239
tggggagaag aagggaccga cga                                            23

<210> SEQ ID NO 240
<211> LENGTH: 46
<212> TYPE: DNA
<213> ORGANISM: Homo sapiens
```

```
<400> SEQUENCE: 240
tggggagaag aagggggacca cgaaggaatc ctgggagata caagaa                    46

<210> SEQ ID NO 241
<211> LENGTH: 22
<212> TYPE: DNA
<213> ORGANISM: Homo sapiens

<400> SEQUENCE: 241
gctccagcgg tgtaaacctg ca                                               22

<210> SEQ ID NO 242
<211> LENGTH: 22
<212> TYPE: DNA
<213> ORGANISM: Homo sapiens

<400> SEQUENCE: 242
cgtgcaaatt caccagaagg ca                                               22

<210> SEQ ID NO 243
<211> LENGTH: 44
<212> TYPE: DNA
<213> ORGANISM: Homo sapiens

<400> SEQUENCE: 243
cgtgcaaatt caccagaagg catcaacttc atttcatagt ctga                       44

<210> SEQ ID NO 244
<211> LENGTH: 20
<212> TYPE: DNA
<213> ORGANISM: Homo sapiens

<400> SEQUENCE: 244
ctttcggttt tcaggggggaa                                                 20

<210> SEQ ID NO 245
<211> LENGTH: 20
<212> TYPE: DNA
<213> ORGANISM: Homo sapiens

<400> SEQUENCE: 245
tggctcacag ttctgcaggc                                                  20

<210> SEQ ID NO 246
<211> LENGTH: 43
<212> TYPE: DNA
<213> ORGANISM: Homo sapiens

<400> SEQUENCE: 246
tggctcacag ttctgcagca ggcaattcct tatggcgcac agg                        43

<210> SEQ ID NO 247
<211> LENGTH: 20
<212> TYPE: DNA
<213> ORGANISM: Homo sapiens

<400> SEQUENCE: 247
ggggtcccgc tcatcaagta                                                  20

<210> SEQ ID NO 248
<211> LENGTH: 20
<212> TYPE: DNA
```

```
<213> ORGANISM: Homo sapiens

<400> SEQUENCE: 248
aactgccaca tcctttgcgt                                              20

<210> SEQ ID NO 249
<211> LENGTH: 40
<212> TYPE: DNA
<213> ORGANISM: Homo sapiens

<400> SEQUENCE: 249
aactgccaca tcctttgcgt ccgcatgaag atgggagctc                        40

<210> SEQ ID NO 250
<211> LENGTH: 21
<212> TYPE: DNA
<213> ORGANISM: Homo sapiens

<400> SEQUENCE: 250
gcttccaagc ccgacctgat g                                            21

<210> SEQ ID NO 251
<211> LENGTH: 21
<212> TYPE: DNA
<213> ORGANISM: Homo sapiens

<400> SEQUENCE: 251
acggtggaaa tggtagtagg a                                            21

<210> SEQ ID NO 252
<211> LENGTH: 40
<212> TYPE: DNA
<213> ORGANISM: Homo sapiens

<400> SEQUENCE: 252
acggtggaaa tggtagtagg actccagccc tgagggttcc                        40

<210> SEQ ID NO 253
<211> LENGTH: 20
<212> TYPE: DNA
<213> ORGANISM: Homo sapiens

<400> SEQUENCE: 253
ggccagaatt tagcaagaca                                              20

<210> SEQ ID NO 254
<211> LENGTH: 20
<212> TYPE: DNA
<213> ORGANISM: Homo sapiens

<400> SEQUENCE: 254
tgactatggg cctagagcag                                              20

<210> SEQ ID NO 255
<211> LENGTH: 41
<212> TYPE: DNA
<213> ORGANISM: Homo sapiens

<400> SEQUENCE: 255
tgactatggg cctagagcag ggcttcttct tttccactgg t                      41

<210> SEQ ID NO 256
<211> LENGTH: 18
```

```
<212> TYPE: DNA
<213> ORGANISM: Homo sapiens

<400> SEQUENCE: 256
ccgaccagat caccctcc                                                 18

<210> SEQ ID NO 257
<211> LENGTH: 18
<212> TYPE: DNA
<213> ORGANISM: Homo sapiens

<400> SEQUENCE: 257
gcttccgcac gtagacct                                                 18

<210> SEQ ID NO 258
<211> LENGTH: 36
<212> TYPE: DNA
<213> ORGANISM: Homo sapiens

<400> SEQUENCE: 258
gcttccgcac gtagacctag ccccgtctcc gcatca                             36

<210> SEQ ID NO 259
<211> LENGTH: 24
<212> TYPE: DNA
<213> ORGANISM: Homo sapiens

<400> SEQUENCE: 259
tttcagaagg tctgccaaca ccaa                                          24

<210> SEQ ID NO 260
<211> LENGTH: 24
<212> TYPE: DNA
<213> ORGANISM: Homo sapiens

<400> SEQUENCE: 260
gtgtccacca aggtcctgag atcc                                          24

<210> SEQ ID NO 261
<211> LENGTH: 48
<212> TYPE: DNA
<213> ORGANISM: Homo sapiens

<400> SEQUENCE: 261
gtgtccacca aggtcctgag atcccatttc tgccagtttc tgctgaaa                48

<210> SEQ ID NO 262
<211> LENGTH: 20
<212> TYPE: DNA
<213> ORGANISM: Homo sapiens

<400> SEQUENCE: 262
aggtgggcaa agggaagtaa                                               20

<210> SEQ ID NO 263
<211> LENGTH: 20
<212> TYPE: DNA
<213> ORGANISM: Homo sapiens

<400> SEQUENCE: 263
tagagcccct gagaagagcc                                               20

<210> SEQ ID NO 264
```

```
<211> LENGTH: 40
<212> TYPE: DNA
<213> ORGANISM: Homo sapiens

<400> SEQUENCE: 264
tagagcccct gagaagagcc cagagaactg acagtccgtg                             40

<210> SEQ ID NO 265
<211> LENGTH: 21
<212> TYPE: DNA
<213> ORGANISM: Homo sapiens

<400> SEQUENCE: 265
ccagccactg ttgcagcatg a                                                 21

<210> SEQ ID NO 266
<211> LENGTH: 21
<212> TYPE: DNA
<213> ORGANISM: Homo sapiens

<400> SEQUENCE: 266
aggcaaatgg gactcataca c                                                 21

<210> SEQ ID NO 267
<211> LENGTH: 42
<212> TYPE: DNA
<213> ORGANISM: Homo sapiens

<400> SEQUENCE: 267
aggcaaatgg gactcataca cgggctggtg ctggagtgac ta                          42

<210> SEQ ID NO 268
<211> LENGTH: 20
<212> TYPE: DNA
<213> ORGANISM: Homo sapiens

<400> SEQUENCE: 268
gctctgagcg agattgagac                                                   20

<210> SEQ ID NO 269
<211> LENGTH: 20
<212> TYPE: DNA
<213> ORGANISM: Homo sapiens

<400> SEQUENCE: 269
caggatcaca cagcagatga                                                   20

<210> SEQ ID NO 270
<211> LENGTH: 40
<212> TYPE: DNA
<213> ORGANISM: Homo sapiens

<400> SEQUENCE: 270
caggatcaca cagcagatga tccacatagt ctaccgcgtg                             40

<210> SEQ ID NO 271
<211> LENGTH: 20
<212> TYPE: DNA
<213> ORGANISM: Homo sapiens

<400> SEQUENCE: 271
tgtgcacaaa tccatcaacc                                                   20
```

```
<210> SEQ ID NO 272
<211> LENGTH: 20
<212> TYPE: DNA
<213> ORGANISM: Homo sapiens

<400> SEQUENCE: 272
gaaaggctcc agggttaggt                                               20

<210> SEQ ID NO 273
<211> LENGTH: 40
<212> TYPE: DNA
<213> ORGANISM: Homo sapiens

<400> SEQUENCE: 273
gaaaggctcc agggttaggt cacggatccg catggccatc                         40

<210> SEQ ID NO 274
<211> LENGTH: 20
<212> TYPE: DNA
<213> ORGANISM: Homo sapiens

<400> SEQUENCE: 274
ccacgctctt ctgcctgctg                                               20

<210> SEQ ID NO 275
<211> LENGTH: 20
<212> TYPE: DNA
<213> ORGANISM: Homo sapiens

<400> SEQUENCE: 275
ctggtaggag acggcgatgc                                               20

<210> SEQ ID NO 276
<211> LENGTH: 40
<212> TYPE: DNA
<213> ORGANISM: Homo sapiens

<400> SEQUENCE: 276
ctggtaggag acggcgatgc gggtttgcta caacatgggc                         40

<210> SEQ ID NO 277
<211> LENGTH: 20
<212> TYPE: DNA
<213> ORGANISM: Homo sapiens

<400> SEQUENCE: 277
gccgcctact tggtgctaac                                               20

<210> SEQ ID NO 278
<211> LENGTH: 20
<212> TYPE: DNA
<213> ORGANISM: Homo sapiens

<400> SEQUENCE: 278
cgtgctgcgc cctgccttat                                               20

<210> SEQ ID NO 279
<211> LENGTH: 40
<212> TYPE: DNA
<213> ORGANISM: Homo sapiens

<400> SEQUENCE: 279
cgtgctcgcc cctgccttag aggagtgcca agtttctatt                         40
```

```
<210> SEQ ID NO 280
<211> LENGTH: 21
<212> TYPE: DNA
<213> ORGANISM: Homo sapiens

<400> SEQUENCE: 280
gattcctatg tgggcgacga g                                               21

<210> SEQ ID NO 281
<211> LENGTH: 20
<212> TYPE: DNA
<213> ORGANISM: Homo sapiens

<400> SEQUENCE: 281
ccatctcttg ctcgaagtcc                                                 20

<210> SEQ ID NO 282
<211> LENGTH: 40
<212> TYPE: DNA
<213> ORGANISM: Homo sapiens

<400> SEQUENCE: 282
ccatctcttg ctcgaagtcc gccagccagg tccagacgca                           40
```